(12) United States Patent
Takhi et al.

(10) Patent No.: US 9,062,002 B2
(45) Date of Patent: Jun. 23, 2015

(54) SUBSTITUTED PYRIDINE DERIVATIVES AS FABI INHIBITORS

(71) Applicants: Aurigene Discovery Technologies Limited, Bangalore (IN); UM Pharmauji Sdn. BHD, Kuala Lumpur (MY)

(72) Inventors: Mohamed Takhi, Hyderabad (IN); Subramanya Hosahalli, Bangalore (IN); Sunil Kumar Panigrahi, Kantamal (IN); Muni Kumar Mahadari, Gadwal (IN); Chandrashekar Reddy Kottam, Shadnagar (IN); Noorsaadah Abd Rahman, Kuala Lumpur (MY); Rohana Yusof, Kajang (MY)

(73) Assignees: Aurigene Discovery Technologies Limited, Bangalore (IN); UM Pharmauji Sdn. BHD, Kuala Lumpur (MY)

( * ) Notice: Subject to any disclaimer, the term of this patent is extended or adjusted under 35 U.S.C. 154(b) by 0 days.

(21) Appl. No.: 14/361,171
(22) PCT Filed: Nov. 29, 2012
(86) PCT No.: PCT/IN2012/000776
§ 371 (c)(1),
(2) Date: May 28, 2014

(87) PCT Pub. No.: WO2013/080222
PCT Pub. Date: Jun. 6, 2013

(65) Prior Publication Data
US 2014/0336153 A1    Nov. 13, 2014

(30) Foreign Application Priority Data

Dec. 2, 2011 (IN) .............. 4176/CHE/2011

(51) Int. Cl.
| | | |
|---|---|---|
| C07D 471/20 | (2006.01) |
| C07D 471/04 | (2006.01) |
| C07D 213/75 | (2006.01) |
| C07D 471/14 | (2006.01) |
| C07D 401/14 | (2006.01) |
| C07F 5/02 | (2006.01) |

(52) U.S. Cl.
CPC ............ *C07D 213/75* (2013.01); *C07D 471/04* (2013.01); *C07D 471/14* (2013.01); *C07D 401/14* (2013.01); *C07D 471/20* (2013.01); *C07F 5/025* (2013.01)

(58) Field of Classification Search
CPC .. C07D 213/75; C07D 471/04; C07D 471/14; C07D 471/20
USPC ................ 514/64, 300, 256, 234.5, 278, 221, 514/237.2, 333; 546/13, 122, 18, 256
See application file for complete search history.

(56) References Cited

U.S. PATENT DOCUMENTS

| | | |
|---|---|---|
| 5,506,261 A | 4/1996 | Brooks et al. |
| 6,326,381 B1 * | 12/2001 | Kelly et al. ................. 514/318 |
| 6,503,903 B1 | 1/2003 | Miller et al. |
| 6,730,684 B1 | 5/2004 | Miller et al. |
| 6,762,201 B1 | 7/2004 | Miller et al. |
| 6,765,005 B2 | 7/2004 | Miller et al. |
| 6,846,819 B1 | 1/2005 | Miller et al. |
| 7,049,310 B2 | 5/2006 | Burgess et al. |
| 7,250,424 B2 | 7/2007 | Burgess et al. |
| 7,524,843 B2 | 4/2009 | Miller et al. |
| 7,557,125 B2 | 7/2009 | Miller et al. |
| 7,741,339 B2 | 6/2010 | Burgess et al. |
| 7,790,716 B2 | 9/2010 | Miller et al. |

FOREIGN PATENT DOCUMENTS

| | | |
|---|---|---|
| WO | 2011061214 | 5/2011 |
| WO | 2013021051 | 2/2013 |
| WO | 2013021052 | 2/2013 |

OTHER PUBLICATIONS

Bergler et al. "Protein EnvM Is the NADH-dependent Enoyl-ACP Reductase (FabI) of *Escherichia coli*", Journal of Biological Chemistry, vol. 269, No. 8, pp. 5493-5496, Feb. 25, 1994.
Heath et al. "Regulation of Fatty Acid Elongation and Initiation by Acyl-Acyl Carrier Protein in *Escherichia coli*", Journal of Biological Chemistry, vol. 271, No. 4, pp. 1833-1836, Jan. 26, 1996.
Grassberger et al. "Preparation and Antibacterial Activities of New 1,2,3-Diazaborine Derivatives and Analogues", Journal of Medicinal Chemistry, vol. 27, pp. 947-953, Aug. 1984.
McMurry et al. "Triclosan targets lipid synthesis", Nature, vol. 394, pp. 531-532, Aug. 6, 1998.
International Search Report for priority PCT Application No. PCT/IN2012/000776, mailed Apr. 25, 2013 (3 pages).
Miller, W.H. "Discovery of aminopyridine-based inhibitors of bacterial enoyl-ACP reductase (FabI)", Journal of Medicinal Chemistry, vol. 45, No. 15, pp. 3246-3256, Jun. 19, 2002.

* cited by examiner

*Primary Examiner* — Niloofar Rahmani
(74) *Attorney, Agent, or Firm* — Winthrop & Weinstine, P.A.

(57) ABSTRACT

The present invention provides substituted pyridine derivatives of formula (I), which may be therapeutically useful as as anti-bacterial agents, more particularly FabI inhibitors. Formula (I) in which R1 to R5 and L have the meanings given in the specification, and pharmaceutically acceptable salts thereof that are useful in the treatment and prevention in diseases or disorder, in particular their use in diseases or disorder where there is an advantage anti-bacterial agents, more particularly FabI inhibitors. The present invention also provides methods for synthesizing and administering the FabI inhibitor compounds. The present invention also provides pharmaceutical formulations comprising at least one of the FabI inhibitor compounds together with a pharmaceutically acceptable carrier, diluent or excipient therefor.

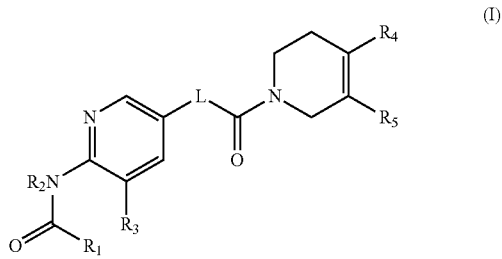

(I)

19 Claims, No Drawings

SUBSTITUTED PYRIDINE DERIVATIVES AS FABI INHIBITORS

This application claims the benefit of Indian provisional application number 4176/CHE/2011 filed on Dec. 2, 2011 which hereby incorporated by reference.

TECHNICAL FIELD

This invention relates to pharmaceutically active compounds which inhibit FabI and are useful for the treatment of bacterial infections.

BACKGROUND

Fatty acid biosynthesis (or Fab) is an essential metabolic process for all living organisms. It is used to synthesize the metabolic precursors for membrane phospholipids in the cell wall. Fatty acids are synthesized by mammals (using enzyme FAS I) and bacteria (using enzyme FAS II) via substantially different biosynthetic mechanisms, thus providing the possibility of bacteria-specific drug targeting. Indeed, inhibitors targeting the various stages of the fatty acid biosynthetic pathway have been investigated as novel anti-bacterial agents. Broadly, the pathway of saturated fatty acid biosynthesis (FAB) is more or less similar in all organisms, however, the fatty acid synthase (FAS) enzymatic biosynthesis systems vary considerably with respect to their structural organization. Mammalian fatty acid synthesis (FAS-I) employs a multifunctional enzyme complex in which all enzymatic activities reside on a single polypeptide. In contrast, bacterial fatty acid synthesis (FAS-II) elongation cycle utilizes several distinct monofunctional enzymes with activity pertaining to respective enzyme peptides effecting fatty acid chain elongation and ultimately cell membrane production. Enoyl acyl carrier protein reductase (FabI) is the component of FAS-II that catalyzes the final reaction in the enzymatic sequence. Hence, there appears to be considerable scope for the selective inhibition of the bacterial FAS system enzymes by exploring newer anti-bacterial agents.

Fab I (a protein enzyme encoded by EnVM gene) acts as an enoyl-ACP reductase (Bergler, et al, (1994), J. Biol. Chem. 269, 5493-5496) in the final step of the reactions involved in each cycle of bacterial fatty acid biosynthesis. Further rounds of this cycle, adding two carbon atoms per cycle, eventually lead to palmitoyl-ACP (16-Carbon), and subsequently the cycle is blocked largely due to feedback inhibition of Fab I by palmitoyl-ACP (Heath, et al, (1996), J. Biol. Chem. 271, 1833-1836).

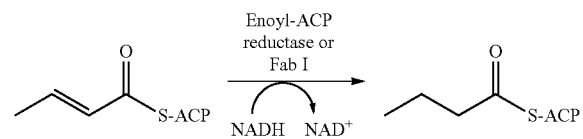

Thus, Fab I is among one of the major biosynthetic enzyme and appears to be a key moderator in the overall bacterial fatty acid biosynthetic pathway. Therefore, Fab I may be one of the meaningful target for acquiring anti-bacterial role.

Though there is plethora of literature on Fab I, which provides different inhibitors, however, among promising literature, it reveals that diazaborine (an antibiotic) inhibit fatty acid, phospholipid and lipopolysaccharide (LPS) biosynthesis via Fab I as one of the anti-bacterial target. Grassberger, et at in J. Med Chem 27, 947-953 (1984) reported derivative of 2b18 (a peptide) possessing non-competitive inhibitory activity of Fab I (Bergler, et al, (1994) J. Biol. Chem. 269, 5493-5496). Bergler et al in J. Biol. Chem. 269, 5493-5496 (1994) reported that inhibition of Fab I either by diazaborine or by raising the temperature in a Fab I temperature sensitive mutant is lethal. These results demonstrate that Fab I appears to be essential for the survival of the organism. McMurry et at in Nature 394, 531-532 (1998) have shown that Fab I is also the target for the well known broad spectrum anti-bacterial agent triclosan. Recent literature including U.S. Pat. Nos. 7,790,716; 7,741,339; 7,557,125; 7,524,843; 7,250,424; 7,049,310; 6,846,819; 6,765,005; 6,762,201; 6,730,684 and 6,503,903 also reveals that diverse compounds are known to possess Fab I inhibitory activity and have anti-bacterial role, and, therefore, may be useful for the treatment of bacterial infections in mammals, particularly in man.

Further various antimicrobial resistances among clinical isolates have been observed as one of the major problem in recent years. Of particular concern has been the increasing incidence of methicillin-resistant *Staphylococcus* spp., vancomycin-resistant *Enterococcus* spp., and penicillin-resistant *Streptococcus pneumoniae.*

Despite various disclosures on Fab I inhibitors, however, with the rise in number of patients affected by diverse bacterial and related microbial diseases and drug resistance, there appears to be unmet need for newer drugs that can treat such diseases more effectively. There is still need for newer antibacterial agentswhich may be further useful in a wide variety of bacterial infections and possessing broader spectrum.

SUMMARY OF THE INVENTION

The present invention relates to novel substituted pyridine derivatives of formula (I) useful as anti-bacterial agents.

In one aspect of the present invention, it relates to compound of formula (I):

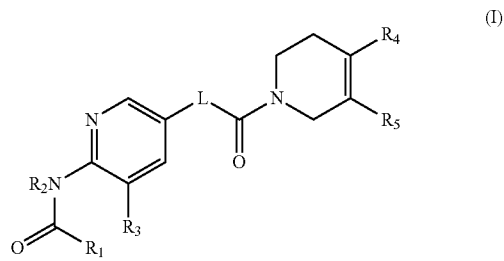

or a pharmaceutically acceptable salts, derivatives, prodrugs, stereoisomer's, solvates or biologically active metabolites thereof;

wherein;

$R_1$ is selected from an optionally substituted alkyl, amino, cycloalkyl, aryl, heterocyclyl, heteroaryl, heterocyclylalkyl or heteroarylalkyl;

$R_2$ is hydrogen; or $R_1$ and $R_2$ may be taken together with the atoms to which they are attached to form an optionally substituted 4-7 membered ring containing 0-3 additional hetero atoms independently selected from N, O and S in any stable combination;

$R_3$ is selected from hydrogen, carboxy, optionally substituted alkyl or heterocyclylalkyl; or $R_1$ and $R_3$ may be taken together with the carbon atoms to which they are attached to form an optionally substituted 6-8 membered ring containing 0-3 additional hetero atoms independently selected from N, O and S in any stable combination; wherein the optional substituent, at each occurrence, is independently selected from one or more $R_6$;

L is a linker selected from —$CH_2$—$CH_2$—, —CH=CH— or —$CH_2$—S—;

$R_4$ is selected from optionally substituted alkyl, optionally substituted alkenyl, optionally substituted alkynyl, optionally substituted alkoxy, optionally substituted amino, optionally substituted aryl, $B(OH)_2$, optionally substituted cycloalkyl, optionally substituted heterocyclyl, optionally substituted heteroaryl, optionally substituted arylalkyl, optionally substituted heteroarylalkyl, optionally substituted heterocyclylalkyl, wherein the optional substituent, in each occurrence, is independently selected from one or more $R_7$;

$R_5$ is hydrogen; or $R_4$ and $R_5$ may be taken together with the carbon atoms to which they are attached to form an optionally substituted 5-8 membered ring optionally containing 0-4 hetero atoms independently selected from N, O and S in any stable combination; wherein the optional substituent, at each occurrence, is independently selected from alkoxy, halo, hydroxyl, an optionally substituted alkyl or an optionally substituted alkenyl;

$R_6$ is independently selected from optionally substituted alkyl, optionally substituted heterocyclylalkyl, —$COOR_8$ or two of the $R_6$ groups on the same atom combined together to form an optionally substituted spiro condensed 3-8 membered ring containing 0-3 hetero atoms independently selected from N, O and S; wherein the optional substituent is independently selected from one or more $R_8$, —$(CH_2)_{1-3}OR_8$, —$COOR_8$, —$COR_8$, —$COCH_2OR_8$, —$CONR_8R_8$, —$NR_8R_8$ or an optionally substituted heterocyclyl;

$R_7$ is independently selected from cyano, nitro, halogen, —$OR_8$, —$NR_8R_8$, —$COOR_8$, —$CONR_8R_8$, —$NR_8COR_8$, haloalkyl, haloalkoxy, —NHC(=$NR_9$)$NHR_9$, —$(CH_2)_{1-3}OR_8$, —C(=NOH)$NH_2$ or optionally substituted alkyl, optionally substituted alkoxy, optionally substituted alkenyl, optionally substituted alkynyl, optionally substituted aryloxy, cyanoalkyl, cyanoalkoxy, cycloalkyl, optionally substituted aryl, optionally substituted heterocyclyl, optionally substituted heteroaryl or optionally substituted heterocyclylalkyl;

$R_8$ at each occurrence is independently selected from hydrogen or optionally substituted alkyl, optionally substituted aryl, optionally substituted arylalkyl, cycloalkyl, heterocyclyl, heteroaryl, —$CH_2C$(=NOH)$NH_2$ or two of the $R_8$ groups on the same atom can be taken together with the atom to which they are attached to form an optionally substituted 3-8 membered ring containing 0-3 hetero atoms independently selected from N, O and S in any stable combination; wherein the optional substituent is independently selected from —$COOC_1$-$C_4$alkyl, halogen, hydroxy, cyano, alkyl, alkoxy, nitro or haloalkoxy;

$R_9$ at each occurrence is independently selected from hydrogen or —$COOC_1$-$C_4$alkyl.

In yet another aspect of the present invention, it relates to process for the preparation of novel substituted pyridine derivatives of formula (I).

In a further aspect of the present invention, it relates to the pharmaceutical composition comprising substituted pyridine derivatives of formula (I) and processes for preparing thereof.

In yet further another aspect of the present invention, it relates to the use of novel substituted pyridine derivatives of formula (I) and their solvates, tautomers, salts and stereoisomers thereof, including mixtures thereof in all suitable ratios wherever applicable as a medicament for the treatment and prevention of disorder or diseases by inhibitory action on enzymes—Fab I.

DETAILED DESCRIPTION OF THE INVENTION

Embodiments of the present application provides novel substituted pyridine derivatives of formula (I) useful as antibacterial agents.

One of the embodiment of the present invention provides compound of formula (I):

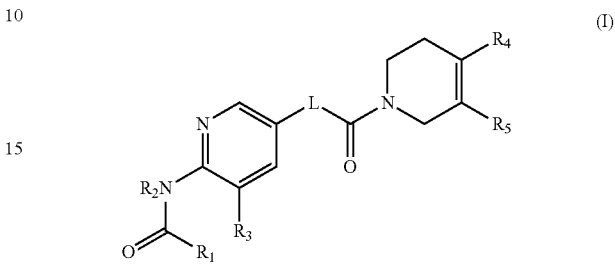

or a pharmaceutically acceptable salts, derivatives, prodrugs, stereoisomers, solvates or biologically active metabolites thereof;

wherein;

$R_1$ is selected from an optionally substituted alkyl, amino, cycloalkyl, aryl, heterocyclyl, heteroaryl, heterocyclylalkyl or heteroarylalkyl;

$R_2$ is hydrogen; or $R_1$ and $R_2$ may be taken together with the atoms to which they are attached to form an optionally substituted 4-7 membered ring containing 0-3 additional hetero atoms independently selected from N, O and S in any stable combination;

$R_3$ is selected from hydrogen, carboxy, optionally substituted alkyl or heterocyclylalkyl; or $R_1$ and $R_3$ may be taken together with the carbon atoms to which they are attached to form an optionally substituted 6-8 membered ring containing 0-3 additional hetero atoms independently selected from N, O and S in any stable combination; wherein the optional substituent, at each occurrence, is independently selected from one or more $R_6$;

L is a linker selected from —$CH_2$—$CH_2$—, —CH=CH— or —$CH_2$—S—;

$R_4$ is selected from optionally substituted alkyl, optionally substituted alkenyl, optionally substituted alkynyl, optionally substituted alkoxy, optionally substituted amino, optionally substituted aryl, $B(OH)_2$, optionally substituted cycloalkyl, optionally substituted heterocyclyl, optionally substituted heteroaryl, optionally substituted arylalkyl, optionally substituted heteroarylalkyl, optionally substituted heterocyclylalkyl, wherein the optional substituent, in each occurrence, is independently selected from one or more $R_7$;

$R_5$ is hydrogen; or $R_4$ and $R_5$ may be taken together with the carbon atoms to which they are attached to form an optionally substituted 5-8 membered ring optionally containing 0-4 hetero atoms independently selected from N, O and S in any stable combination; wherein the optional substituent, at each occurrence, is independently selected from alkoxy, halo, hydroxyl, an optionally substituted alkyl or an optionally substituted alkenyl;

$R_6$ is independently selected from optionally substituted alkyl, optionally substituted heterocyclylalkyl, —$COOR_8$ or two of the $R_6$ groups on the same atom combined together to form an optionally substituted spiro condensed 3-8 membered ring containing 0-3 hetero atoms independently selected from N, O and S; wherein the optional substituent is independently selected from one or more $R_8$, —$(CH_2)_{1-3}$ $OR_8$, —$COOR_8$, —$COR_8$, —$COCH_2OR_8$, —$CONR_8R_8$, —$NR_8R_8$ or an optionally substituted heterocyclyl;

$R_7$ is independently selected from cyano, nitro, halogen, —$OR_8$, —$NR_8R_8$, —$COOR_8$, —$CONR_8R_8$, —$NR_8COR_8$, haloalkyl, haloalkoxy, —$NHC(=NR_9)NHR_9$, —$(CH_2)_{1-3}$ $OR_8$, —$C(=NOH)NH_2$ or optionally substituted alkyl, optionally substituted alkoxy, optionally substituted alkenyl, optionally substituted alkynyl, optionally substituted aryloxy, cyanoalkyl, cyanoalkoxy, cycloalkyl, optionally substituted aryl, optionally substituted heterocyclyl, optionally substituted heteroaryl or optionally substituted heterocyclylalkyl;

$R_8$ at each occurrence is independently selected from hydrogen or optionally substituted alkyl, optionally substituted aryl, optionally substituted arylalkyl, cycloalkyl, heterocyclyl, heteroaryl, —$CH_2C(=NOH)NH_2$ or two of the $R_8$ groups on the same atom can be taken together with the atom to which they are attached to form an optionally substituted 3-8 membered ring containing 0-3 hetero atoms independently selected from N, O and S in any stable combination; wherein the optional substituent is independently selected from —$COOC_1$-$C_4$alkyl, halogen, hydroxy, cyano, alkyl, alkoxy, nitro or haloalkoxy;

$R_9$ at each occurrence is independently selected from hydrogen or —$COOC_1$-$C_4$alkyl.

In a particular embodiment, the linker L denotes —$CH=CH$— and the remaining groups are same as defined in formula (I).

In another particular embodiment, the linker L denotes —$CH_2$—$CH_2$— and the remaining groups are same as defined in formula (I).

In another particular embodiment, the linker L denotes —$CH_2$—$S$— and the remaining groups are same as defined in formula (I).

In a particular embodiment, the $R_1$ and $R_3$ can be taken together with the carbon atoms to which they are attached to form a 3-8 membered ring optionally substituted with one or more $R_6$ and the remaining groups are same as defined in formula (I).

In another particular embodiment, the above said 3-8 membered ring denotes naphthyridin-2(1H)-one or pyrido diazepin-2(3H)-one and the remaining groups are same as defined in formula (I).

In another particular embodiment, the above two $R_6$ groups on the same atom combined together to form an optionally substituted spiro condensed 3-8 membered ring containing 0-3 hetero atoms independently selected from N, O and S; wherein the optional substituent is independently selected from —$COOR_8$, —$COR_8$, —$COCH_2OR_8$—$CONR_8R_8$, —$NR_8R_8$ or an optionally substituted heterocyclyl.

In another particular embodiment, the above said $R_6$ group denotes alkyl, heterocyclylalkyl or —$COOR_8$ wherein $R_8$ is $C_{1-4}$ alkyl.

In another particular embodiment, the above said $R_6$ group denotes hydrogen or two of the $R_6$ groups on the same atom combined together to form an optionally substituted piperidine and the remaining groups are same as defined in formula (I).

In a particular embodiment, the $R_4$ group denotes alkyl substituted with heteroaryl and the said heteroaryl may be optionally substituted and the remaining groups are same as defined in formula (I);

In a particular embodiment of the compound of formula (I), the invention comprises a particular series of compound of formula (IA):

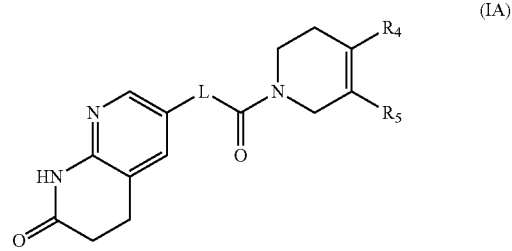

wherein L, $R_4$ and $R_5$ are as defined in formula (I); or a pharmaceutically acceptable salt thereof.

In another particular embodiment of the compound of formula (I), the invention comprises another particular series of compound of formula (IB):

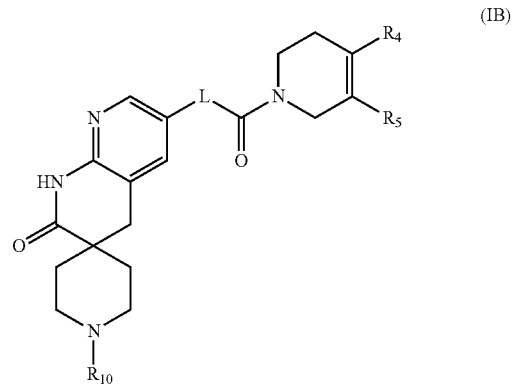

wherein $R_{10}$ is selected from optionally substituted alkyl, —$(CH_2)_{1-3}OR_8$, —$COR_8$, —$COCH_2OR_8$ or —$CONR_8R_8$, and L, $R_4$, $R_5$ and $R_8$ are as defined in formula (I); or a pharmaceutically acceptable salt thereof.

In another particular embodiment of the compound of formula (I), the invention comprises another particular series of compound of formula (IC):

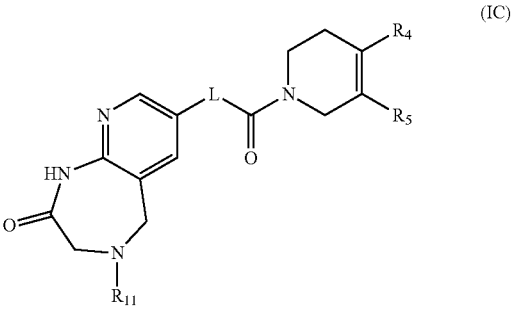

wherein $R_{11}$ is selected from hydrogen, optionally substituted alkyl, heterocyclylalkyl or —$COOR_8$; and L, $R_4$, $R_5$ and $R_8$ are as defined in formula (I); or a pharmaceutically acceptable salt thereof.

In another particular embodiment of the compound of formula (I), the invention comprises another particular series of compound of formula (ID):

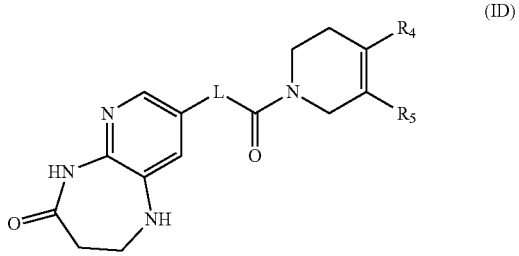

(ID)

wherein L, R$_4$ and R$_5$ are as defined in formula (I); or a pharmaceutically acceptable salt thereof.

In another embodiment of the present invention, it provides the process for preparation of novel substituted pyridine derivatives of formula (I).

The procedure for the compounds of formula (I) is detailed herein below in the specification stepwise including the general synthesis of various intermediates involved in process of manufacture of the compounds according to the present invention.

In yet another embodiment, the present invention relates to substituted pyridine derivatives of formula (I) for use in the treatment of bacterial infections. More preferably, the present invention relates to the use of compounds of formula (I) for the treatment and prevention in diseases or disorder, in particular their use in diseases or disorder, where there is an advantage in inhibiting enzymes—Fab I.

Further embodiments of the invention includes use of compounds of formula (I) and pharmaceutically acceptable derivatives, solvates, tautomers, salts and stereoisomers thereof, including mixtures thereof in all ratios as a medicament.

Use of compounds as above and pharmaceutically usable derivatives, salts, tautomers, solvates and stereoisomers thereof, including mixtures thereof in all ratios, for the preparation of a medicament for the treatment and prevention in diseases or disorder, where there is an advantage in inhibiting enzymes—Fab I.

Use of compounds as above and pharmaceutically usable derivatives, salts, tautomers, solvates and stereoisomers thereof, including mixtures thereof in all ratios, for the preparation of a medicament for the treatment and prevention of bacterial diseases, where there is an advantage in inhibiting enzymes—Fab I.

Use of compounds as above wherein there is an advantage in inhibiting enzymes—Fab I for antibacterial or antimicrobial diseases.

Use of the compounds as above for the preparation of a medicament for the treatment and prophylaxis of cancer diseases, inflammatory bowel disease or rheumatoid arthritis.

The invention further provides the use of substituted pyridine derivatives of formula (I) in combination with anti-bacterial agents such as cephalosporins, quinolones and fluoroquinolones, penicillins, penicillins and beta lactamase inhibitors, carbepenems, monobactams, macrolides and lincosamines, glycopeptides, rifampin, oxazolidonones, tetracyclines, aminoglycosides, streptogramins, sulfonamides, and the like. Other general categories of antibiotic agents which may be part of a subject composition include those agents known to those of skill in the art as antibiotics and that qualify as (with defined terms being in quotation marks): "drug articles" recognized in the official United States Pharmacopoeia or official National Formulary (or any supplement thereto); "new drug" and "new animal drug" approved by the FDA of the U.S. as those terms are used in title 21 of the United States Code; any drug that requires approval of a government entity, in the U.S. or abroad ("approved drug"); any drug that it is necessary to obtain regulatory approval so as to comply with 21 U.S.C. [section]355(a) ("regulatory approved drug"); any agent that is or was subject to a human drug application under 21 U.S.C. [section]379(g) ("human drug"). (All references to statutory code for this definition refer to such code as of the original filing date of this provisional application). Other antibiotic agents are disclosed herein, and are known to those of skilled in the art. In certain embodiments, the term "antibiotic agent" does not include an agent that is a FabI inhibitor, so that the combinations of the present invention in certain instances will include one agent that is a FabI inhibitor and another agent that is not other anti-bacterial compounds. A preferred composition is comprising a compound of formula (I) and Cyclosporin A, FK506, rapamycin, 40-(2-hydroxy)ethyl-rapamycin. Another preferred composition may comprise a compound of Formula (I) and a rheumatoid arthritis active agent selected from leflunomide, etanercept (Enbrel), infliximab (Remicade), anakinra (Kineret), adalimumab (Humira), rituximab (Rituxan), and abatacept (Orencia).

Without limiting the scope of present invention, the following definitions are provided in order to aid those skilled in the art in understanding the detailed description of the present invention.

"Alkyl" refers to a hydrocarbon chain that may be a straight chain or branched chain, containing the indicated number of carbon atoms, for example, a $C_1$-$C_{10}$ alkyl group may have from 1 to 10 (inclusive) carbon atoms in it. Examples of $C_1$-$C_4$ and $C_1$-$C_6$ alkyl groups include, but are not limited to methyl, ethyl, propyl, butyl, pentyl, hexyl, isopropyl, isobutyl, sec-butyl, tert-butyl, isopentyl, neopentyl, and isohexyl. An alkyl group can be unsubstituted or substituted with one or more suitable groups.

"Alkenyl" refers to a straight or branched chain unsaturated hydrocarbon containing 2-18 carbon atoms and at least one double bond. Examples of alkenyl group include but are not limited to 1-butylene, 2-butylene, isobutylene, sec-butylene, isopentene, 1-hexene, 2-hexene, 3-hexene, isohexene, 3-decene, 4-decene and 5-decene. An alkenyl group can be unsubstituted or substituted with one or more suitable groups.

"Alkynyl" refers to a straight or branched chain unsaturated hydrocarbon containing 2-18 carbon atoms and at least one triple bond. Examples of alkynyl group include, but are not limited to acetylene, propyne, 1-butyne, isobutyne, sec-butyne, 1-pentyne, 2-pentyne, 2-hexyne, 3-hexyne, 1-octyne, 4-octyne, 1-nonyne, 4-decyne and 5-decyne. An alkynyl group can be unsubstituted or substituted with one or more suitable groups.

"Alkylene" refers to an alkyl group in which one of the alkyl group's hydrogen atoms has been replaced with a bond. Examples of an alkylene include —CH$_2$—, —CH$_2$CH$_2$—, —CH$_2$CH$_2$CH$_2$—.

"Alkoxy" refers to the group alkyl-O— or —O-alkyl, where alkyl group is as defined above. Exemplary alkoxy groups include but are not limited to methoxy, ethoxy, n-propoxy, iso-propoxy, n-butoxy and t-butoxy. An alkoxy group can be unsubstituted or substituted with one or more suitable groups.

"Amino" refers to an —N— group, the nitrogen atom of said group being attached to a hydrogen, alkyl, cycloalkyl, aryl, heterocycloalkyl, heteroaryl or any suitable groups. Representative examples of an amino group include, but are not limited to —NH$_2$, —NHCH$_3$, —NHCH$_2$-phenyl, and —NH-cyclopropyl. An amino group can be unsubstituted or substituted with one or more of the suitable groups.

"Aminoalkyl" refers to an alkyl group, as defined above, wherein one or more of the alkyl group's hydrogen atom has been replaced, with an amino group as defined above. Representative examples of an aminoalkyl group include, but are not limited to —$CH_2NH_2$, —$CH_2CH_2NH_2$, —$CH(CH_3)NH_2$, —$CH_2CH(CH_3)NH_2$. An aminoalkyl group can be unsubstituted or substituted with one or more suitable groups.

"Amido" refers to a —C(O)N— or —NC(O)— groups, the nitrogen atom of said group being attached to a hydrogen, alkyl, cycloalkyl, aryl or any suitable groups. Representative examples of an amido group include —$C(O)NH_2$, —$C(O)NH$-phenyl, —$C(O)NH$-Me, —$C(O)N(Me)_2$, —$C(O)NH$-cyclobytyl and —$C(O)NH$-pyridyl. An amido group can be unsubstituted or substituted with one or more suitable groups.

"Aryl" refers to an optionally substituted monocylic, bicyclic or polycyclic aromatic hydrocarbon ring system of about 6 to 14 carbon atoms. Examples of a $C_6$-$C_{14}$ aryl group include, but are not limited to phenyl, naphthyl, biphenyl, anthryl, tetrahydronaphthyl, fluorenyl, indanyl, biphenylenyl, and acenaphthyl. Aryl group which can be unsubstituted or substituted with one or more suitable groups.

"Aryloxy" refers to an aryl group as defined above attached via an oxygen linkage to the rest of the molecule. Examples of aryloxy moiety include, but are not limited to phenoxy and naphthoxy. Unless set forth or recited to the contrary, all aryloxy groups described herein may be substituted or unsubstituted.

"Arylalkyl" refers to an alkyl group, as defined above, wherein one or more of the alkyl group's hydrogen atom has been replaced with an aryl group as defined above. Examples of arylalkyl group include, but are not limited to benzyl, benzhydryl, 1-phenylethyl, 2-phenylethyl, 3-phenylpropyl, 2-phenylpropyl, 1-naphthylmethyl, 2-naphthylmethyl. An arylalkyl group can be unsubstituted or substituted with one or more suitable groups.

"Carboxyl or Carboxy" refers to a —COO— group, the carboxy group being attached to any suitable groups. Representative examples of carboxy include, but are not limited to —COOH, —$COOCH_3$, —COO-aryl. A carboxy group can be unsubstituted or substituted with one or more of the suitable groups.

"Cyano" refers to —CN group.

"Cyanoalkyl" refers to an alkyl group, as defined above, wherein one or more of the alkyl group's hydrogen atoms have been replaced with a cyano group as defined above. cyanoalkyl moieties include but are not limited to —$CH_2CN$ and —$CH_2CH_2CN$. A cyanoalkyl group can be unsubstituted or substituted with one or more suitable groups.

"Cyanoalkoxy" refers to an alkoxy group, as defined above, wherein one or more of the alkoxy group's hydrogen atoms have been replaced with a cyano group as defined above. Cyanoalkoxy moieties include, but are not limited to —O—$CH_2CN$ and —O—$CH_2CH_2CN$. A cyanoalkoxy group can be unsubstituted or substituted with one or more suitable groups.

"Cycloalkyl" refers to a non-aromatic, saturated or unsaturated, monocyclic, bicyclic or polycyclic hydrocarbon ring system. Representative examples of a cycloalkyl include, but are not limited to, cyclopropyl, cyclopentyl, cycloheptyl, cyclooctyl, decahydronaphthalen-1-yl, octahydro-1H-inden-2-yl and decahydro-1H-benzo[7]annulen-2-yl. A cycloalkyl can be unsubstituted or substituted with one or more suitable groups.

"Haloalkyl" refers to an alkyl group, as defined above, wherein one or more of the alkyl group's hydrogen atoms has been replaced with —F, —Cl, —Br, or —I. Examples of a haloalkyl group include, but are not limited to, —$CH_2F$, —$CCl_3$, —$CF_3$, —$CH_2CF_3$, —$CH_2CH(Br)CH_3$, —$CH_2CH(Cl)CH_2CH_3$, —$CH(F)CH_2CH_3$ and —$C(CH_3)_2(CH_2Cl)$. A haloalkyl group can be unsubstituted or substituted with one or more suitable groups;

"Haloalkoxy" refers to an alkoxy group, as defined above, wherein one or more of the alkoxy group's hydrogen atoms has been replaced with —F, —Cl, —Br or —I. A haloalkoxy group can be unsubstituted or substituted with one or more suitable groups;

"Halogen" or "halo" includes fluorine, chlorine, bromine or iodine.

"Heterocyclyl" or "Heterocyclylalkyl" refers to a non-aromatic saturated or unsaturated monocyclic or polycyclic ring system of 3 to 10 member having at least one heteroatom or heterogroup selected from O, N, S, or —$SO_2$. Additionally, each of any two hydrogen atoms on the same carbon atom of the heterocyclyl ring can be replaced by an oxygen atom to form an oxo (=O) substituent. Exemplary heterocyclyl groups include aziridinyl, pyrrolidinyl, piperidinyl, piperazinyl, morpholinyl, thiomorpholinyl, thiazolidinyl, 1,3-dioxolanyl, 1,4-dioxanyl and the like. A heterocyclyl group can be unsubstituted or substituted with one or more suitable groups;

"Heteroaryl" refers to a monocyclic, bicyclic, or polycyclic aromatic ring system containing at least one heteroatomselected fromoxygen, sulfur or nitrogen. Examples of $C_1$-$C_{10}$ heteroaryl groups include furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic $C_1$-$C_9$heteroaryl groups include those where a phenyl, pyridine, pyrimidine or pyridazine ring is fused to a 5 or 6-membered monocyclic heterocyclyl, heteroaryl ring having one or two nitrogen atoms in the ring, one nitrogen atom together with either one oxygen or one sulfur atom in the ring, or one O or S ring atom. A heteroaryl group can be unsubstituted or substituted with one or more suitable groups.

"Heteroatom" refers to a sulfur; nitrogen, or oxygen atom.

"Heterocyclylalkyl" or "heterocycloalkyl" refers to an alkyl group, as defined above, wherein one or more of the alkyl group's hydrogen atoms have been replaced with a heterocyclyl or heterocycloalkyl group as defined above. Heterocyclylalkyl moieties include but are not limited to pyrrolidin-1-ylmethyl, 2-pyridylmethyl, 1-piperazinylethyl, 4-morpholinylpropyl, and 6-piperazinylhexyl. A heterocycloalkylalkyl group can be unsubstituted or substituted with one or more suitable groups.

"Heteroarylalkyl" refers to an alkyl group, as defined above, wherein one or more of the alkyl group's hydrogen atoms have been replaced with a heteroaryl group as defined above. Heteroaryl moieties include but are not limited to pyridine-1-ylmethyl, pyridine-2-yl ethyl, and pyrimidine-1-yl methyl. A heteroarylalkyl group can be unsubstituted or substituted with one or more suitable groups.

"Hydroxylalkyl-" or "Hydroxyalkyl" refers to an alkyl group, as defined above, wherein one or more of the alkyl group's hydrogen atoms have been replaced with hydroxyl groups. Examples of hydroxylalkyl moieties include but are not limited to —$CH_2OH$, —$CH_2CH_2OH$, —$CH_2CH_2CH_2OH$, —$CH_2CH(OH)CH_2OH$, —$CH_2CH(OH)CH_3$, —$CH(CH_3)CH_2OH$.

"Hydroxy" or "Hydroxyl" refers to —OH group.

"Nitro" refers to —NO$_2$ group.

"Oxo" refers to =O group.

"Thio" refers to an —S— group, the sulphur atom of said group being attached to a hydrogen, alkyl, cycloalkyl, aryl, amino, oxo or any suitable groups. Representative examples of a thiogroup include, but are not limited to —SH (thiol), —SCH$_3$, —SOCH$_3$, —SO$_2$CH$_3$, —SO$_2$NHCH$_3$. A thio group can be unsubstituted or substituted with one or more of the suitable groups.

"3-8-membered ring containing 0-3 heteroatoms" refers to a monocyclic or bicyclic aromatic or non-aromatic cyclic rings in which 1-4 of the ring carbon atoms have been independently replaced with a N, O or S atom. Representative examples of a 3- to 8-membered ring include, but are not limited to morpholine, pyrrole, cyclobytyl, phenyl, pyridine, pyridinone, tetrahydroisoquinoline.

"Optionally substituted" as used herein means that at least one or two hydrogen atoms of the optionally substituted group has been substituted with suitable substitutions as exemplified but not limited to alkyl, alkenyl, alkoxy, alkynyl, aryl, amido, amino, carboxy, cyano, cycloalkyl, halogen, hydroxy, nitro, haloalkyl, haloalkoxy, heteroaryl, heterocyclyl, —COOalkyl, oxo(=O), thio(=S), —P(O)$_3$H, —P(O)$_2$NH$_2$, —P(O)$_2$NH(alkyl), —P(O)$_2$NH(cycloalkyl), —P(O)$_2$NH(heterocycloalkyl), —P(O)$_2$NH(aryl), —P(O)$_2$NH(heteroaryl), —C(O)(alkyl), —C(O)(aryl), —C(O)(cycloalkyl), —C(O)(heterocyclyl), —C(O)(heteroaryl), —NHC(=NH)NH$_2$, —NHC(=NH)N(COO(CH$_3$))$_2$, —C(=NOH)NH$_2$ or two substituents on the same carbon atom combined together to form an optionally substituted 3-8 member ring containing 0-3 hetero atoms independently selected form N, O and S in any stable combination; "Comprise" or "Comprising" is generally used in the sense of include, that is to say permitting the presence of one or more features or components.

"Pharmaceutically acceptable salt" or "pharmaceutically acceptable derivatives" is taken to mean an active ingredient, which comprises a compound of the formula (I) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The term "prodrug derivatives" or "prodrug" is taken to mean compounds of the formula (I) which have been modified with, for example alkyl or acyl groups, sugars or oligopeptides and which are rapidly cleaved in the organism to form the active compounds. These also include biodegradable polymer derivatives of the compounds according to the invention, as described, for example, in Int. J. Pharm. 115, 61-67 (1995).

The use of the term "including" as well as other forms, such as "include", "includes," and "included," is not limiting.

As used herein, the terms "treat", "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms. The terms "treat," "treating" or "treatment", include, but are not limited to prophylactic and/or therapeutic treatments.

As used herein the terms "subject" or "patient" are well-recognized in the art and are used interchangeably herein to refer to a mammal, including dog, cat, rat, mouse, monkey, cow, horse, goat, sheep, pig, camel, and, most preferably, a human. In some embodiments the subject is a subject in need of treatment or a subject with a disease or disorder. However, in other embodiments, the subject can be a normal subject. The term does not denote a particular age or sex. Thus adult and newborn subjects, whether male or female are intended to be covered.

As used herein the term "therapeutically effective amount" refers to a sufficient amount of a compound or a composition being administered which will relieve to some extent one or more of the symptoms of the disease or condition being treated. The result can be reduction and/or alleviation of the signs, symptoms, or causes of a disease, or any other desired alteration of a biological system.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term "stereoisomers" refers to any enantiomers, diastereoisomers, or geometrical isomers of the compounds of formula (I), wherever they are chiral or when they bear one or more double bond. When the compounds of the formula (I) and related formulae are chiral, they can exist in racemic or in optically active form. Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis. In the case of racemic amines, diastereomers are formed from the mixture by reaction with an optically active resolving agent. Examples of suitable resolving agents are optically active acids such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel).

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example combining the active ingredient with the excipient(s) or adjuvant(s).

Pharmaceutical formulations adapted for oral administration can be administered as separate units such as, for example capsules or tablets; powders or granules; solutions or suspensions in aqueous or non-aqueous liquids; edible foams or foam foods; or oil-in-water liquid emulsions or water-in-oil liquid emulsions. For example in the case of oral administration as tablet or capsule, the active-ingredient component can be combined with an oral, non-toxic and pharmaceutically acceptable inert excipient such as, for example ethanol, glycerol, water and the like. Powders are prepared by comminuting the compound to a suitable fine size and mixing it with a pharmaceutical excipient comminuted in a similar manner such as, for example an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form can be added to the powder mixture before the filling operation. A disintegrant or solubiliser such as, for example agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example carboxymethylcellulose, an alginate, gelatine or polyvinyl-pyrrolidone, a dissolution retardant, such as, for example paraffin, an absorption accelerator, such as, for example, a quaternary salt, and/or an absorbant, such as, for example bentonite, kaolin or dicalcium phosphate. The powder mixture can be granulated by wetting it with a binder, such as, for example syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking, to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example ethoxylated isostearyl alcohols and polyoxyethylene sorbitol ethers, preservatives, flavour additives, such as, for example peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example by coating or embedding of particulate material in polymers, wax and the like.

Novel substituted pyridine derivatives of formula (I) and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from suitable lipids or phospholipids or both, such as, for example, cholesterol, stearylamine or phosphatidylcholines or the like.

Pharmaceutical compounds adapted for topical administration can be formulated as ointments, creams, suspensions, lotions, powders, solutions, pastes, gels, sprays, aerosols or oils.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example in the range 20-500 microns, which is administered in the manner in which snuff is taken i.e., by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations. Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example formulations which are suitable for oral administration may comprise flavours.

A therapeutically effective amount of a compound of the formula (I) and of the other active ingredient depends on a number of factors, including, for example the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus the actual amount per day for an adult mammal weighing 0.70 kg is usually between 70 and 700 mg, where this amount can be administered as an individual dose per day or usually in a series of part-doses (such as, for example two, three, four, five or six) per day so that the total daily dose is the same. An effective amount of a salt or solvate or of a physiologically functional derivative thereof can be determined as the fraction of the effective amount of the compound per se.

In a further aspect, the present invention relates to a process for preparing substituted pyridine derivatives of formula (I).

An embodiment of the present invention provides the FABI inhibitor compounds according to of formula (I) may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used but such conditions can be determined by the person skilled in the art, using routine optimisation procedures. Moreover, by utilizing the procedures described in detail, one of ordinary skill in the art can prepare additional compounds of the present invention claimed herein. All temperatures are in degrees Celsius (° C.) unless otherwise noted.

In a further aspect, the compounds of the present invention can also contain unnatural proportions of atomic isotopes at one or more of the atoms that constitute such compounds. For example the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention and their uses. Exemplary isotopes that can be incorporated in to compounds of the invention include isotopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically labeled compounds of the present inventions can generally be prepared by following procedures analogous to those disclosed in the Schemes and/or in the Examples herein below, by substituting an isotopically labeled reagent for a non-isotopically labeled reagent.

The abbreviations used in the entire specification may be summarized hereinbelow with their particular meaning.

° C. (degree Celsius); δ (delta); % (percentage); $Ag_2CO_3$ (Silver carbonate); AIBN (Azobisisobutyronitrile); AcOH (Acetic acid); ACN (Acetonitrile); $Ac_2O$ (Acetic anhydride); brine (NaCl solution); Br or $Br_2$ (Bromine); n-BuLi (n-Butyl lithium); BnBr (Benzyl bromide); t-BuOH (tert-butanol); $(BoC)_2O$ (Di tert-butyl dicarbonate); bs or brs (Broad singlet); CuI (Cuprous iodide); CAN (Ceric ammonium nitrate); CDI (Carbonyl diimidazole); $CDCl_3$ (Deuteriated chloro-form); $CH_2Cl_2$/DCM (Dichloromethane); $Cs_2CO_3$ (Cesium carbonate); $CCl_4$ (Carbon tetrachloride); $CBr_4$ (Carbon tetrabromide); $CH_3SO_2Cl$/$MeSO_2Cl$ (Methanesulfonyl chloride); $CuNO_2$ (Copper(II)nitrate); DDQ (2,3-Dichloro-5,6-dicyano-1,4-benzoquinone); DMF (Dimethyl formamide); DMA (Dimethyl acetamide); DMSO (Dimethyl sulphoxide); DME(Dimethoxy ethane); DIPEA/DIEA (N,N-Diisopropyl ethylamine); DMAP (Dimethyl amino pyridine); DCE (Dichloro ethane); DEAD (Diethyl azodicarboxylate); DIAD (D iisopropylazodicarboxylate), DCC (Dicyclohexylcarbodiimide); DMSO-$d_6$ (Deuteriated DMSO); d (Doublet); dd (Doublet of doublet); dt (Doublet of triplet); EDC.HCl (1-(3-Dimethyl aminopropyl)-3-carbodiimide hydrochloride); EtOH (Ethanol); $Et_2O$ (Diethyl ether); EtOAc (Ethyl acetate); Fe (Iron powder); g or gr (gram); H or $H_2$-(Hydrogen); $H_2O$ (Water); HOBt (1-Hydroxy benzotriazole); $H_2SO_4$ (Sulphuric acid); HBr (Hydrobromic acid); HCl (Hydrochloric acid); h or hr (Hours); HATU (2-(1H-7-Azabenzotriazol-1-yl)-1,1,3,3-tetramethyl uranium hexafluoro phosphate methanaminium); Hz (Hertz); HPLC (High-performance liquid chromatography); $I_2$ (Iodine); J (Coupling constant); $K_2CO_3$ (Potassium carbonate); $K_3PO_4$ (Potassium phosphate); $KH_2PO_4$ (Mono potassium phosphate); KOBu$^t$ (Potassium tert-butoxide), LDA (Lithium diisopropylamide); LAH (Lithium aluminium hydride); LiOH.$H_2O$ (Lithium hydroxide mono hydrate); LiHMDS (Lithium bis(trimethylsilyl)amide); MeOH/$CH_3OH$ (Methanol); MP (Melting point); mmol (Millimol); M (Molar); µl (Micro litre); ml (Millilitre); mg (Milli gram); m (Multiplet); mm (Millimeter); MHz (Megahertz); MS (ES) (Mass spectroscopy-electro spray); min (Minutes); NaOBu$^t$ (Sodium tert-butoxide); $NaOCH_3$ (Sodium methoxide); NaOAc (Sodium acetate); NaOH (Sodium hydroxide); $NaBH_4$ (Sodium borohydride); $NaCNBH_3$ (Sodiumcyanoborohydride); NaH (Sodium hydride); $Na_2SO_4$ (Sodium sulphate); $N_2$ (Nitrogen); NMR (Nuclear magnetic resonance spectroscopy); $NH_4Cl$ (Ammonium chloride); $NH_3$ (Ammonia); $Na_2CO_3$ (Sodium carbonate); $NH_2OH.HCl$ (Hydroxylamine hydrochloride; 10% Pd/C (10% palladium activated carbon); $Pd(PPh_3)_2Cl_2$ (Bis (triphenylphosphine)palladium(II) dichloride); Pd $(OAc)_2$ (Palladium di acetate); $Pd(dppf)_2Cl_2$(1,1'-Bis(diphenylphosphino)ferrocene) palladium(II) dichloride; $Pd_2$ $(dba)_3$ (Trisdibenzylidene acetone) dipalladium; $Pd(pph_3)_4$ [Tetrakistriphenylphosphine palladium(0)]; $PPh_3$ (Triphenyl phosphine); $P(Me)_3$ (Trimethyl phosphine); $P(Et)_3$ (Triethyl phosphine); $P(Bu)_3$ (Tributyl phosphine); P (o-tolyl)$_3$ (Tri-o-tolyl phosphine); P (m-tolyl)$_3$ (Tri-m-tolyl phosphine); P (p-tolyl)$_3$ (Tri-P-tolyl phosphine); $P(OMe_3)_3$ (Trimethylphosphite); PhS(O)Me (Phenyl methyl sulphoxide); PhMe (Toluene); $PBr_3$ (Phosphorous tribromide); PPA (Polyphosphoric acid); $SOCl_2$ (Thionyl chloride); S (Singlet); TEA (Triethyl amine); TFA (Trifluoroacetic acid); TLC (Thin Layer Chromatography); THF (Tetrahydrofuran); Ti ($^i$Opr)$_4$ (Titanium tetra isopropoxide); TFA/$CF_3COOH$ (Trifluoro acetic acid); t (Triplet); Xantphos (4,5-Bis(diphenylphosphino)-9,9-dimethylxanthene); Zn (Zinc) etc.

Another embodiment of the present invention provides methods useful for making the compounds of formula (I) are set forth in the examples below and generalized in schemes 1-10. One of skill in the art will recognize that schemes 1-10 can be adapted to produce the compounds of formula (I) and pharmaceutically accepted salts of compounds of formula (I) according to the present invention. Wherein all symbols/variables are as defined earlier unless otherwise stated. The process is represented by Schemes 1-10.

Scheme-1

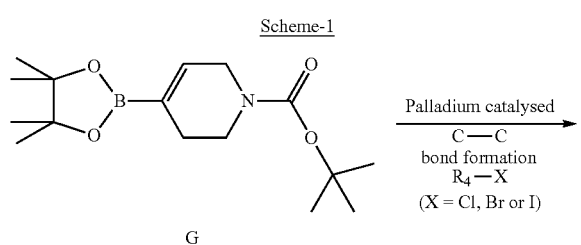

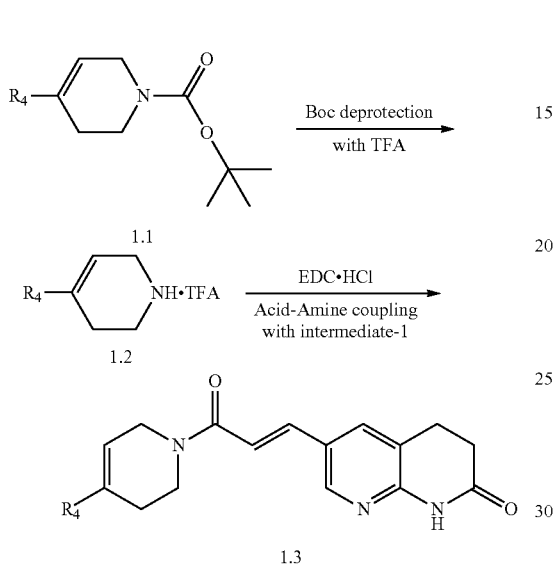

As shown in the scheme-1, the novel compounds of the present invention formula 1.3 can be synthesized from Compound-G. The compound G can undergo Pd-catalyzed C—C coupling reaction with substituted aryl halides, aralkyl halides, heteroaryl halides, heterocyclic halides ($R_4$—X) to provide 1.1. The coupling reaction can be carried out in suitable polar solvents such as THF, DMF, DMA and DMSO and the like. The Pd-catalyzed C—C coupling reaction can be carried out in a suitable base such as $Na_2CO_3$, $K_2CO_3$, $Cs_2CO_3$, $K_3PO_4$, $NaOBu^t$, NaOAc, NaOH and KOH and the like and their molar solutions; catalysts such as $Pd(dppf)_2Cl_2$, $Pd(PPh_3)_4$, $Pd_2(dba)_3$, $Pd(OAc)_2$ and the like at a temperature of about 80-120° C. for about 12-48 h in conventional method or under microwave heating for about 15 min to 1 h. The reaction progress can be monitored at 20-35° C. by conventional methods such as TLC or NMR.

The deprotection of 1.1 by using the suitable deprotecting agents such as TFA, diethylether-HCl solutions to provide 1.2. The deprotection reaction can be carried out in suitable solvents such as DCM and DCM/THF (1:1, 1:2, 1:5) and the like at a temperature of about 20-35° C. for about 2-6 h in conventional method. The reaction progress can be monitored at 20-35° C. by conventional methods such as TLC or NMR.

The acid-amine coupling of compound 1.2 with Intermediate-1 can be carried out by a conventional amide bond formation method by using a suitable coupling reagents such as HATU, benzotriazole-containing coupling reagents such as N-hydroxybenzotriazole, benzotriazol-1-yloxytris(dimethylamino)phosphoniumhexafluorophosphate and 2-(1H-benzotriazol-1-yl)-1,1,3,3-tetramethyluronium hexafluorophosphate and an azabenzotriazole-containing reagent such as O-(7-azabenzotriazole-1-yl)-N and also the dicarboimides containing reagent such as 1-Ethyl-3-(3-dimethylaminopropyl)carbodiimide hydrochloride, dicyclohexylcarbodiimide and the like, in a suitable solvent such as DMF, THF, DMSO or DCM and the like, in the presence of suitable bases such as TEA, DIPEA and/or DMAP and the like at a temperature of about 20-35° C. for about 12-48 h to provide compound 1.3. The reaction progress can be monitored at 20-35° C. by conventional methods such as TLC or NMR.

Scheme-2

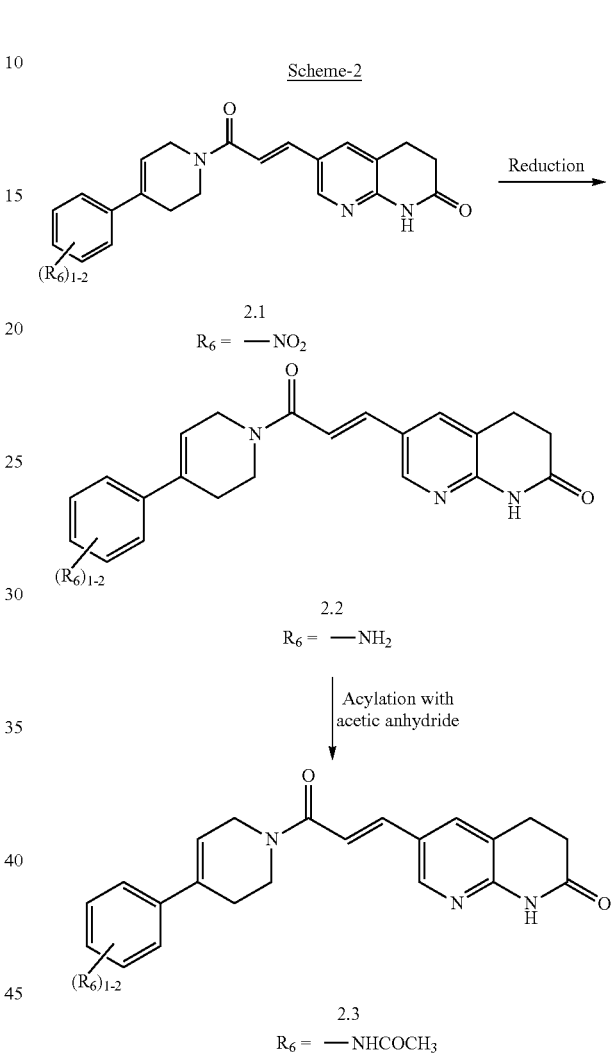

As shown in the scheme-2, the compound 2.3 can be synthesized from compound 2.1 with nitro and methyl groups as substituents. The nitro group of compound 2.1 can be reduced to amino group of compound 2.2 by using suitable reducing agents such as Fe/HCl, Fe/$NH_4Cl$ or Zn/$NH_3$ and the like, in the presence of polar solvents such as ethanol/water (8:2 or 9:1), at a temperature of 80-100° C. for about 1-6 h. The reaction progress can be monitored at 20-35° C. by conventional methods such as TLC or NMR.

The acylation of the amine compound 2.2 can be carried out in the presence of acetyl chloride or acetic anhydride and the like, in the presence of suitable bases such as Pyridine, TEA, DIPEA or Leutidine and the like, in a suitable organic solvent such as THF or DCM and the like at a temperature of about 20-35° C. for about 12-24 h to provide compound 2.3. The reaction progress can be monitored at 20-35° C. by conventional methods such as TLC or NMR Scheme-3

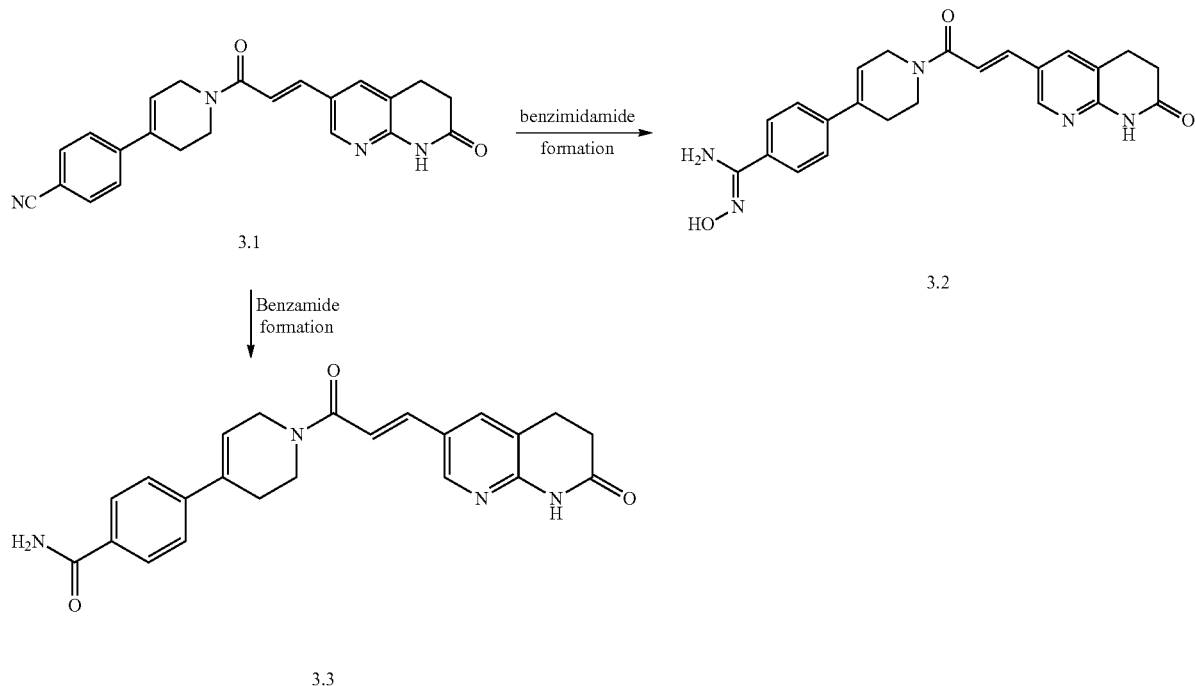

As shown in the scheme-3, the cyano group of compound 3.1 can be converted to benzimidamide of compound 3.2 by using suitable reagent such as hydroxylamine hydrochloride in the presence of bases such as $K_2CO_3$, $Cs_2CO_3$, NaOH and KOH and the like and their molar solutions in suitable polar solvents such as EtOH or MeOH and the like, at a temperature of about 80-100° C. for about 6-16 h in conventional method. The reaction progress can be monitored at 20-35° C. by conventional methods such as TLC or NMR.

The cyano group of compound 3.1 can be converted to amide of compound 3.3 by using the mixture of $TFA/H_2SO_4$ (4:1) and the like, at a temperature of 20-35° C. for about 16-48 h in conventional method. The reaction progress can be monitored at 20-35° C. by conventional methods such as TLC or NMR.

Scheme-4

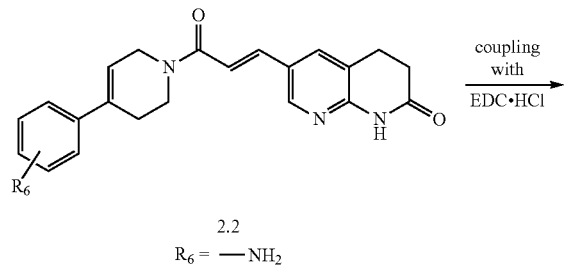

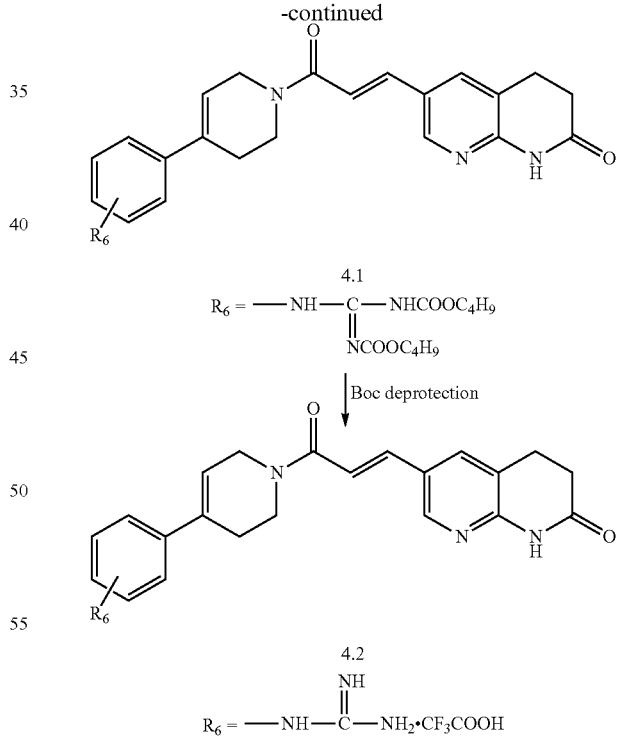

As shown in the scheme 4, the amino group of compound 2.2 can be converted to Boc-protected guanidine of compound 4.1 by using suitable reagent such as N;N'-Bistert-butoxycarbonylthiourea, in presence of benzotriazole-containing coupling reagents such as N-hydroxybenzotriazole, benzotriazol-1-yloxytris(dimethylamino) phosphoniumhexafluorophosphate and 2-(1H-benzotriazol-1-yl)-1,1,3,3-- tetramethyluronium hexafluorophosphate and an azabenzotriazole containing reagent such as O-(7-azabenzotriazole-1-yl)-N and also the dicarboimides containing reagent such as 1-Ethyl-3-(3-dimethylaminopropyl)carbodiimide hydrochloride and the like, in a suitable organic solvent such as DMF, THF and DMSO and the like at a temperature of about 20-35° C. for about 12-48 h. The reaction progress can be monitored at 20-35° C. by conventional methods such as TLC or NMR.

The deprotection of compound 4.1 to 4.2 can be carried out by the similar method described in scheme-1.

Scheme-5

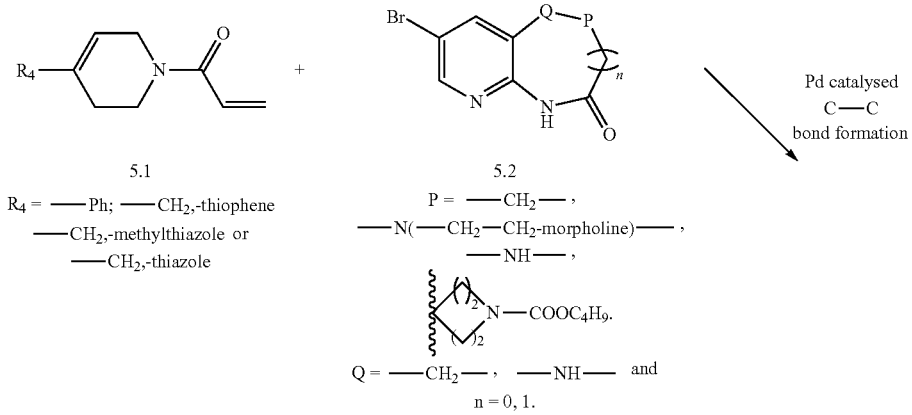

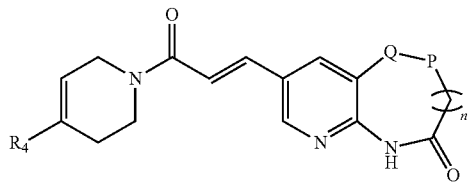

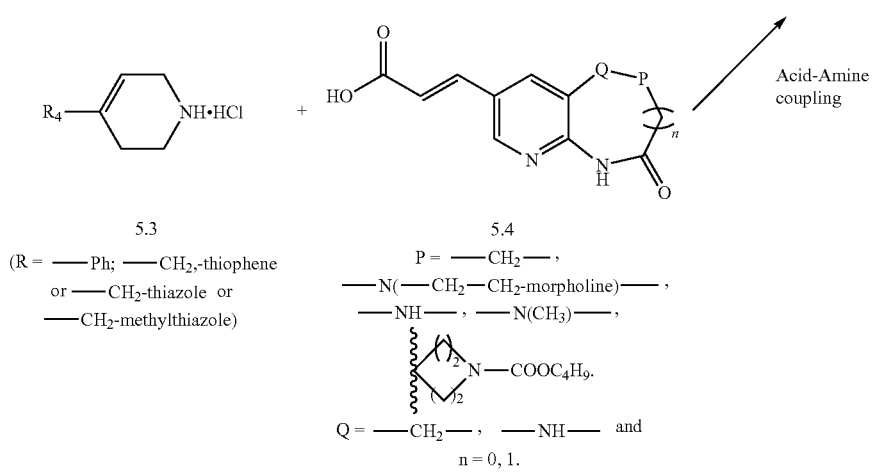

As shown in the scheme-5, the compound 5.1 can undergo Pd-catalyzed C—C coupling reaction with the compound 5.2 to provide compound 5.5. The coupling reaction can be carried out in suitable polar solvents such as DMF, propionitrile, ACN, THF or DMSO and the like, in a suitable organic bases such as TEA, DIPEA and the like by using catalysts such as Pd(OAc)$_2$, Pd(PPh$_3$)$_2$Cl$_2$ or Pd$_2$(dba)$_3$ and the like, in presence of ligands P(o-tolyl)$_3$, P(m-tolyl)$_3$ or P(p-tolyl)$_3$ and the like, at a temperature of about 80-120° C. for about 12-48 h in conventional method or under microwave heating for about 15 min to 1 h. The reaction progress can be monitored at 20-35° C. by conventional methods such as TLC or NMR.

The acid-amine coupling of compound 5.3 with compound 5.4 can be carried out by similar method described in scheme-1.

Scheme-6

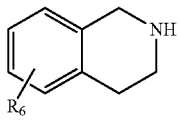

6.1

5.2

6.2

P = —CH$_2$—, —N(—CH$_2$—CH$_2$-morpholine)-,
—NH—, —N(CH$_3$)—,

Q = —CH$_2$—, —NH— and n = 0, 1.

As shown in the scheme-6, the compound 6.1 can undergo Pd-catalyzed C—C coupling reaction with the compound 5.2 to provide 6.2. The coupling reaction can be carried out by similar method described in scheme-5.

Scheme-7

7.1
7.1 = Free amine or acidic salt
R$_6$ = —H or any Substitution 5.4
P = —CH$_2$—,
—N(—CH$_2$—CH$_2$-morpholine)—,
—NH—, —N(CH$_3$)—, Q = —CH$_2$—, —NH— and
n = 0, 1.

7.2

As shown in the scheme-7, the peptide coupling of the acidic-amine salt compound 7.1 with acid compound 5.4 can be carried out by similar method described in scheme-1.

Scheme-8

5.1

8.1
R$_1$ = —CH$_2$-triazole

As shown in the scheme-8, the compound 5.1 can undergo Pd-catalyzed C—C coupling reaction with the compound 8.1 to provide compound 8.3. The coupling reaction can be carried out by similar method described in scheme-5.

As shown in the scheme-8, the acid-amine coupling of compound 5.3 with compound 8.2 can be carried out by similar method described in scheme-1.

As shown in the scheme-9, the intermediate-5 can undergo C—N bond coupling with heterocycles ($R_6$) to provide 9.1. The C—N bond coupling reaction can be carried out in suitable polar solvents such as DMF, ACN, THF and 1,4-dioxane and the like, in presence of suitable bases such as $K_2CO_3$, $Cs_2CO_3$ and TEA and the like, at a temperature of about 80-120° C. for about 12-48 h in conventional method or under microwave heating for about 15 min to 1 h. The reaction progress can be monitored at 20-35° C. by conventional methods such as TLC or NMR.

Conversion of compound 9.1 to compound 9.3 (de protection of Boc and, amide formation) can be carried out by the similar methods described in scheme-1.

-continued

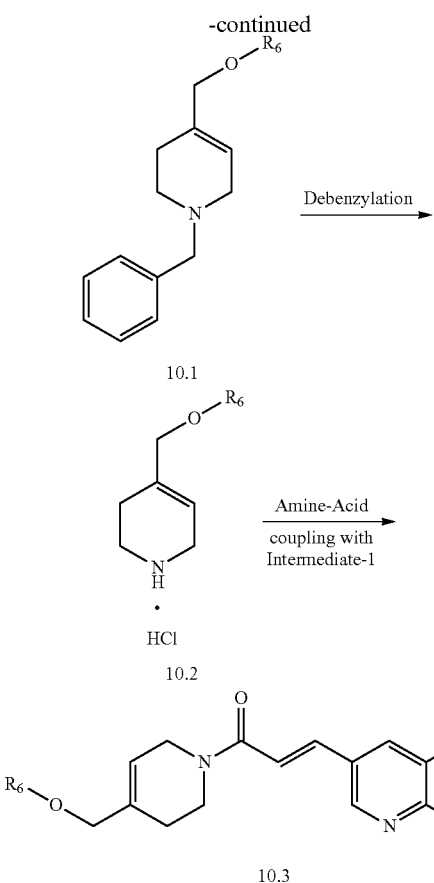

As shown in the scheme 10, the intermediate-6 can undergo ether linker formation with phenols, mono substituted phenols, di substituted phenols or tri substituted phenols and the like to provide 10.1. The ether linker formation can be carried out in suitable polar solvents such as THF, DCM or 1,4-dioxane and the like, in the presence of suitable reagents such as DEAD, DIAD, DCC and EDC.HCl and the like, in the presence of ligands such as $PPh_3$, $P(Me)_3$, $P(Et)_3$ and $P(Bu)_3$ and the like, at a temperature of about 20-35° C. for about 6-48 h in conventional method or under microwave heating for about 15 min to 1 h. The reaction progress can be monitored at 20-35° C. by conventional methods such as TLC or NMR.

Conversion of compound 10.1 to compound 10.2 can be carried out in presence of suitable reagent such as 1-chloroethyl chloroformate, ethylchloroformate, CAN, DDQ and the like, in suitable solvents such as THF, DCM, DCE and methanol and the like, at a temperature of about 80-120° C. for about 120-48 h in conventional method or under microwave heating for about 15 min to 1 h. The reaction progress can be monitored at 20-35° C. by conventional methods such as TLC or NMR.

The acid-amine coupling of the compound 10.2 with intermediate-1 can be carried out by similar method described in scheme-1.

EXAMPLES

Although the invention has been illustrated by certain of the preceding examples, it is not to be construed as being limited thereby; but rather the invention encompasses the generic area as herein before disclosed. Various modifications and embodiments can be made without departing from the spirit and scope thereof.

The MS data provided in the examples described below were obtained as follows:

Mass spectrum: LC/MS Agilent 6120 Quadrapole LC/MS

The NMR data provided in the examples described below were obtained as follows:

$^1$H-NMR: Varian 400 MHz.

The microwave chemistry was performed on a CEM Explorer.

The procedure for the compounds of formula (I) are detailed hereinbelow stepwise including the general synthesis of various intermediates involved in process of manufacture of the compounds according to the present invention.

Intermediate-1

Synthesis of (E)-3-(7-oxo-5,6,7,8-tetrahydro-1,8-naphthyridin-3-yl) acrylic acid hydrochloride

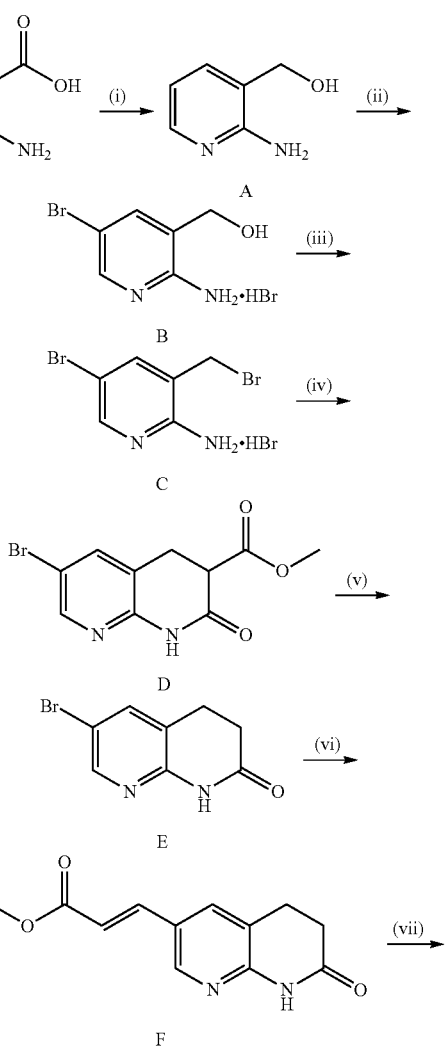

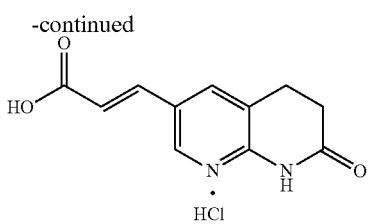

(Intermediate-1)

(i) LAH, Dry THF, reflux, 16 h; (ii) Br$_2$, HOAc, 20-35° C., 3 h; (iii) 48% HBr, reflux, 16 h; (iv) NaOCH$_3$, dimethyl malonate, CH$_3$OH, 20-35° C., 16 h; (v) NaOH, CH$_3$OH, reflux, 4 h, then HCl, reflux, 16 h; (vi) tert-butyl acrylate, Pd(OAc)$_2$, P(o-tolyl)$_3$, DIEA, DMF, Propionitrile, 90° C., 16 h; (vii) TFA, CH$_2$Cl$_2$, 20-35° C., 4 h, then 4% dioxane. HCl, 20-35° C., 2 h.
(Reference for Step-(i); WO 2005095391 and Step-(ii-vii): J. Med. Chem. 2003, 46, 1627-1635)

Intermediate-2

Synthesis of 1-(4-phenyl-5,6-dihydropyridin-1(2H)-yl)prop-2-en-1-one

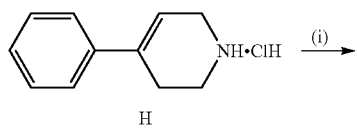

(Intermediate-2)

(i) Acryloyl chloride, triethylamine, CH$_2$Cl$_2$, 20-35° C., 16 h;

Step-(i)

To a stirred suspension of compound H (2 g, 10.2 mmol) in anhydrous CH$_2$Cl$_2$ (20 ml) was added triethylamine (7.1 ml, 51.99 mmol) and acryloyl chloride (1.34 g, 14.88 mmol) at 0° C. The reaction mixture was stirred at 20-35° C. for 16 h. The progress of the reaction was monitored by TLC. After 16 h of stirring, the reaction mixture was diluted with water (100 ml) and extracted with ethyl acetate (2×100 ml). The combined organic layers were washed with brine (100 ml), followed by drying over anhydrous Na$_2$SO$_4$ and filtering. The filtrate was rotary evaporated to get residue which was purified by column chromatography using a mixture of 20% ethyl acetate/pet ether as an eluent to get the desired compound as a pale brown liquid (1.5 g, 69%); $^1$H NMR (400 MHz, DMSO-d$_6$) δ 7.45-7.43 (m, 2H), 7.35 (m, t, J=7.5 Hz, 2H), 7.27 (t, J=7.1 Hz, 1H), 6.96-6.76 (m, 1H), 6.20-6.12 (m, 2H), 5.70 (dd, J=10.3, 2.5 Hz, 1H), 4.30-4.22 (m, 1H), 4.20-4.14 (m, 1H), 3.79-3.73 (m, 2H), 2.56-2.51 (m, 2H).

Intermediate-3 and 4

Synthesis of 4-(thiophen-2-ylmethyl)-1,2,3,6-tetrahydro pyridine hydro-chloride and 1-(4-(thiophen-2-ylmethyl)-5,6-dihydropyridin-1(2H)-yl)prop-2-en-1-one

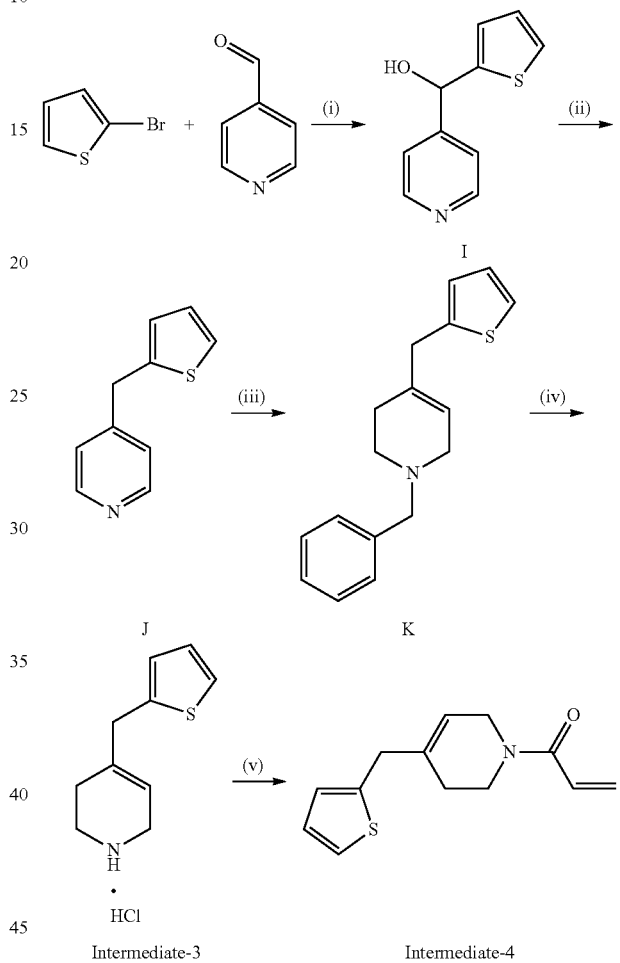

Intermediate-3    Intermediate-4

(i) n-BuLi (1.6M in hexane), Dry THF, -78° C., 2 h; (ii) Zn, AcOH, reflux, 16 h, (iii) (a) Benzyl bromide, DMF, 100° C., 3 h, (b) NaBH$_4$, EtOH, 70-80° C., 2 h; (iv) (a) 1-Chloroethyl chloroformate, DCM, 20-35° C., 3 h, (b) MeOH, 70-80° C., 1 h; (v) Acryloyl chloride, triethylamine, CH$_2$Cl$_2$, 20-35° C., 16 h.

Step-(i)

Synthesis of pyridin-4-yl (thiophen-2-yl)methanol (I)

To a stirred solution of 2-bromothiophene (10 g, 61.34 mmol) in dry THF (42 ml) was dropwise added a solution of n-butyl lithium in n-hexane (1.6M, 42.0 ml, 67.48 mmol) at −78° C. The resulting suspension was stirred at the same temperature for 30 min. After 30 min, a solution of isonicotinaldehyde (6.56 g, 61.34 mmol) in dry THF (30 ml) was dropwise added and continued the stirring at −78° C. for another 2 h. The progress of the reaction was monitored by TLC. The reaction was quenched with NH$_4$Cl solution (10 ml) and diluted with diethyl ether (500 ml). The organic layer was washed with water (50 ml), brine (50 ml), dried over anhydrous $Na_2SO_4$ and evaporated. The crude compound was triturated with hexane and diethyl ether to get the desired compound as an off-white solid (4.0 g, 34%). $^1$H NMR (400 MHz, DMSO-$d_6$) δ 8.52 (dd, J=4.9, 1.5 Hz, 2H), 7.45-7.38 (m, 3H), 6.97-6.93 (m, 2H), 6.45 (d, J=4.4 Hz, 1H), 5.97 (d, J=4.4 Hz, 1H).

Step-(ii)

Synthesis of 4-(thiophen-2-ylmethyl)pyridine (J)

To a stirred solution of I(4 g, 20.94 mmol) in acetic acid (40 ml) was added Zn powder (11.69 g, 208.73 mmol) portion wise at 70° C. and the reaction mixture was allowed to reflux for 16 h. The progress of the reaction was monitored by TLC. After 16 h, the reaction mixture was filtered and washed with ethyl acetate. The volatiles in the filtrate were removed under vacuum; resultant residue was diluted with water, basified with $Na_2CO_3$ solution to pH 9 at 0° C. and diluted with diethyl ether. The organic layer was washed with water (50 ml), brine (50 ml), dried over anhydrous $Na_2SO_4$ and evaporated to get the desired compound as an oily liquid (3.2 g, 87%). $^1$H NMR (400 MHz, DMSO-$d_6$) δ 8.48 (dd, J=4.4, 1.5 Hz, 2H), 7.37 (dd, J=4.9, 1.5 Hz, 1H), 7.26 (d, J=5.9 Hz, 2H), 6.99-6.93 (m, 2H), 4.19 (s, 2H).

Step-(iii)

Synthesis of 1-benzyl-4-(thiophen-2-ylmethyl)-1,2,3,6-tetrahydropyridine (K)

To a stirred solution of J (3.1 g, 11.52 mmol) in DMF (10 ml) was added benzyl bromide (2.16 g, 12.67 mmol) at 20-35° C. and the reaction mixture was stirred at 100° C. for 3 h. After 3 h, the reaction mixture was cooled to 20-35° C., diluted with ethanol (30 ml) and $NaBH_4$ (0.65 g, 17.28 mmol) was added slowly portion wise at 0° C., then heated at 70-80° C. for 2 h. The progress of the reaction was monitored by TLC. The excess ethanol was removed under vacuum and resultant residue diluted with ethyl acetate (100 ml). The organic layer was washed with water (50 ml), brine (50 ml), dried over anhydrous $Na_2SO_4$ and evaporated. The crude compound was purified by column chromatography using a mixture of 20% ethyl acetate/pet ether as an eluent to get the desired compound as a pale brown oily liquid (3.3 g, 67%). $^1$H NMR (400 MHz, DMSO-$d_6$) δ 7.33-7.28 (m, 5H), 7.28-7.22 (m, 1H), 6.94 (dd, J=5.4, 3.4 Hz, 1H), 6.84-6.82 (m, 1H), 5.46 (s, 1H), 3.51 (s, 2H), 3.46 (s, 2H), 2.87 (s, 2H), 2.46 (t, J=5.9 Hz, 2H), 1.98 (s, 2H).

Step-(iv) Intermediate-3

Synthesis of 4-(thiophen-2-ylmethyl)-1,2,3,6-tetrahydro pyridine hydrochloride

To a stirred solution of K (3.3 g, 12.26 mmol) in dichloromethane (50 ml) was added 1-chloroethyl chloroformate (12.27 g, 85.87 mmol) at 0° C. and the reaction mixture was stirred at 20-35° C. for 3 h. The progress of the reaction was monitored by TLC. After 3 h, the reaction mixture was diluted with $CH_2Cl_2$ (100 ml) and washed with water (50 ml), followed by brine (50 ml), dried over anhydrous $Na_2SO_4$ and evaporated. The resultant crude residue was dissolved in methanol (20 ml) and heated at 70-80° C. for 1 h. The progress of the reaction was monitored by TLC. After 1 h, the reaction mixture was concentrated under vacuum and washed with diethyl ether to get the desired compound as a brown solid (2.5 g, quantitative). $^1$H NMR (400 MHz, DMSO-$d_6$) δ 9.04-8.92 (m, 2H), 7.38 (dd, J=5.4, 1.5 Hz, 1H), 6.97 (dd, J=5.4, 3.4 Hz, 1H), 6.90 (dd, J=3.4, 1.0 Hz, 1H), 5.54 (s, 1H), 3.56 (s, 2H), 3.54-3.52 (m, 2H), 3.14-3.11 (m, 2H), 2.24-2.16 (m, 2H).

Step-(v) Intermediate-4

Synthesis of 1-(4-(thiophen-2-ylmethyl)-5,6-dihydropyridin-1(2H)-yl)prop-2-en-1-one To a stirred suspension of Intermediate-3 (1.5 g, 6.96 mmol) in anhydrous $CH_2Cl_2$(15 ml) was added triethylamine (2.91 ml, 20.88 mmol) and acryloyl chloride (0.82 g, 9.05 mmol) at 0° C. The reaction mixture was stirred at 20-35° C. for 16 h. The progress of the reaction was monitored by TLC. After 16 h of stirring, the reaction mixture was diluted with water (50 ml) and extracted with ethyl acetate (2×50 ml). The combined organic layers were washed with brine (50 ml), followed by drying over anhydrous $Na_2SO_4$ and filtering. The filtrate was rotary evaporated to get residue which was purified by column chromatography using a mixture of 20% ethyl acetate/pet ether as an eluent to get the desired compound as a pale brown liquid (0.7 g, 43%). $^1$H NMR (400 MHz, DMSO-$d_6$) δ7.34 (dd, J=5.4, 1.0 Hz, 1H), 6.95 (dd, J=4.9, 3.4 Hz, 1H), 6.86 (d, J=2.5 Hz, 1H), 6.80 (dd, J=16.6, 10.3 Hz, 1H), 6.14-6.06 (m, 1H), 5.66 (dt, J=4.9, 2.5 Hz, 1H), 5.57-5.51 (m, 1H), 3.98 (s, 2H), 3.62-3.3.55 (m, 2H), 3.52 (s, 2H), 2.08-2.02 (m, 2H); MS (ES) m/e 234.1 (M+H)$^+$.

Intermediate-5

Synthesis of tert-butyl 4-(chloromethyl)-5,6-dihydropyridine-1(2H)-carboxylate

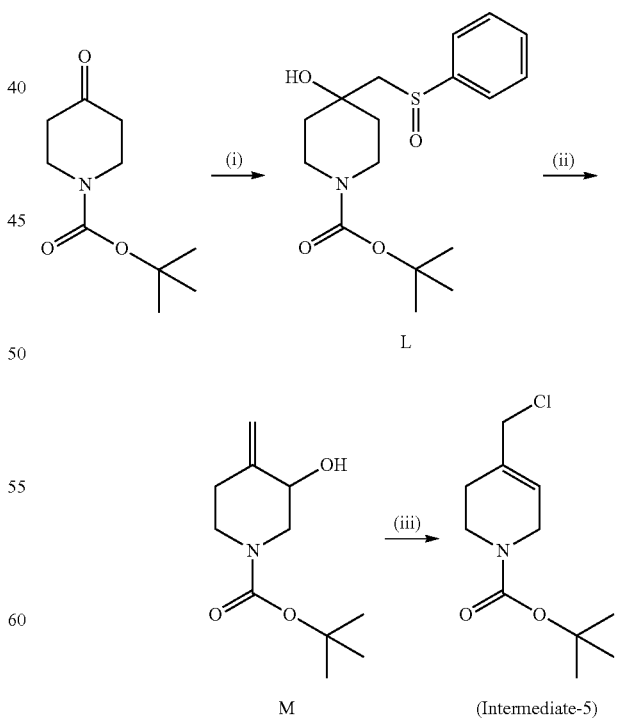

M  (Intermediate-5)

(i) PhS(O)Me, LDA, THF, -75° C. to 23° C., 18 h; (ii) KO$^t$Bu, t-BuOH, 20-35° C., 2 h; (iii) SOCl$_2$, PhMe, 60° C., 25 min.
(Ref. for steps-(i-iii): Bioorg. Med. Chem. Lett, 18, 2114-2121, 2008)

Intermediate-6

Synthesis of (1-benzyl-1,2,3,6-tetrahydropyridin-4-yl)methanol

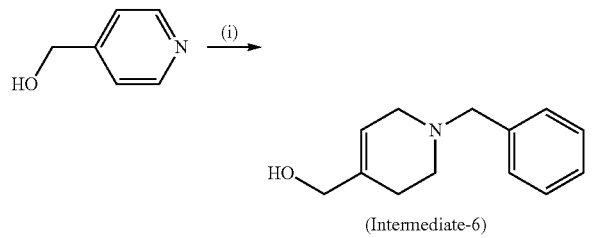

(Intermediate-6)

(i) (a) Benzyl bromide, DMF, 100° C., 3 h, (b) NaBH₄, EtOH, 70-80° C., 2 h.
(Ref. for Step-(i): WO2012004378)

Preparation of Intermediates-7 and 8

Synthesis of 2-((1,2,3,6-tetrahydropyridin-4-yl)methyl)thiazole 2,2,2-trifluoroacetate and 1-(4-(thiazol-2-ylmethyl)cyclohex-3-en-1-yl)prop-2-en-1-one

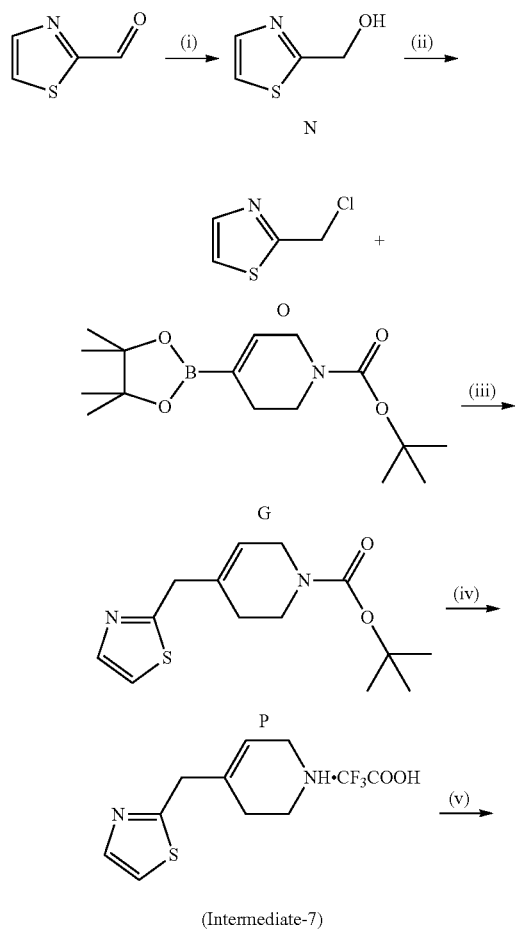

(Intermediate-7)

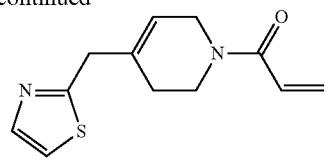

(Intermediate-8)

(i) NaBH₄, MeOH, 20-35° C., 4 h; (ii) SOCl₂, DCM, 20° C., 0.5 h; (iii) Pd(dppf)₂Cl₂, K₂CO₃, DMF, 110° C., 14 h; (iv) CF₃COOH, CH₂Cl₂, 20-35° C., 2 h; (v) Acryloyl chloride, triethylamine, CH₂Cl₂, 20-35° C., 16 h.
(Ref. for step-(i-ii): US2009/082403)

Step-(iii)

A stirred solution of O (0.97 g, 6.46 mmol), G (1 g, 3.23 mmol) and potassium carbonate (1.33 g, 9.69 mmol) in dry DMF (10 ml) was degassed with nitrogen for 10 minutes. After 10 minutes Pd(dppf)₂Cl₂ (260 mg, 0.32 mmol) was added, again degassed with nitrogen for 10 minutes and the reaction mixture was stirred at 110° C. for 14 h. The progress of the reaction was monitored by TLC. After 14 h of stirring, the mixture was cooled to 20-35° C., diluted with water (100 ml) and extracted with ethyl acetate (2×100 ml). The combined organic layers were washed with brine (100 ml), followed by drying over anhydrous Na₂SO₄ and filtering. The filtrate was rotary evaporated to get residue which was purified by column chromatography using a mixture of 30% ethyl acetate/hexane as an eluent to get the desired compound as a pale brown liquid (400 mg, 44%). ¹H NMR (400 MHz, DMSO-d₆) δ 7.70 (d, J=3.4 Hz, 1H), 7.60 (d, J=3.5 Hz, 1H), 5.60 (s, 1H), 3.82 (s, 2H), 3.71 (s, 2H), 3.38 (t, J=5.9 Hz, 2H), 2.06-1.96 (m, 2H), 1.40 (s, 9H).

Step-(iv)

Synthesis of 2-((1,2,3,6-tetrahydropyridin-4-yl)methyl)thiazole.trifluoro acetic acid (Intermediate-7)

A stirred solution of P(1.5 g, 5.36 mmol) in CH₂Cl₂(2 ml) was treated with trifluoro acetic acid (1 ml) at 20-35° C. for 2 h. The progress of the reaction was monitored by TLC. After 2 h of stirring, the clear solution was concentrated under vacuum to get the desired compound as a brown liquid (1.6 g, quantitative) and was used to next reaction without characterization.

Step-(v)

Synthesis of 1-(4-(thiazol-2-ylmethyl)-5,6-dihydropyridin-1(2H)-yl)prop-2-en-1-one (Intermediate-8)

To a stirred suspension of Intermediate-7(1.52 g, 5.17 mmol) in anhydrous CH₂Cl₂ (15 ml) was added triethyl amine (2.2 ml, 15.51 mmol) and acryloyl chloride (0.5 ml, 5.69 mmol) at 0° C. The reaction mixture was stirred at 20-35° C. for 16 h. The progress of the reaction was monitored by TLC. After 16 h of stirring, the reaction mixture was diluted with water (100 ml) and extracted with dichloromethane (2×100 ml). The combined organic layers were washed with brine (100 ml), followed by drying over anhydrous Na₂SO₄ and filtering. The filtrate was rotary evaporated to get residue which was purified by column chromatography using a mixture of 20% ethyl acetate/pet ether as an eluent to get the desired compound as a pale brown liquid (320 mg, 26%). ¹H NMR (400 MHz, DMSO-d₆) E. 7.70 (s, 1H), 7.24 (d, J=3.4 Hz, 1H), 6.55 (dt, J=16.6, 11.0 Hz, 1H), 6.29 (dd, J=16.6, 5.8 Hz, 1H), 5.74-5.66 (m, 1H), 5.58 (s, 1H), 4.16 & 4.08 (rotamer & s, 2H), 3.76-3.70 (m, 2H), 3.62 (t, J=5.6 Hz, 2H), 2.06-1.96 (m, 2H).

Key Intermediate for Compound 32

Synthesis of 2-(4-iodophenoxy)acetonitrile

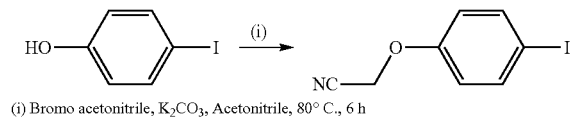

(i) Bromo acetonitrile, K₂CO₃, Acetonitrile, 80° C., 6 h

To a stirred solution of 4-iodo phenol (700 mg, 3.1 mmol) in acetonitrile (7 ml) was added K₂CO₃ (1.31 g, 9.5 mmol), followed by bromo acetonitrile (410 mg, 3.4 mmol) at 20-35° C. and the reaction mixture was stirred at 80° C. for 6 h. The progress of the reaction was monitored by TLC. After 6 h of stirring, the mixture was cooled to 20-35° C., diluted with water (50 ml) and extracted with ethyl acetate (2×50 ml). The combined organic layers were washed with brine (50 ml), followed by drying over anhydrous Na₂SO₄ and filtering. The filtrate was rotary evaporated to get residue which was purified by column chromatography using a mixture of 15% ethyl acetate/hexane as an eluent to get the desired compound as a pale yellow liquid (400 mg, 51%). ¹H NMR (400 MHz, DMSO-d₆) δ 7.65 (dt, J=5.4, 2.9 Hz, 2H), 6.79-6.77 (m, 2H), 4.74 (s, 2H).

Key Intermediate for Compound 34

Synthesis of 4-((4-iodophenoxy)methyl)benzonitrile

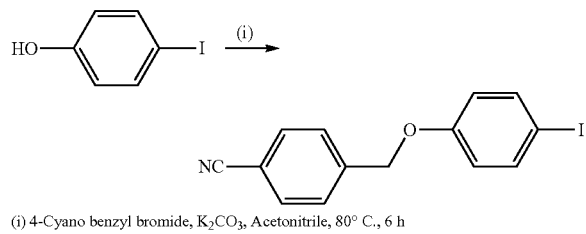

(i) 4-Cyano benzyl bromide, K₂CO₃, Acetonitrile, 80° C., 6 h

To a stirred solution of 4-iodo phenol (620 mg, 3.18 mmol) in acetonitrile (6 ml) was added K₂CO₃ (1.31 g, 9.54 mmol), followed by 4-cyanobenzyl bromide (700 mg, 3.18 mmol) at 20-35° C. and the reaction mixture was stirred at 80° C. for 6 h. The progress of the reaction was monitored by TLC. After 6 h of stirring, the mixture was cooled to 20-35° C., diluted with water (50 ml) and extracted with ethyl acetate (2×50 ml). The combined organic layers were washed with brine (50 ml), followed by drying over anhydrous Na₂SO₄ and filtering. The filtrate was rotary evaporated to get residue which was purified by column chromatography using a mixture of 10% ethyl acetate/hexane as an eluent to get the desired compound as a to pale yellow solid (800 mg, 75%). ¹H NMR (400 MHz, DMSO-d₆) δ 7.86 (d, J=8.3 Hz, 2H), 7.64-7.59 (m, 4H), 6.90-6.85 (m, 2H), 5.21 (s, 2H).

Key Intermediate for Compound 35

Synthesis of 4-((4-iodobenzyl)oxy)benzonitrile

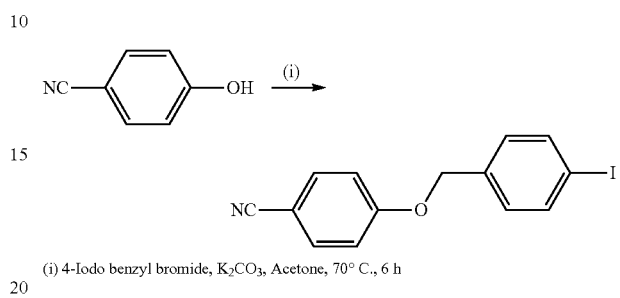

(i) 4-Iodo benzyl bromide, K₂CO₃, Acetone, 70° C., 6 h

To a stirred solution of 4-cyano phenol (1 g, 8.4 mmol) in acetone (15 ml) was added K₂CO₃ (3.48 g, 25.0 mmol), followed by 4-iodobenzyl bromide (2.7 g, 9.2 mmol) at 20-35° C. and the reaction mixture was stirred at 70° C. for 6 h. The progress of the reaction was monitored by TLC. After 6 h of stirring, the mixture was cooled to 20-35° C., diluted with water (50 ml) and extracted with ethyl acetate (2×50 ml). The combined organic layers were washed with brine (50 ml), followed by drying over anhydrous Na₂SO₄ and filtering. The filtrate was rotary evaporated to get residue which was purified by column chromatography using a mixture of 5% ethyl acetate/hexane as an eluent to get the desired compound as a white solid (700 mg, 35%). ¹H NMR (400 MHz, DMSO-d₆) δ 7.80-7.75 (m, 4H), 7.26 (d, J=8.3 Hz, 2H), 7.19-7.15 (m, 2H), 5.18 (s, 2H).

Key Intermediate for Compound 36

Synthesis of 4-(3-bromobenzyl)morpholine

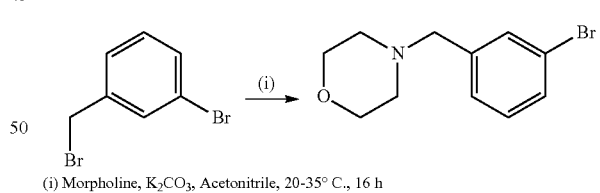

(i) Morpholine, K₂CO₃, Acetonitrile, 20-35° C., 16 h

To a stirred solution of morpholine (0.5 g, 5.8 mmol) in acetonitrile (5 ml) was added K₂CO₃ (2.4 g, 17.44 mmol), followed by 3-bromobenzyl bromide (1.45 g, 5.8 mmol) at 0° C. and the reaction mixture was stirred at 20-35° C. for 16 h. The progress of the reaction was monitored by TLC. After 16 h of stirring, the mixture was diluted with water (50 ml) and extracted with ethyl acetate (2×50 ml). The combined organic layers were washed with brine (50 ml), followed by drying over anhydrous Na₂SO₄ and filtering. The filtrate was rotary evaporated to get residue which was purified by column chromatography using a mixture of 5% ethyl acetate/hexane as an eluent to get the desired compound as a white solid (700 mg, 35%). $^1$H NMR (400 MHz, DMSO-$d_6$) δ 7.26 (d, J=8.3 Hz, 2H), 7.19-7.15 (m, 2H), 5.18 (s, 2H), 3.56 (t, J=4.6 Hz, 4H), 2.58 (t, J=4.4 Hz, 4H).

Key Intermediate for Compound 47

Synthesis of 2-(4-iodobenzyl)isoindoline-1,3-dione

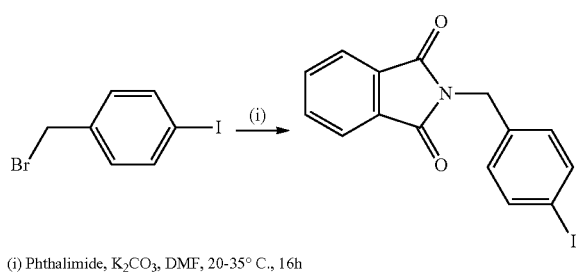

(i) Phthalimide, K$_2$CO$_3$, DMF, 20-35° C., 16h

To a stirred solution of phthalimide (0.6 g, 4.0 mmol) in DMF (5 ml) was added K$_2$CO$_3$ (2.25 g, 16.00 mmol), followed by 4-iodobenzyl bromide (1.33 g, 4.4 mmol) at 0° C. and the reaction mixture was stirred at 20-35° C. for 16 h. The progress of the reaction was monitored by TLC. After 16 h of stirring, the mixture was diluted with water (50 ml) and extracted with ethyl acetate (2×50 ml). The combined organic layers were washed with brine (50 ml), followed by drying over anhydrous Na$_2$SO$_4$ and filtering. The filtrate was rotary evaporated to get residue which was washed with diethyl ether to get the desired compound as a white solid (700 mg, 50%). $^1$H NMR (400 MHz, DMSO-$d_6$) δ 7.91-7.84 (m, 4H), 7.70-7.66 (m, 2H), 7.12 (d, J=8.3 Hz, 2H), 4.72 (s, 2H).

Key Intermediate for Compound 48

Synthesis of 2-(3-bromobenzyl)isoindoline-1,3-dione

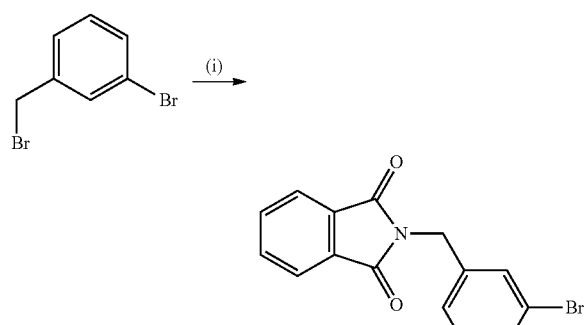

(i) Phthalimide, K$_2$CO$_3$, DMF, 20-35° C., 16h

To a stirred solution of phthalimide (0.64 g, 4.4 mmol) in DMF (10 ml) was added K$_2$CO$_3$ (1.65 g, 12.00 mmol), followed by 3-bromobenzyl bromide (1 g, 4.0 mmol) at 0° C. and the reaction mixture was stirred at 20-35° C. for 16 h. The progress of the reaction was monitored by TLC. After 16 h of stirring, the mixture was diluted with cool water (50 ml), resultant solid was filtered and dried under vacuum for 3 h to get the desired compound as a white solid (1.2 g, 95%). $^1$H NMR (400 MHz, DMSO-$d_6$) δ 7.92-7.84 (m, 4H), 7.54 (s, 1H), 7.50-7.45 (m, 1H), 7.33-7.26 (m, 2H), 4.77 (s, 2H).

Key Intermediate for Compound 57

Synthesis of 2-(chloromethyl)-5-methylthiazole (57b)

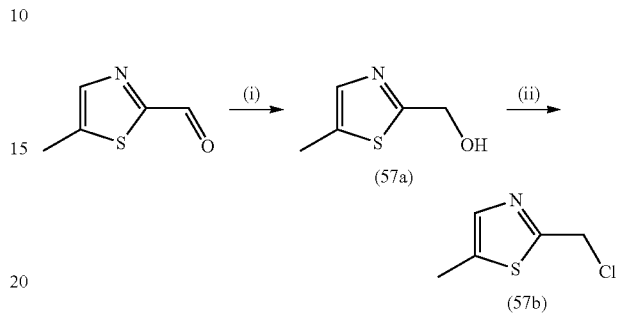

(i) NaBH$_4$, MeOH, 0° C. to 20-35° C., 1 h; (ii) SOCl$_2$, DCM, 20-35° C., 1 h.
(Ref. for step-(i): J. Med. Chem. 48(5), 1367-1383, 2005)

Step-(ii)

Synthesis of 2-(chloromethyl)-5-methylthiazole (57b)

To a stirred solution of 57a (1 g, 6.53 mmol) in DCM (10 ml) was added thionyl chloride (0.45 ml, 7.18 mmol) at 0° C. and the reaction mixture was stirred at 20-35° C. for 1 h. The progress of the reaction was monitored by TLC. After 1 h, the reaction mixture was poured into sodium bicarbonate solution and diluted with dichloromethane. The organic layer was washed with water (50 ml), brine (30 ml), dried over anhydrous Na$_2$SO$_4$ and evaporated to get the desired compound as a brown liquid (800 mg, 72%). The crude compound was directly used to next reaction without characterization.

Key Intermediate for Compound 84

Synthesis of 2-(bromomethyl)thiophene

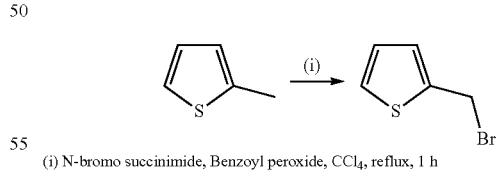

(i) N-bromo succinimide, Benzoyl peroxide, CCl$_4$, reflux, 1 h

To a stirred solution of 2-methyl thiophene (3 g, 30.61 mmol) in CCl$_4$ (75 ml) was added N-bromo succinimide (2.67 g, 15.00 mmol), followed by benzoyl peroxide (60 mg, 6.0 mmol) at 20-35° C. and the reaction mixture was refluxed for 1 h. The progress of the reaction was monitored by TLC. After cooling to 20-35° C., hexane (300 ml) was added to the reaction mixture, the resultant precipitate was removed via filtration and the filtrate was collected, concentrated to get the desired compound as a brown liquid (4.2 g, 78%). $^1$H NMR (400 MHz, CDCl$_3$) δ 7.33-7.24 (m, 1H), 7.11 (d, J=4.4 Hz, 1H), 6.93 (dd, J=4.9, 3.4 Hz, 1H), 4.75 (s, 2H).

Key Intermediate for Compound 86

Synthesis of 2-(bromomethyl)-3-methyl thiophene

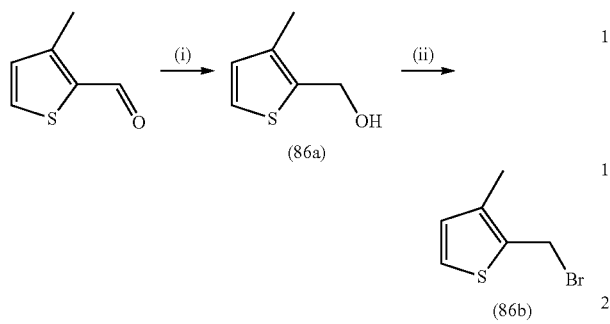

(i) NaBH$_4$, MeOH, 0° C. to 20-35° C., 12 h; (ii) CBr$_4$, PPh$_3$, DIPEA, DCM, 20-35° C., 12 h. (Ref. for step-(i): WO2008030520)

Step-(ii)

Synthesis of 2-(bromomethyl)-3-methylthiophene (86b)

To a stirred solution of 86a (0.5 g, 3.90 mmol) in DCM (10 ml) were added CBr$_4$ (2.6 g, 7.80 mmol), PPh$_3$ (2.04 g, 7.80 mmol) and DIPEA (1.06 ml, 7.80 mmol) at 20-35° C. and the reaction mixture was stirred at 20-35° C. for 12 h. The progress of the reaction was monitored by TLC. The resultant precipitate was removed via filtration and the filtrate was collected, concentrated to get the desired compound as a brown liquid (200 mg, 27%). The crude compound was directly used to next reaction without characterization.

Key Intermediate for Compound 87

Synthesis of 2-(bromomethyl)-3-chlorothiophene

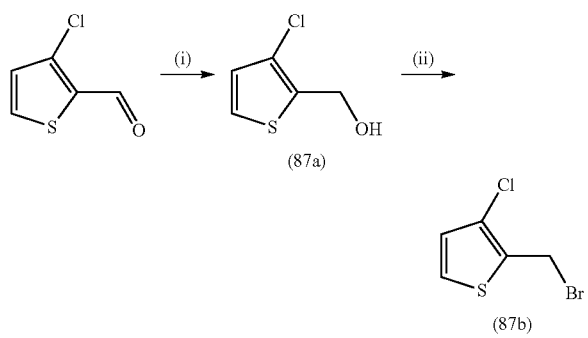

(i) NaBH$_4$, MeOH, 0° C. to 20-35° C., 16 h; (ii) PBr$_3$, DCM, 20-35° C., 16 h. (Ref. for step-(ii): WO2010132999)

Step-(i)

Synthesis of (3-chlorothiophen-2-yl)methanol (87a)

To a stirred solution of 3-chlorothiophene-2-carboxaldehyde (1 g, 6.85 mmol) in MeOH (15 ml) was added NaBH$_4$ (1.3 g, 34.25 mmol) at 0° C. and the reaction mixture was stirred at 20-35° C. for 16 h. The progress of the reaction was monitored by TLC. The reaction mixture was diluted with water (50 ml) and extracted with ethyl acetate (2×50 ml). The combined organic layers were washed with brine (50 ml), followed by drying over anhydrous Na$_2$SO$_4$ and filtering. The filtrate was rotary evaporated to get residue which was purified, by column chromatography using a mixture of 15% ethyl acetate/hexane as an eluent to get the desired compound as an oily liquid (900 mg, 88%). $^1$H NMR (400 MHz, DMSO-d$_6$) δ 6.89 (d, J=4.9 Hz, 1H), 6.73 (d, J=4.9 Hz, 1H), 4.91 (d, J=3.9 Hz, 2H), 4.13 (t, J=3.9 Hz, 1H).

Key Intermediate for Compound 97

Synthesis of 2-(bromomethyl)thiazole

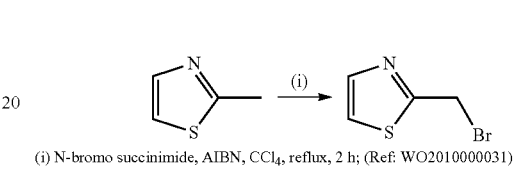

(i) N-bromo succinimide, AIBN, CCl$_4$, reflux, 2 h; (Ref: WO2010000031)

Key Intermediate for Compound 105

Synthesis of 2-(bromomethyl)-3-methylbenzo furan

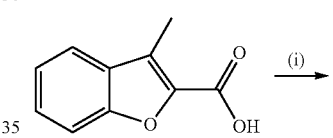

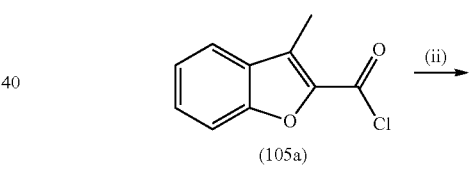

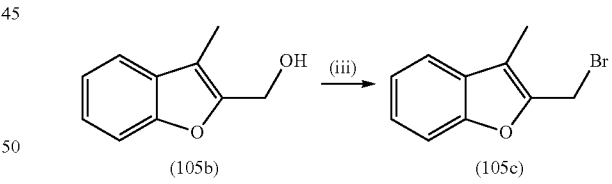

(i) Oxalyl chloride, DCM, DMF, 0° C. to 20-35° C., 16 h; (ii) NaBH$_4$, EtOH/THF, 0° C. to 20-35° C., 3 h; (iii) PBr$_3$, Diethyl ether, 0° C. to 20-35° C., 3-4 h; (Ref. for step-(i): WO2008098374) and step-(ii & iii): WO2006068991)

Key Intermediate for Compound-122

Synthesis of 6-bromo-1,2,3,4-tetrahydroisoquinoline

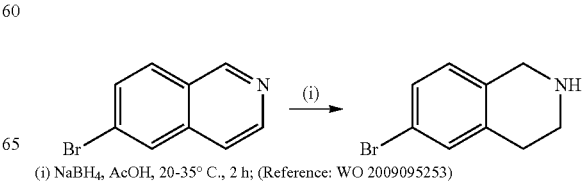

(i) NaBH$_4$, AcOH, 20-35° C., 2 h; (Reference: WO 2009095253)

Key Intermediate for Compound-123

Synthesis of 6-methoxy1,2,3,4-tetrahydroisoquinoline

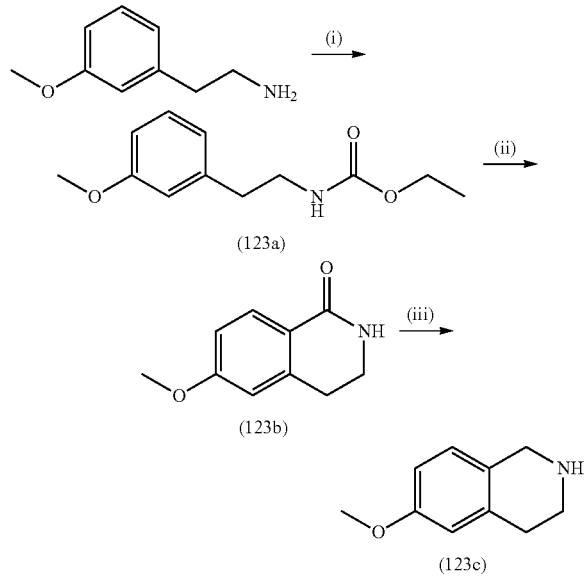

(i) Ethyl chloro formate, THF, 20-35° C., 16 h; (ii) PPA, 145° C., 5 min; (iii) LAH, THF, reflux, 3 h.
(Reference for Steps(i-iii): *Journal of medicinal chemistry*, 30, 2208-2218, 1987)

Key-Intermediate for Compound-124

Synthesis of 1,2,3,4-tetrahydroisoquinolin-6-ol Hydrobromide

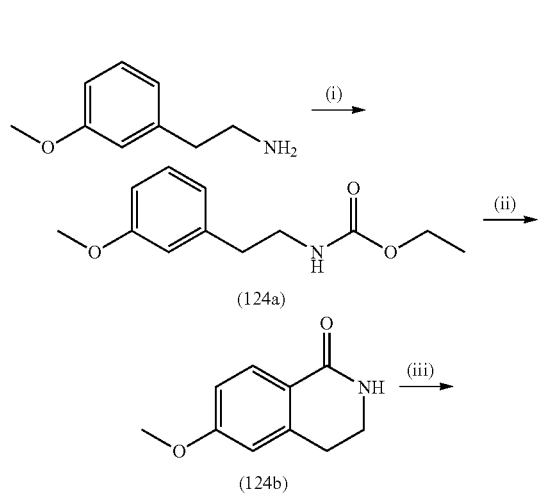

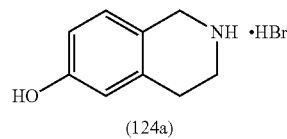

(124a)

(i) Ethyl chloro formate, THF, 20-35° C., 16 h; (ii) PPA, 145° C., 5 min; (iii) LAH, THF, reflux, 3 h.; (iv) Aq HBr, reflux, 3 h;
(Reference for Step-(i-iv): *Journal of medicinal chemistry*, 30, 2208-2218, 1987)

Key-Intermediate for Compound-125

Synthesis of (E)-1-(pyrrolidin-1-yl)-3-(1,2,3,4-tetrahydroisoquinolin-6-yl) prop-2-en-1-one trifluoro acetic acid

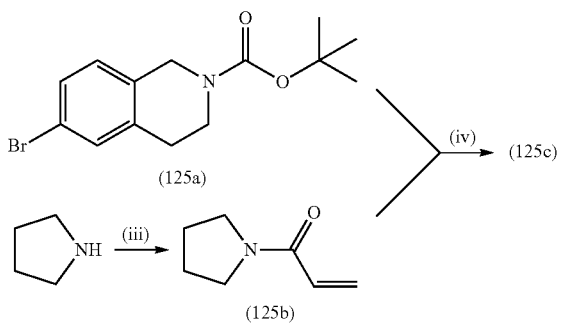

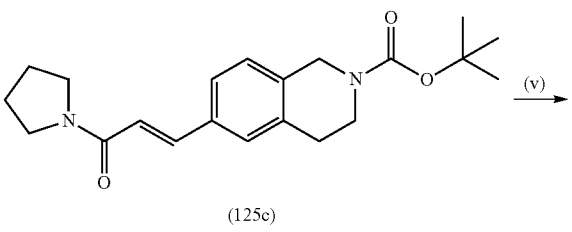

-continued

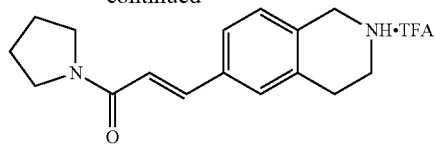

(125d)

(i) NaBH₄, AcOH, 20-35° C., 2 h; (ii) (BoC)₂O, Triethylamine, CH₂Cl₂, 20-35° C., 16 h; (iii) Acryloyl chloride, CH₂Cl₂, Triethylamine, 20-35° C., 16 h; (iv) Pd(OAc)₂, P(o-tolyl)₃, DIPEA, Propionitrile, DMF, 110° C., 16 h; (v) CF₃COOH, CH₂Cl₂, 20-35° C., 16 h; (Reference for Step-(i): WO 2009/095253)

Step-(ii)

Synthesis of tert-butyl 6-bromo-3,4-dihydroisoquinoline-2(1H)-carboxylate (125a)

To a stirred solution of 122a (700 mg, 3.31 mmol) in anhydrous DCM (10 ml) was added triethylamine (0.92 ml, 6.63 mmol) and di-tert-butyl dicarbonate (1.44 g, 6.63 mmol) at 0° C. The reaction mixture was stirred at 20-35° C. for 16 h. The progress of the reaction was monitored by TLC. After 16 h of stirring, the reaction mixture was diluted with water (30 ml) and extracted with dichloromethane (2×30 ml). The combined organic layers were washed with brine (30 ml), followed by drying over anhydrous Na₂SO₄ and filtering. The filtrate was rotary evaporated to get residue which was purified by column chromatography using a mixture of 10% ethyl acetate/pet ether as an eluent to get the desired compound as an oily liquid (900 mg, 87%). ¹H NMR (400 MHz, DMSO-d₆) δ 7.39 (s, 1H), 7.36 (dd, J=7.8, 1.9 Hz, 1H), 7.14 (d, J=8.3 Hz, 1H), 4.45 (s, 2H), 3.52 (t, J=5.9 Hz, 2H), 2.77 (t, J=5.9 Hz, 2H), 1.47 (s, 9H).

Step-(iii)

Synthesis of 1-(pyrrolidin-1-yl)prop-2-en-1-one (125b)

To a stirred solution of pyrrolidine (2 g, 28.16 mmol) in anhydrous DCM (30 ml) was added triethylamine (15.56 ml, 111.88 mmol) and acryloyl chloride (3.04 g, 33.77 mmol) at 0° C. The reaction mixture was stirred at 20-35° C. for 16 h. The progress of the reaction was monitored by TLC. After 16 h of stirring, the reaction mixture was diluted with water (50 ml) and extracted with ethyl acetate (2×50 ml). The combined organic layers was washed with brine (50 ml), followed by drying over anhydrous Na₂SO₄ and filtering. The filtrate was rotary evaporated to get the desired compound as a brown liquid (1.1 g, 31%). ¹H NMR (400 MHz, DMSO-d₆) δ 6.49-6.33 (m, 2H), 5.66 (dd, J=9.8, 2.4 Hz, 1H), 3.54 (dt, J=6.8, 3.9 Hz, 4H), 2.02-1.91 (m, 2H), 1.90-1.82 (m, 2H).

Step-(iv)

Synthesis of (E)-tert-butyl 6-(3-oxo-3-(pyrrolidin-1-yl) prop-1-en-1-yl)-3,4-dihydroisoquinoline-2(1H)-carboxylate (125c)

DIPEA (1.44 ml, 8.36 mmol) was added to a solution of 125a (650 mg, 2.09 mmol), 125b (287 mg, 2.29 mmol), Pd-(OAc)₂ (46 mg, 0.21 mmol) and P(o-tol)₃ (127 mg, 0.42 mmol) in propionitrile/DMF (8 ml/2 ml) and the reaction mixture was purged with nitrogen for 10 minutes, then was heated at 110° C. for 16 h. The progress of the reaction was monitored by TLC. After 16 h of stirring, the mixture was cooled to 20-35° C. and filtered on celite. The filtrate was concentrated and resultant residue diluted with water (30 ml) and extracted with ethyl acetate (2×30 ml). The combined organic layers were washed with brine (30 ml), followed by drying over anhydrous Na₂SO₄ and filtering. The filtrate was rotary evaporated to get residue which was purified by column chromatography using a mixture of 50% ethyl acetate/pet ether as an eluent to get the desired compound as an off-white solid (400 mg, 54%). ¹H NMR (400 MHz, DMSO-d₆) δ 7.50 (d, J=6.8 Hz, 2H), 7.41 (d, J=15.7 Hz, 1H), 7.20 (d, J=8.3 Hz, 1H), 6.94 (d, J=15.7 Hz, 1H), 4.56-4.46 (m, 2H), 3.63 (t, J=6.6 Hz, is 2H), 3.55 (t, J=5.9 Hz, 2H), 3.41-3.34 (m, 2H), 2.79 (t, J=5.9 Hz, 2H), 1.96-1.88 (m, 2H); 1.87-1.76 (m, 2H), 1.43 (s, 9H).

Step-(v)

Synthesis of (E)-1-(pyrrolidin-1-yl)-3-(1,2,3,4-tetrahydroisoquinolin-6-yl)prop-2-en-1-one trifluoro acetic acid (125d)

A solution of 125c (400 mg, 1.12 mmol) in CH₂Cl₂ (4 ml) was treated with TFA (1.28 g, 11.21 mmol)) at 20-35° C. for 16 h. The progress of the reaction was monitored by TLC. After 16 h of stirring, the clear solution was concentrated under vacuum and the resultant solid was washed with diethyl ether to get the desired compound as a gummy liquid (380 mg, 91%). ¹H NMR (400 MHz, DMSO-d₆) δ 9.05 (bs, 2H), 7.58 (d, J=8.3 Hz, 2H), 7.43 (d, J=15.6 Hz, 1H), 7.25 (d, J=7.8 Hz, 1H), 6.99 (d, J=15.6 Hz, 1H), 4.32-4.24 (m, 2H), 3.63 (t, J=6.9 Hz, 2H), 3.39 (t, J=6.9 Hz, 4H), 3.01 (t, J=6.1 Hz, 2H), 1.98-1.89 (m, 2H), 1.88-1.76 (m, 2H).

Preparation of Compound-1

Synthesis of (E)-(1-(3-(7-oxo-5,6,7,8-tetrahydro-1,8-naphthyridin-3-yl)acryloyl)-1,2,3,6-tetrahydropyridin-4-yl)boronic acid

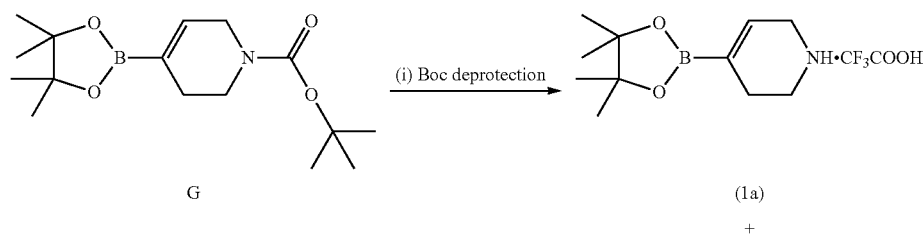

-continued

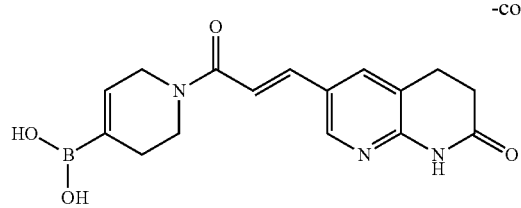

Compound-1

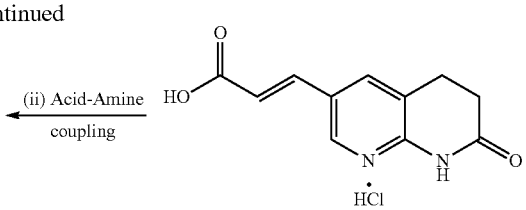

(Intermediate-1)

(i) CF₃COOH, CH₂Cl₂, 20-35° C., 2 h; (ii) HOBt, EDC·HCl, DIPEA, DMF, 20-35° C., 16 h

Step-(i)

Synthesis of 4-(4,4,5,5-tetramethyl-1,3,2-dioxaborolan-2-yl)-1,2,3,6-tetrahydro pyridine.trifluoroacetic acid (1a)

A solution of G (300 mg, 0.97 mmol) in CH₂Cl₂ (15 ml) was treated with trifluoro acetic acid (220 mg, 1.94 mmol) at 20-35° C. for 2 h. The progress of the reaction was monitored by TLC. After 2 h of stirring, the clear solution was concentrated under vacuum and the resultant solid was washed with pet ether to get the desired compound as a brown liquid (202 mg). MS (ES) m/e 209.2 (M-CF₃COOH).

Step-(ii)

Synthesis of (E)-(1-(3-(7-oxo-5,6,7,8-tetrahydro-1,8-naphthyridin-3-yl)acryloyl)-1,2,3,6-tetrahydropyridin-4-yl)boronic acid DIPEA (0.35 ml, 1.92 mmol) was added to a stirred solution of Intermediate-1 (140 mg, 0.64 mmol), 1a (160 mg, 0.77 mmol), anhydrous HOBt (172 mg, 1.28 mmol) and EDC.HCl (245 mg, 1.28 mmol) in dry DMF (15 ml) at 20-35° C. The reaction mixture was stirred at 20-35° C. for 16 h. The progress of the reaction was monitored by TLC. After 16 h of stirring, the mixture was diluted with water (50 ml) and extracted with ethyl acetate (2×50 ml). The combined organic layers were washed with brine (50 ml), followed by drying over anhydrous Na₂SO₄ and filtering. The filtrate was rotary evaporated to get residue which was purified by using preparative HPLC to get the desired compound-1 as a white solid (30 mg, 14%). ¹H NMR (400 MHz, DMSO-d₆) δ 10.63 (bs, 1H), 8.32 (d, J=11.7 Hz, 1H), 8.20-8.14 (m, 1H), 7.45 (d, J=15.1 Hz, 1H), 7.35-7.15 (m, 1H), 6.40 (bs, 1H), 4.30 (bs, 1H), 4.06 (bs, 1H), 3.70-3.56 (m, 2H), 2.91 (t, J=7.6 Hz, 2H), 2.54 (d, J=8.3 Hz, 2H), 2.45-2.22 (m, 2H); 2-OH protons were unrevealed by ¹H NMR instrument; MS (ES) m/e 328.2 (M+H)⁺.

Preparation of Compound-2

Synthesis of (E)-6-(3-oxo-3-(4-phenyl-5,6-dihydro pyridin-1(2H)-yl)prop-1-en-1-yl)-3,4-dihydro-1,8-naphthyridin-2(1H)-one

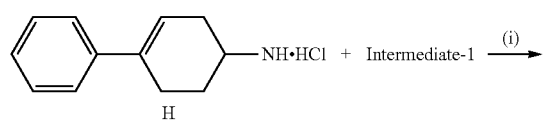

-continued

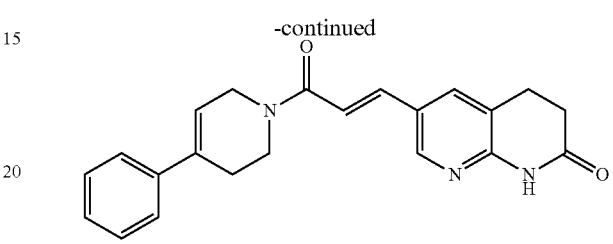

Compound-2

(i) HOBt, EDC·HCl, DIPEA, DMF, 20-35° C., 16 h

The details and specifics of the process are mentioned below.

Step-(i)

Synthesis of (E)-6-(3-oxo-3-(4-phenyl-5,6-dihydropyridin-1(2H)-yl)prop-1-en-1-yl)-3,4-dihydro-1,8-naphthyridin-2(1H)-one The process of this step was adopted from step-(ii) of compound-1. The desired Compound-2 obtained as creamy white solid (50 mg, 27%). ¹H NMR (400 MHz, DMSO-d₆) δ 10.65 (s, 1H), 8.37 (s, 1H), 8.11 (d, J=16.2 Hz, 1H), 7.52-7.45 (m, 3H), 7.36 (t, J=7.6 Hz, 3H), 7.30-7.22 (m, 1H), 6.24-6.18 (m, 1H), 4.46-4.37 (m, 1H), 4.28-4.20 (m, 1H), 3.94-3.88 (m, 1H), 3.85-3.74 (m, 1H), 2.95-2.90 (m, 2H), 2.63-2.57 (m, 2H), 2.56-2.52 (m, 2H); MS (ES) m/e 359.9 (M+H)⁺.

Preparation of Compound-3

Synthesis of (E)-6-(3-(4-(3-methylbenzofuran-2-yl)-5,6-dihydropyridin-1(2H)-yl)-3-oxoprop-1-en-1-yl)-3,4-dihydro-1,8-naphthyridin-2(1H)-one

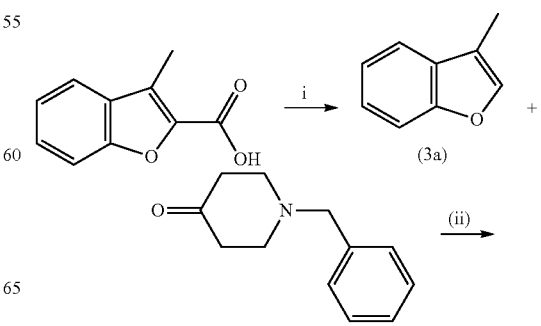

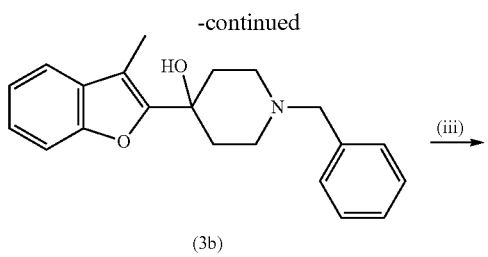

(3b)

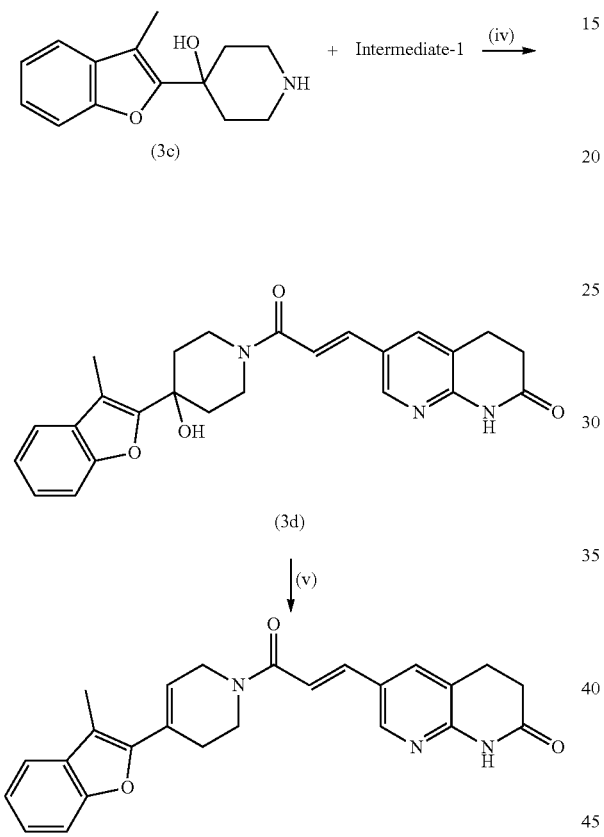

(i) Ag₂CO₃, AcOH, DMSO, 130° C., 16 h; (ii) n-BuLi, dry THF, -78° C., 2 h, then 20-35° C., 16 h; (iii) 10% Pd/C, MeOH, H₂-gas, 20-35° C., 3 h; (iv) HOBt, EDC·HCl, DIPEA, DMF, 20-35° C., 16 h; (v) 10% HCl solution, Reflux, 6 h.

(Reference for Step-(i): Organic Letters, 11(24),5710-5713, 2009)

Step-(ii)

Synthesis of 1-benzyl-4-(3-methylbenzofuran-2-yl) piperidin-4-ol (3b)

To a stirred solution of 3a (500 mg, 3.79 mmol) in dry THF (5 ml) was dropwise added a solution of n-butyl lithium in n-hexane (1.6M, 2.69 ml, 4.38 mmol) at −78° C. The resulting suspension was stirred at the same temperature for 0.5 h and treated dropwise with a solution of 1-benzylpiperidin-4-one (1.08 g, 5.68 mmol) in dry THF (10 ml). The reaction mixture was stirred −78° C. for 2 h, slowly warmed to 20-35° C. and continued stirring at 20-35° C. for 16 h. The progress of the reaction was monitored by TLC. The reaction mixture was quenched with NH₄Cl solution (2 ml), diluted with water (20 ml) and extracted with ethyl acetate (2×50 ml). The combined organic layers were washed with brine (50 ml), followed by drying over anhydrous Na₂SO₄ and filtering. The filtrate was rotary evaporated to get residue which was purified by column chromatography using a mixture of 20% ethyl acetate/hexane as an eluent to get the desired compound as an off-white waxy solid (260 mg, 21%).

$^1$H NMR (400 MHz, DMSO-$d_6$) δ 7.51 (dd, J=6.6, 2.2 Hz, 1H), 4.45 (dd, J=7.0, 1.2 Hz, 1H), 7.37-7.30 (m, 4H), 7.29-7.18 (m, 3H), 5.21 (bs, 1H), 3.50 (s, 2H), 2.56 (d, J=10.8 Hz, 2H), 2.51-2.42 (m, 2H), 2.32 (s, 3H), 2.11 (dt, J=12.9, 4.4 Hz, 2H), 1.83 (d, J=12.7 Hz, 2H); MS (ES) m/e 322.0 (M+H)⁺.

Step-(iii)

Synthesis of 4-(3-methylbenzofuran-2-yl)piperidin-4-ol (3c)

To a stirred solution of 3b (260 mg, 0.81 mmol) in methanol (5 ml) was added 10% Pd/C (130 mg). The mixture was degassed with nitrogen for 10 minutes and continued stirring at 20-35° C. under H₂ gas atmosphere for 3 h. The progress of the reaction was monitored by TLC. The reaction mixture was filtered on celite bed, celite bed washed with methanol and resultant filtrate concentrated to get the desired product as a yellow waxy solid (180 mg, 96%). $^1$H NMR (400 MHz, DMSO-$d_6$) δ 7.52 (dd, J=6.8, 2.0 Hz, 1H), 7.47-7.44 (m, 1H), 7.26-7.18 (m, 2H), 5.20 (bs, 1H), 2.92 (s, 1H), 2.73 (d, J=10.7 Hz, 2H), 2.44 (t, J=10.5 Hz, 2H), 2.34 (s, 3H), 2.15-2.07 (m, 2H), 1.84 (d, J=12.7 Hz, 2H); MS (ES) m/e 232.1 (M+H)⁺.

Step-(iv)

Synthesis of (E)-6-(3-(4-hydroxy-4-(3-methylbenzofuran-2-yl)piperidin-1-yl)-3-oxoprop-1-en-1-yl)-3,4-dihydro-1,8-naphthyridin-2(1H)-one (3d)

The process of this step was adopted from step-(ii) of compound-1 and compound-(3d) obtained as a creamy white solid (80 mg, 24%). $^1$H NMR (400 MHz, DMSO-$d_6$) δ 10.64 (s, 1H), 8.36 (d, J=2.0 Hz, 1H), 8.10 (s, 1H), 7.53 (dd, J=6.4, 2.2 Hz, 1H), 7.48 (d, J=15.2 Hz, 1H), 7.44 (d, J=2.0 Hz, 1H), 7.31 (d, J=15.6 Hz, 1H), 7.27-7.20 (m, 2H), 5.59 (bs, 1H), 4.33 (d, J=11.7 Hz, 1H), 4.17 (dd, J=12.2 Hz, 1H), 3.56 (t, J=12.0 Hz, 1H), 3.17 (t, J=11.0 Hz, 1H), 2.92 (t, J=7.5 Hz, 2H), 2.56-2.53 (m, 2H), 2.36 (s, 3H), 2.12-2.04 (m, 1H), 2.02-1.88 (m, 3H); MS (ES) m/e 432.3 (M+H)⁺.

Step-(v)

Synthesis of (E)-6-(3-(4-(3-methylbenzofuran-2-yl)-5,6-dihydropyridin-1(2H)-yl)-3-oxoprop-1-en-1-yl)-3,4-dihydro-1,8-naphthyridin-2(1H)-one A solution of 3d (50 mg, 0.11 mmol) in 10% HCl solution (5 ml) was stirred at 100° C. for 6 h. The progress of the reaction was monitored by TLC. After 6 h of stirring, the mixture was cooled to 0° C. and basified with NaHCO₃ solution. The resultant solid was filtered, washed with water and dried under vacuum for 16 h. The crude compound was purified by column chromatography using a mixture of 1% methanol/chloroform as an eluent to get the desired compound-3 as a pale brown solid (15 mg, 33%). $^1$H NMR (400

MHz, DMSO-d$_6$) δ 10.65 (s, 1H), 8.38 (s, 1H), 8.11 (d, J=16.7 Hz, 1H), 7.59 (d, J=7.3 Hz, 1H), 7.53-7.47 (m, 2H), 7.38-7.22 (m, 3H), 6.42-6.34 (m, 1H), 4.56-4.44 (m, 1H), 4.38-4.24 (m, 1H), 3.98-3.90 (m, 1H), 3.89-3.77 (m, 1H), 2.93 (t, J=7.5 Hz, 2H), 2.78-2.70 (m, 1H), 2.67-2.64 (m, 1H), 2.57-2.54 (m, 2H), 2.35 (s, 3H); MS (ES) m/e 414.1 (M+H)$^+$.

Preparation of Compound-4

Synthesis of (E)-6-(3-(5,6-dihydro-[4,4'-bipyridin]-1(2H)-yl)-3-oxoprop-1-en-1-yl)-3,4-dihydro-1,8-naphthyridin-2(1H)-one

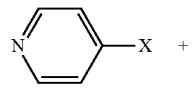

X = Cl, Br or I

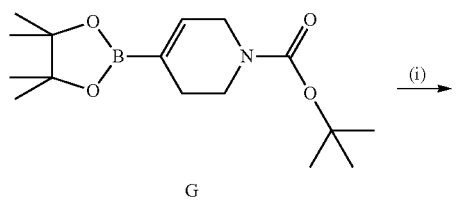

G

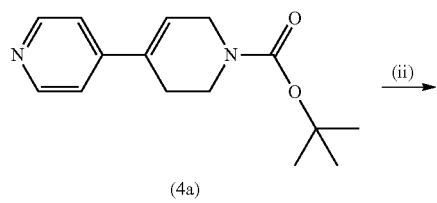

(4a)

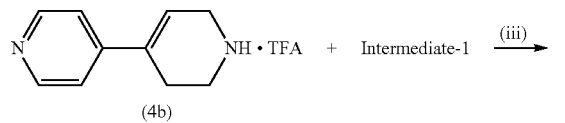

(4b)

Compound-4

(i) Pd(dppf)$_2$Cl$_2$, K$_2$CO$_3$, DMF, 80° C., 16 h; (ii) CF$_3$COOH, CH$_2$Cl$_2$, 20-35° C., 2 h; (iii) HOBt, EDC•HCl, DIPEA, DMF, 20-35° C., 16 h.

Step-(i)

Synthesis of tert-butyl 5,6-dihydro-[4,4'-bipyridine]-1(2H)-carboxylate (4a)

A solution of 4-iodopyridine (360 mg, 1.75 mmol), G (500 mg, 1.62 mmol) and potassium carbonate (450 mg, 3.50 mmol) in dry DMF (5 ml) was degassed with nitrogen for 10 minutes. After 10 minutes Pd(dppf)$_2$Cl$_2$(130 mg, 0.17 mmol) was added, again degassed with nitrogen for 10 minutes and the reaction mixture was stirred, at 80° C. for 16 h. The progress of the reaction was monitored by TLC. After 16 h of stirring, the reaction mixture was cooled to 20-35° C., diluted with water (50 ml) and extracted with ethyl acetate (2×50 ml). The combined organic layers were washed with brine (50 ml), followed by drying over anhydrous Na$_2$SO$_4$ and filtering. The filtrate was rotary evaporated to get residue which was purified by column chromatography using a mixture of 40% ethyl acetate/hexane as an eluent to get the desired compound as a pale brown solid (120 mg, 29%). $^1$H NMR (400 MHz, DMSO-d$_6$) δ 8.57-8.54 (m, 2H), 7.25 (d, J=2.0 Hz, 2H), 6.30-6.20 (m, 1H), 4.11 (d, J=2.5 Hz, 2H), 3.65 (t, J=5.4 Hz, 2H), 2.56-2.46 (m, 2H), 1.49 (s, 9H); MS (ES) m/e 261.1 (M+H)$^+$.

Step-(ii)

Synthesis of 1,2,3,6-tetrahydro-4,4'-bipyridine trifluoro acetic acid (4b)

The process of this step was adopted from step-(i) of compound-1. $^1$H NMR (400 MHz, DMSO-d$_6$) δ 9.04 (bs, 2H), 8.71 (d, J=5.8 Hz, 2H), 7.74 (d, J=6.3 Hz, 2H), 6.69 (s, 1H), 3.88-3.82 (m, 2H), 3.36 (d, J=4.9 Hz, 2H), 2.71 (d, J=2.0 Hz, 2H); MS (ES) m/e 161.1 (M-CF$_3$COOH).

Step-(iii)

Synthesis of (E)-6-(3-(5,6-dihydro-[4,4'-bipyridin]-1(2H)-yl)-3-oxoprop-1-en-1-yl)-3,4-dihydro-1,8-naphthyridin-2(1H)-one The process of this step was adopted from step-(ii) of compound-1. The desired compound-4 obtained as a pale brown solid (30 mg, 23%). $^1$H NMR (400 MHz, DMSO-d$_6$) δ 10.65 (s, 1H), 8.53 (d, J=5.3 Hz, 2H), 8.37 (s, 1H), 8.11 (d, J=17.1 Hz, 1H), 7.52-7.45 (m, 3H), 7.38-7.22 (m, 1H), 6.60-6.46 (m, 1H), 4.50-4.40 (m, 1H), 4.38-4.24 (m, 1H), 4.00-3.90 (m, 1H), 3.88-3.74 (m, 1H), 2.91 (dd, J=13.9, 6.6 Hz, 2H), 2.64-2.50 (m, 4H); MS (ES) m/e 361.2 (M+H)$^+$.

The compounds prepared by following the process according to compound-4 and their to physicochemical characteristics are summarized hereinbelow in the Table-I.

TABLE-I

| Comp. No | R₄ | ¹H NMR (400 MHz, DMSO-d₆); δ (ppm) and MS(ES) m/e |
|---|---|---|
| 5 |  | 10.65 (s, 1H), 8.70 (s, 1H), 8.48 (dd, J = 4.7, 1.2 Hz, 1H), 8.37 (s, 1H), 8.12 (d, J = 15.7 Hz, 1H), 7.86 (d, J = 7.8 Hz, 1H), 7.50 (d, J = 15.1 Hz, 1H), 7.40-7.38 (m, 1H), 7.37-7.36 (m, 1H), 6.34-6.32 (m, 1H), 4.44-4.42 (m, 1H), 4.26-4.24 (m, 1H), 3.95-3.93 (m, 1H), 3.81-3.79 (m, 1H), 2.9 (t, J = 7.6 Hz, 2H), 2.61-2.52 (m, 4H); MS (ES) m/e 361.2 (M + H) ⁺. |
| 6 |  | 10.65 (s, 1H), 8.80 (d, J = 4.9 Hz, 2H), 8.37 (s, 1H), 8.14-8.08 (m, 1H), 7.50 (d, J = 15.7 Hz, 1H), 7.36 (t, J = 4.9 Hz, 2H), 7.28-7.21 (m, 1H) 4.58-4.46 (m, 1H), 4.38-4.30 (m, 1H), 3.96-3.88 (m, 1H), 3.86-3.76 (m, 1H), 2.93 (t, J = 7.3 Hz, 2H), 2.80-2.70 (m, 1H), 2.68-2.62 (m, 1H), 2.58-2.50 (m, 2H); MS (ES) m/e 362.3 (M + H) ⁺. |
| 7 | 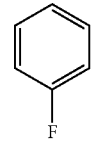 | 10.65 (s, 1H), 9.09 (s, 1H), 8.93 (s, 2H), 8.37 (s, 1H), 8.12 (d, J = 15.6 Hz, 1H), 7.50 (d, J = 15.2 Hz, 1H), 7.39-7.23 (m, 1H), 6.48-6.42 (m, 1H), 4.50-4.40 (m, 1H), 4.36-4.24 (m, 1H), 3.98-3.90 (m, 1H), 3.86-3.76 (m, 1H), 2.94-2.89 (m, 2H), 2.70-2.60 (m, 1H), 2.59-2.44 (m, 3H); MS (ES) m/e 362.2 (M + H) ⁺. |
| 8 | 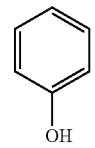 | 8.42 (s, 1H), 8.35 (s, 1H), 7.65 (d, J = 15.1 Hz, 2H), 7.34 (dd, J = 8.3, 5.4 Hz, 2H), 7.04 (t, J = 8.8 Hz, 2H), 6.89-6.80 (m, 1H), 6.07-5.99 (m, 1H), 4.39-4.31 (m, 2H), 3.98-3.92 (m, 1H), 3.90-3.81 (m, 1H), 3.01 (t, J = 7.6 Hz, 2H), 2.74-2.69 (m, 2H), 2.62-2.58 (m, 2H); MS (ES) m/e 378.1 (M + H) ⁺. |
| 9 | 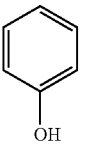 | 10.64 (s, 1H), 9.43 (bs, 1H), 8.36 (s, 1H), 8.11 (d, J = 15.7 Hz, 1H), 7.51-7.44 (s, 1H), 7.33 (d, J = 15.7 Hz, 1H), 7.27 (d, J = 7.8 Hz, 2H), 6.73 (d, J = 8.3 Hz, 2H), 6.03 (s, 1H), 4.42-4.38 (m, 1H), 4.22-4.18 (m, 1H), 3.90-3.81 (m, 1H), 3.76-3.71 (m, 1H), 2.94-2.89 (m, 2H), 2.61-2.54(m, 4H); MS (ES) m/e 374 (M − H). |
| 10 | 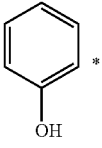 | 10.64 (s, 1H), 9.38 (s, 1H), 8.36 (s, 1H), 8.11 (d, J = 17.1 Hz, 1H), 7.48 (d, J = 15.1 Hz, 1H), 7.36-7.16 (m, 1H), 7.13 (d, J = 7.8 Hz, 1H), 6.88 (d, J = 6.8 Hz, 1H), 6.82 (s, 1H), 6.68 (d, J = 7.9 Hz, 1H), 6.15-6.12 (m, 1H), 4.44-4.38 (m, 1H), 4.21-4.19 (m, 1H), 3.91-3.89 (m, 1H), 3.78-3.76 (m, 1H), 2.94-2.89 (m, 2H), 2.56-2.54 (m, 4H); MS (ES) m/e 374.2(M − H). |
| 11 | 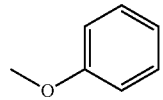 | 10.64 (s, 1H), 9.41 (s, 1H), 8.36 (d, J = 1.9 Hz, 1H), 8.11 (d, J = 14.2 Hz, 1H), 7.49 (d, J = 15.7 Hz, 1H), 7.38-7.19 (m, 1H), 7.05-7.01 (m, 2H), 6.82 (d, J = 7.8 Hz, 1H), 6.76 (t, J = 7.3 Hz, 1H), 5.87 (s, 1H), 4.42-4.38 (m, 1H), 4.20-4.12 (m, 1H), 3.92-3.82 (m, 1H), 3.80-3.72 (m, 1H), 2.92 (t, J = 7.9 Hz, 2H), 2.60-2.54 (m, 4H); MS (ES) m/e 376.2 (M + H) ⁺ |
| 12 | 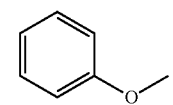 | 10.64 (s, 1H), 8.37 (d, J = 9.3 Hz, 1H), 8.07 (d, J = 15.7 Hz, 1H), 7.55 (d, J = 15.6 Hz, 1H), 7.39 (d, J = 7.8 Hz, 2H), 7.36-7.22 (m, 1H), 6.92 (d, J = 8.8 Hz, 2H), 6.08-6.02 (m, 1H), 4.41-4.38 (m, 1H), 4.22-4.18 (m, 1H), 3.92-3.85 (m, 1H), 3.80-3.76 (m, 1H), 3.75 (s, 3H), 2.92 (t, J = 7.3 Hz, 2H), 2.88-2.67 (m, 4H); MS (ES) m/e 390(M + H) ⁺. |
| 13 |  | 10.64 (s, 1H), 8.37 (s, 1H), 8.11 (d, J = 17.1 Hz, 1H), 7.48 (d, J = 15.2 Hz, 1H), 7.37-7.22 (m, 2H), 7.03 (d, J = 7.9 Hz, 1H), 6.98 (s, 1H), 6.85 (dd, J = 7.9, 2.0 Hz, 1H), 6.23-6.21 (m, 1H), 4.42-4.39 (m, 1H), 4.24-4.20 (m, 1H), 3.92-3.90 (m, 1H), 3.79-3.78 (m, 1H), 3.77 (s, 3H), 2.92 (t, J = 7.6 Hz, 2H), 2.56-2.52 (m, 4H); MS (ES) m/e 388.1 (M − H). |

TABLE-I-continued

Structure: R₄-substituted tetrahydropyridine-N-C(=O)-CH=CH-(3,4-dihydro-1,8-naphthyridin-2(1H)-one)

| Comp. No | R₄ | ¹H NMR (400 MHz, DMSO-$d_6$); δ (ppm) and MS(ES) m/e |
|---|---|---|
| 14 | 2-methoxyphenyl | 10.64 (s, 1H), 8.37 (d, J = 2.0 Hz, 1H), 8.11 (d, J = 14.6 Hz, 1H), 7.52-7.50 (m, 1H), 7.48-7.21 (m, 2H), 7.16-7.14 (m, 1H), 7.00 (d, J = 8.3 Hz, 1H), 6.94-6.90 (m, 1H), 5.82-5.80 (m, 1H), 4.38-4.36 (m, 1H), 4.20-4.16 (m, 1H), 3.88-3.85 (m, 1H), 3.76 (s, 3H), 3.76-3.74 (m, 1H), 2.90 (t, J = 7.4 Hz, 2H), 2.67-2.57 (m, 4H); MS (ES) m/e 390.3(M + H)⁺. |
| 15 | 2-(trifluoromethoxy)phenyl | 10.65 (s, 1H), 8.37 (s, 1H), 8.09 (d, J = 16.2 Hz, 1H), 7.60 (d, J = 6.8 Hz, 2H), 7.53 (d, J = 15.7 Hz, 1H), 7.47-7.28 (m, 3H), 6.23 (s, 1H), 4.41-4.38 (m, 1H), 4.22-4.18 (m, 1H), 3.91-3.85 (m, 1H), 3.80-3.76 (m, 1H), 2.92 (t, J = 7.4 Hz, 2H), 2.56-2.52 (m, 4H); MS (ES) m/e 444.4 (M + H)⁺. |
| 16 | 4-methylphenyl | 10.64 (s, 1H), 8.36 (s, 1H), 8.11 (d, J = 15.6 Hz, 1H), 7.48 (d, J = 15.8 Hz, 1H), 7.35 (d, J = 7.3 Hz, 2H), 7.25-7.21 (m, 1H), 7.16 (d, J = 7.8 Hz, 2H), 6.17-6.15 (m 1H), 4.41-4.39 (m, 1H), 4.22-4.20 (m, 1H), 3.92-3.90 (m, 1H), 3.79-3.77 (m, 1H), 2.92 (t, J = 7.4 Hz, 2H), 2.56-2.54 (m, 4H), 2.29 (s, 3H); MS (ES) m/e 374.1 (M + H)⁺. |
| 17 | 3-cyanophenyl | 10.65 (s, 1H), 8.37 (s, 1H), 8.12 (d, J = 16.2 Hz, 1H), 7.93 (s, 1H), 7.81 (d, J = 6.9 Hz, 1H), 7.74 (d, J = 7.9 Hz, 1H), 7.57 (t, J = 7.9 Hz, 1H), 7.50 (d, J = 15.6 Hz, 1H), 7.37-7.22 (m, 1H), 6.41-6.37 (m, 1H), 4.48-4.40 (m, 1H), 4.30-4.22 (m, 1H), 3.98-3.90 (m, 1H), 3.89-3.78 (m, 1H), 2.92 (t, J = 7.3 Hz, 2H), 2.61-2.54 (m, 4H); MS (ES) m/e 385.2 (M + H)⁺. |
| 18 | 4-cyanophenyl | 10.65 (s, 1H), 8.37 (s, 1H), 8.13-8.09 (m, 1H), 7.82 (d, J = 8.3 Hz, 2H), 7.70-7.64 (m, 2H), 7.49 (d, J = 15.2 Hz, 1H), 7.37-7.22 (m, 1H), 6.45-6.40 (m, 1H), 4.45-4.43 (m, 1H), 4.27-4.26 (m, 1H), 3.94-3.92 (m, 1H), 3.80-3.79 (m, 1H), 2.92 (t, J = 7.4 Hz, 2H), 2.56-2.52 (m, 4H); MS (ES) m/e 385.2 (M + H)⁺. |
| 20 | 4-nitrophenyl | 10.65 (s, 1H), 8.37 (s, 1H), 8.22 (d, J = 8.8 Hz, 2H), 8.12 (d, J = 16.2 Hz, 1H), 7.75 (d, J = 7.4 Hz, 2H), 7.50 (d, J = 15.2 Hz, 1H), 7.38-7.23 (m, 1H), 6.54-6.48 (m, 1H), 4.49-4.47 (m, 1H), 4.31-4.28 (m, 1H), 3.96-3.94 (m, 1H), 3.88-3.80 (m, 1H), 2.93 (t, J = 7.3 Hz, 2H), 2.67-2.52 (m, 4H); MS (ES) m/e 405.2 (M + H)⁺. |
| 23 | 3-nitrophenyl | 10.65 (s, 1H), 8.37 (s, 1H), 8.23 (s, 1H), 8.13 (dd, J₁ = 7.5, 2.2 Hz, 2H), 7.95 (d, J = 7.4 Hz, 1H), 7.67 (t, J = 8.0 Hz, 1H), 7.50 (d, J = 15.2 Hz, 1H), 7.38-7.23 (m, 1H), 6.50-6.42 (m, 1H), 4.49-4.42 (m, 1H), 4.60-4.53 (m, 1H), 3.97-3.92 (m, 1H), 3.62-3.57 (m, 1H), 2.94-2.89 (m, 2H), 2.67 (d, J = 2.0 Hz, 1H), 2.56-2.52 (m, 3H); MS (ES) m/e 405 (M + H)⁺. |
| 26 | 4-(ethoxycarbonyl)phenyl | 10.65 (s, 1H), 8.37 (s, 1H), 8.11 (d, J = 17.1 Hz, 1H), 7.94 (d, J = 8.3 Hz, 2H), 7.61 (d, J = 7.4 Hz, 2H), 7.49 (d, J = 15.1 Hz, 1H), 7.38-7.34 (m, 1H), 6.42-6.38 (m, 1H), 4.47-4.44 (m, 1H), 4.31 (q, J = 7.2 Hz, 2H), 4.27-4.25 (m, 1H), 3.95-3.93 (m, 1H), 3.81-3.79 (m, 1H), 2.92 (t, J = 7.6 Hz, 2H), 2.56-2.52 (m, 4H), 1.32 (t, J = 7.1 Hz, 3H); MS (ES) m/e 432.3 (M + H)⁺. |

TABLE-I-continued

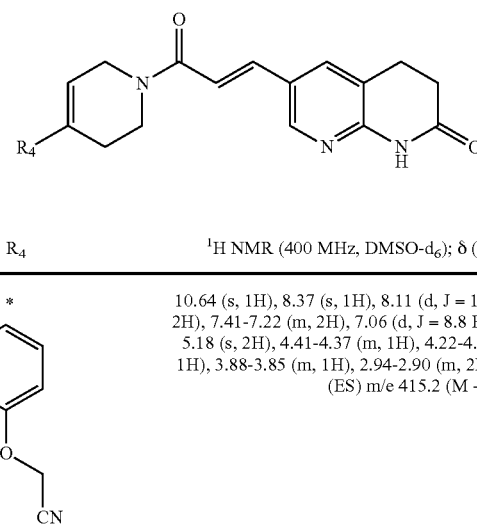

| Comp. No | R₄ | ¹H NMR (400 MHz, DMSO-d₆); δ (ppm) and MS(ES) m/e |
|---|---|---|
| 32 | 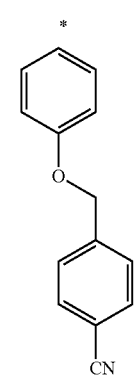 | 10.64 (s, 1H), 8.37 (s, 1H), 8.11 (d, J = 15.6 Hz, 1H), 7.51-7.47 (m, 2H), 7.41-7.22 (m, 2H), 7.06 (d, J = 8.8 Hz, 2H), 6.18-6.14 (m, 1H), 5.18 (s, 2H), 4.41-4.37 (m, 1H), 4.22-4.20 (m, 1H), 3.93-3.90 (m, 1H), 3.88-3.85 (m, 1H), 2.94-2.90 (m, 2H), 2.56-2.54 (m, 4H); MS (ES) m/e 415.2 (M + H) ⁺. |
| 34 | 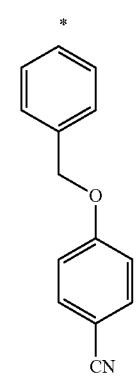 | 10.64 (s, 1H), 8.36 (s, 1H), 8.12 (d, J = 16.2 Hz, 1H), 7.87 (d, J = 8.3 Hz, 2H), 7.64 (d, J = 8.3 Hz, 2H), 7.48 (d, J = 15.7 Hz, 1H), 7.41 (d, J = 7.3 Hz, 2H), 7.36-7.21 (m, 1H), 7.00 (d, J = 8.8 Hz, 2H), 6.15-6.10 (m, 1H), 5.24 (s, 2H), 4.42-4.38 (m, 1H), 4.22-4.18 (m, 1H), 3.98-3.92 (m, 1H), 3.90-3.78 (m, 1H), 2.92 (t, J = 7.9 Hz, 2H), 2.66-2.56 (m, 4H); MS (ES) m/e 491.5 (M + H) ⁺. |
| 35 | 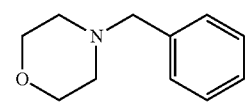 | 10.64 (s, 1H), 8.37 (s, 1H), 8.11 (d, J = 16.1 Hz, 1H), 7.78 (d, J = 8.8 Hz, 2H), 7.51-7.37 (m, 6H), 7.18 (d, J = 8.8 Hz, 2H), 6.26-6.22 (m, 1H), 5.21 (s, 2H), 4.43-4.41 (m, 1H), 4.25-4.21 (m, 1H), 3.94-3.91 (m, 1H), 3.81-3.78 (m, 1H), 2.94-2.89 (m, 2H), 2.59-2.54 (m, 4H); MS (ES) m/e 491.2 (M + H) ⁺. |
| 36 | 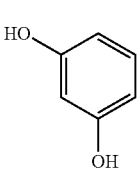 | 10.65 (s, 1H), 8.37 (s, 1H), 8.10 (d, J = 16.1 Hz, 1H), 7.49 (d, J = 15.7 Hz, 1H), 7.38 (s, 1H), 7.33 (s, 1H), 7.30 (d, J = 7.4 Hz, 1H), 4.26 (s, 1H), 7.21 (d, J = 6.4 Hz, 1H), 6.22-6.18 (m, 1H), 4.42-4.38 (m, 1H), 4.28-4.22 (m, 1H), 3.96-3.92 (m, 1H), 3.82-3.78 (m, 1H), 3.60-3.54 (m, 4H), 3.48-3.44 (m, 2H), 2.92 (t, J = 7.1 Hz, 2H), 2.64-2.58 (m, 4H), 2.38-2.30 (m, 4H); MS (ES) m/e 459.1 (M + H) ⁺. |
| 37 | HO—⬡—OH * | 10.64 (s, 1H), 9.21 (s, 2H), 8.36 (s, 1H), 8.10 (d, J = 17.2 Hz, 1H), 7.48 (d, J = 15.2 Hz, 1H), 7.35-7.31 (m, 1H), 6.28 (s, 2H), 6.14 (s, 1H), 6.08-6.04 (m, 1H), 4.40-4.36 (m, 1H), 4.21-4.17 (m, 1H), 3.92-3.88 (m, 1H), 3.80-3.76 (m, 1H), 2.94-2.920 (m, 2H), 2.56-2.52 (m, 4H); MS (ES) m/e 392.3 (M + H) ⁺. |

TABLE-I-continued

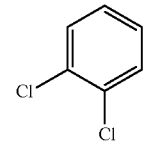

| Comp. No | R₄ | ¹H NMR (400 MHz, DMSO-d₆); δ (ppm) and MS(ES) m/e |
|---|---|---|
| 38 | 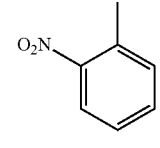 | 10.65 (s, 1H), 8.37 (s, 1H), 8.11 (d, J = 15.1 Hz, 1H), 7.71 (s, 1H), 7.61 (d, J = 8.3 Hz, 1H), 7.51-7.42 (m, 2H), 7.38-7.22 (m, 1H), 6.36 (s, 1H), 4.44-4.40 (m, 1H), 4.28-4.20 (m, 1H), 3.86-3.82 (m, 1H), 3.82-3.74 (m, 1H), 2.92 (t, J = 7.8 Hz, 2H), 2.58-2.54 (m, 4H); MS (ES) m/e 428.3(M + H)⁺. |
| 39 | 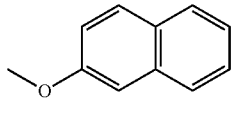 | 10.64 (s, 1H), 8.37 (d, J = 1.4 Hz, 1H), 8.11 (d, J = 8.4 Hz, 1H), 7.80 (dd, J = 7.8, 1.5 Hz, 1H), 7.51 (d, J = 15.1 Hz, 1H), 7.45 (d, J = 7.3 Hz, 1H), 7.41 (d, J = 7.9 Hz, 1H), 7.36-7.22 (m, 1H), 5.79-5.75 (m, 1H), 4.42-4.40 (m, 1H), 4.22-4.20 (m, 1H), 3.99-3.94 (m, 1H), 3.84-3.80 (m, 1H), 2.93-2.89 (m, 2H), 2.60-2.54 (m, 2H), 2.41-2.36 (m, 2H), 2.34 (m, 3H); MS (ES) m/e 419.1 (M + H)⁺. |
| 42 |  | 10.65 (s, 1H), 8.38 (s, 1H), 8.12 (d, J = 16.6 Hz, 1H), 7.88-7.78 (m, 3H), 7.76-7.64 (m, 1H), 7.50 (d, J = 15.2 Hz, 1H), 7.42-7.24 (m, 1H), 7.30 (d, J = 1.9 Hz, 1H), 7.15 (dd, J = 8.8, 2.4 Hz, 1H), 6.38-6.6.35 (m, 1H), 4.46-4.42 (m, 1H), 4.27-4.25 (m, 1H), 3.98-3.3.94 (m, 1H), 3.87 (s, 3H), 3.86-3.82 (m, 1H), 2.96-2.86 (m, 2H), 2.58-2.2.52 (m, 4H); MS (ES) m/e 440.4 (M + H)⁺. |
| 43 |  | 10.64 (s, 1H), 8.36 (s, 1H), 8.10 (d, J = 18.6 Hz, 1H), 7.48 (d, J = 15.7 Hz, 1H), 7.43-7.41 (m, 1H), 7.36-7.23 (m, 1H), 7.21-7.12 (m, 1H), 7.03 (dd, J = 4.9, 3.4 Hz, 1H), 6.18-6.10 (m, 1H), 4.42-4.36 (m, 1H), 4.26-4.16 (m, 1H), 3.94-3.86 (m, 1H), 3.82-3.74 (m, 1H), 2.92 (t, J = 7.3 Hz, 2H), 2.62-2.54 (m, 4H); MS (ES) m/e 366.3 (M + H)⁺. |
| 44 | 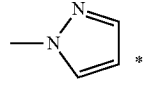 | 10.65 (s, 1H), 8.37 (s, 1H), 8.13-8.08 (m, 1H), 7.82 (d, J = 2.9 Hz, 1H), 7.67 (d, J = 2.5 Hz, 1H), 7.50 (d, J = 15.6 Hz, 1H), 7.40-7.21 (m, 1H), 6.65-6.62 (m, 1H), 4.46-4.42 (m, 1H), 4.26-4.22 (m, 1H), 3.98-3.90 (m, 1H), 3.90-3.81 (m, 1H), 2.92 (t, J = 7.4 Hz, 2H), 2.71-2.61 (m, 2H), 2.56-2.50 (m, 2H); MS (ES) m/e 367.1 (M + H)⁺. |
| 46 | 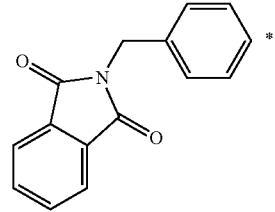 | 10.64 (s, 1H), 8.36 (s, 1H), 8.09 (d, J = 14.6 Hz, 1H), 7.77 (s, 1H), 7.58 (s, 1H), 7.47 (d, J = 15.7 Hz, 1H), 7.34-7.20 (m, 1H), 5.98-5.94 (m, 1H), 4.33-4.31 (m, 1H), 4.16-4.12 (m, 1H), 3.87-3.84 (m, 1H), 3.80 (s, 3H), 3.76-3.74 (m, 1H), 2.91 (t, J = 7.3 Hz, 2H), 2.56-2.52 (m, 4H); MS (ES) m/e 364.2(M + H)⁺. |
| 47 | 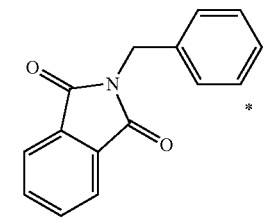 | 10.63 (s, 1H), 8.36 (s, 1H), 8.10 (d, J = 16.1 Hz, 1H), 7.95-7.85 (m, 4H), 7.50-7.41 (m, 4H), 7.30 (d, J = 8.3 Hz, 2H), 6.19-6.17 (m, 1H), 4.77 (s, 2H), 4.41-4.38 (m, 1H), 4.21-4.19 (m, 1H), 3.91-3.89 (m, 1H), 3.78-3.76 (m, 1H), 2.98-2.91 (m, 2H), 2.56-2.52 (m, 4H); MS (ES) m/e 519.4 (M + H)⁺ |
| 48 | 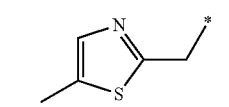 | 10.65 (s, 1H), 8.36 (s, 1H), 8.11 (d, J = 18.6 Hz, 1H), 7.91-7.85 (m, 4H), 7.48 (d, J = 15.2 Hz, 1H), 7.48-7.25 (m, 4H), 7.20 (d, J = 7.1 Hz, 1H), 6.19 (s, 1H), 4.78 (s, 2H), 4.44-4.38 (m, 1H), 4.28-4.20 (m, 1H), 3.96-3.88 (m, 1H), 3.86-3.78 (m, 1H), 2.92 (t, J = 7.4 Hz, 2H), 2.56-2.52 (m, 4H); MS (ES) m/e 519.2 (M + H)⁺ |
| 57 |  | 10.63 (s, 1H), 8.34 (d, J = 2.0 Hz, 1H), 8.09 (s, 1H), 7.45 (d, J = 15.1 Hz, 1H), 7.35 (d, J = 1.0 Hz, 1H), 7.23-7.18 (m, 1H), 5.67-5.64 (m, 1H), 4.24-4.22 (m, 1H), 4.05-4.01 (m, 1H), 3.76-3.73 (m, 1H), 3.65-3.63 (m, 3H), 2.90 (t, J = 7.3 Hz, 2H), 2.55-2.51 (m, 2H), 2.39 (d, J = 1.0 Hz, 3H), 2.19-2.12 (m, 2H); MS (ES) m/e 393.2 (M − H). |

TABLE-I-continued

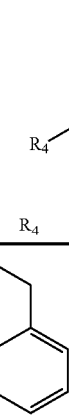

| Comp. No | R₄ | ¹H NMR (400 MHz, DMSO-d₆); δ (ppm) and MS(ES) m/e |
|---|---|---|
| 62 | 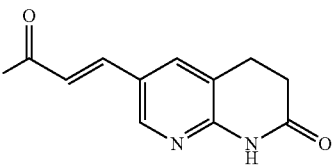 | 10.63 (s, 1H), 8.33 (s, 1H), 8.07 (s, 1H), 7.43 (d, J = 15.2 Hz, 1H), 7.32-7.16 (m, 6H), 5.48 (s, 1H), 4.24-4.18 (m, 1H), 4.08-4.02 (m, 1H), 3.78-3.70 (m, 1H), 3.70-3.62 (m, 1H), 3.33 (s, 2H), 2.90 (t, J = 7.4 Hz, 2H), 2.56-2.52 (m, 2H), 2.03-1.96 (m, 2H); MS (ES) m/e 374.2 (M + H)⁺. |
| 63 | 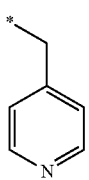 | 10.64 (s, 1H), 8.43 (s, 2H), 8.33 (s, 1H), 8.07 (s, 1H), 7.60 (d, J = 7.4 Hz, 1H), 7.43 (d, J = 15.7 Hz, 1H), 7.33 (dd, J = 7.3, 4.9 Hz, 1H), 7.26-7.15 (m, 1H), 5.52-5.50 (m, 1H), 4.21-4.19 (m, 1H), 4.03-4.01 (m, 1H), 3.74-3.72 (m, 1H), 3.62-3.60 (m, 1H), 2.90 (t, J = 7.4 Hz, 2H), 2.66-2.52 (m, 2H), 2.09-2.03 (m, 4H); MS (ES) m/e 375.3 (M + H)⁺ |
| 64 | 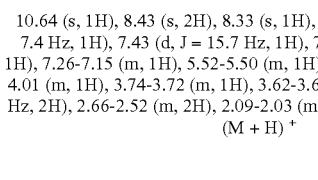 | 10.62 (s, 1H), 8.33 (s, 1H), 8.06 (s, 1H), 7.43 (d, J = 15.7 Hz, 1H), 7.25-7.21 (m, 3H), 7.14-7.09 (m, 2H), 5.47 (s, 1H), 4.23-4.17 (m, 1H), 4.12-4.02 (m, 1H), 3.78-3.70 (m, 1H), 3.65-3.60 (m, 1H), 3.31 (s, 2H), 2.91-2.87 (m, 2H), 2.54-2.52 (m, 2H), 2.02-1.96 (m, 2H); MS (ES) m/e 392.4 (M + H)⁺. |
| 65 | 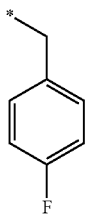 [SMILES: *Cc1ccc(F)cc1] | 10.63 (s, 1H), 8.33 (s, 1H), 8.07 (s, 1H), 7.44 (d, J = 15.2 Hz, 1H), 7.37-7.32 (m, 1H), 7.26-7.16 (m, 1H), 7.05-7.01 (m, 3H), 5.51 (s, 1H), 4.22-4.18 (m, 1H), 4.03-4.01 (m, 1H), 3.73-3.71 (m, 1H), 3.62-3.60 (m, 1H), 3.37-3.35 (m, 2H), 2.90 (t, J = 7.6 Hz, 2H), 2.55-2.52 (m, 2H), 2.12-1.98 (m, 2H); MS (ES) m/e 392.3 (M + H)⁺. |
| 66 | 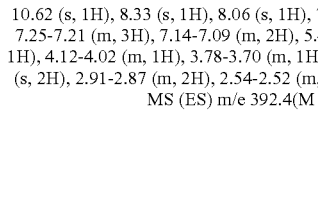 | 10.63 (s, 1H), 8.33 (d, J = 2.0 Hz, 1H), 8.07 (d, J = 8.3 Hz, 1H), 7.44 (d, J = 15.2 Hz, 1H), 7.31-7.23 (m, 3H), 7.18-7.13 (m, 2H), 5.40 (s, 1H), 4.22-4.18 (m, 1H), 4.04-3.98 (m, 1H), 3.78-3.70 (m, 1H), 3.68-3.60 (m, 1H), 3.35 (s, 2H), 2.90 (t, J = 7.9 Hz, 2H), 2.54-2.52 (m, 2H), 2.18-1.987 (m, 2H); MS (ES) m/e 392.3 (M + H)⁺. |
| 67 | 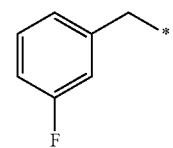 | 10.63 (s, 1H), 8.33 (s, 1H), 8.07 (s, 1H), 7.43 (d, J = 15.2 Hz, 1H), 7.34 (d, J = 7.9 Hz, 1H), 7.27 (d, J = 7.8 Hz, 1H), 7.26 (s, 1H), 7.21 (d, J = 8.8 Hz, 1H), 7.16 (d, J = 7.4 Hz, 1H), 5.51 (s, 1H), 4.21 and 4.02 (rotamer and s, 2H); 3.72 and 3.61 (rotamer and s, 2H); 3.34 (s, 2H), 2.90 (t, J = 7.8 Hz, 2H), 2.55-2.51 (m, 2H), 2.03 and 1.96 (rotamer and s, 2H); MS (ES) m/e 406.4 (M − H). |
| 68 | 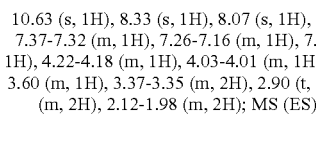 | 10.63 (s, 1H), 8.33 (s, 1H), 8.06 (s, 1H), 7.43 (d, J = 15.7 Hz, 1H), 7.37-7.32 (m, 2H), 7.26-7.20 (m, 3H), 5.49 (s, 1H), 4.24-4.16 (m, 1H), 4.04-3.96 (m, 1H), 3.76-3.68 (m, 1H), 3.64-3.56 (m, 1H), 3.32 (s, 2H), 2.90 (t, J = 7.6 Hz, 2H), 2.55-2.51 (m, 2H), 2.08-1.88 (m, 2H). |
| 69 | 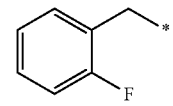 | 10.63 (s, 1H), 8.33 (s, 1H), 8.06 (s, 1H), 7.66 (d, J = 7.8 Hz, 2H), 7.47-7.41 (m, 3H), 7.27-7.19 (m, 1H), 5.53 (s, 1H), 4.24-4.16 (m, 1H), 4.04-3.96 (m, 1H), 3.78-3.72 (m, 1H), 3.66-3.58 (m, 1H), 3.43 (s, 2H), 2.90 (t, J = 7.6 Hz, 2H), 2.55-2.51 (m, 2H), 2.08-1.92 (m, 2H). |
| 70 | 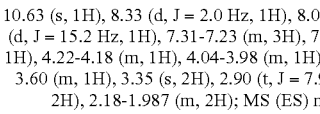 | 10.62 (s, 1H), 8.33 (s, 1H), 8.06 (s, 1H), 7.43 (d, J = 15.2 Hz, 1H), 7.24-7.15 (m, 1H), 7.11-7.05 (m, 4H), 5.47 (s, 1H), 4.21-4.19 (m, 1H), 4.05-4.01 (m, 1H), 3.79-3.73 (m, 1H), 3.61-3.57 (m, 1H), 3.26 (s, 2H), 2.91-2.88 (m, 2H), 2.54-2.52 (m, 2H), 2.26 (s, 3H), 2.01-1.94 (m, 2H); MS (ES) m/e 388.2 (M + H)⁺ |

TABLE-I-continued

| Comp. No | R₄ | ¹H NMR (400 MHz, DMSO-d₆); δ (ppm) and MS(ES) m/e |
|---|---|---|
| 71 | 3-methylbenzyl | 10.63 (s, 1H), 8.33 (s, 1H), 8.07 (s, 1H), 7.43 (d, J = 15.2 Hz, 1H), 7.18 (d, J = 7.4 Hz, 2H), 7.02-6.96 (m, 3H), 5.48 (s, 1H), 4.21-4.19 (m, 1H), 4.02-4.00 (m, 1H), 3.73-3.71 (m, 1H), 3.61-3.60 (m, 1H), 3.28 (s, 2H), 2.90 (t, J = 7.3 Hz, 2H), 2.54-2.52 (m, 2H), 2.27 (s, 3H), 2.03-2.01 (m, 2H); MS (ES) m/e 388.1 (M + H)⁺. |
| 72 | 2-methylbenzyl | 10.63 (s, 1H), 8.34 (d, J = 2.0 Hz, 1H), 8.06 (d, J = 11.3 Hz, 1H), 7.44 (d, J = 15.6 Hz, 1H), 7.27-7.09 (m, 5H), 5.26 (s, 1H), 4.22-4.18 (m, 1H), 4.08-3.98 (m, 1H), 3.80-3.70 (m, 1H), 3.70-3.62 (m, 1H), 3.32 (s, 2H), 2.90 (t, J = 7.4 Hz, 2H), 2.55-2.52 (m, 2H), 2.23 (s, 3H), 2.14-2.01 (m, 2H); MS (ES) m/e 388.3(M + H)⁺. |
| 73 | 4-cyanobenzyl | 10.63 (s, 1H), 8.33 (s, 1H), 8.07 (s, 1H), 7.77 (d, J = 8.3 Hz, 2H), 7.45-7.40 (m, 3H), 7.25-7.17 (m, 1H), 5.52 (s, 1H), 4.26-4.21 (m, 1H), 4.08-4.02 (m, 1H), 3.78-3.70 (m, 1H), 3.62-3.60 (m, 1H), 3.43 (s, 2H), 2.90 (t, J = 7.4 Hz, 2H), 2.55-2.52 (m, 2H), 2.08-1.94 (m, 2H); MS (ES) m/e 399.3 (M + H)⁺. |
| 74 | 3-cyanobenzyl | 10.63 (s, 1H), 8.34 (s, 1H), 8.06 (s, 1H), 7.70-7.67 (m, 2H), 7.56-7.52 (m, 2H), 7.43 (d, J = 15.7 Hz, 1H), 7.26-7.16 (m, 1H), 5.52-5.50 (m, 1H), 4.22-4.20 (m, 1H), 4.03-4.01 (m, 1H), 3.74-3.70 (m, 1H), 3.62-3.60 (m, 1H), 3.40 (s, 2H), 2.90 (t, J = 7.4 Hz, 2H), 2.56-2.52 (m, 2H), 2.05-1.95 (m, 2H); MS (ES) m/e 399.4 (M + H)⁺. |
| 75 | 2-cyanobenzyl | 10.63 (s, 1H), 8.34 (s, 1H), 8.08 (s, 1H), 7.81 (d, J = 7.8 Hz, 1H), 7.67 (dt, J = 7.9, 7.3 Hz, 1H), 7.47-7.44 (m, 2H), 7.42 (s, 1H), 7.27-7.15 (m, 1H), 5.42 (s, 1H), 4.20 and 4.04 (rotamer and s, 2H), 3.75 and 3.63 (rotamer and s, 2H), 3.54 (s, 2H), 2.90 (t, J = 7.8 Hz, 2H), 2.58-2.52 (m, 2H), 2.10 and 2.02 (rotamer and s, 2H); MS (ES) m/e 399.2(M + H)⁺. |
| 76 | 4-trifluoromethoxybenzyl | 10.63 (s, 1H), 8.33 (s, 1H), 8.06 (s, 1H), 7.43 (d, J = 15.2 Hz, 1H), 7.33-7.15 (m, 5H), 5.50 (bs, 1H), 4.21 (bs, 1H), 4.02 (bs, 1H), 3.73 (bs, 1H), 3.61 (bs, 1H), 3.36 (s, 2H), 2.90 (t, J = 7.6 Hz, 2H), 2.53 (d, J = 7.8 Hz, 2H), 2.03-1.96 (m, 2H); MS (ES) m/e 458.3 (M + H)⁺. |
| 77 | 3-trifluoromethoxybenzyl | 10.63 (s, 1H), 8.34 (s, 1H), 8.07 (s, 1H), 7.45-7.43 (m, 2H), 7.26-7.12 (m, 4H), 5.53-5.51 (m, 1H), 4.22-4.20 (m, 1H), 4.04-4.02 (m, 1H), 3.74-3.70 (m, 1H), 3.62-3.60 (m, 1H), 3.40 (s, 2H), 2.91-2.89 (m, 2H), 2.58-2.54 (m, 2H), 2.03-1.97 (m, 2H); MS (ES) m/e 458.3(M + H)⁺. |
| 78 | 2-trifluoromethoxybenzyl | 10.63 (s, 1H), 8.33 (d, J = 1.5 Hz, 1H), 8.07 (s, 1H), 7.44 (d, J = 15.1 Hz, 1H), 7.40-7.34 (m, 4H), 7.33-7.14 (m, 1H), 5.43 (s, 1H), 4.19 and 4.01 (rotamer and s, 2H), 3.74 and 3.62 (rotamer and s, 2H), 3.39 (s, 2H), 2.90 (t, J = 7.8 Hz, 2H), 2.56-2.52 (m, 2H), 2.05 and 1.97 (rotamer and s, 2H); MS (ES) m/e 458.3 (M + H)⁺. |
| 79 | 2-nitrobenzyl | 10.63 (s, 1H), 8.33 (s, 1H), 8.07 (d, J = 10.3 Hz, 1H), 7.74 (d, J = 7.8 Hz, 1H), 7.68 (t, J = 7.9 Hz, 1H), 7.53-7.46 (m, 2H), 7.42 (s, 1H), 7.27-7.17 (m, 1H), 5.27 (s, 1H), 4.16-3.96 (rotamer and s, 2H), 3.73 and 3.62 (rotamer and s, 2H), 3.62 (s, 2H), 2.90 (t, J = 7.4 Hz, 2H), 2.55-2.52 (m, 2H), 2.07 and 2.00 (rotamer and s, 2H). |
| 80 | 3-nitrobenzyl | 10.63 (s, 1H), 8.33 (s, 1H), 8.09 (d, J = 9.3 Hz, 1H), 8.07 (s, 1H), 7.70-7.64 (m, 2H), 7.62-7.57 (m, 1H), 7.44 (d, J = 15.7 Hz, 1H), 7.18 (d, J = 15.7 Hz, 1H), 5.60-5.52 (m, 1H), 4.25-4.21 (m, 1H), 4.05-4.01 (m, 1H), 3.78-3.72 (m, 1H), 3.64-3.60 (m, 1H), 3.32 (s, 2H), 2.92-2.88 (m, 2H), 2.56-2.52 (m, 2H), 2.06-1.98 (m, 2H); MS (ES) m/e 419.0 (M + H)⁺. |

TABLE-I-continued

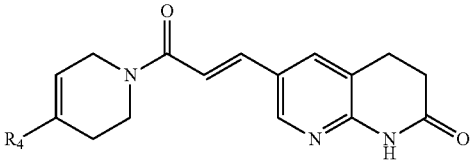

| Comp. No | R₄ | ¹H NMR (400 MHz, DMSO-d₆); δ (ppm) and MS(ES) m/e |
|---|---|---|
| 82 | 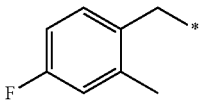 [SMILES: *Cc1ccc(F)cc1C] | 10.62 (s, 1H), 8.33 (s, 1H), 8.07 (d, J = 10.3 Hz, 1H), 7.44 (d, J = 15.2 Hz, 1H), 7.27-7.14 (m, 2H), 7.11-7.09 (m, 1H), 6.97 (d, J = 8.3 Hz, 1H), 6.88 (t, J = 7.3 Hz, 1H), 5.35 (s, 1H), 4.22-4.18 (m, 1H), 4.04-3.98 (m, 1H), 3.77 (s, 3H), 3.77-3.70 (m, 1H), 3.70-3.60 (m, 1H), 3.28 (s, 2H), 2.90 (t, J = 7.8 Hz, 2H), 2.55-2.52 (m, 2H), 2.16-2.02 (m, 2H); MS (ES) m/e 404.3 (M + H) ⁺. |
| 83 | 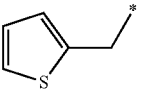 [SMILES: *Cc1cccs1] | 10.63 (s, 1H), 8.33 (d, J = 1.5 Hz, 1H), 8.06 (d, J = 11.8 Hz, 1H), 7.44 (d, J = 15.1 Hz, 1H), 7.15-7.11 (m, 2H), 7.02-6.92 (m, 2H), 5.24 (s, 1H), 4.18-4.12 (m, 1H), 4.00-3.92 (m, 1H), 3.76-3.72 (m, 1H), 3.65-3.61 (m, 1H), 3.29 (s, 2H), 2.92-2.88 (m, 2H), 2.54-2.52 (m, 2H), 2.22 (s, 3H), 2.06-1.98 (m, 2H); MS (ES) m/e 406.3 (M + H) ⁺. |
| 84 | 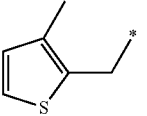 [SMILES: *Cc1sccc1C] | 10.63 (s, 1H), 8.34 (s, 1H), 8.07 (s, 1H), 7.45 (d, J = 15.1 Hz, 1H), 7.35-7.33 (m, 1H), 7.18 (d, J = 15.0 Hz, 1H), 6.95 (dd, J = 4.8, 3.4 Hz, 1H), 6.87 (d, J = 2.9 Hz, 1H), 5.60-5.54 (m, 1H), 4.23-4.19 (m, 1H), 4.04-3.98 (m, 1H), 3.78-3.72 (m, , 1H), 3.66-3.62 (m, 1H), 3.54 (s, 2H), 2.95-2.91 (m, 2H), 2.57-2.52 (m, 2H), 2.18-2.01 (m, 2H); MS (ES) m/e 380.2 (M + H) ⁺. |
| 86 | 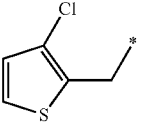 [SMILES: *Cc1sccc1Cl] | 10.63 (s, 1H), 8.33 (d, J = 1.9 Hz, 1H), 8.08 (s, 1H), 7.44 (d, J = 15.6 Hz, 1H), 7.30-7.18 (m, 2H), 6.84 (d, J = 4.9 Hz, 1H), 5.46 (s, 1H), 4.19 and 4.04 (rotamer and s, 2H), 3.74 and 3.62 (rotamer and s, 2H), 3.43 (s, 2H), 2.9 (t, J = 7.3 Hz, 2H), 2.55-2.51 (m, 2H), 2.11 (s, 3H), 2.10 and 2.02 (rotamer and s, 2H); MS (ES) m/e 393.9 (M + H) ⁺. |
| 87 | 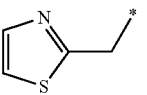 | 10.63 (s, 1H), 8.34 (s, 1H), 8.09 (s, 1H), 7.53 (d, J = 5.3 Hz, 1H), 7.45 (d, J = 15.2 Hz, 1H), 7.30-7.16 (m, 1H), 7.03 (d, J = 5.4 Hz, 1H), 5.52 (s, 1H), 4.22-4.18 (m, 1H), 4.08-4.00 (m, 1H), 3.80-3.62 (m, 2H), 3.52 (s, 2H), 2.91 (t, J = 7.3 Hz, 2H), 2.58-2.52 (m, 2H), 2.14-2.02 (m, 2H); MS (ES) m/e 412.1 (M − H). |
| 97 | 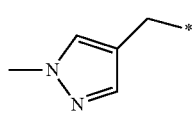 [SMILES: *Cc1cnn(C)c1] | 10.64 (s, 1H), 8.34 (d, J = 1.5 Hz, 1H), 8.08 (s, 1H), 7.71 (d, J = 3.4 Hz, 1H), 7.61 (d, J = 3.0 Hz, 1H), 7.45 (d, J = 15.6 Hz, 1H), 7.28-7.17 (m, 1H), 5,67-5.65 (m, 1H), 4.24-4.22 (m, 1H), 4.05-4.02 (m, 1H), 3.75 (s, 2H), 3.74-3.72 (m, 1H), 3.64-3.62 (m, 1H), 2.99 (t, J = 7.5 Hz, 2H), 2.55-2.51 (m, 2H), 2.19-2.07 (m, 2H); MS (ES) m/e 381.3 (M + H) ⁺. |
| 98 | 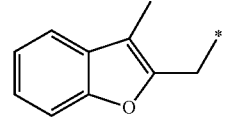 [SMILES: *Cc1oc2ccccc2c1C] | 10.63 (s, 1H), 8.34 (d, J = 1.5 Hz, 1H), 8.07 (d, J = 8.8 Hz, 1H), 7.46 (s, 1H), 7.42 (s, 1H), 7.27-7.14 (m, 2H), 5.45-5.43 (m, 1H), 4.18-4.16 (m, 1H), 4.01-3.98 (m, 1H), 3.77(s, 3H), 3.74-3.72 (m, 1H), 3.62-3.60 (m, 1H), 3.12 (s, 2H), 2.91 (t, J = 7.3 Hz, 2H), 2.55-2.53 (m, 2H), 2.08-2.00 (m, 2H); MS (ES) m/e 378.5 (M + H) ⁺. |
| 105 | 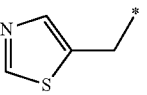 | 10.63 (bs, 1H), 8.33 (s, 1H), 8.07 (s, 1H), 7.52-7.50 (m, 1H), 7.46-7.44 (m, 1H), 7.41 (s, 1H), 7.26-7.19 (m, 3H), 5.54 (s, 1H), 4.21-4.02 (m, 2H), 3.74-3.63 (m, 2H), 3.52 (s, 2H), 2.89 (t, J = 7.8 Hz, 2H), 2.67-2.52 (m, 2H), 2.18 (s, 3H), 2.12-2.04 (m, 2H). |
| 145 |  | 10.63 (s, 1H), 8.96 (s, 1H), 8.34 (s, 1H), 8.08 (s, 1H), 7.69 (s, 1H), 7.44 (d, J = 15.7 Hz, 1H), 7.30-7.12 (m, 1H), 5.58 (s, 1H), 4.28-4.16 (m, 1H), 4.10-4.02 (m, 1H), 3.80-3.70 (m, 1H), 3.68-3.56 (m, 3H), 2.91 (t, J = 7.5 Hz, 2H), 2.54-2.51 (m, 2H), 2.14-1.96 (m, 2H); MS (ES) m/e 381.4 (M + H) ⁺. |

Note:
*Bonding position of R₄.

Preparation of Compound-19

Synthesis of (Z)—N'-hydroxy-4-(1-(E)-3-(7-oxo-5,6,7,8-tetrahydro-1,8-naphthyridin-3-yl)acryloyl)-1,2,3,6-tetrahydropyridin-4-yl)benzimidamide

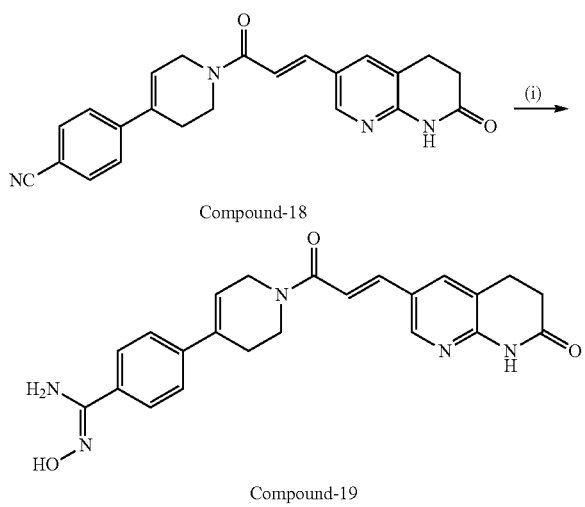

Compound-18

Compound-19

(i) NH$_2$OH·HCl, Aq. Na$_2$CO$_3$, EtOH, 80° C.-90° C., 6-8 h

Step-(i)

To a stirred solution of Compound-18 (50 mg, 0.13 mmol) in ethanol (2 ml) was added hydroxylamine hydrochloride (13 mg, 0.19 mmol), followed by Aq. Na$_2$CO$_3$ solution (41 mg, 0.39 mmol) and the reaction mixture was stirred at 90° C. for 6-8 h. The progress of the reaction was monitored by TLC. Then the reaction mixture was concentrated under vacuum, resultant residue diluted with water (50 ml). The resultant solid was filtered, washed with water and dried under vacuum to get the desired compound-19 as an off-white solid (30 mg, 55%). $^1$H NMR (400 MHz, DMSO-d$_6$) δ 11.00 (s, 1H), 10.65 (s, 1H), 8.37 (s, 1H), 8.12 (d, J=17.1 Hz, 1H), 7.66 (d, J=8.8 Hz, 1H), 7.57-7.42 (m, 3H), 7.37-7.24 (m, 1H), 6.28 (s, 1H), 5.80 (bs, 1H), 4.43-4.40 (m, 1H), 4.28-4.20 (m, 1H), 3.98-3.88 (m, 1H), 3.88-3.78 (m, 1H), 2.92 (t, J=7.1 Hz, 2H), 2.61-2.54 (m, 4H), —NH$_2$ protons were unrevealed by NMR instrument; MS (ES) m/e 418.2 (M+H)$^+$.

Preparation of Compound-21

Synthesis of (E)-6-(3-(4-(4-aminophenyl)-5,6-dihydro pyridin-1(2H)-yl)-3-oxoprop-1-en-1-yl)-3,4-dihydro-1,8-naphthyridin-2(1H)-one

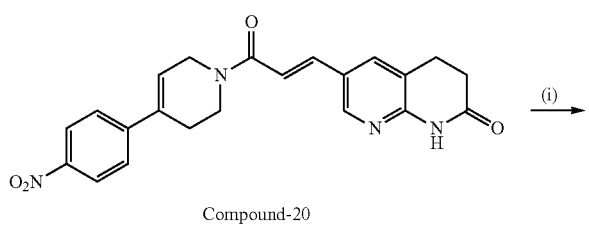

Compound-20

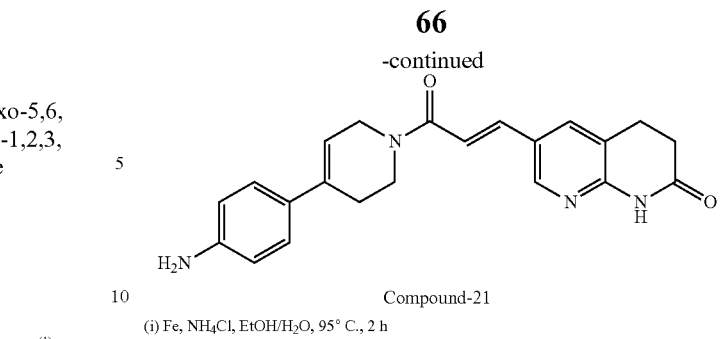

Compound-21

(i) Fe, NH$_4$Cl, EtOH/H$_2$O, 95° C., 2 h

To a stirred suspension of Compound-20 (300 mg, 0.74 mol) in a mixture of ethanol (8 ml) and H$_2$O (2 ml), NH$_4$Cl (393 mg, 7.42 mmol) and iron powder (124 mg, 2.22 mmol) were added. The resulting suspension was stirred at 95° C. for 2 h. The progress of the reaction was monitored by TLC. After completion of the reaction; the reaction mixture was filtered to remove the iron residues, washed with ethanol and concentrated. The resultant solid was diluted with water, filtered and dried under vacuum to get the desired compound-21 as a brown solid (100 mg, 36%).

Compounds-24 and 40 were prepared by the following methodology adopted similar to described above for the Compound-21.

Preparation of Compound-22

Synthesis of (E)-N-(4-(1-(3-(7-oxo-5,6,7,8-tetrahydro-1,8-naphthyridin-3-yl)acryloyl)-1,2,3,6-tetrahydropyridin-4-yl)phenyl)acetamide

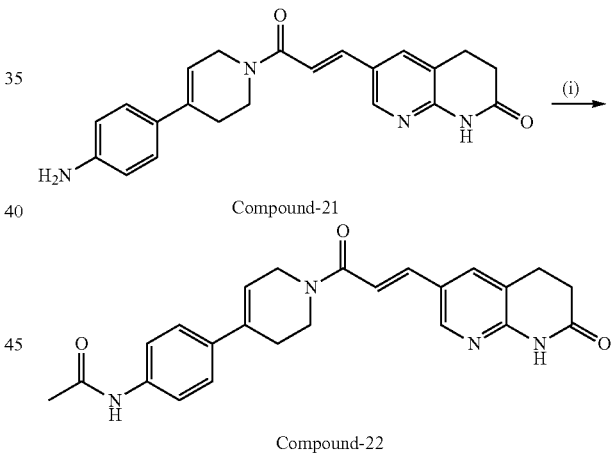

Compound-21

Compound-22

(i) Acetic anhydride, Triethylamine, CH$_2$Cl$_2$, 20-35° C., 16 h

To a stirred solution of Compound-21 (100 mg, 0.26 mmol) in CH$_2$Cl$_2$ (10 ml) were added triethyl amine (0.055 ml, 0.40 mmol) and acetic anhydride (0.037 ml, 0.40 mmol). at 0° C. and the reaction mixture was slowly warmed to 20-35° C. and continued the stirring at same temperature for 16 h. The progress of the reaction was monitored by TLC. After completion, the reaction mixture was concentrated. The resultant solid was diluted with water, filtered and dried under vacuum to get the desired compound-22 as an off-white solid (30 mg, 27%).

Compounds 25 and 41 were prepared by the following methodology adopted similar to described above for the Compound 22.

The compounds prepared by following the process according to compounds 21 and 22 and their physico-chemical characteristics are summarized here in below in the Table-II.

TABLE-II

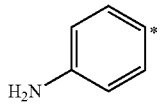

| Comp No | R₄ | ¹H NMR (400 MHz, DMSO-d₆); δ (ppm) and MS (ES) m/e |
|---|---|---|
| 21 | 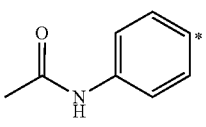 | 10.65 (s, 1H), 8.36 (s, 1H), 8.11 (d, J = 15.2 Hz, 1H), 7.48 (d, J = 15.6 Hz, 1H), 7.35-7.34 (m, 1H), 7.20 (d, J = 8.3 Hz, 2H), 6.64 (d, J = 8.3 Hz, 2H), 6.20-5.95 (m, 2H), 5.99 (s, 1H), 4.41-4.36 (m, 1H), 4.21-4.18 (m, 1H), 3.95-3.86 (m, 1H), 3.79-3.70 (m, 1H), 2.94-2.90 (m, 2H), 2.56-2.53 (m, 2H), 2.45-2.39 (m, 2H); MS (ES) m/e 375.3 (M + H)⁺. |
| 22 | 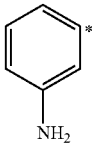 | 10.64 (s, 1H), 9.95 (s, 1H), 8.36 (s, 1H), 8.11 (d, J = 16.6 Hz, 1H), 7.56 (d, J = 8.3 Hz, 2H), 7.48 (d, J = 15.6 Hz, 1H), 7.40-7.38 (m, 2H), 7.38-7.30 (m, 1H), 6.20-6.12 (m, 1H), 4.42-4.38 (m, 1H), 4.28-4.17 (m, 1H), 3.91-3.82 (m, 1H), 3.82-3.78 (m, 1H), 2.92 (t, J = 7.3 Hz, 2H), 2.61-2.54 (m, 2H), 2.44-2.41 (m, 2H), 2.04 (s, 3H); MS (ES) m/e 417.2 (M + H)⁺. |
| 24 | 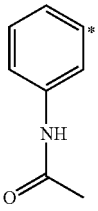 | 10.64 (s, 1H), 8.36 (s, 1H), 8.10 (d, J = 16.2 Hz, 1H), 7.48 (d, J = 15.1 Hz, 1H), 7.45-7.32 (m, 1H), 6.97 (d, J = 7.9 Hz, 1H), 6.63 (s, 1H), 6.60 (d, J = 6.4 Hz, 1H), 6.47 (d, J = 7.9 Hz, 1H), 6.07-6.02 (m, 1H), 5.04 (s, 2H), 4.42-4.38 (m, 1H), 4.24-4.18 (m, 1H), 3.93-3.88 (m, 1H), 3.80-3.76 (m, 1H), 2.92 (t, J = 7.3 Hz, 2H), 2.58-2.52 (m, 2H), 2.48-2.42 (m, 2H); MS (ES) m/e 375.0 (M + H)⁺. |
| 25 | 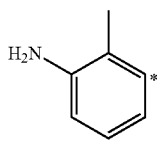 | 10.64 (s, 1H), 9.93 (s, 1H), 8.36 (s, 1H), 8.10 (d, J = 16.6 Hz, 1H), 7.69 (s, 1H), 7.49-7.47 (m, 2H), 7.28-7.24 (m, 2H), 7.13 (d, J = 7.4 Hz, 1H), 6.15 (s, 1H), 4.41 and 3.79 (rotamer and s, 2H), 3.92 and 3.79 (rotamer and s, 2H), 2.92 (t, J = 7.4 Hz, 2H), 2.67-2.45 (m, 4H), 2.03 (s, 3H); MS (ES) m/e 417.5 (M + H)⁺. |
| 40 | 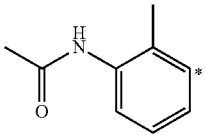 | 10.64 (s, 1H), 8.27 (s, 1H), 8.11 (d, J = 6.1 Hz, 1H), 7.50 (d, J = 15.2 Hz, 1H), 7.35-7.23 (m, 1H), 6.89 (t, J = 7.5 Hz, 1H), 6.64 (d, J = 7.8 Hz, 1H), 6.43 (d, J = 5.9 Hz, 1H), 5.73 (bs, 2H), 5.52-5.49 (m, 1H), 4.41-4.35 (m, 1H), 4.21-4.16 (m, 1H), 3.92-3.85 (m, 1H), 3.81-3.75 (m, 1H), 2.91 (t, J = 7.3 Hz, 2H), 2.56-2.54 (m, 2H), 2.37-2.23 (m, 2H), 1.99 (s, 3H); MS (ES) m/e 389.1 (M + H)⁺. |
| 41 | | 10.64 (s, 1H), 9.31 (s, 1H), 8.37 (s, 1H), 8.12 (s, 1H), 7.50 (d, J = 15.2 Hz, 1H), 7.34 (d, J = 15.2 Hz, 1H), 7.28-7.26 (m, 1H), 7.14-7.10 (m, 1H), 6.93 (d, J = 6.8 Hz, 1H), 5.61-5.57 (m, 1H), 4.42-4.38 (m, 1H), 4.21-4.18 (m, 1H), 3.92-3.87 (m, 1H), 3.81-3.74 (m, 1H), 2.92 (t, J = 7.3 Hz, 2H), 2.56-2.54 (m, 2H), 2.48-2.29 (m, 2H), 2.11 (s, 3H), 2.05 (s, 3H); MS (ES) m/e 431.2 (M + H)⁺. |

Note:

* Bonding position of R₄.

Preparation of Compound-27

Synthesis of (E)-4-(1-(3-(7-oxo-5,6,7,8-tetrahydro-1, 8-naphthyridin-3-yl)acryloyl)-1,2,3,6-tetrahydropyridin-4-yl)benzoic acid

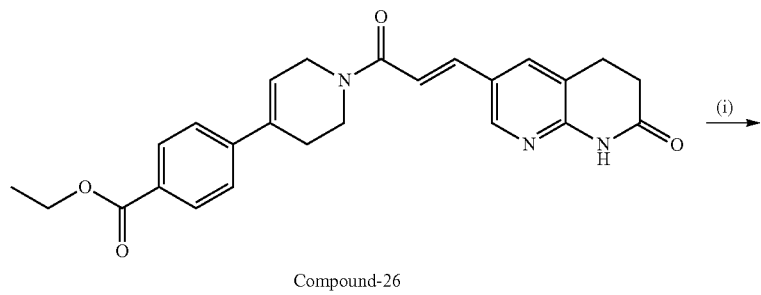

Compound-26

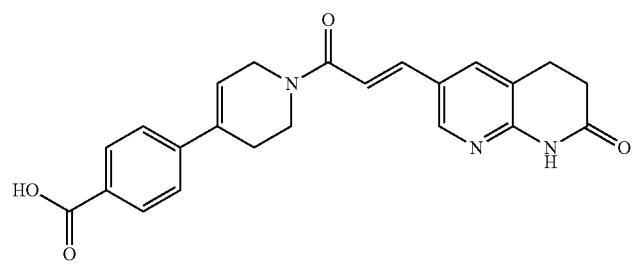

Compound-27

(i) LiOH·H$_2$O, THF/H$_2$O, 20-35° C., 16 h

Step-(i)

To a stirred solution of Compound-26 (80 mg, 0.18 mmol) in a mixture of THF/H$_2$O (2 ml/2 ml) was added lithium hydroxide (80 mg, 0.2 mmol). The reaction mixture was stirred at 20-35° C. for 16 h. The progress of the reaction was monitored by TLC. After 16 h, the reaction mixture was concentrated under vacuum to get residue which was neutralized with 1N HCl solution at 0° C. The resultant solid was filtered, washed with water and dried under vacuum to get the desired compound-27 as a white solid (8 mg, 12%). $^1$H NMR (400 MHz, DMSO-d$_6$) δ 10.65 (s, 1H), 8.37 (s, 1H), 8.11 (d, J=17.1 Hz, 1H), 7.92 (d, J=7.8 Hz, 2H), 7.59 (d, J=5.9 Hz, 2H), 7.49 (d, J=15.1 Hz, 1H), 7.38-7.26 (m, 1H), 6.39-6.37 (m, 1H), 4.45-4.43 (m, 1H), 4.27-4.24 (m, 1H), 3.94-3.92 (m, 1H), 3.81-3.79 (m, 1H), 2.92 (t, J=7.6 Hz, 2H), 2.56-2.54 (m, 4H); Acid proton was unrevealed by ¹H NMR instrument. MS (ES) m/e 402.0 (M−H)⁺.

Preparation of Compound-28

Synthesis of (E)-4-(1-(3-(7-oxo-5,6,7,8-tetrahydro-1,8-naphthyridin-3-yl)acryloyl)-1,2,3,6-tetrahydropyridin-4-yl)benzamide

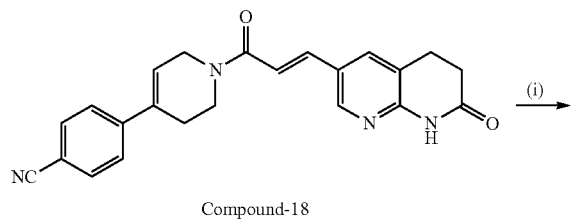

Compound-18

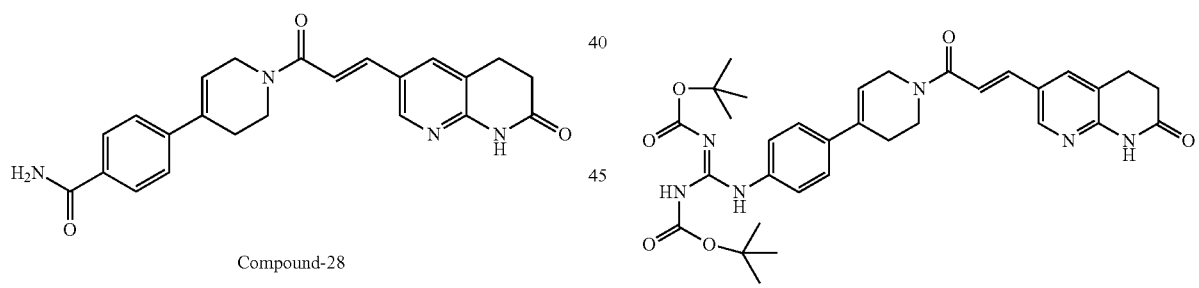

Compound-28

(i) CF₃COOH, H₂SO₄, 20-35° C., 16 h

Step-(i)

To a stirred solution of Compound-18 (30 mg, 0.078 mmol) in trifluoroacetic acid (2 ml) was added conc. H₂SO₄ (0.5 ml) and the reaction mixture was stirred at 20-35° C. for 16 h. The progress of the reaction was monitored by TLC. After 16 h, the reaction mixture was diluted with ice cold water (10 ml) and stirred for 20 minutes, filtered, washed with water and dried under vacuum to get the desired compound-28 as a pale yellow solid (10 mg, 32%). ¹H NMR (400 MHz, DMSO-d₆) δ 10.65 (s, 1H), 8.37 (s, 1H), 8.12 (d, J=17.2 Hz, 1H), 7.95 (s, 1H), 7.86 (d, J=8.2 Hz, 2H), 7.55-7.53 (m, 2H), 7.49 (d, J=15.6 Hz, 1H), 7.37-7.21 (m, 2H), 6.38-6.32 (m, 1H), 4.44-4.40 (m, 1H), 4.32-4.25 (m, 1H), 3.94-3.88 (m, 1H), 3.88-3.80 (m, 1H), 2.93 (t, J=7.8 Hz, 2H), 2.61-2.54 (m, 4H); MS (ES) m/e 403.0 (M+H)⁺.

Preparation of Compound-29

Synthesis of (E)-di-tert-butoxycarbonyl-1-(4-(1-(3-(7-oxo-5,6,7,8-tetrahydro-1,8-naphthyridin-3-yl)acryloyl)-1,2,3,6-tetrahydropyridin-4-yl)phenyl)guanidine

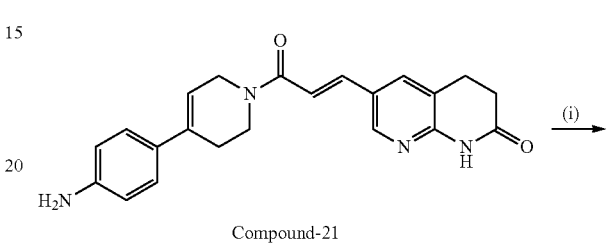

Compound-21

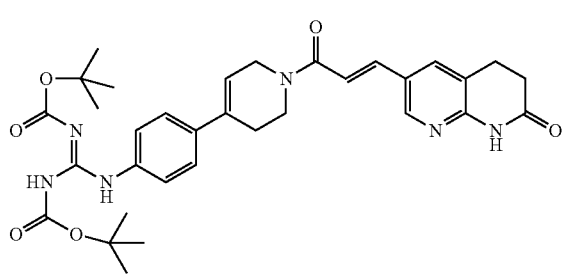

Compound-29

(i) N,N′-Bis-tert-butoxycarbonylthiourea, HOBt, EDC•HCl, DMF, 20-35° C., 16 h

Step-(i)

To a stirred solution of Compound-21 (30 mg, 0.80 mmol) in DMF (0.5 ml) was added N,N′-Bis-tert-butoxycarbonylthiourea (24 mg, 0.88 mmol), HOBt (16 mg, 0.12 mmol), EDC.HCl (30 mg, 0.16 mmol) at 20-35° C. and the reaction mixture was stirred at 20-35° C. for 16 h. The progress of the reaction was monitored by TLC. After 16 h of stirring, the reaction mixture was diluted with cold water (20 ml) and the resultant solid was filtered, washed with water, dried under vacuum for 2 h to get the desired compound-29 as an off-white solid (8 mg, 16%).

Preparation of Compound-30
Synthesis of (E)-1-(4-(1-(3-(7-oxo-5,6,7,8-tetrahydro-1,8-naphthyridin-3-yl)acryloyl)-1,2,3,6-tetrahydropyridin-4-yl)phenyl)guanidine trifluoro acetic acid
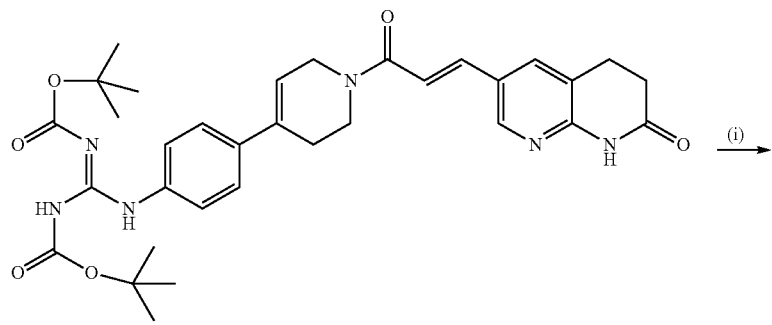
Compound-29
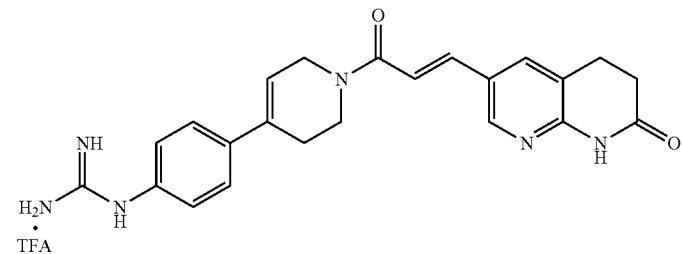
Compound-30
(i) TFA, CH$_2$Cl$_2$, 20-35° C., 16 h

Step-(i)

A solution of Compound-29 (20 mg, 0.032 mmol) in $CH_2Cl_2$ (2 ml) was treated with trifluoro acetic acid (15 mg, 0.13 mmol)) at 0° C. and the reaction mixture was stirred at 20-35° C. for 16 h. The progress of the reaction was monitored by TLC. After 16 h of stirring, the clear solution was concentrated in vacuum and the resultant solid was washed with diethyl ether to get the desired compound-30 as a yellow solid (30 mg, 23%).

Compound 31 was prepared by the following methodology adopted similar to described above for the Compound 30.

The compounds prepared by following the process according to Compounds 29 and 30 and their physico-chemical characteristics are summarized here in below in the Table-III.

TABLE-III

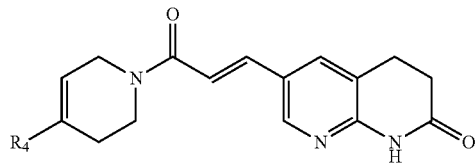

| Comp No | $R_4$ | $^1$H NMR (400 MHz, DMSO-$d_6$); δ (ppm) and MS (ES) m/e |
|---|---|---|
| 29 | (Bis-Boc guanidinyl phenyl group) | ($CDCl_3$): 11.64 (bs, 1H), 10.36 (s, 1H), 8.33 (s, 1H), 8.16 (s, 1H), 7.65 (d, J = 15.7 Hz, 1H), 7.61-7.59 (m, 3), 7.34 (d, J = 8.3 Hz, 2H), 6.98-6.82 (m, 1H), 6.10-5.98 (m, 1H), 4.35 (bs, 2H), 3.98-3.90 (m, 1H), 3.90-3.82 (m, 1H), 3.01 (t, J = 7.8 Hz, 2H), 2.71 (t, J = 7.3 Hz, 2H), 2.63 (bs, 2H), 1.54 (s, 9H), 1.51 (s, 9H); MS (ES) m/e 617.5 (M + H)$^+$. |
| 30 | $CF_3COOH$ · guanidinyl phenyl group | δ10.65 (s, 1H), 9.65 (s, 1H), 8.37 (s, 1H), 8.12 (d, J = 15.2 Hz, 1H), 7.53 (d, J = 8.3 Hz, 2H), 7.49 (d, J = 15.6 Hz, 1H), 7.44-7.25 (m, 5H), 7.23 (d, J = 8.8 Hz, 2H), 6.24 (s, 1H), 4.48-4.30 (m, 1H), 4.30-4.22 (m, 1H), 3.93-3.75 (m, 2H), 2.92 (t, J = 7.3 Hz, 2H), 2.62-2.52 (m, 4H); MS (ES) m/e 417.3 (M + H)$^+$. |
| 31 | guanidinyl phenyl group | 10.63 (s, 1H), 9.78 (s, 1H), 8.36 (s, 1H), 8.10 (d, J = 15.2 Hz, 1H), 7.54-7.13 (m, 9H), 6.27 (s, 1H), 4.48-4.30 (m, 1H), 4.30-4.22 (m, 1H), 3.93-3.75 (m, 2H), 2.92 (t, J = 7.3 Hz, 2H), 2.62-2.52 (m, 4H); MS (ES) m/e 417.1 (M + H)$^+$. |

Note:
* Bonding position of $R_4$.

Preparation of Compound-33

Synthesis of (Z)—N'-hydroxy-2-(4-(1-((E)-3-(7-oxo-5,6,7,8-tetrahydro-1,8-naphthyridin-3-yl)acryloyl)-1,2,3,6-tetrahydropyridin-4-yl)phenoxy)acetimidamide

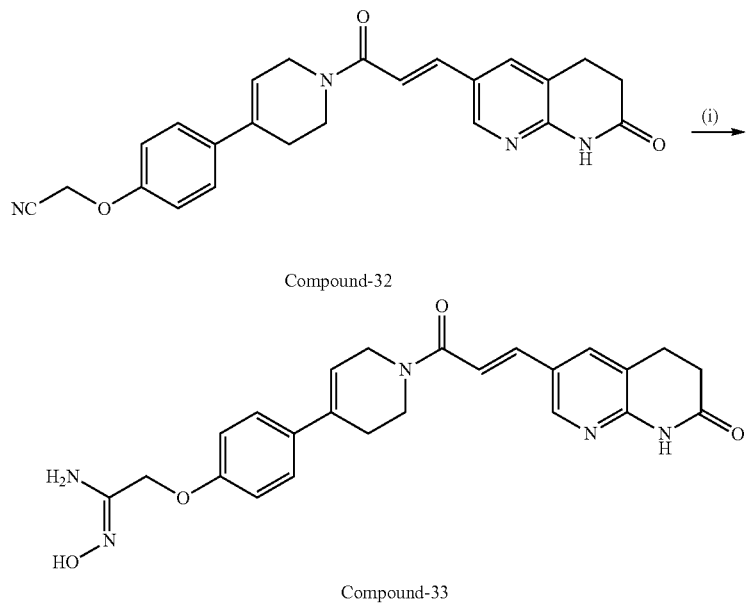

(i) $NH_2OH \cdot HCl$, Aq. $Na_2CO_3$, EtOH/$H_2O$, 80° C., 8 h

Step-(i)

The process of this step was adopted from step-(i) of compound-19. The desired compound-33 obtained as a yellow solid (20 mg, 40%). $^1$H NMR (400 MHz, DMSO-$d_6$) δ 10.65 (s, 1H), 9.27 (s, 1H), 8.36 (s, 1H), 8.10 (d, J=17.8 Hz, 1H), 7.48 (d, J=15.1 Hz, 1H), 7.38 (d, J=7.8 Hz, 2H), 7.21-7.19 (m, 1H), 6.99-6.92 (m, 2H), 6.1-1 (s, 1H), 5.59 (s, 2H), 4.48-4.45 (m, 1H), 4.42 (s, 2H), 4.21-4.19 (m, 1H), 3.91-3.89 (m, 1H), 3.78-3.76 (m, 1H), 2.92 (t, J=7.6 Hz, 2H), 2.56-2.52 (m, 4H); MS (ES) m/e 448.4 (M+H)$^+$.

Preparation of Compound-45

Synthesis of (E)-6-(3-(4-(1-methyl-1H-imidazol-2-yl)-5,6-dihydropyridin-1(2H)-yl)-3-oxoprop-1-en-1-yl)-3,4-dihydro-1,8-naphthyridin-2(1H)-one

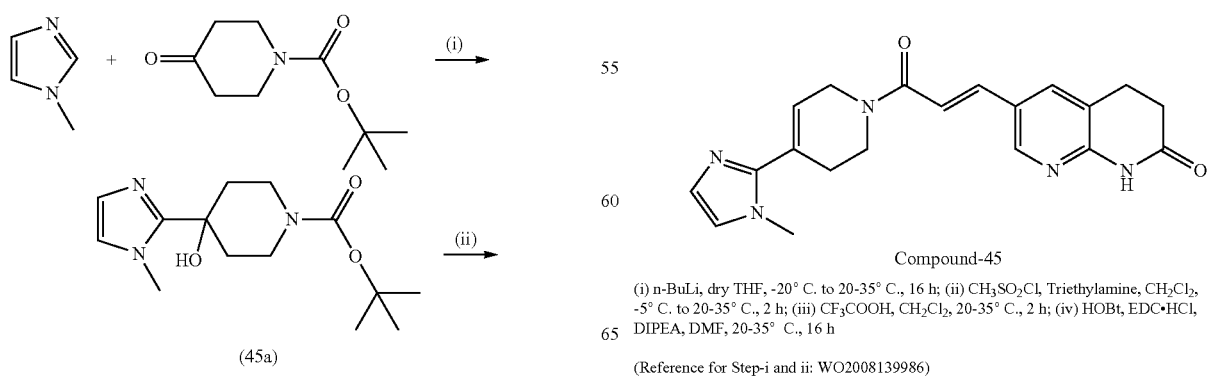

(i) n-BuLi, dry THF, -20° C. to 20-35° C., 16 h; (ii) $CH_3SO_2Cl$, Triethylamine, $CH_2Cl_2$, -5° C. to 20-35° C., 2 h; (iii) $CF_3COOH$, $CH_2Cl_2$, 20-35° C., 2 h; (iv) HOBt, EDC·HCl, DIPEA, DMF, 20-35° C., 16 h (Reference for Step-i and ii: WO2008139986)

Step-(iii)

Synthesis of 4-(1-methyl-1H-imidazol-2-yl)-1,2,3,6-tetrahydropyridine trifluoro acetic acid salt (45c)

The process of this step was adopted from step-(i) of compound-1 MS (ES) m/e 163.1 (M-CF$_3$COOH).

Step-(iv) Preparation of Compound-45

Synthesis of (E)-6-(3-(4-(1-methyl-1H-imidazol-2-yl)-5,6-dihydropyridin-1(2H)-yl)-3-oxoprop-1-en-1-yl)-3,4-dihydro-1,8-naphthyridin-2(1H)-one The process of this step was adopted from step-(ii) of compound-1. The desired compound-45 obtained as a pale yellow solid (15 mg, 9%). $^1$H NMR (400 MHz, DMSO-d$_6$) δ 10.64 (s, 1H), 8.37 (d, J=2.0 Hz, 1H), 8.10 (d, J=17.6 Hz, 1H), 7.50 (d, J=15.7 Hz, 1H), 7.35-7.31 (m, 1H), 7.13 (s, 1H), 6.87 (d, J=1.0 Hz, 1H), 6.14-6.10 (m, 1H), 4.46-4.42 (m, 1H), 4.27-4.23 (m, 1H), 3.88 (d, J=4.4 Hz, 1H), 3.78-3.74 (m, 1H), 3.70 (s, 3H), 2.92 (t, J=7.3 Hz, 2H), 2.56-2.52 (m, 4H); MS (ES) m/e 364.3 (M+H)$^+$.

Preparation of Compound-49

Synthesis of 6-(3-oxo-3-(4-phenyl-5,6-dihydropyridin-1(2H)-yl)propyl)-3,4-dihydro-1,8-naphthyridin-2(1H)-one

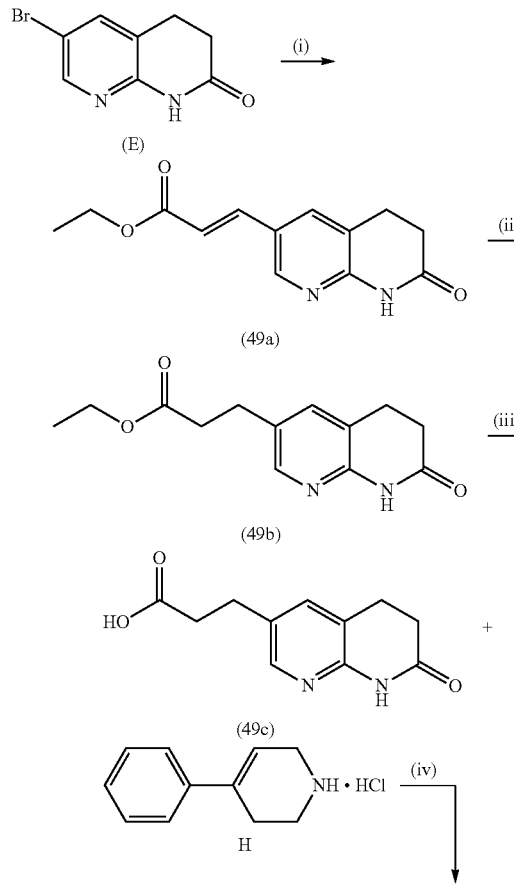

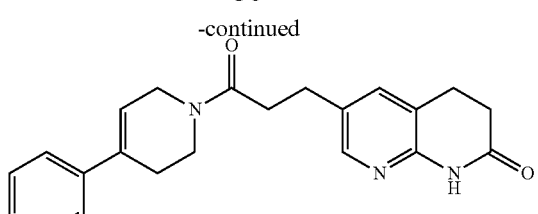

Compound-49

(i) Ethylacrylate, Pd(OAc)$_2$, P(O-tolyl)$_3$, DIPEA, Propionitrile: DMF, 100-110° C., 16 h; (ii) H$_2$, Pd/C, MeOH, 20-35° C., 16 h; (iii) LiOH•H$_2$O, THF/H$_2$O, 20-35° C., 16 h; (iv) HOBt, EDC•HCl, DIPEA, DMF, 20-35° C., 16 h

Step-(i)

Synthesis of (E)-ethyl 3-(7-oxo-5,6,7,8-tetrahydro-1,8-naphthyridin-3-yl)acrylate (49a)

A solution of E (from intermediate-1) (15 g, 66.07 mmol), ethyl acrylate (33.0 g, 33.0 mmol), Pd(OAc)$_2$ (1.48 g, 6.6 mmol), P(o-tolyl)$_3$ (4 g, 13.15 mmol), and DIPEA (22.9 ml, 131.78 mmol) in dimethyl formamide/propionitrile (60 ml/250 ml) was degassed with nitrogen for 15 minutes and then heated to 100-110° C. for 16 h. The progress of the reaction was monitored by TLC. After 16 h, the mixture was cooled to 20-35° C., filtered through celite and concentrated. The crude compound was purified by column chromatography using a mixture of 50% ethyl acetate/hexane as an eluent to get the desired compound as an off-white solid (7.7 g, 43.2%); $^1$H NMR (400 MHz, DMSO-d$_6$) δ 10.70 (s, 1H), 8.39 (d, J=2.0 Hz, 1H), 8.06 (s, 1H), 7.61 (d, J=16.1 Hz, 1H), 6.61 (d, J=16.1 Hz, 1H), 4.19-4.16 (m, 2H), 2.92-2.88 (m, 2H), 2.54-2.53 (m, 2H), 1.26 (t, J=7.1 Hz, 3H); MS (ES) m/e 247.0 (M+H)$^+$.

Step-(ii)

Synthesis of ethyl 3-(7-oxo-5,6,7,8-tetrahydro-1,8-naphthyridin-3-yl)propionate (49b)

To a stirred solution of 49a (7.7 g, 34.3 mmol) in methanol (150 ml) was added 10% Pd/C (3 g) under nitrogen. The reaction mixture was stirred in presence of H$_2$ gas at 20-35° C. for 16 h. The progress of the reaction was monitored by TLC. After the reaction was completed, the reaction mixture was filtered through celite and concentrated to get the desired compound as a white solid (7 g, 90.2%); $^1$H NMR (400 MHz, DMSO-d$_6$) δ 10.35 (s, 1H), 7.95 (s, 1H), 7.48 (s, 1H), 4.05 (q, J=7.1 Hz, 2H), 2.83 (t, J=7.6 Hz, 2H), 2.79-2.60 (m, 4H), 2.58-2.55 (m, 2H), 1.16 (m, 3H); MS (ES) m/e 249.1 (M+H)$^+$.

Step-(iii)

Synthesis of 3-(7-oxo-5,6,7,8-tetrahydro-1,8-naphthyridin-3-yl)propanoic acid (49c)

The process of this step was adopted from step-(i) of compound-27. The desired compound obtained as a pale yellow solid (90 mg, 44%). $^1$H NMR (400 MHz, DMSO-d$_6$) δ 12.15 (bs, 1H), 10.34 (s, 1H), 7.95 (d, J=1.5 Hz, 1H), 7.48 (s, 1H), 2.84 (t, J=7.6 Hz, 2H), 2.74 (d, J=7.6 Hz, 2H), 2.67-2.45 (m, 4H); MS (ES) m/e 221.0 (M+H)$^+$.

Step-(iv) Preparation of Compound-49

Synthesis of 6-(3-oxo-3-(4-phenyl-5,6-dihydro pyridin-1(2H)-yl)propyl)-3,4-dihydro-1,8-naphthyridin-2(1H)-one The process of this step was adopted from step-(ii) of compound-1. The desired compound-49 obtained as an off-white solid (30 mg, 21%). $^1$H NMR (400 MHz, DMSO-$d_6$) δ 10.31 (d, J=5.4 Hz, 1H), 7.98 (dd, J=4.9, 2.0 Hz, 1H), 7.50 (d, J=6.4 Hz, 1H), 7.42 (t, J=7.4 Hz, 2H), 7.35 (t, J=7.6 Hz, 2H), 7.28-7.7.24 (m, 1H), 6.18-6.12 (m, 1H), 4.15-4.10 (m, 2H), 3.65 (dt J=11.3, 5.4 Hz, 2H), 2.85-2.80 (m, 2H), 2.80-2.75 (m, 2H), 2.75-2.71 (m, 1H), 2.70-2.63 (m, 1H), 2.50-2.41 (m, 4H); MS (ES) m/e 362.2 (M+H)$^+$.

Preparation of Compound-50

Synthesis of 6-((2-oxo-2-(4-phenyl-5,6-dihydropyridin-1(2H)-yl)ethyl)thio)-3,4-dihydro-1,8-naphthyridin-2(1H)-one

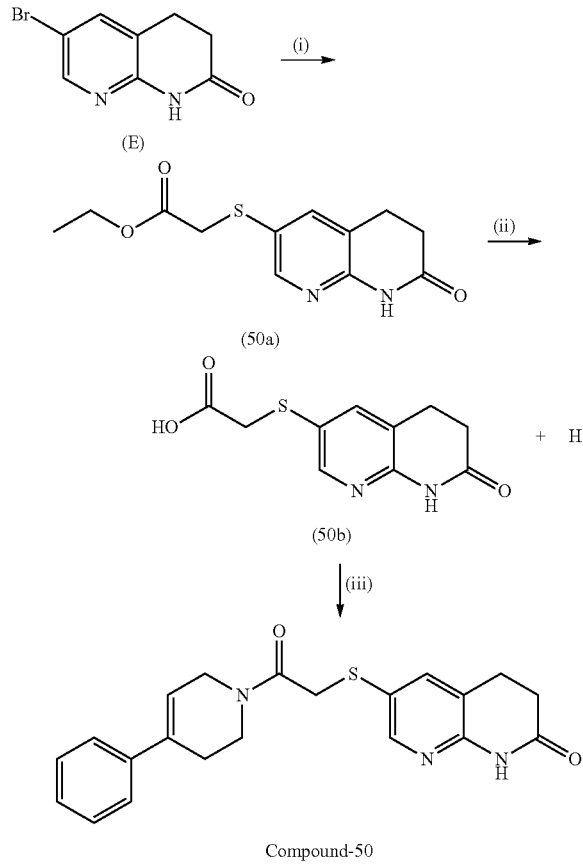

Compound-50

(i) ethyl 2-mercaptoacetate, Pd$_2$(dba), Xantphos, DIPEA, 1,4-dioxane, 80° C., 6 h;
(ii) LiOH•H$_2$O, THF/H$_2$O, 20-35° C., 16 h; (iii) HOBt, EDC•HCl, DIPEA, DMF, 20-35° C., 16 h.

Step-(i)

Synthesis of ethyl 2-((7-oxo-5,6,7,8-tetrahydro-1,8-naphthyridin-3-yl)thio)acetate (50a)

A solution of E (from intermediate-1) (2 g, 8.8 mmol), ethyl-2-mercaptoacetate (1.16 g, 9.6 mmol), Pd$_2$(dba)$_3$ (806 mg, 0.80 mmol), Xantphos (1 g, 1.75 mmol), and DIPEA (3.05 ml, 17.5 mmol) in 1,4-dioxane (30 ml) was degassed with nitrogen for 10 min and then stirred at 80° C. for 6 h. The progress of the reaction was monitored by TLC. After 6 h, the mixture was cooled to 20-35° C., filtered through celite and celite bed washed with ethyl acetate. The organic layer was washed with water (50 ml), brine (50 ml), dried over anhydrous Na$_2$SO$_4$ and evaporated. The crude compound was purified by column chromatography using a mixture of 15% ethyl acetate/dichloromethane as an eluent to get the desired compound as a yellow solid (1.12 g, 50%); NMR (400 MHz, DMSO-$d_6$) δ 8.70 (bs, 1H), 8.29 (d, J=2.4 Hz, 1H), 7.65 (d, J=1.0 Hz, 1H), 4.17 (q, J=7.3 Hz, 2H), 3.52 (s, 2H), 2.96 (t, J=7.8 Hz, 2H), 2.68 (t, J=7.8 Hz, 2H), 1.25 (t, J=7.3 Hz, 3H); MS (ES) m/e 267 (M–H)$^+$.

Step-(ii)

Synthesis of 2-((7-oxo-5,6,7,8-tetrahydro-1,8-naphthyridin-3-yl)thio)acetic acid (50b)

The process of this step was adopted from step-(i) of compound-27. The desired compound obtained as a yellow solid (630 mg, 63%). $^1$H NMR (400 MHz, DMSO-$d_6$) δ 12.64 (bs, 1H), 10.54 (s, 1H), 8.11 (d, J=2.0 Hz, 1H), 7.71 (d, J=1.4 Hz, 1H), 3.70 (s, 2H), 2.87 (t, J=7.5 Hz, 2H), 2.54-2.50 (m, 2H); MS (ES) m/e 237 (M–H)$^+$.

Step-(iii) Preparation of Compound-50

Synthesis of 6-((2-oxo-2-(4-phenyl-5,6-dihydropyridin-1(2H)-yl)ethyl)thio)-3,4-dihydro-1,8-naphthyridin-2(1H)-one The process of this step was adopted from step-(ii) of compound-1. The desired compound-50 obtained as a yellow solid (80 mg, 50%). $^1$H NMR (400 MHz, DMSO-$d_6$) δ 10.52 (d, J=4.9 Hz, 1H), 8.12 (dd, J=5.8, 1.9 Hz, 1H), 7.72 (d, J=9.8 Hz, 1H), 7.44 (t, J=6.6 Hz, 2H), 7.37-7.33 (m, 2H), 7.27 (d, J=6.9 Hz, 1H), 6.19-6.16 (m, 1H), 4.21-4.18 (m, 1H), 4.10-4.07 (m, 1H), 4.00-3.98 (m, 1H), 3.95-3.92 (m, 1H), 3.67 (q, J=5.9 Hz, 2H), 2.84 (q, J=7.6 Hz, 2H), 2.59-2.54 (m, 2H), 2.46-2.42 (m, 2H); MS (ES) m/e 380.1 (M+H)$^+$.

Preparation of Compound-51

Synthesis of (E)-tert-butyl 2-oxo-6-(3-oxo-3-(4-phenyl-5,6-dihydropyridin-1(2H)-yl)prop-1-en-1-yl)-2,4-dihydro-1H-spiro[[1,8]naphthyridine-3,4'-piperidine]-1'-carboxylate

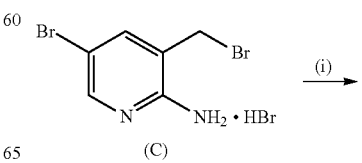

(C)

83

-continued

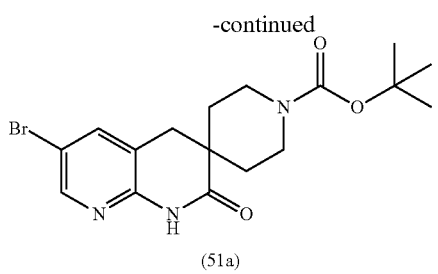

(51a)

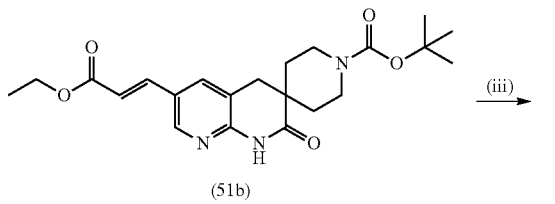

(51b)

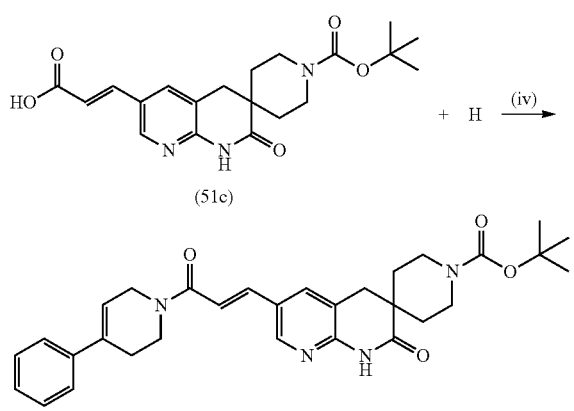

(51c)

Compound-51

(i) 1-tert-butyl 4-ethyl piperidine-1,4-dicarboxylate, LDA (1M in THF), dry THF, -78° C., 2 h then 20-35° C., 16 h; (ii) Ethylacrylate, Pd(OAc)₂, P(O-tolyl)₃, DIPEA, Propionitrile: DMF, 100-110° C., 36 h; (iii) LiOH·H₂O, THF/H₂O, 20-35° C., 16 h; (iv) EDC·HCl, HOBt, DIPEA, DMF, 20-35° C., 16 h; (Reference for Step-(i): WO2007067416A2)

Step-(ii)

Synthesis of (E)-tert-butyl 6-(3-ethoxy-3-oxoprop-1-en-1-yl)-2-oxo-2,4-dihydro-1H-spiro[[1,8]naphthyridine-3,4'-piperidine]-1'-carboxylate (51b)

The process of this step was adopted from step-(i) of compound-49. The desired compound obtained as a creamy white solid (200 mg, 43%); ¹H NMR (400 MHz, DMSO-d₆) δ 8.89 (bs, 1H), 8.34 (d, J=2.0 Hz, 1H), 7.67 (d, J=1.0 Hz, 1H), 7.62 (d, J=15.9 Hz, 1H), 6.40 (d, J=15.9 Hz, 1H), 4.27 (q, J=7.0 Hz, 2H), 3.68-3.61 (m, 2H), 3.52-3.45 (m, 2H), 2.89 (s, 2H), 1.99-1.1.94 (m, 2H), 1.49-1.40 (m, 2H), 1.46 (s, 9H), 1.34 (t, J=7.1 Hz, 3H); MS (ES) m/e 416.2 (M+H)⁺.

Step-(iii)

Synthesis of (E)-3-(1'-(tert-butoxycarbonyl)-2-oxo-2,4-dihydro-1H-spiro[[1,8]naphthyridine-3,4'-piperidin]-6-yl)acrylic acid (51c)

The process of this step was adopted from step-(i) of compound-27. The desired compound obtained as an off-white solid (160 mg, 86%). ¹H NMR (400 MHz, DMSO-d₆) δ 12.34 (bs, 1H), 10.78 (s, 1H), 8.38 (d, J=2.0 Hz, 1H), 8.02 (d, J=1.0 Hz, 1H), 7.55 (d, J=15.8 Hz, 1H), 6.47 (d, J=15.8 Hz, 1H), 3.57-3.52 (m, 2H), 3.28-3.20 (m, 2H), 2.95 (s, 2H), 1.78-1.68 (m, 2H), 1.39 (s, 9H), 1.36-1.33 (m, 2H); MS (ES) m/e 388.1 (M+H)⁺.

Step-(iv) Preparation of Compound-51

Synthesis of (E)-tert-butyl 2-oxo-6-(3-oxo-3-(4-phenyl-5,6-dihydropyridin-1(2H)-yl)prop-1-en-1-yl)-2,4-dihydro-1H-spiro[[1,8]naphthyridine-3,4'-piperidine]-1'-carboxylate The process of this step was adopted from step-(ii) of compound-1. The desired compound-51 obtained as an off-white solid (120 mg, 55%). ¹H NMR (400 MHz, DMSO-d₆) δ 10.74 (s, 1H), 8.38 (d, J=11.2 Hz, 1H), 8.16-8.08 (m, 1H), 7.51-7.45 (m, 3H), 7.36 (t, J=7.5 Hz, 2H), 7.30-7.27 (m, 2H), 6.24-6.16 (m, 1H), 4.46-4.40 (m, 1H), 4.28-4.20 (m, 1H), 3.96-3.88 (m, 1H), 3.86-3.78 (m, 1H), 3.60-3.52 (m, 2H), 2.96 (s, 2H), 2.64-2.56 (m, 2H), 1.78-1.64 (m, 3H), 1.39 (s, 9H), 1.38-1.34 (m, 3H); MS (ES) m/e 529.2 (M+H)⁺.

Preparation of Compound-52

Synthesis of (E)-6-(3-oxo-3-(4-phenyl-5,6-dihydropyridin-1(2H)-yl)prop-1-en-1-yl)-1H-spiro[[1,8]naphthyridine-3,4'-piperidin]-2(4H)-one trifluoro acetic acid

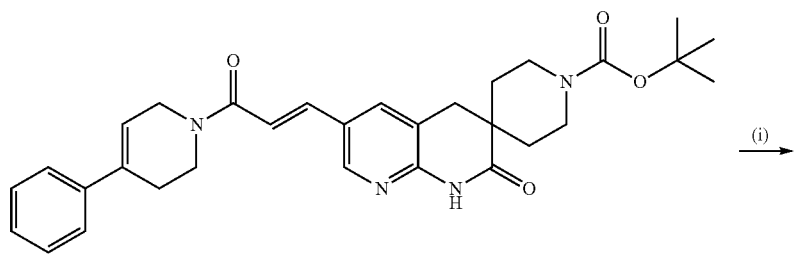

Compound-51

-continued

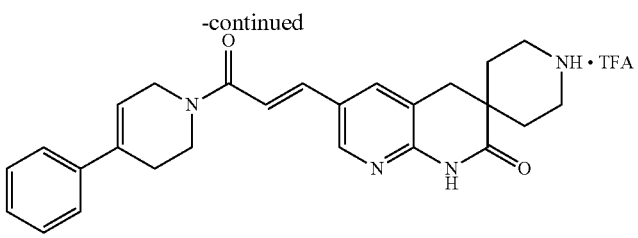

Compound-52

(i) TFA/CH$_2$Cl$_2$, 20-35° C., 2 h

Step-(i)

The process of this step was adopted from step-(i) of compound-1. The desired compound-52 obtained as a creamy white solid (80 mg, 87%). $^1$H NMR (400 MHz, DMSO-d$_6$) δ 10.89 (s, 1H), 8.58-8.48 (m, 2H), 8.45 (s, 1H), 8.12 (d, J=13.7 Hz, 1H), 7.54-7.45 (m, 3H), 7.39-7.21 (m, 4H), 6.30-6.20 (m, 1H), 4.50-4.38 (m, 1H), 4.30-4.20 (m, 1H), 3.98-3.88 (m, 1H), 3.86-3.76 (m, 1H), 3.30-3.06 (m, 4H), 2.99 (s, 2H), 2.66-2.50 (m, 2H), 2.08-1.90 (m, 2H), 1.66-1.50 (m, 2H); MS (ES) m/e 428.9 (M-CF$_3$COOH).

Preparation of Compound-53

Synthesis of (E)-3-(2-morpholinoethyl)-6-(3-oxo-3-(4-phenyl-5,6-dihydropyridin-1(2H)-yl)prop-1-en-1-yl)-3,4-dihydropyrido[2,3-d]pyrimidin-2(1H)-one

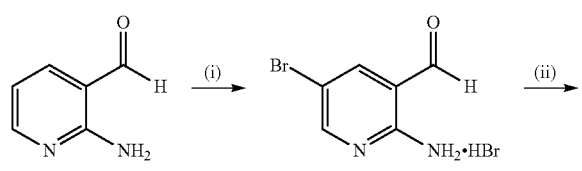

(53a)

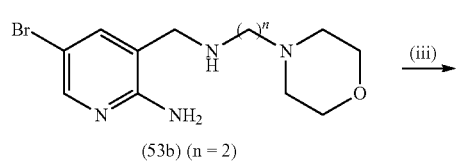

(53b) (n = 2)

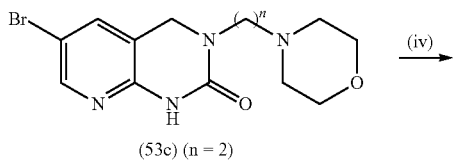

(53c) (n = 2)

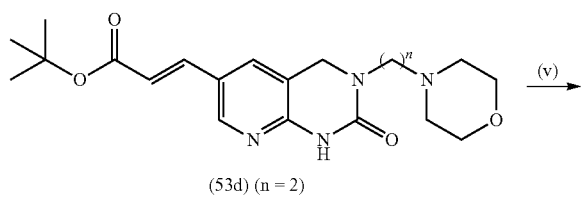

(53d) (n = 2)

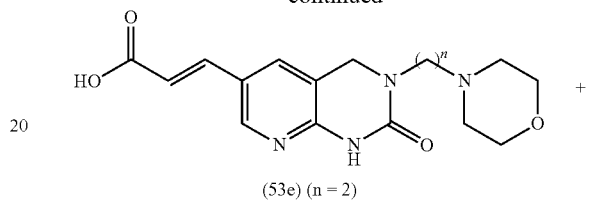

(53e) (n = 2)

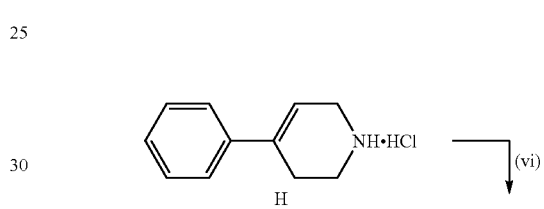

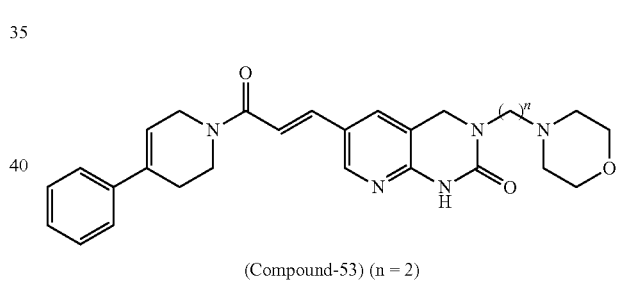

(Compound-53) (n = 2)

(i) Br$_2$/AcOH, 20-35° C., 3 h; (ii) Triethyl amine, MeOH, 4-(2-Aminoethyl)morpholine, 20-35° C., 16 h then NaBH$_4$, 20-35° C., 16 h; (iii) CDI, Dioxane, 80° C., 14 h; (iv) tert-butylacrylate, Pd(OAc)$_2$, P(O-tolyl)$_3$, DIPEA, Propionitrile:DMF, 100° C., 14 h; (v) CH$_2$Cl$_2$, TFA, 20-35° C., 2 h; (vi) EDC•HCl, HOBt, DIPEA, DMF, 20-35° C., 16 h
(Ref. for Step-(i-v): WO2004052890)

Step-(vi) Preparation of Compound-53

Synthesis of (E)-3-(2-morpholinoethyl)-6-(3-oxo-3-(4-phenyl-5,6-dihydropyridin-1(2H)-yl)prop-1-en-1-yl)-3,4-dihydropyrido[2,3-d]pyrimidin-2(1H)-one The process of this step was adopted from step-(ii) of compound-1. The desired compound-53 obtained as a brown solid (30 mg, 23%). $^1$H NMR (400 MHz, DMSO-d$_6$) δ 9.87 (s, 1H), 8.36 (s, 1H), 8.11 (d, J=16.1 Hz, 1H), 7.49-7.46 (m, 3H), 7.36 (t, J=7.6 Hz, 2H), 7.29-7.27 (m, 2H), 6.22-6.20 (m, 1H), 4.55 (s, 2H), 4.40-4.38 (m, 1H), 4.24-4.21 (m, 1H), 3.92-3.90 (m, 1H), 3.80-3.78 (m, 1H), 3.56 (t, J=4.2 Hz, 4H), 3.46 (t, J=6.1 Hz, 2H), 3.38-3.33 (m, 2H), 2.59-2.56 (m, 2H), 2.44-2.40 (m, 4H); MS (ES) m/e 474.2 (M+H)⁺.

Preparation of Compound-54

Synthesis of (E)-7-(3-oxo-3-(4-phenyl-5,6-dihydro-pyridin-1(2H)-yl)prop-1-en-1-yl)-4,5-dihydro-1H-pyrido[2,3-e][1,4]diazepin-2(3H)-one trifluoro acetic acid

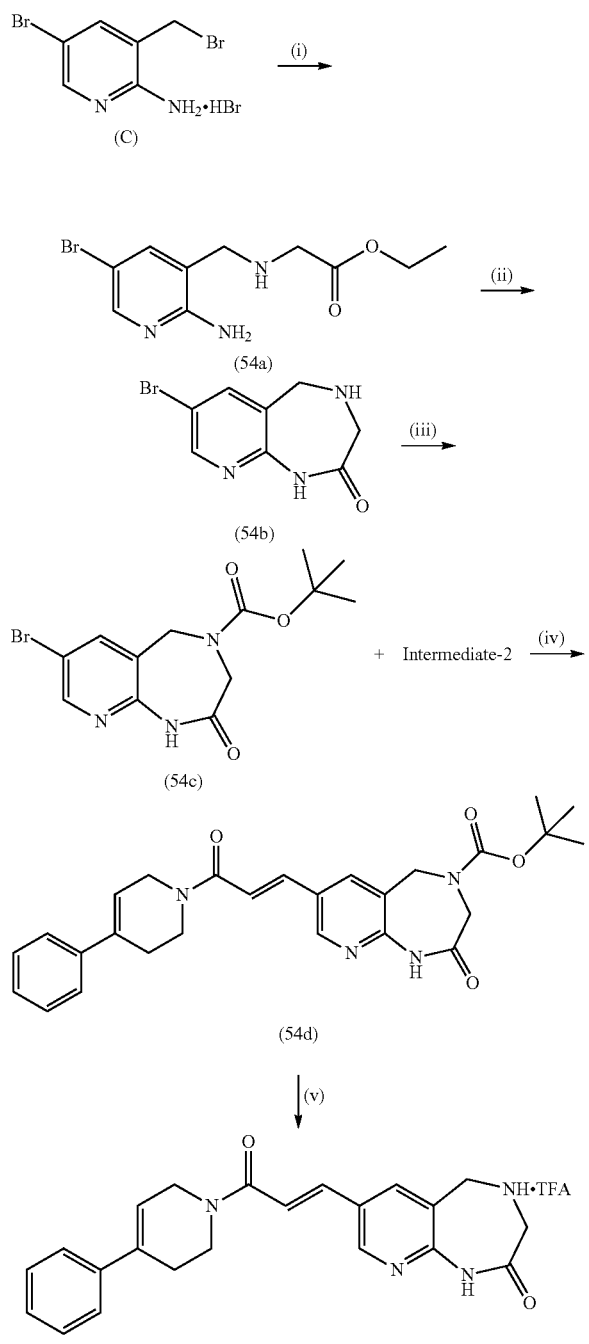

(i) glycine ethyl ester hydrochloride, triethylamine, DMF, 20-35° C., 5 h;
(ii) NaH, DMSO, 20-35° C., 5 h; (iii) (Boc)₂O; TEA; CH₂Cl₂, 20-35° C., 16 h;
(iv) Pd(OAc)₂, P(o-tolyl)₃, DIPEA, Propionitrile, DMF, 100° C., 16 h;
(v) TFA, CH₂Cl₂, 20-35° C., 2 h.
(Reference for Step-(i-ii): US20060142265A1)

Step-(iii)

Synthesis of tert-butyl 7-bromo-2-oxo-2,3-dihydro-1H-pyrido[2,3-e][1,4]diazepine-4(5H)-carboxylate (54c)

To a stirred solution of 54b (1.2 g, 4.97 mmol) in anhydrous DCM (30 ml) were added triethylamine (1.37 ml, 9.94 mmol) and (Boc)₂O (1.3 g, 5.96 mmol) at 0° C. The reaction mixture was stirred at 20-35° C. for 16 h. The progress of the reaction was monitored by TLC. After 16 h of stirring, the reaction mixture was diluted with water (50 ml) and extracted with ethyl acetate (2×50 ml). The combined organic layers were washed with brine (50 ml), followed by drying over anhydrous Na₂SO₄ and filtering. The filtrate was rotary evaporated to get the desired compound as a pale brown solid (1 g, 60%); ¹H NMR (400 MHz, DMSO-d₆) δ 10.0 (bs, 1H), 8.30 (d, J=2.5 Hz, 1H), 7.90 (s, 1H), 4.49 (s, 2H), 4.31 (s, 2H), 1.47 (s, 9H); MS (ES) m/e 340.0 (M+H)⁺.

Step-(iv)

Synthesis of (E)-tert-butyl 2-oxo-7-(3-oxo-3-(4-phenyl-5,6-dihydropyridin-1(2H)-yl)prop-1-en-1-yl)-2,3-dihydro-1H-pyrido[2,3-e][1,4]diazepine-4(5H)-carboxylate (54d)

DIPEA (0.1 ml, 0.58 mmol) was added to a stirred solution of 54c (100 mg, 0.29 mmol), Intermediate-2 (62 mg, 0.29 mmol), Pd-(OAc)₂ (7 mg, 0.029 mmol) and P(o-tol)₃ (17 mg, 0.058 mmol) in propionitrile/DMF (4 ml/1 ml) and the reaction mixture was purged with nitrogen for 10 minutes, then was stirred at 100° C. for 16 h. The progress of the reaction was monitored by TLC. After 16 h of stirring, the reaction mixture was diluted with water (20 ml) and extracted with ethyl acetate (2×20 ml). The combined organic layers were washed with brine (20 ml), followed by drying over anhydrous Na₂SO₄ and filtering. The filtrate was rotary evaporated to get residue which was purified by column chromatography using a mixture of 4% methanol/dichloromethane as an eluent to get the desired compound as a pale yellow solid (30 mg, 22%). ¹H NMR (400 MHz, DMSO-d₆) δ 10.40 (bs, 1H), 8.53-8.50 (m, 1H), 8.26-8.16 (m, 1H), 7.56-7.44 (m, 4H), 7.42-7.30 (m, 2H), 7.29-7.23 (m, 1H), 6.26-6.19 (m, 1H), 4.62-4.48 (m, 2H), 4.47-4.38 (m, 1H), 4.37-4.28 (m, 2H), 4.26-4.20 (m, 1H), 3.98-3.88 (m, 1H), 3.86-3.76 (m, 1H), 2.62-2.56 (m, 2H), 1.48 (s, 9H); MS (ES) m/e 475.3 (M+H)⁺.

Step-(v) Preparation of Compound-54

Synthesis of (E)-7-(3-oxo-3-(4-phenyl-5,6-dihydro-pyridin-1(2H)-yl)prop-1-en-1-yl)-4,5-dihydro-1H-pyrido[2,3-e][1,4]diazepin-2(3H)-one trifluoro acetic acid The process of this step was adopted from step-(i) of compound-1. The desired compound-54 obtained as a pale yellow solid (15 mg, 7%). ¹H NMR (400 MHz, DMSO-d₆) δ 11.08 (s, 1H), 9.64 (bs, 2H), 8.79 (s, 1H), 8.34-8.26 (m, 1H), 7.56 (d, J=15.6 Hz, 1H), 7.52-7.42 (m, 2H), 7.37 (t, J=7.6 Hz, 2H), 7.30-7.25 (m, 2H), 6.24-6.21 (m, 1H), 4.44-4.39 (m, 1H), 4.28 (s, 2H), 4.27-4.21 (m, 1H), 3.98-3.90 (m, 1H), 3.87 (s, 2H), 3.84-3.76 (m, 1H), 2.66-2.58 (m, 2H); MS (ES) m/e 375.0 (M-CF$_3$COOH)$^+$.

Preparation of Compound-55

Synthesis of (E)-4-methyl-7-(3-oxo-3-(4-phenyl-5,6-dihydropyridin-1(2H)-yl)prop-1-en-1-yl)-4,5-dihydro-1H-pyrido[2,3-e][1,4]diazepin-2(3H)-one

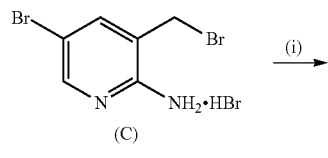

Compound-55

(i) sarcosine ethyl ester hydrochloride, triethylamine, DMF, 24° C., 4 h;
(ii) NaH, DMSO, 24° C., 4 h; (iii) Pd(OAc)$_2$, P(o-tolyl)$_3$, DIPEA,
Propionitrile, DMF, 100° C., 16 h;
(Reference for Step-(i-ii): PCT/US2006/0142265 A1)

Step-(iii) Preparation of Compound-55

Synthesis of (E)-4-methyl-7-(3-oxo-3-(4-phenyl-5,6-dihydropyridin-1(2H)-yl)prop-1-en-1-yl)-4,5-dihydro-1H-pyrido[2,3-e][1,4]diazepin-2(3H)-one The process of this step was adopted from step-(iv) of compound-54. The desired compound-55 obtained as a pale yellow solid (3 mg, 2%). $^1$H NMR (400 MHz, DMSO-d$_6$) δ 10.35 (s, 1H), 8.54 (s, 1H), 8.19 (d, J=14.7 Hz, 1H), 7.52 (d, J=15.2 Hz, 1H), 7.48-7.43 (m, 2H), 7.36 (t, J=7.5 Hz, 2H), 7.27 (t, J=7.1 Hz, 2H), 6.28-6.22 (m, 1H), 4.46-4.40 (m, 1H), 4.28-4.20 (m, 1H), 3.98-3.90 (m, 1H), 3.86-3.78 (m, 1H), 3.80 (s, 2H), 3.43 (s, 2H), 2.64-2.56 (m, 2H), 2.38 (s, 3H); MS (ES) m/e 387.3 (M–H)$^+$.

Preparation of Compound-56

Synthesis of (E)-4-(2-morpholinoethyl)-7-(3-oxo-3-(4-phenyl-5,6-dihydropyridin-1(2H)-yl)prop-1-en-1-yl)-4,5-dihydro-1H-pyrido[2,3-e][1,4]diazepin-2(3H)-one

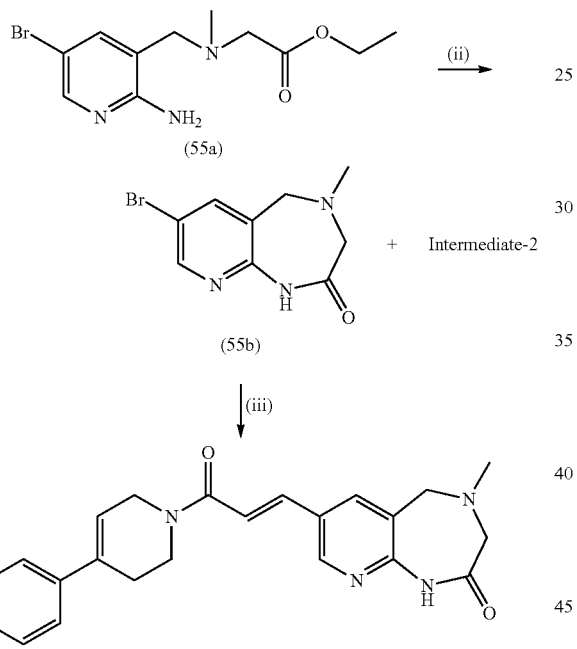

91

-continued

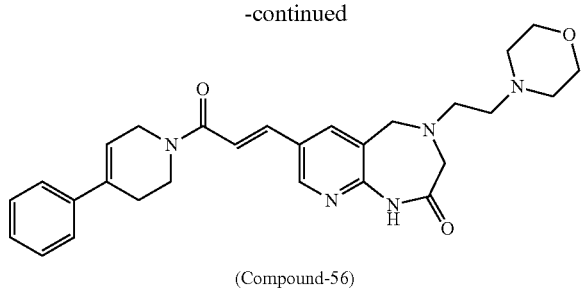

(Compound-56)

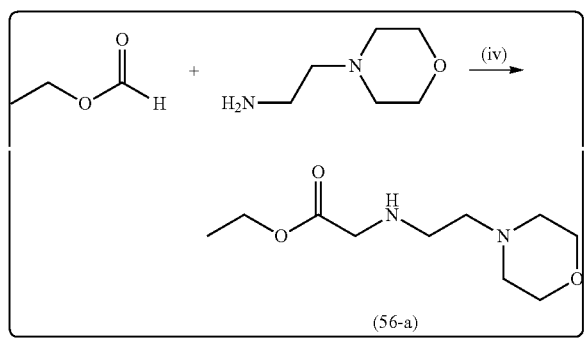

(56-a)

(i) (56a), triethylamine, DMF, 24° C., 4 h; (ii) NaH, DMSO, 24° C., 4 h;
(iii) Pd(OAc)₂, P(o-tolyl)₃, DIPEA, Propionitrile, DMF,
100° C., 16 h; (iv) Ethyl formate, 4-(2-aminoethyl)morpholine,
NaBH₃CN, AcOH, MeOH, 24° C., 4 h
(Refrerence for Step-(i-ii and iv): US20060142265A1)

92

Step-(iii) Preparation of Compound-56

Synthesis of (E)-4-(2-morpholinoethyl)-7-(3-oxo-3-(4-phenyl-5,6-dihydropyridin-1(2H)-yl)prop-1-en-1-yl)-4,5-dihydro-1H-pyrido[2,3-e][1,4]diazepin-2(3H)one The process of this step was adopted from step-(iv) of compound-54. The desired compound-56 obtained as a brown solid (4 mg, 3%). $^1$H NMR (400 MHz, DMSO-$d_6$) δ 10.31 (s, 1H), 8.52 (s, 1H), 8.17 (d, J=14.7 Hz, 1H), 7.51 (d, J=15.1 Hz, 1H), 7.48-7.43 (m, 2H), 7.39-7.32 (m, 2H), 7.27 (t, J=7.3 Hz, 2H), 6.23-6.20 (m, 1H), 4.44-4.40 (m, 1H), 4.26-4.21 (m, 1H), 3.93 (s, 2H), 3.92-3.86 (m, 1H), 3.84-3.76 (m, 1H), 3.58 (s, 2H), 3.53 (t, J=4.4 Hz, 4H), 2.70-2.56 (m, 3H), 2.52-2.42 (m, 3H), 2.40-2.30 (m, 4H); MS (ES) m/e 488.3 (M+H)$^+$.

Preparation of Compound-58

Synthesis of (E)-2-morpholino-N-(5-(3-oxo-3-(4-phenyl-5,6-dihydro pyridine-1(2H)-yl)prop-1-en-1-yl)pyridin-2-yl)acetamide

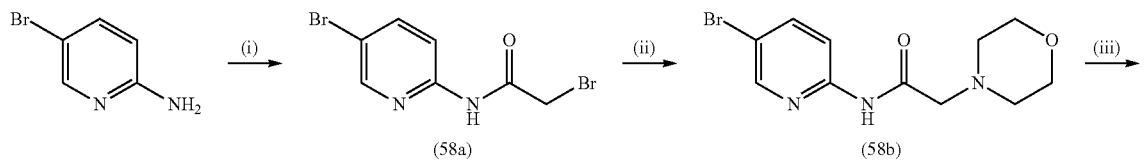

(58a) (58b)

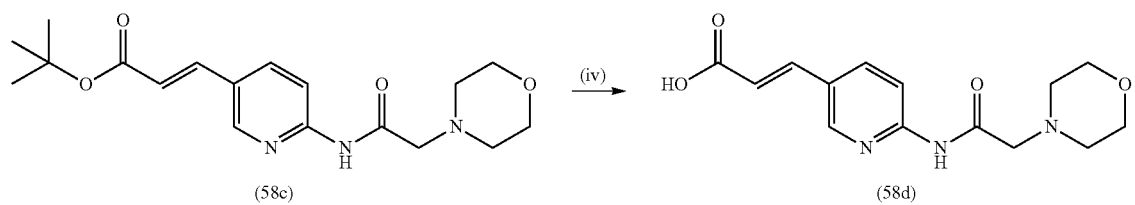

(58c) (58d)

+

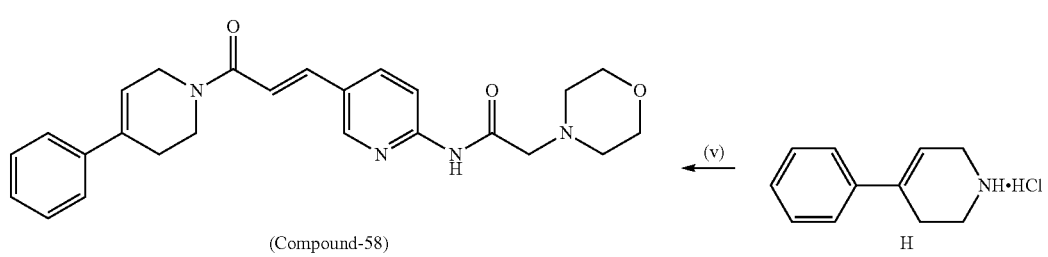

(Compound-58)

(i) Bromo acetyl bromide, DMF, 20-35° C., 16 h; (ii) Morpholine, triethylamine, 1, 4-dioxane, 80-90° C., 2-4 h; (iii) tert-butyl
acrylate, Pd(OAc)₂, P(o-tolyl)₃, DIPEA, Propionitrile, DMF, 100-110° C., 16 h; (iv) CF₃COOH, CH₂Cl₂, 20-35° C., 2 h;
(v) EDC•HCl, HOBt, DIPEA, DMF, 20-35° C., 16 h.
(Reference for Step-(i): Chemistry of Natural Compounds, 46, 1, 66-67, 2010)

Step-(ii)

Synthesis of N-(5-bromopyridin-2-yl)-2-morpholinoacetamide (58b)

To a stirred suspension of 58a (1 g, 3.42 mmol) in anhydrous 1,4-dioxane (10 ml) was added triethylamine (0.95 ml, 6.84 mmol), morpholine (0.45 g, 5.13 mmol) and heated for 2-4 h at 80-90° C. The progress of the reaction was monitored by TLC. After 4 h of stirring, the reaction mixture was cooled to 20-35° C., filtered and concentrated. The resultant residue was diluted with water (50 ml) and extracted with ethyl acetate (2×50 ml). The combined organic layers were washed with brine (50 ml), followed by drying over anhydrous $Na_2SO_4$ and filtering. The filtrate was rotary evaporated to get the desired compound as a creamy white solid (650 mg, 63%); $^1$H NMR (400 MHz, DMSO-$d_6$) δ 10.15 (bs, 1H), 8.44 (d, J=2.4 Hz, 1H), 8.10-8.01 (m, 2H), 3.62 (t, J=4.6 Hz, 4H), 3.20 (s, 2H), 2.56-2.50 (m, 4H); MS (ES) m/e 299.9 (M+H)$^+$.

Step-(iii)

Synthesis of (E)-tert-butyl 3-(6-(2-morpholinoacetamido)pyridin-3-yl)acrylate (58c)

A solution of 58b (640 mg, 2.14 mmol), tert-butyl acrylate (1.37 g, 10.7 mmol), DIPEA (0.74 ml, 4.28 mmol), Pd-(OAc)$_2$ (47 mg, 0.21 mmol) and P(o-tol)$_3$ (129 mg, 0.42 mmol) in propionitrile (8 ml) and DMF (2 ml) was purged with nitrogen for 10 minutes, and then was heated at 100-110° C. for 16 h. The progress of the reaction was monitored by TLC. After 16 h of stirring, the reaction mixture was cooled to 20-35° C., filtered through celite, and then concentrated. The resultant residue was diluted with water (50 ml) and extracted with ethyl acetate (2×50 ml). The combine organic layers were washed with brine (50 ml), followed by drying over anhydrous $Na_2SO_4$ and filtering. The filtrate was rotary evaporated to get residue which was purified by column chromatography using a mixture of 60% ethyl acetate/pet ether as an eluent to get the desired compound as an off-white solid (560 mg, 75%). $^1$H NMR (400 MHz, DMSO-$d_6$) δ 10.17 (s, 1H), 8.60 (d, J=2.0 Hz, 1H), 8.20 (dd, J=8.8, 2.5 Hz, 1H), 8.11 (d, J=8.8 Hz, 1H), 7.53 (d, J=16.1 Hz, 1H), 6.56 (d, J=16.2 Hz, 1H), 3.62 (t, J=4.4 Hz, 4H), 3.21 (s, 2H), 2.55-2.51 (m, 4H), 1.48 (s, 9H); MS (ES) m/e 348.0 (M+H)$^+$.

Step-(iv)

Synthesis of (E)-3-(6-(2-morpholinoacetamido)pyridin-3-yl)acrylic acid (58d)

A solution of 58c (550 mg, 1.58 mmol) in $CH_2Cl_2$ (10 ml) was treated with trifluoro acetic acid (1.22 ml) at 20-35° C. for 2 h. The progress of the reaction was monitored by TLC. After 16 h of stirring, the clear solution was concentrated under vacuum and the resultant solid was washed with diethyl ether to get the desired compound as a creamy white solid (400 mg, 87%). MS (ES) m/e 290.1 (M–H)$^+$.

Step-(v)

Preparation of Compound-58: Synthesis of (E)-2-morpholino-N-(5-(3-oxo-3-(4-phenyl-5,6-dihydropyridin-1(2H)-yl)prop-1-en-1-yl)pyridin-2-yl)acetamide The process of this step was adopted from step-(ii) of compound-1. The desired compound-58 obtained as a white solid (50 mg, 22%).

Compound-59 was prepared by the following methodologies adopted similar to described below for the Compound 58.

The compounds prepared by following the process according to compound 58 and their physicochemical characteristics are summarized here in below in the Table-IV.

TABLE-IV

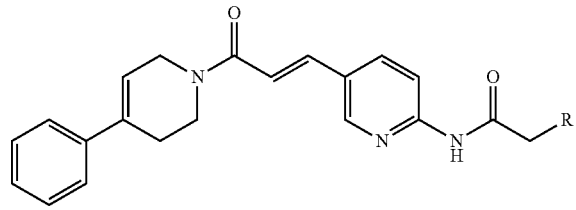

| Comp No | R | $^1$H NMR (400 MHz, DMSO-$d_6$); δ (ppm) and MS (ES) m/e |
|---|---|---|
| 58 | *N⌒O (morpholine) | 10.17 (s, 1H), 8.63 (s, 1H), 8.29-8.24 (m, 1H), 8.12 (d, J = 8.8 Hz, 1H), 7.52 (d, J = 15.6 Hz, 1H), 7.47-7.42 (m, 2H), 7.41-7.32 (m, 3H), 7.31-7.24 (m, 1H), 6.22-6.18 (m, 1H), 4.42-4.40 (m, 1H), 4.30-4.23 (m, 1H), 3.93-3.90 (m, 1H), 3.84-3.80 (m, 1H), 3.64-3.61 (m, 4H), 3.22 (s, 2H), 2.60-2.52 (m, 6H); MS (ES) m/e 433.1 (M + H)$^+$. |
| 59 | imidazole | 11.03 (s, 1H), 8.67 (s, 1H), 8.28-8.24 (m, 1H), 8.06 (d, J = 8.3 Hz, 1H), 7.64 (s, 1H), 7.52 (d, J = 15.1 Hz, 1H), 7.46-7.42 (m, 2H), 7.36 (t, J = 7.6 Hz, 3H), 7.27 (t, J = 7.1 Hz, 1H), 7.17 (s, 1H), 6.90 (s, 1H), 6.23-6.20 (m, 1H), 4.99 (s, 2H), 4.44-4.40 (m, 1H), 4.25-4.21 (m, 1H), 3.95-3.91 (m, 1H), 3.80-3.78 (m, 1H), 2.59-2.55 (m, 2H); MS (ES) m/e 414.3 (M + H)$^+$. |

\* Bonding position of R

Preparation of Compound-60

Synthesis of (E)-N-(5-(3-oxo-3-(4-phenyl-5,6-dihydro pyridin-1(2H)-yl)prop-1-en-1-yl)pyridin-2-yl)-2-(1H-1,2,3-triazol-1-yl)acetamide

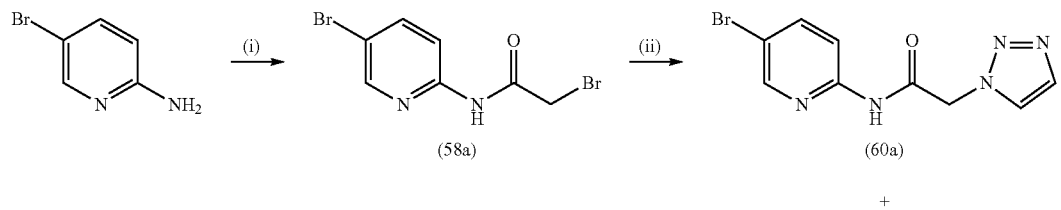

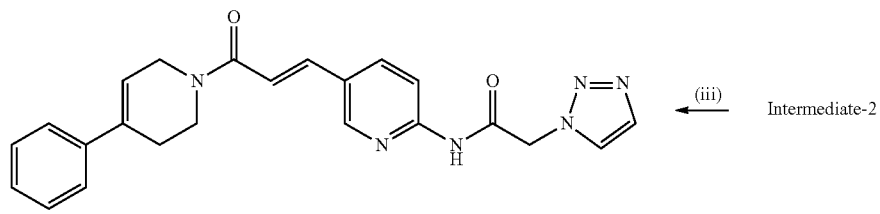

Compound-60

(i) Bromo acetyl bromide, DMF, 20-35° C., 16 h; (ii) 1, 2, 3-triazole, triethylamine, 1,4-dioxane, 90° C., 2 h;
(iii) Pd(OAc)$_2$, P(o-tolyl)$_3$, DIPEA, Propionitrile, DMF, 100-110° C., 16 h;
(Reference for Step-(i): Chemistry of Natural Compounds, 46, 1, 66-67, 2010)

Step-(ii)

Synthesis of N-(5-iodopyridin-2-yl)-2-(1H-1,2,3-triazol-1-yl)acetamide (60a)

The process of this step is adopted from step-(ii) of compound-58. The desired compound obtained as a white solid (1.8 g, 34%); MS (ES) m/e 203.9 (M−127)$^+$.

Step-(iii)

Preparation of Compound-60: Synthesis of (E)-N-(5-(3-oxo-3-(4-phenyl-5,6-dihydropyridin-1(2H)-yl) prop-1-en-1-yl)pyridin-2-yl)-2-(1H-1,2,3-triazol-1-yl)acetamide The process of this step was adopted from step-(vii) of compound-54. The desired compound-60 obtained as an off-white solid (4 mg, 3%). $^1$H NMR (400 MHz, DMSO-d$_6$) δ 11.2 (bs, 1H), 8.69 (bs, 1H), 8.28 (d, J=8.3 Hz, 1H), 8.16 (s, 1H), 8.04 (d, J=7.9 Hz, 1H), 7.77 (s, 1H), 7.53 (d, J=15.1 Hz, 1H), 7.47-7.42 (m, 2H), 7.38-7.32 (m, 3H), 7.28-7.22 (m, 1H), 6.23-6.21 (m, 1H), 5.46 (s, 2H), 4.44-4.41 (m, 1H), 4.28-4.22 (m, 1H), 3.98-3.92 (m, 1H), 3.86-3.78 (m, 1H), 2.60-2.51 (m, 2H).

Preparation of Compound-61

Synthesis of (E)-N-(3-(morpholinomethyl)-5-(3-oxo-3-(4-phenyl-5,6-dihydropyridin-1(2H)-yl)prop-1-en-1-yl)pyridin-2-yl)acetamide

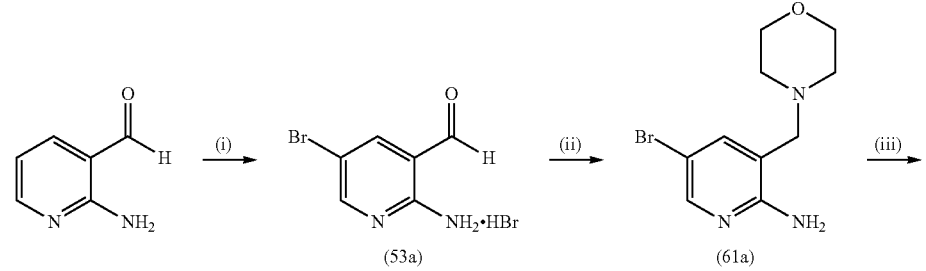

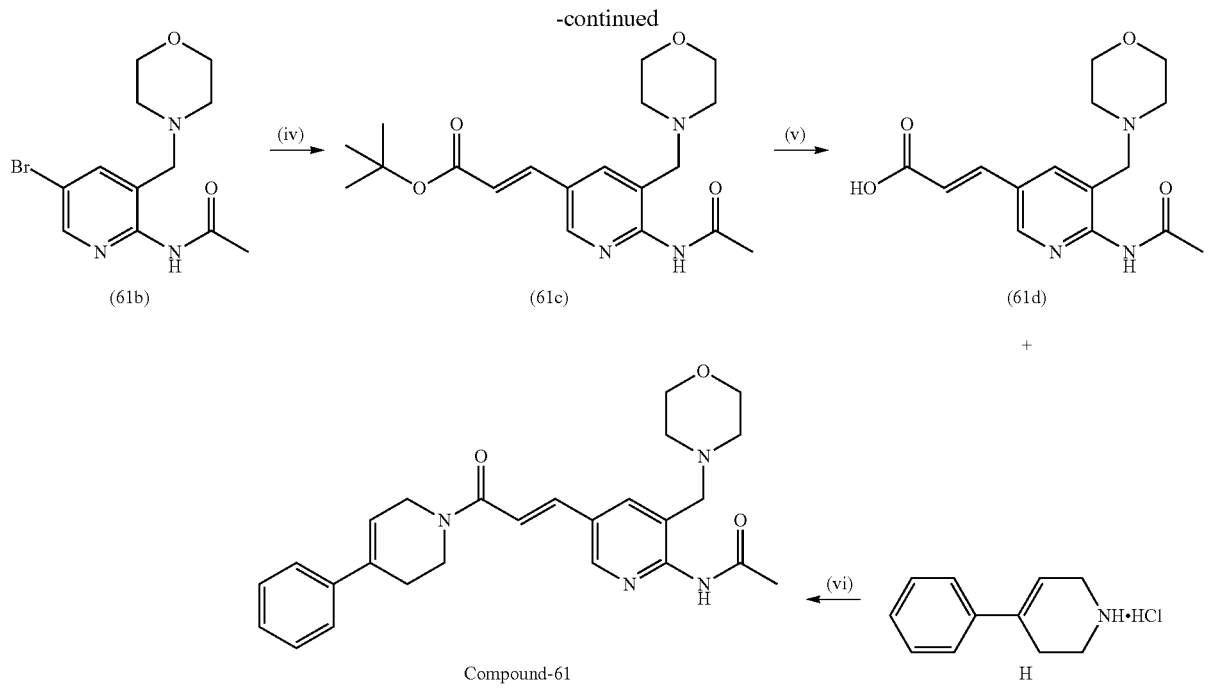

Compound-61

(i) Br$_2$/AcOH, 20-35° C., 3 h; (ii) Morpholine, Triethyl amine, MeOH, 20-35° C., 6 h then NaBH$_4$, 20-35° C., 8 h; (iii) Acetic anhydride, pyridine, 20-35° C., 16 h; (iv) tert-butylacrylate, Pd(OAc)$_2$, P(O-tolyl)$_3$, DIPEA, Propionitrile:DMF, 110° C., 16 h; (v) CH$_2$Cl$_2$, TFA, 20-35° C., 4 h; (vi) EDC•HCl, HOBt, DIPEA, DMF, 20-35° C., 16 h.
(Reference for Step-(i-ii): WO2004052890)

Step-(iii)

Synthesis of N-(5-bromo-3-(morpholinomethyl)pyridin-2-yl)acetamide (61b)

To a stirred solution of 61a (400 mg, 1.47 mmol) in pyridine (5 ml) was added acetic anhydride (450 mg, 4.41 mmol) at 20-35° C. and the reaction mixture was stirred at 20-35° C. for 16 h. The progress of the reaction was monitored by TLC. After 16 h of stirring, the reaction mixture was concentrated under vacuum. The resultant solid was diluted with water (30 ml) and extracted with ethyl acetate (2×30 ml). The combined organic layers were washed with brine (30 ml), followed by drying over anhydrous Na$_2$SO$_4$ and filtering. The filtrate was rotary evaporated to get the desired compound as pale yellow liquid (400 mg, 89%). $^1$H NMR (400 MHz, DMSO-d$_6$) δ 10.26 (s, 1H), 8.40 (d, J=2.4 Hz, 1H), 8.01 (d, J=2.4 Hz, 1H), 3.58 (t, J=4.6 Hz, 4H), 3.43 (s, 2H), 2.34 (t, J=4.2 Hz, 4H), 2.12 (s, 3H).

Step-(iv)

Synthesis of (E)-tert-butyl 3-(6-acetamido-5-(morpholinomethyl)pyridin-3-yl)acrylate (61c)

The process of this step was adopted from step-(iii) of compound-58. The desired compound obtained as a yellow liquid (150 mg, 33%). $^1$H NMR (400 MHz, DMSO-d$_6$) δ 10.39 (s, 1H), 8.54 (d, J=2.5 Hz, 1H), 8.01 (d, J=2.4 Hz, 1H), 7.55 (d, J=15.6 Hz, 1H), 6.57 (d, J=16.1 Hz, 1H), 3.60-3.57 (m, 6H), 3.50 and 3.43 (s and rotamer, 3H), 2.42-2.32 (m, 4H), 1.48 (s, 9H).

Step-(v)

Synthesis of (E)-3-(6-acetamido-5-(morpholinomethyl)pyridin-3-yl)acrylic acid (61d)

The process of this step was adopted from step-(iv) of compound-58. The desired compound obtained as a pale brown solid (100 mg, 83%). $^1$H NMR (400 MHz, DMSO-d$_6$) δ 12.58 (bs, 1H), 10.50 (s, 1H), 8.80-8.70 (m, 1H), 8.40-8.34 (m, 1H), 7.63 (d, J=16.2 Hz, 1H), 6.63 (d, J=16.1 Hz, 1H), 4.40-4.10 (m, 3H), 4.09-3.80 (m, 4H), 3.79-3.50 (m, 3H), 2.17 (s, 3H).

Step-(vi)

Preparation of Compound-61: Synthesis of (E)-N-(3-(morpholinomethyl)-5-(3-oxo-3-(4-phenyl-5,6-dihydropyridin-1(2H)-yl) prop-1-en-1-yl)pyridin-2-yl) acetamide The process of this step was adopted from step-(ii) of compound-1. The desired compound-61 obtained as greenish waxy solid (8 mg, 8%). $^1$H NMR (400 MHz, DMSO-d$_6$) δ 10.39 (bs, 1H), 8.59 (bs, 1H), 8.17 (d, J=9.3 Hz, 1H), 7.53 (d, J=15.1 Hz, 1H), 7.49-7.43 (m, 2H), 7.36 (t, J=7.5 Hz, 2H), 7.28 (t; J=7.1 Hz, 2H), 6.24-6.18 (m, 1H), 4.46-4.37 (m, 1H), 4.28-4.21 (m, 1H), 3.98-3.89 (m, 1H), 3.85-3.74 (m, 1H), 3.68-3.56 (m, 4H), 3.53 (s, 2H), 2.66-2.56 (m, 2H), 2.42-2.32 (m, 4H), 2.20 (s, 3H); MS (ES) m/e 447.1 (M+H)$^+$.

Preparation of Compound-81

Synthesis of (E)-6-(3-(4-(3-aminobenzyl)-5,6-dihydropyridin-1(2H)-yl)-3-oxoprop-1-en-1-yl)-3,4-dihydro-1,8-naphthyridin-2(1H)-one

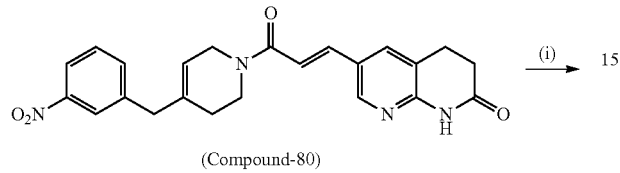

(Compound-80)

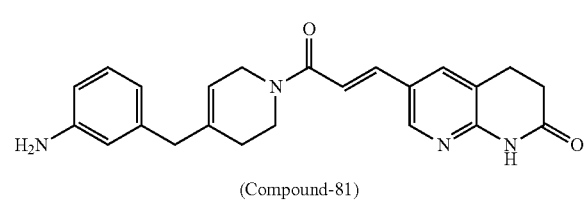

(Compound-81)

(i) Fe, NH$_4$Cl, EtOH/H$_2$O, 95° C., 4 h

Step-(i)

The process of this step was adopted from step-(i) of compound-21. The desired compound-81 obtained, as a yellow solid (20 mg, 27%). $^1$H NMR (400 MHz, DMSO-d$_6$) δ 10.63 (s, 1H), 8.33 (s, 1H), 8.07 (s, 1H), 7.44 (d, J=15.6 Hz, 2H), 7.28-7.10 (m, 3H), 6.76-6.66 (m, 3H), 5.58-5.52 (m, 1H), 4.24-4.18 (m, 1H), 4.06-4.02 (m, 1H), 3.78-3.72 (m, 1H), 3.61-3.57 (m, 1H), 3.36-3.28 (m, 2H), 2.96-2.92 (m, 2H), 2.56-2.52 (m, 2H), 2.02-1.88 (m, 2H); MS (ES) m/e 389.4 (M+H)$^+$.

Preparation of Compound-85

Synthesis of (E)-6-(3-(4-((5-nitrothiophen-2-yl)methyl)-5,6-dihydropyridin-1(2H)-yl)-3-oxoprop-1-en-1-yl)-3,4-dihydro-1,8-naphthyridin-2(1H)-one

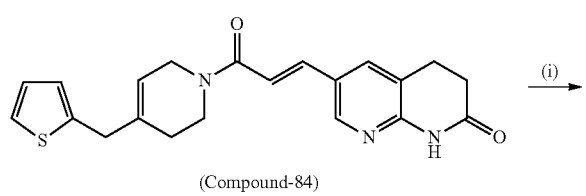

(Compound-84)

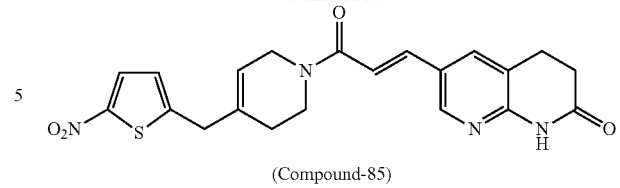

(Compound-85)

(i) CuNO$_2$,TFA, 20-35° C., 48 h

Step-(i)

To a stirred solution of Compound-84 in TFA (2 ml) was added copper nitrate (36 mg, 0.20 mmol) at 20-35° C. and the reaction mixture was stirred at 20-35° C. for 48 h. The progress of the reaction was monitored by TLC. After 48 h of stirring, the reaction mixture was adjusted to pH 5 with aq.NaOH solution (2M) and was diluted with ethyl acetate (30 ml). The ethyl acetate layer was washed with water (30 ml), brine (30 ml), dried over anhydrous Na$_2$SO$_4$ and evaporated to get the desired compound as a brick red solid (23 mg, 26%). $^1$H NMR (400 MHz, DMSO-d$_6$) δ 10.63 (s, 1H), 8.35 (s, 1H), 8.08 (s, 1H), 8.02 (d, J=4.4 Hz, 1H), 7.45 (d, J=15.6 Hz, 1H), 7.28-7.18 (m, 1H), 7.05 (d, J=3.9 Hz, 1H), 5.69-5.67 (m, 1H), 4.25-4.23 (m, 1H), 4.06-4.02 (m, 1H), 3.78-3.76 (m, 1H), 3.67-3.63 (m, 3H), 2.90 (t, J=7.3 Hz, 2H), 2.56-2.54 (m, 2H), 2.18-2.12 (m, 2H); MS (ES) m/e 425.3 (M+H)$^+$.

Preparation of Compound-88

Synthesis of (E)-N-(5-(3-oxo-3-(4-(thiophen-2-ylmethyl)-5,6-dihydropyridin-1(2H)-yl)prop-1-en-1-yl)pyridin-2-yl)acetamide

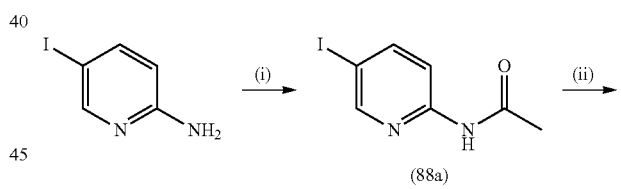

(88a)

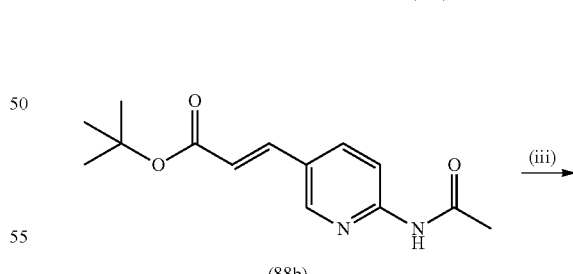

(88b)

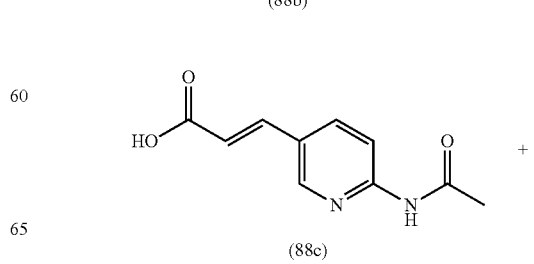

(88c)

101

-continued

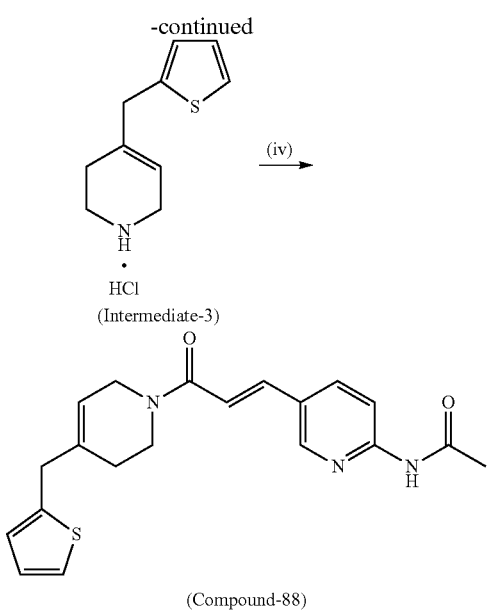

(i) Pyridine, Acetic anhydride, 20-35° C., 16 h; (ii) tert-butyl acrylate, Pd(OAc)$_2$, P(o-tolyl)$_3$, DIPEA, Propionitrile, DMF, 100-110° C., 16 h;
(iii) CF$_3$COOH, CH$_2$Cl$_2$, 20-35° C., 2 h; (iv) EDC•HCl, HOBt, DIPEA, DMF, 20-35° C., 16 h.

Step-(i)

Synthesis of N-(5-bromopyridin-2-yl)acetamide (88a)

The process of this step was adopted from step-(iii) of compound-61. The desired compound obtained as an off-white solid (1.5 g, 63%). $^1$H NMR (400 MHz, DMSO-d$_6$) δ 10.59 (s, 1H), 8.51 (d, J=2.4 Hz, 1H), 8.08 (dd, J=8.8, 2.4 Hz, 1H), 7.95 (d, J=8.8 Hz, 1H), 2.08 (s, 3H); MS (ES) m/e 261.1 (M−H).

Step-(ii)

Synthesis of (E)-tert-butyl 3-(6-acetamidopyridin-3-yl)acrylate (88b)

The process of this step was adopted from step-(iii) of compound-58. The desired compound obtained as an off-white solid (900 mg, 90%). $^1$H NMR (400 MHz, DMSO-d$_6$) δ 10.69 (s, 1H), 8.57 (d, J=2.4 Hz, 1H), 8.16 (dd, J=8.8, 2.4 Hz, 1H), 8.09 (d, J=8.8 Hz, 1H), 7.52 (d, J=16.1 Hz, 1H), 6.54 (d, J=16.2 Hz, 1H), 2.11 (s, 3H), 1.48 (s, 9H); MS (ES) m/e 261.2 (M−H).

Step-(iii)

Synthesis of (E)-3-(6-acetamidopyridin-3-yl)acrylicacid (88c)

The process of this step was adopted from step-(iv) of compound-58. The desired compound obtained as a creamy white solid (700 mg, 99%). $^1$H NMR (400 MHz, DMSO-d$_6$) δ 12.40 (bs, 1H), 10.69 (s, 1H), 8.5.7 (d, J=1.9 Hz, 1H), 8.15 (dd, J=8.8, 2.4 Hz, 1H), 8.10 to (d, J=8.8 Hz, 1H), 7.56 (d, J=16.1 Hz, 1H), 6.54 (d, J=16.1 Hz, 1H), 2.11 (s, 3H); MS (ES) m/e 205.1 (M−H).

102

Step-(iv) Preparation of Compound-88

Synthesis of (E)-N-(5-(3-oxo-3-(4-(thiophen-2-ylmethyl)-5,6-dihydropyridin-1(2H)-yl)prop-1-en-1-yl)pyridin-2-yl)acetamide The process of this step was adopted from step-(ii) of compound-1. The desired compound-88 obtained as a pale yellow solid (25 mg, 12%). $^1$H NMR (400 MHz, DMSO-d$_6$) δ 10.65 (s, 1H), 8.59 (d, J=2.0 Hz, 1H), 8.16 (d, J=8.8 Hz, 1H), 8.08 (d, J=8.8 Hz, 1H), 7.46 (d, J=15.1 Hz, 1H), 7.34 (dd, J=4.9, 1.0 Hz, 1H), 7.31-7.20 (m, 1H), 6.95 (dd, J=5.3, 3.4 Hz, 1H), 6.87 (dd, J=3.4, 1.0 Hz, 1H), 5.57 (s, 1H), 4.22 and 4.03 (rotamer and s, 2H), 3.74 and 3.63 (rotamer and s, 2H), 3.54 (s, 2H), 2.10 (s, 3H), 2.14 and 2.02 (rotamer and s, 2H); MS (ES) m/e 366.1 (M−H).

Preparation of Compound-89

Synthesis of (E)-2-morpholino-N-(5-(3-oxo-3-(4-(thiophen-2-ylmethyl)-5,6-dihydropyridin-1(2H)-yl)prop-1-en-1-yl)pyridin-2-yl)acetamide

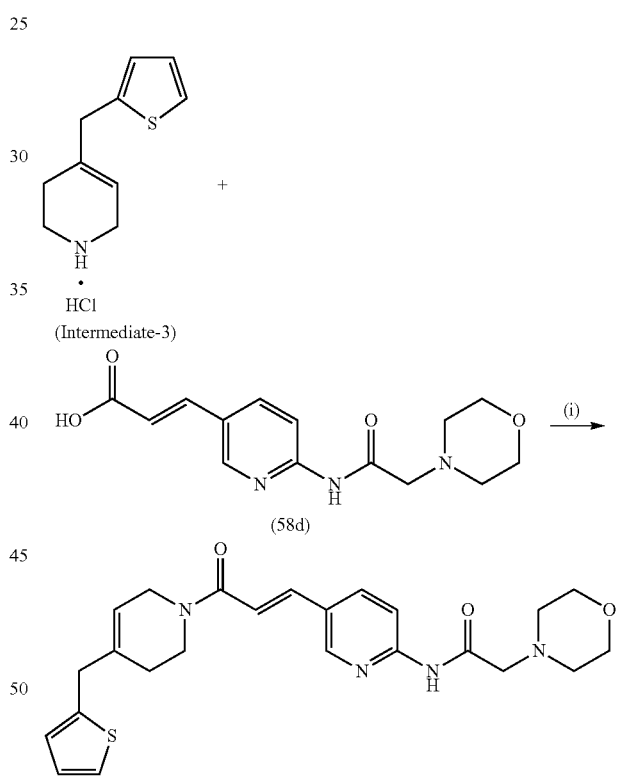

Compound-89

(i) EDC•HCl, HOBt, DIPEA, DMF, 20-35° C., 16 h.

Step-(i)

The process of this step was adopted from step-(ii) of compound-1. The desired compound-89 obtained as a pale brown waxy solid (20 mg, 8%). $^1$H NMR (400 MHz, DMSO-d$_6$) δ 10.16 (s, 1H), 8.60 (d, J=2.0 Hz, 1H), 83.22 (d, J=9.3 Hz, 1H), 8.10 (d, J=8.8 Hz, 1H), 7.47 (d, J=15.1 Hz, 1H), 7.35 (dd, J=1.0, 1.0 Hz, 1H), 7.32-7.25 (m, 1H), 6.95 (dd, J=4.8, 3.4 Hz, 1H), 6.87 (d, J=2.4 Hz, 1H), 5.58-5.56 (m, 1H), 4.23-4.21

(m, 1H), 4.03 (d, J=6.9 Hz, 1H), 3.75-3.73 (m, 1H), 3.64-3.60 (m, 5H), 3.54 (s, 2H), 3.21 (s, 2H), 2.54-2.52 (m, 4H), 2.09-1.91 (m, 2H); MS (ES) m/e 453.3 (M+H)+.

Preparation of Compound-90

Synthesis of (E)-3-(2-morpholinoethyl)-6-(3-oxo-3-(4-(thiophen-2-ylmethyl)-5,6-dihydropyridin-1(2H)-yl)prop-1-en-1-yl)-3,4-dihydro pyrido[2,3-d]pyrimidin-2(1H)-one

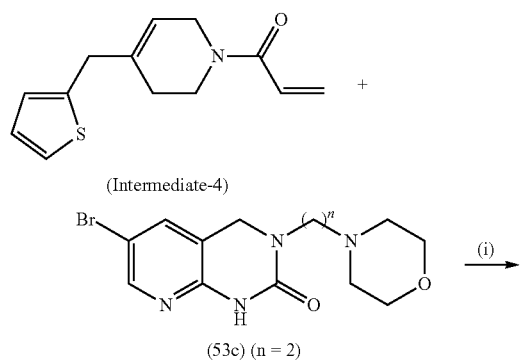

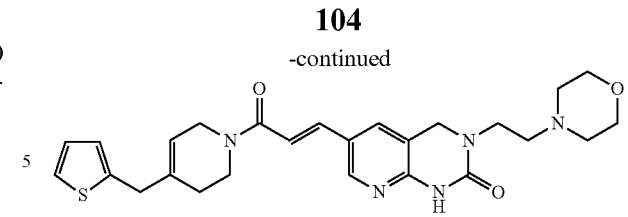

Compound-90

(i) Pd(OAc)$_2$, P(O-tolyl)$_3$, DIPEA, Propionitrile:DMF, 100-110° C., 16 h;

Step-(i)

The process of this step was adopted from step-(iv) of compound-54. The desired compound-90 obtained as a yellow solid (20 mg, 6%). $^1$H NMR (400 MHz, DMSO-d$_6$) δ 9.88 (s, 1H), 8.33 (s, 1H), 8.14-8.06 (m, 1H), 7.98 (s, 1H), 7.43 (d, J=15.2 Hz, 1H), 7.35 (d, J=4.9 Hz, 1H), 7.22-7.12 (m, 1H), 6.97-6.95 (m, 1H), 6.88 (s, 1H), 5.57 (s, 1H), 4.53 (s, 2H), 4.20 and 4.03 (rotamer and s, 2H), 3.73-3.39 (m, 10H), 3.37-3.32 (m, 2H), 2.50-2.32 (m, 3H), 2.09 and 2.02 (rotamer and s, 2H); MS (ES) m/e 494.3 (M+H)+.

Preparation of Compound-91

Synthesis of (E)-8-(3-oxo-3-(4-(thiophen-2-ylmethyl)-5,6-dihydropyridin-1(2H)-yl)prop-1-en-1-yl)-2,3-dihydro-1H-pyrido[2,3-b][1,4]diazepin-4(5H)-one

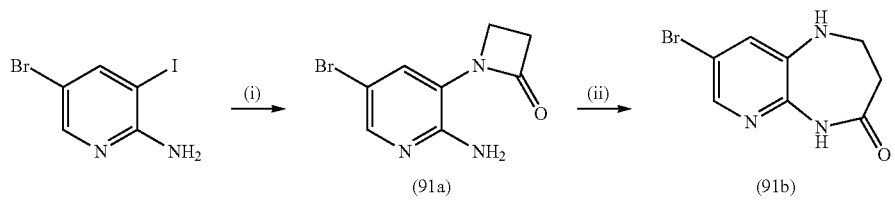

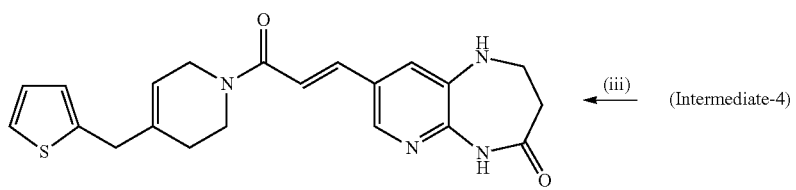

Compound-91

(i) Azetidin-2-one, Pd$_2$(dba)$_3$, Xantphos, Cs$_2$CO$_3$, Toluene, 90° C., 19 h; (ii) Ti($^i$OPr)4, Toluene, 110° C., 15 h;
(iii) Pd(OAc)$_2$, P(O-tolyl)$_3$, DIPEA, Propionitrile:DMF, 100-110° C., 16 h;
(Ref. for step-(i-ii): WO2007067416)

Step-(iii) Preparation of Compound-91

Synthesis of (E)-8-(3-oxo-3-(4-(thiophen-2-ylmethyl)-5,6-dihydropyridin-1(2H)-yl)prop-1-en-1-yl)-2,3-dihydro-1H-pyrido[2,3-b][1,4]diazepin-4(5H)-one The process of this step was adopted from step-(iv) of compound-54. The desired compound-91 obtained as a pale yellow solid (30 mg, 8%). $^1$H NMR (400 MHz, DMSO-d$_6$) δ 9.73 (s, 1H), 8.00 (s, 1H), 7.38-7.34 (m, 3H), 7.14-7.03 (m, 1H), 6.96 (dd, J=4.8, 3.4 Hz, 1H), 6.87 (d, J=2.5 Hz, 1H), 5.99-5.97 (m, 1H), 5.58-5.56 (m, 1H), 4.20-4.16 (m, 1H), 4.00-3.91 (m, 1H), 3.71-3.69 (m, 1H), 3.62-3.60 (m, 1H), 3.54 (s, 2H), 3.45-3.41 (m, 2H), 2.59-2.56 (m, 2H), 2.09-2.02 (m, 2H); MS (ES) m/e 395.0 (M+H)$^+$.

Preparation of Compound-92

Synthesis of (E)-7-(3-oxo-3-(4-(thiophen-2-ylmethyl)-5,6-dihydropyridin-1(2H)-yl)prop-1-en-1-yl)-4,5-dihydro-1H-pyrido[2,3-e][1,4]diazepin-2(3H)-one

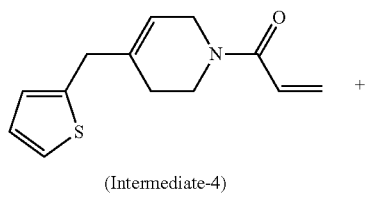

(Intermediate-4)

+

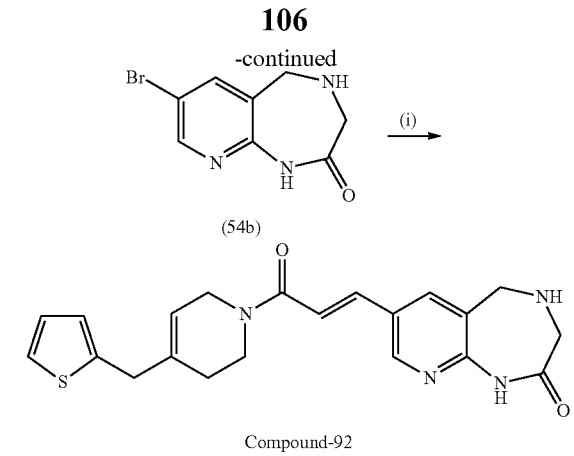

(54b)

Compound-92

(i) Pd(OAc)$_2$, P(O-tolyl)$_3$, DIPEA, Propionitrile:DMF, 100-110° C., 16 h;

Step-(i)

The process of this step was adopted from step-(iv) of compound-54. The desired compound-92 obtained as a cream solid (30 mg, 9%). $^1$H NMR (400 MHz, DMSO-d$_6$) 11.02 (s, 1H), 9.60-9.40 (m, 1H), 8.73 (d, J=2.4 Hz, 1H), 8.26 (s, 1H), 7.52 (d, J=15.7 Hz, 1H), 7.49-7.27 (m, 2H), 6.97-6.95 (m, 1H), 6.87 (d, J=2.4 Hz, 1H), 5.59 (s, 1H), 4.24 (s, 2H), 4.22 and 4.05 (rotamer and s, 2H), 3.85 (s, 2H), 3.75 and 3.64 (rotamer and s, 2H), 3.55 (s, 2H), 2.11 and 2.03 (rotamer and s, 2H); MS (ES) m/e 395.2 (M+H)$^+$.

Preparation of Compound-93

Synthesis of (E)-4-methyl-7-(3-oxo-3-(4-(thiophen-2-ylmethyl)-5,6-dihydropyridin-1(2H)-yl)prop-1-en-1-yl)-4,5-dihydro-1H-pyrido[2,3-e][1,4]diazepin-2(3H)-one

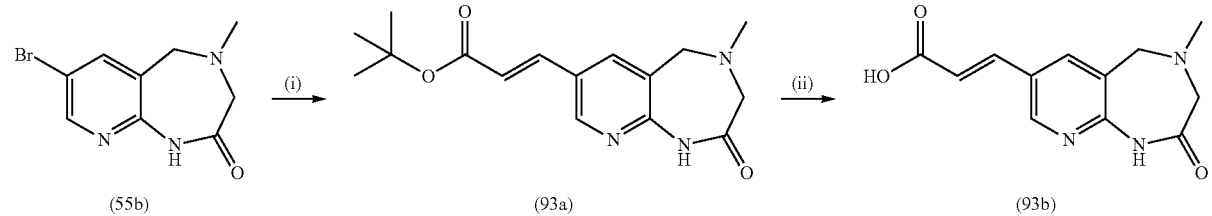

Compound-93 ← (Intermediate-3)

(i) tert-butyl acrylate, Pd(OAc)$_2$, P(o-tolyl)$_3$, DIPEA, Propionitrile, DMF, 100° C., 16 h;
(ii) CF$_3$COOH, CH$_2$Cl$_2$, 20-35° C., 2 h; (iii) HOBt, EDC•HCl, DIPEA, DMF, 20-35° C., 16 h.
(Reference for Steps-(i-ii): US20060142265A1)

Step-(iii) Preparation of Compound-93

Synthesis of (E)-4-methyl-7-(3-oxo-3-(4-(thiophen-2-ylmethyl)-5,6-dihydropyridin-1(2H)-yl)prop-1-en-1-yl)-4,5-dihydro-1H-pyrido[2,3-e][1,4]diazepin-2(3H)-one The process of this step was adopted from step-(ii) of compound-1. The desired compound-93 obtained as a brown solid (10 mg, 11%). $^1$H NMR (400 MHz, DMSO-$d_6$) δ 10.34 (s, 1H), 8.51 (s, 1H), 8.15 (s, 1H), 7.48 (d, J=15.7 Hz, 1H), 7.36-7.23 (m, 2H), 6.97-6.95 (m, 1H), 6.88-6.86 (m, 1H), 5.58 (s, 1H), 4.23 and 4.04 (rotamer and s, 2H), 3.79 (s, 2H), 3.75 and 3.63 (rotamer and s, 2H), 3.54 (s, 2H), 3.42 (s, 2H), 2.37 (s, 3H), 2.10 and 2.03 (rotamer and s, 2H); MS (ES) m/e 409.4 (M+H)$^+$.

Preparation of Compound-94

Synthesis of (E)-tert-butyl 2-oxo-6-(3-oxo-3-(4-(thiophen-2-ylmethyl)-5,6-dihydropyridin-1(2H)-yl)prop-1-en-1-yl)-2,4-dihydro-1H-spiro[[1,8]naphthyridine-3,4'-piperidine]-1'-carboxylate

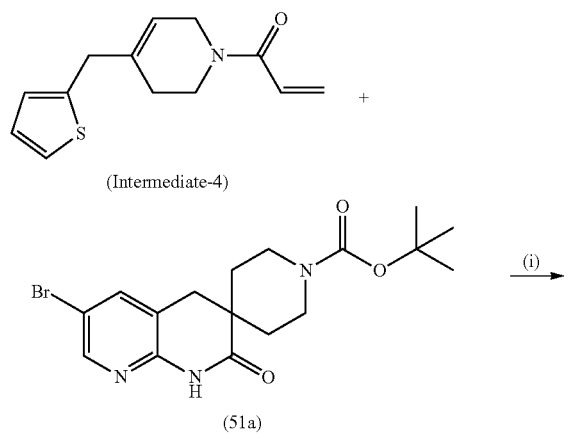

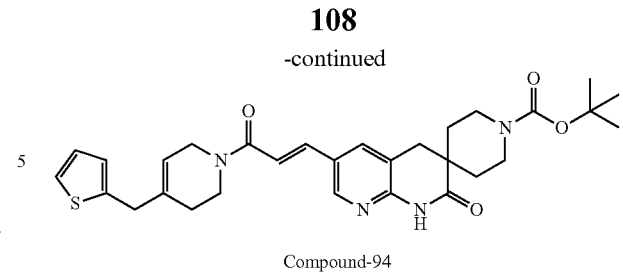

Compound-94

(i) Pd(OAc)$_2$, P(O-tolyl)$_3$, DIPEA, Propionitrile:DMF, 100-110° C., 16 h;

Step-(i)

The process of this step was adopted from step-(iv) of compound-54. The desired compound obtained as a brown solid (70 mg, 34%). $^1$H NMR (400 MHz, DMSO-$d_6$) δ 10.73 (s, 1H), 8.36 (d, J=2.0 Hz, 1H), 8.08 (s, 1H), 7.45 (d, J=15.1 Hz, 1H), 7.35 (dd, J=5.2, 1.2 Hz, 1H), 7.26-7.18 (m, 1H), 6.96 (dd, J=4.9, 4.9 Hz, 1H), 6.89-6.86 (m, 1H), 5.58 (s, 1H), 4.21 and 4.03 (rotamer and s, 2H), 3.74 and 3.63 (rotamer and s, 2H), 3.60-3.50 (m, 4H), 3.29-3.23 (m, 2H), 2.94 (s, 2H), 2.14-2.02 (m, 2H), 1.80-1.66 (m, 2H), 1.40 (s, 9H), 1.37-1.30 (m, 2H); MS (ES) m/e 547.6 (M−H).

Preparation of Compound-95

Synthesis of (E)-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one trifluoro acetic acid

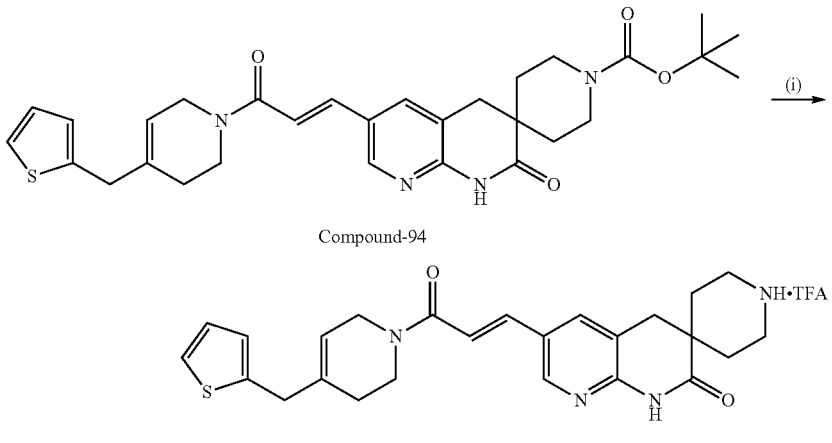

(i) TFA, DCM, 20-35° C., 2 h

Step-(i)

The process of this step was adopted from step-(i) of compound-1. The desired compound-95 obtained as pale brown solid (40 mg, 65%). $^1$H NMR (400 MHz, DMSO-$d_6$) δ 10.88 (s, 1H), 8.51-8.44 (m, 2H), 8.41 (d, J=1.4 Hz, 1H), 8.07 (s, 1H), 7.46 (d, J=15.1 Hz, 1H), 7.35 (d, J=4.4 Hz, 1H), 7.27-7.14 (m, 1H), 6.96 (dd, J=5.2, 3.6 Hz, 1H), 6.87 (d, J=2.4 Hz, 1H), 5.58 (s, 1H), 4.21 and 4.03 (rotamer and s, 2H), 3.74 and 3.63 (rotamer and s, 2H), 3.55 (s, 2H), 3.26-3.06 (m, 4H), 2.97 (s, 2H), 2.10-1.94 (m, 4H), 1.59-1.52 (m, 2H); MS (ES) m/e 449.2 (M+H)$^+$.

Preparation of Compound-96

Synthesis of (E)-1'-acetyl-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one

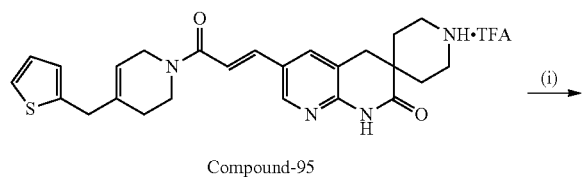

Compound-95

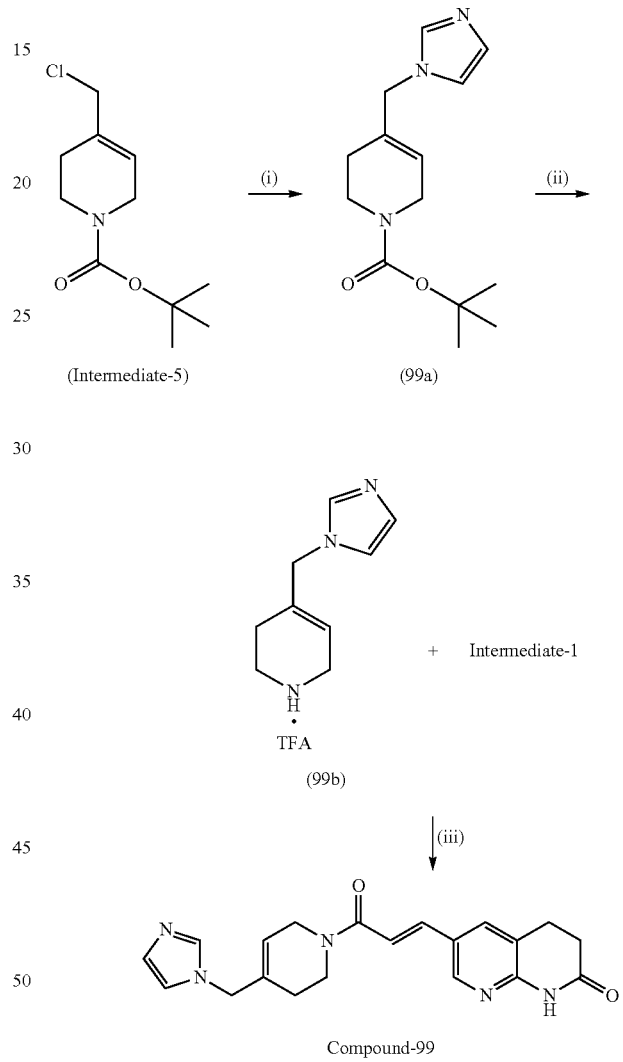

Compound-96

(i) Acetic anhydride, Pyridine, 20-35° C., 24 h

Step-(i)

The process of this step was adopted from step-(iii) of compound-61. The desired compound-96 obtained as a grey solid (12 mg, 46%). $^1$H NMR (400 MHz, DMSO-$d_6$) δ 10.76 (s, 1H), 8.38 (s, 1H), 8.09 (s, 1H), 7.45 (d, J=15.1 Hz, 1H), 7.35 (d, J=4.9 Hz, 1H), 7.21 (dd, J=27.6, 15.4 Hz, 1H), 6.96 (m, 1H), 6.88 (s, 1H), 5.58 (s, 1H), 4.23 and 4.03 ((rotamer and s, 2H), 3.75-3.71 (m, 2H), 3.70-3.61 (m, 2H), 3.58 (s, 2H), 3.57-3.53 (m, 2H), 2.95 (s, 2H), 2.10-1.81 (m, 2H), 1.99 (s, 3H), 1.88-1.76 (m, 1H), 1.74-1.60 (m, 1H), 1.44-1.26 (m, 2H); MS (ES) m/e 489.4 (M−H).

Preparation of Compound-99

Synthesis of (E)-6-(3-(4-((1H-imidazol-1-yl)methyl)-5,6-dihydropyridin-1(2H)-yl)-3-oxoprop-1-en-1-yl)-3,4-dihydro-1,8-naphthyridin-2(1H)-one Compound-99

(i) Imidazole, K$_2$CO$_3$, Acetonitrile, 80° C., 16 h;
(ii) TFA, CH$_2$Cl$_2$, 20-35° C., 2 h;
(iii) EDC•HCl, HOBt, DIPEA, DMF, 20-35° C., 16 h.

Step-(i)

Synthesis of tert-butyl 4-((1H-imidazol-1-yl)methyl)-5,6-dihydropyridine-1(2H)-carboxylate (99a)

To a stirred solution of Intermediate-5 (500 mg, 2.16 mmol) and imidazole (180 mg, 2.60 mmol) in acetonitrile (4 ml) was added K₂CO₃ (900 mg, 6.49 mmol) and the reaction mixture was stirred at 80° C. for 16 h. The progress of the reaction was monitored by TLC. After 16 h, the mixture was cooled to 20-35° C., diluted with ethyl acetate (50 ml), washed with water (50 ml), brine (30 ml), dried over anhydrous Na₂SO₄ and evaporated. The crude compound was purified by column chromatography using a mixture of 5% methanol/dichloromethane as an eluent to get the desired compound as a yellow liquid (200 mg, 35%). ¹H NMR (400 MHz, DMSO-d₆) δ 7.58 (s, 1H), 7.07 (s, 1H), 6.90 (s, 1H), 5.48 (s, 1H), 4.57 (s, 2H), 3.80 (s, 2H), 3.37 (t, J=5.6 Hz, 2H), 1.90-1.82 (m, 2H), 1.39 (s, 9H).

Step-(ii)

Synthesis of 4-((1H-imidazol-1-yl)methyl)-1,2,3,6-tetrahydropyridine trifluoro acetic acid (99b)

The process of this step was adopted from step-(i) of compound-1. The resultant liquid was directly used to next reaction without characterization (150 mg, 71%).

Step-(iii)

Preparation of Compound-99: Synthesis of (E)-6-(3-(4-((1H-imidazol-1-yl)methyl)-5,6-dihydropyridin-1(2H)-yl)-3-oxoprop-1-en-1-yl)-3,4-dihydro-1,8-naphthyridin-2(1H)-one The process of this step was adopted from step-(ii) of compound-1. The desired compound-99 obtained as an off-white solid (15 mg, 7%). ¹H NMR (400 MHz, DMSO-d₆) δ 10.64 (s, 1H), 8.34 (d, J=1.9 Hz, 1H), 8.07 (d, J=6.9 Hz, 1H), 7.61 (s, 1H), 7.44 (d, J=15.2 Hz, 1H), 7.27-7.19 (m, 1H), 7.10 (s, 1H), 6.91 (s, 1H), 5.55-5.52 (m, 1H), 4.58 (s, 2H), 4.23-4.21 (m, 1H), 4.04-3.98 (m, 1H), 3.76-3.74 (m, 1H), 3.64-3.62 (m, 1H), 2.91 (t, J=7.5 Hz, 2H), 2.55-2.51 (m, 2H), 2.02-1.94 (m, 2H); MS (ES) m/e 364.0 (M−H).

The compounds prepared by following the process according to compound 99 and their physicochemical characteristics are summarized here in below in the Table-V.

TABLE-V

| Comp No | R₆ | ¹H NMR (400 MHz, DMSO-d₆); δ (ppm) and MS (ES) m/e |
|---|---|---|
| 100 | 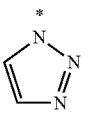 | 10.63 (s, 1H), 8.34 (d, J = 1.9 Hz, 1H), 8.08 (s, 1H), 7.70 (d, J = 1.9 Hz, 1H), 7.46-7.42 (m, 2H), 7.27-7.23 (m, 1H), 6.26 (d, J = 1.9 Hz, 1H), 5.53-5.49 (m, 1H), 4.72 (s, 2H), 4.22-4.20 (m, 1H), 4.04-4.02 (m, 1H), 3.74-3.72 (m, 1H), 3.62-3.60 (m, 1H), 2.91 (t, J = 7.04 Hz, 2H), 2.53-2.52 (m, 2H), 1.99-1.93 (m, 2H); MS (ES) m/e 364.3 (M + H)⁺. |
| 101 | 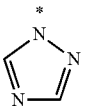 | 10.64 (s, 1H), 8.34 (d, J = 1.4 Hz, 1H), 8.09-8.08 (m, 2H), 7.75 (s, 1H), 7.45 (d, J = 15.7 Hz, 1H), 7.27-7.19 (m, 1H), 5.62 (d, J = 11.8 Hz, 1H), 5.02 (s, 2H), 4.24 and 4.05 (rotamer and s, 2H), 3.75 and 3.63 (rotamer and s, 2H), 2.90 (t, J = 7.8 Hz, 2H), 2.55-2.53 (m, 2H), 2.02 and 1.96 (rotamer and s, 2H); MS (ES) m/e 365.1 (M + H)⁺. |
| 102 | 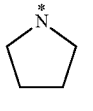 | 10.64 (s, 1H), 8.53 (s, 1H), 8.34 (d, J = 1.9 Hz, 1H), 8.07 (d, J = 6.9 Hz, 1H), 7.98 (s, 1H), 7.45 (d, J = 15.7 Hz, 1H), 7.27-7.15 (m, 1H), 5.62-5.60 (m, 1H), 4.80 (s, 2H), 4.24-4.22 (m, 1H), 4.05-4.03 (m, 1H), 3.75-3.73 (m, 1H), 3.63-3.61 (m, 1H), 2.91 (t, J = 7.5 Hz, 2H), 2.55-2.52 (m, 2H), 2.08-2.01 (m, 2H); MS (ES) m/e 365.1 (M + H)⁺. |
| 103 | 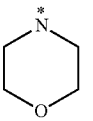 | 10.65 (s, 1H), 8.36 (s, 1H), 8.11 (d, J = 14.6 Hz, 1H), 7.48 (d, J = 15.2 Hz, 1H), 7.32-7.17 (m, 1H), 6.00 (s, 1H), 4.30-4.28 (m, 1H), 4.11-4.09 (m, 1H), 3.83-3.81 (m, 1H), 3.77 (s, 2H), 3.69-3.67 (m, 1H), 3.47-3.45 (m, 2H), 3.03-2.98 (m, 2H), 2.91 (t, J = 7.5 Hz, 2H), 2.57-2.53 (m, 2H), 2.26-2.22 (m, 2H), 2.19-2.01 (m, 2H), 1.97-1.83 (m, 2H); MS (ES) m/e 367.4 (M + H)⁺. |
| 104 |  | 10.63 (s, 1H), 8.34 (s, 1H), 8.07 (d, J = 11.7 Hz, 1H), 7.45 (d, J = 15.1 Hz, 1H), 7.30-7.18 (m, 1H), 5.64-5.62 (m, 1H), 4.21-4.19 (m, 1H), 4.03-4.01 (m, 1H), 3.76-3.74 (m, 1H), 3.65-3.63 (m, 1H), 3.56 (t, J = 4.4 Hz, 4H), 2.92 (t, J = 7.5 Hz, 2H), 2.85 (s, 2H), 2.55-2.52 (m, 2H), 2.28 (s, 4H), 2.08-1.91 (m, 2H); MS (ES) m/e 383.4 (M + H)⁺. |

Note:
* Bonding position of R₆.

Preparation of Compound-106

Synthesis of (E)-6-(3-oxo-3-(4-(phenylethynyl)-5,6-dihydropyridin-1(2H)-yl)prop-1-en-1-yl)-3,4-dihydro-1,8-naphthyridin-2(1H)-one

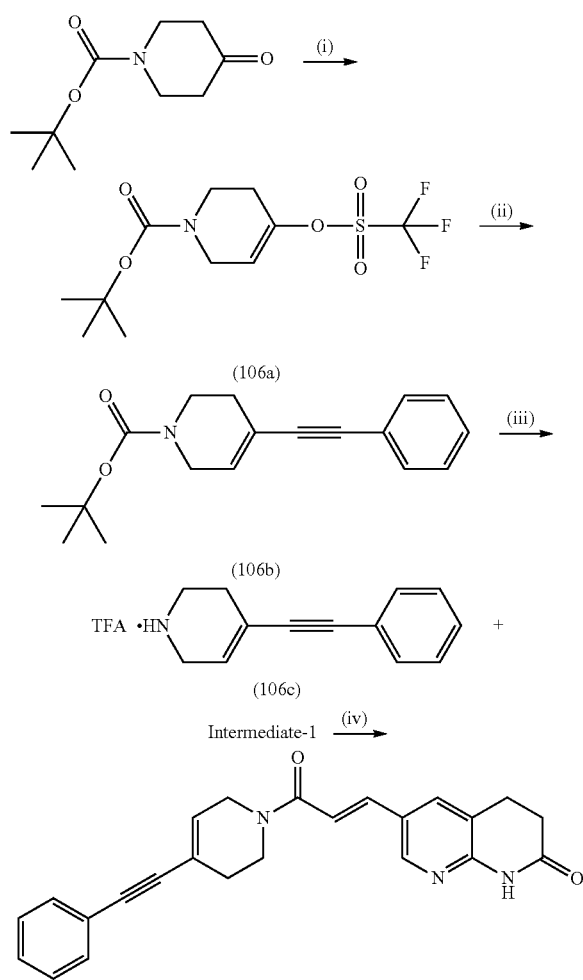

Compound-106

(i) LiHMDS, N-Phenyl-bis(trifluoromethanesulfonimide), THF, -78° C. to 20-35° C., 16 h; (ii) Triethylamine, Pd(PPh₃)₂Cl₂, CuI, Acetonitrile, 90° C., 16 h; (iii) TFA, DCM, 20-35° C., 3 h; (iv) HOBt, EDC·HCl, DIPEA, DMF, 20-35° C., 16 h.
(Ref. for step-(i): Bioorg. Med. Chem. Letters, 18, 4993-4996, 2008)

Step-(ii)

Synthesis of tert-butyl 4-(phenylethynyl)-5,6-dihydropyridine-1(2H)-carboxylate (106b)

To a stirred solution of 106a (200 mg, 0.60 mmol), phenyl acetylene (70 mg, 0.66 mmol), CuI (11 mg, 0.06 mmol) and triethylamine (0.25 ml, 1.81 mmol) in dimethylformamide (2 ml) was added Pd(PPh₃)₂Cl₂ (21 mg, 0.03 mmol) and the mixture was degassed with nitrogen for 1.5 minutes and then heated at 90° C. for 16 h. The progress of the reaction was monitored by TLC. After 16 h, the mixture was cooled to 20-35° C., filtered through celite and concentrated. The resultant residue was diluted with water (50 ml) and extracted with ethyl acetate (2×50 ml). The combined organic layers were washed with brine (50 ml), dried over anhydrous Na₂SO₄ and evaporated. The crude compound was purified by column chromatography using a mixture of 10% ethyl acetate/pet-ether as an eluent to get the desired compound as a yellow solid (150 mg, 88%). $^1$H NMR (400 MHz, DMSO-d₆) δ 7.45-7.41 (m, 2H), 7.39-7.24 (m, 3H), 6.18 (s, 1H), 3.95 (s, 2H), 3.45 (d, J=5.6 Hz, 2H), 2.28-2.24 (m, 2H), 1.42 (s, 9H).

Step-(iii)

Synthesis of 4-(phenylethynyl)-1,2,3,6-tetrahydropyridine trifluoro acetic acid (106c)

The process of this step was adopted from step-(i) of compound-1. The desired compound obtained as a pale brown solid (150 mg, 95%). $^1$H NMR (400 MHz, DMSO-d₆) δ 9.06-8.96 (m, 2H), 7.52-7.43 (m, 2H), 7.42-7.38 (m, 3H), 6.19 (dd, J=3.4, 1.9 Hz, 1H), 3.73 (d, J=2.0 Hz, 2H), 3.25 (d, J=5.4 Hz, 2H), 2.49-2.45 (m, 2H); MS (ES) m/e 183.8 (M-CF₃COOH)⁺.

Step-(iv) Preparation of Compound-106

Synthesis of (E)-6-(3-oxo-3-(4-(phenyl ethynyl)-5,6-dihydropyridin-1(2H)-yl)prop-1-en-1-yl)-3,4-dihydro-1,8-naphthyridin-2(1H)-one The process of this step was adopted from step-(ii) of compound-1. The desired compound-106 obtained as a brown solid (16 mg, 8%). $^1$H NMR (400 MHz, DMSO-d₆) δ 10.65 (s, 1H), 8.36 (d, J=1.9 Hz, 1H), 8.10 (d, J=8.7 Hz, 1H), 7.48 (d, J=15.6 Hz, 1H), 7.47-7.42 (m, 2H), 7.41-7.36 (m, 3H), 7.33-7.28 (m, 1H), 6.28-6.23 (m, 1H), 4.44-4.36 (m, 1H), 4.26-4.16 (m, 1H), 3.90-3.81 (m, 1H), 3.78-3.68 (m, 1H), 2.92 (t, J=7.8 Hz, 2H), 2.54 (t, J=7.8 Hz, 2H), 2.42-2.34 (m, 1H), 2.33-2.26 (m, 1H); MS (ES) m/e 384.3 (M+H)⁺.

Preparation of Compound-107

Synthesis of (E)-6-(3-oxo-3-(4-(phenoxymethyl)-5,6-dihydropyridin-1(2H)-yl)prop-1-en-1-yl)-3,4-dihydro-1,8-naphthyridin-2(1H)-one

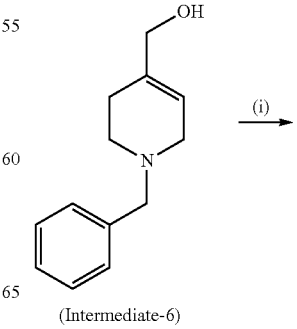

(Intermediate-6)

115
-continued

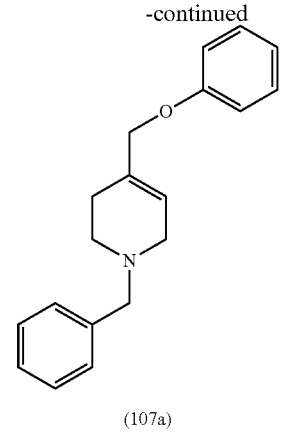

(107a)

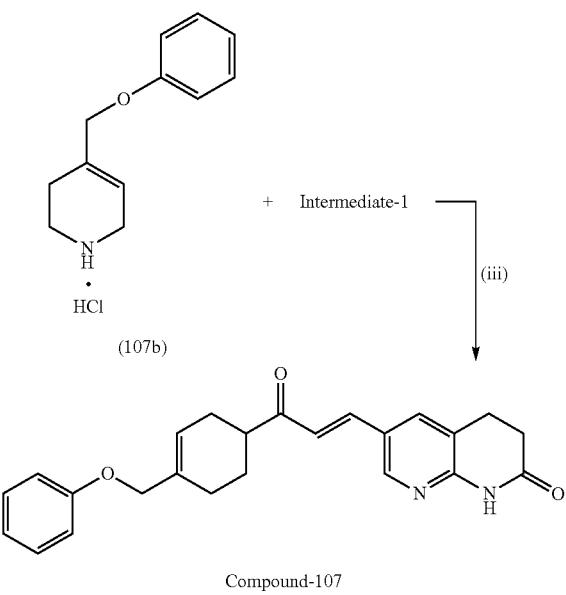

(107b)

Compound-107

(i) Phenol, PPh₃, DEAD, THF, 20-35° C., 16 h;
(ii) 1-Chloroethyl chloroformate, DCM, 20-35° C., 3 h, then MeOH, 70-80° C., 1 h;
(iii) HOBt, EDC·HCl, DIPEA, DMF, 20-35° C., 16 h.
(Ref. for Step-(i): WO2006092731)

116

Step-(ii)

Synthesis of 4-(phenoxymethyl)-1,2,3,6-tetrahydropyridine hydrochloride (107b)

To a stirred solution of 107a (400 mg, 1.43 mmol) in DCM (10 ml) was added 1-chloroethyl chloroformate (1.02 g, 7.16 mmol) at 0° C. and the reaction mixture was stirred at 20-35° C. for 3 h. The progress of the reaction was monitored by TLC. After 3 h, the reaction mixture was diluted with dichloromethane (50 ml) and washed with water (50 ml), followed by brine (50 ml), dried over anhydrous Na₂SO₄ and evaporated. The resultant crude residue dissolved in methanol (10 ml) and stirred at 70-80° C. for 1 h. The progress of the reaction was monitored by TLC. After 1 h, the reaction mixture was concentrated under vacuum, washed with diethyl ether to get the desired compound as a brown solid (200 mg, quantitative) and was used to next reaction without characterization.

Step-(iii) Preparation of Compound-107

Synthesis of (E)-6-(3-oxo-3-(4-(phenoxy methyl)-5,6-dihydropyridin-1(2H)-yl)prop-1-en-1-yl)-3,4-dihydro-1,8-naphthyridin-2(1H)-one The process of this step was adopted from step-(ii) of compound-1. The desired compound-107 obtained as an off-white solid (30 mg, 12%). ¹H NMR (400 MHz, DMSO-d₆) 10.64 (s, 1H), 8.35 (s, 1H), 8.09 (d, J=16.6 Hz, 1H), 7.46 (d, J=15.2 Hz, 1H), 7.34-7.16 (m, 3H), 6.98-6.90 (m, 3H), 5.86 (s, 1H), 4.49 (s, 2H), 4.32-4.24 (m, 1H), 4.10-4.02 (m, 1H), 3.85-3.79 (m, 1H), 3.72-3.66 (m, 1H), 2.91 (t, J=7.3 Hz, 2H), 2.56-2.52 (m, 2H), 2.35-2.31 (m, 1H), 2.24-2.16 (m, 1H).

The compounds prepared by following the process according to compound 107 and their physicochemical characteristics are summarized here in below in the Table-VI.

TABLE-VI

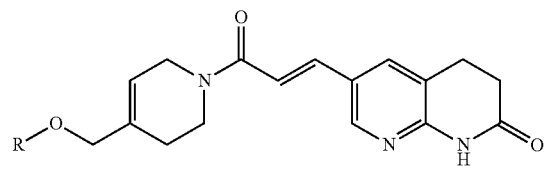

| Comp No | R | ¹H NMR (400 MHz, DMSO-d₆); δ (ppm) and MS (ES) m/e |
|---|---|---|
| 108 | *-C₆H₄-F (2-fluorophenyl) | 10.63 (s, 1H), 8.34 (s, 1H), 8.09 (s, 1H), 7.50-6.80 (m, 6H), 5.86 (s, 1H), 4.56 (s, 2H), 4.25 and 4.06 (rotamer and s, 2H), 3.79 and 3.68 (rotamer and s, 2H), 2.89 (s, 2H), 2.60-2.50 (m, 2H), 2.23 and 2.16 (rotamer and s, 2H); MS (ES) m/e 408.2 (M + H)⁺. |
| 109 | *-C₆H₄-F (3-fluorophenyl) | 10.64 (s, 1H), 8.35 (s, 1H), 8.09 (d, J = 16.1 Hz, 1H), 7.47 (d, J = 15.2 Hz, 1H), 7.45-7.28 (m, 2H), 6.86-6.72 (m, 3H), 5.87 (s, 1H), 4.52 (s, 2H), 4.26 and 4.08 (rotamer and s, 2H), 3.81 and 3.69 (rotamer and s, 2H), 2.93-2.89 (m, 2H), 2.56-2.54 (m, 2H), 2.23 and 2.16 (rotamer and s, 2H); MS (ES) m/e 406.3 (M +H )⁺. |

TABLE-VI-continued

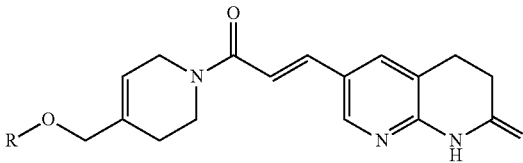

| Comp No | R | $^1$H NMR (400 MHz, DMSO-d$_6$); δ (ppm) and MS (ES) m/e |
|---|---|---|
| 110 |  | 10.64 (s, 1H), 8.35 (s, 1H), 8.09 (d, J = 16.6 Hz, 1H), 7.47 (d, J = 15.1 Hz, 1H), 7.13-7.08 (m, 3H), 6.99-6.95 (m, 2H), 5.85 (s, 1H), 4.47 (s, 2H), 4.25 and 4.07 (rotamer and s, 2H), 3.81 and 3.68 (rotamer and s, 2H), 2.93-2.89 (m, 2H), 2.67-2.54 (m, 2H), 2.23 and 2.15 (rotamer and s, 2H); MS (ES) m/e 406.4 (M + H)$^+$. |
| 111 | 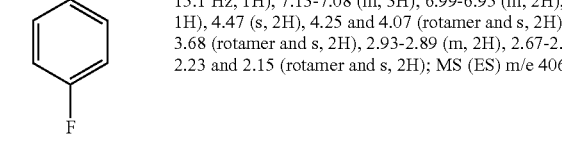 | 10.64 (s, 1H), 8.35 (s, 1H), 8.09 (d, J = 16.7 Hz, 1H), 7.49-7.41 (m, 2H), 7.32-7.22 (m, 2H), 7.17 (d, J = 7.3 Hz, 1H), 6.98-6.94 (m, 1H), 5.89 (s, 1H), 4.60 (s, 2H), 4.27 and 4.09 (rotamer and s, 2H), 3.82 and 3.70 (rotamer and s, 2H), 2.93-2.89 (m, 2H), 2.55-2.51 (m, 2H), 2.27 and 2.18 (rotamer and s, 2H); MS (ES) m/e 422.3 (M + H)$^+$ |
| 112 |  | 10.64 (s, 1H), 8.35 (s, 1H), 8.09 (d, J = 16.6 Hz, 1H), 7.47 (d, J = 15.7 Hz, 1H), 7.30 (t, J = 7.8 Hz, 2H), 7.06-6.93 (m, 3H), 5.87 (s, 1H), 4.53 (s, 2H), 4.26 and 4.08 (rotamer and s, 2H), 3.81 and 3.69 (rotamer and s, 2H), 2.91 (t, J = 7.8 Hz, 2H), 2.55-2.51 (m, 2H), 2.23 and 2.16 (rotamer and s, 2H); MS (ES) m/e 424.3 (M + H)$^+$. |
| 113 | 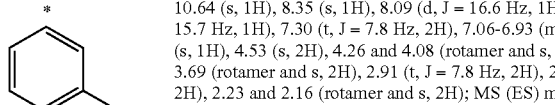 | 10.64 (s, 1H), 8.35 (s, 1H), 8.11-8.07 (m, 1H), 7.46 (d, J = 15.1 Hz, 1H), 7.34-7.27 (m, 3H), 7.01-6.97 (m, 2H), 5.85 (s, 1H), 4.49 (s, 2H), 4.25 and 4.07 (rotamer and s, 2H), 3.80 and 3.68 (rotamer and s, 2H), 2.93-2.89 (m, 2H), 2.55-2.51 (m, 2H), 2.23 and 2.15 (rotamer and s, 2H); MS (ES) m/e 422.3 (M + H)$^+$. |
| 114 |  | 10.64 (s, 1H), 8.35 (s, 1H), 8.11-8.07 (m, 1H), 7.47 (d, J = 15.2 Hz, 1H), 7.32-7.15 (m, 1H), 6.99-6.83 (m, 4H), 5.84 (s, 1H), 4.47 (s, 2H), 4.25 and 4.07 (rotamer and s, 2H), 3.81 and 3.72 (rotamer and s, 2H), 3.75 (s, 3H), 2.92 (t, J = 7.3 Hz, 2H), 2.60-2.40 (m, 2H), 2.25 and 2.17 (rotamer and s, 2H); MS (ES) m/e 418.3 (M + H)$^+$. |
| 115 | 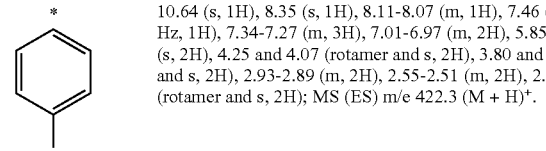 | 10.63 (s, 1H), 8.35 (s, 1H), 8.09 (d, J = 16.1 Hz, 1H), 7.46 (d, J = 15.1 Hz, 1H), 7.31-7.15 (m, 1H), 6.90-6.83 (m, 4H), 5.84-5.82 (m, 1H), 4.42 (s, 2H), 4.25-4.23 (m, 1H), 4.07-4.05 (m, 1H), 3.78 (d, J = 14.7 Hz, 2H), 3.69 (s, 3H), 2.91 (t, J = 7.5 Hz, 2H), 2.67-2.53 (m, 2H), 2.28-1.98 (m, 2H); MS (ES) m/e 418.3 (M + H)$^+$. |
| 116 |  | 10.64 (s, 1H), 8.35 (s, 1H), 8.08 (d, J = 16.6 Hz, 1H), 7.47 (d, J = 15.7 Hz, 1H), 7.49-7.28 (m, 3H), 7.08-7.04 (m, 2H), 5.87-5.85 (m, 1H), 4.52 (s, 2H), 4.27-4.25 (m, 1H), 4.09-4.07 (m, 1H), 3.82-3.80 (m, 1H), 3.70-3.68 (m, 1H), 2.91 (t, J = 7.5 Hz, 2H), 2.67-2.65 (m, 2H), 2.24-2.16 (m, 2H); MS (ES) m/e 474.3 (M+ H)$^+$. |
| 117 | 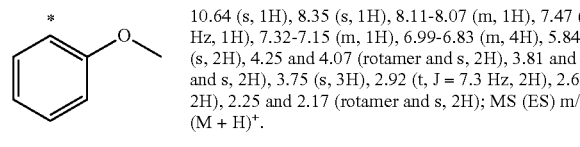 | 10.64 (s, 1H), 8.35 (s, 1H), 8.09 (d, J = 17.1 Hz, 1H), 7.46 (d, J = 15.6 Hz, 1H), 7.32-7.17 (m, 1H), 6.85-6.78 (m, 2H), 6.64 (d, J = 6.8 Hz, 1H), 5.81 (s, 1H), 4.42 (s, 2H), 4.24 and 4.06 (rotamer and s, 2H), 3.78 and 3.68. (rotamer and s, 2H), 3.74 (s, 3H), 2.91 (t, J = 7.4 Hz, 2H), 2.55-2.51 (m, 2H), 2.23 (s, 3H), 2.20 and 2.15 (rotamer and s, 2H); MS (ES) m/e 434.4 (M + H)$^+$. |

TABLE-VI-continued

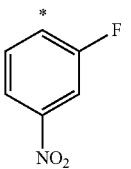

| Comp No | R | ¹H NMR (400 MHz, DMSO-d$_6$); δ (ppm) and MS (ES) m/e |
|---|---|---|
| 118 | 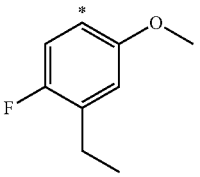 | 10.64 (s, 1H), 8.35 (s, 1H), 8.19-8.10 (m, 3H), 7.49-7.31 (m, 3H), 5.93 (s, 1H), 4.77 (s, 2H), 4.30 and 4.10 (rotamer and s, 2H), 3.82 and 3.70 (rotamer and s, 2H), 2.93-2.89 (m, 2H), 2.56-2.50 (m, 2H), 2.27 and 2.25 (rotamer and s, 2H); MS (ES) m/e 451.7 (M + H)⁺. |
| 119 | 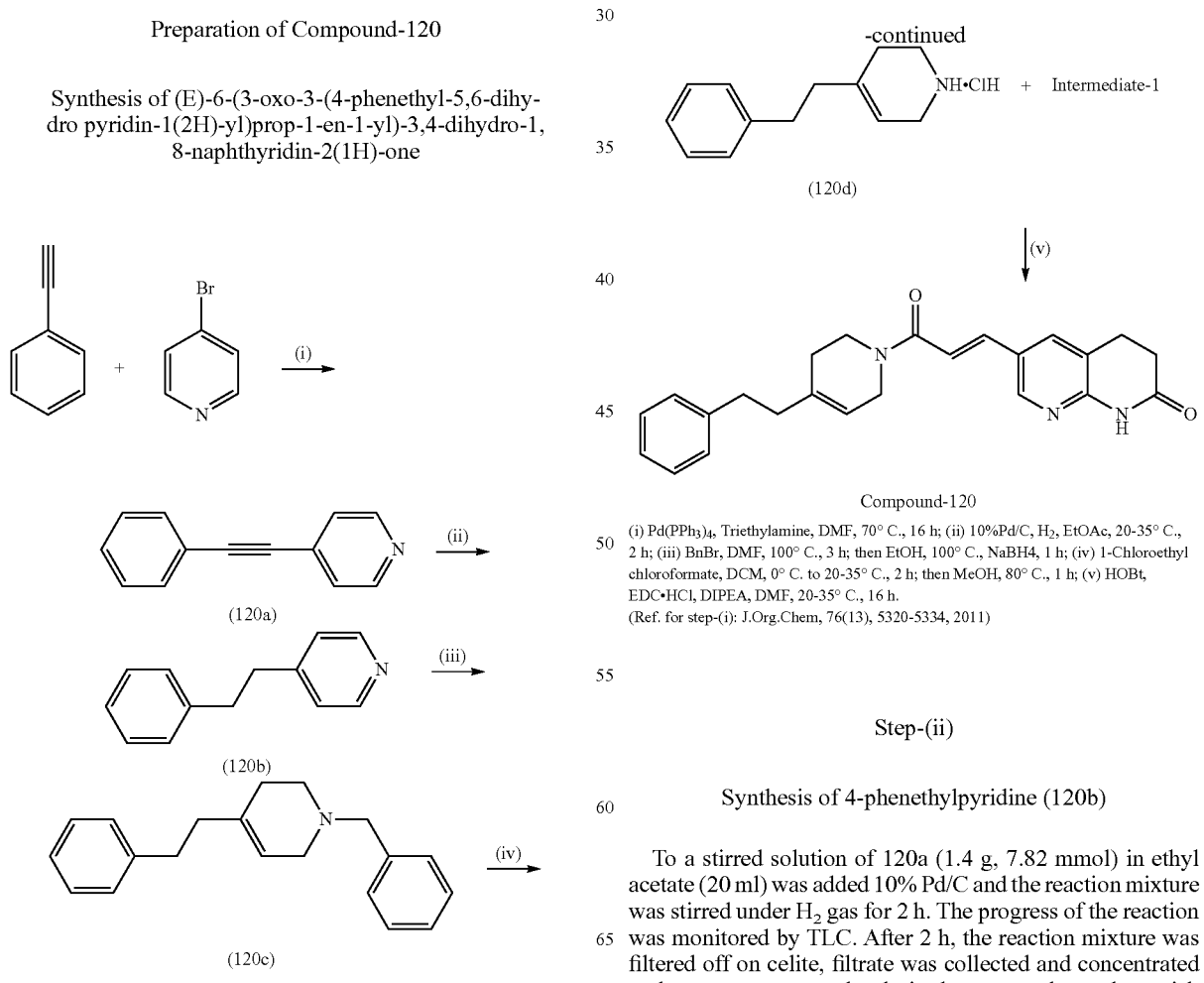 | 10.64 (s, 1H), 8.35 (s, 1H), 8.10 (d, J = 17.1 Hz, 1H), 7.46 (d, J = 15.1 Hz, 1H), 7.32-7.17 (m, 1H), 6.86-6.84 (m, 2H), 5.86-5.82 (m, 1H), 4.46 (s, 2H), 4.26-4.22 (m, 1H), 4.08-4.04 (m, 1H), 3.81-3.79 (m, 1H), 3.74 (s, 3H), 3.69-3.67 (m, 1H), 2.91 (t, J = 7.1 Hz, 2H), 2.56-2.52 (m, 4H), 2.21-1.98 (m, 2H), 1.14 (t, J = 7.2 Hz, 3H); MS (ES) m/e 466.4 (M + H)⁺. |

Note:
* Bonding position of R.

Preparation of Compound-120

Synthesis of (E)-6-(3-oxo-3-(4-phenethyl-5,6-dihydro pyridin-1(2H)-yl)prop-1-en-1-yl)-3,4-dihydro-1,8-naphthyridin-2(1H)-one Compound-120

(i) Pd(PPh$_3$)$_4$, Triethylamine, DMF, 70° C., 16 h; (ii) 10%Pd/C, H$_2$, EtOAc, 20-35° C., 2 h; (iii) BnBr, DMF, 100° C., 3 h; then EtOH, 100° C., NaBH4, 1 h; (iv) 1-Chloroethyl chloroformate, DCM, 0° C. to 20-35° C., 2 h; then MeOH, 80° C., 1 h; (v) HOBt, EDC•HCl, DIPEA, DMF, 20-35° C., 16 h.
(Ref. for step-(i): J.Org.Chem, 76(13), 5320-5334, 2011)

Step-(ii)

Synthesis of 4-phenethylpyridine (120b)

To a stirred solution of 120a (1.4 g, 7.82 mmol) in ethyl acetate (20 ml) was added 10% Pd/C and the reaction mixture was stirred under H$_2$ gas for 2 h. The progress of the reaction was monitored by TLC. After 2 h, the reaction mixture was filtered off on celite, filtrate was collected and concentrated under vacuum to get the desired compound as a brownish waxy solid (500 mg, 35%). ¹H NMR (400 MHz, DMSO-d₆) δ 8.43 (d, J=5.9 Hz, 2H), 7.30-7.15 (m, 7H), 2.90 (s, 4H); MS (ES) m/e 184.0 (M+H)⁺.

Step-(iii)

Synthesis of 1-benzyl-4-phenethyl-1,2,3,6-tetrahydropyridine (120c)

To a stirred solution of 120b (500 mg, 2.73 mmol) in DMF (5 ml) was added benzyl bromide (810 mg, 4.05 mmol) at 20-35° C. and the reaction mixture was stirred at 100° C. for 3 h. After 3 h, the reaction mixture was cooled to 20-35° C., diluted with ethanol (10 ml) and NaBH₄ (110 mg, 2.97 mmol) was added slowly portion wise at 0° C., then heated at 100° C. for 1 h. The progress of the reaction was monitored by TLC. The reaction mixture was quenched with NaOH solution at 20-35° C., excess ethanol was removed under vacuum and resultant residue was diluted with ethyl acetate (50 ml). The organic layer was washed with water (50 ml), brine (50 ml), dried over anhydrous Na₂SO₄ and evaporated. The crude compound was triturated with pet ether to get the desired compound as a yellow sticky solid (440 mg, 58%). ¹H NMR (400 MHz, DMSO-d₆) δ 7.56-7.43 (m, 5H), 7.38-7.7.28 (m, 2H), 7.27-7.20 (m, 2H), 7.19-7.12 (m, 1H), 5.44 (s, 1H), 4.61 (d, J=12.7 Hz, 1H), 4.41 (d, J=12.7 Hz, 1H), 3.62-3.56 (m, 2H), 3.39 (t, J=6.1 Hz, 2H), 2.79 (t, J=7.6 Hz, 2H), 2.62-2.52 (m, 2H), 2.41 (t, J=7.6 Hz, 2H).

Step-(iv)

Synthesis of 4-phenethyl-1,2,3,6-tetrahydropyridine-hydrochloride (120d)

The process of this step was adopted from step-(ii) of compound-107. The desired compound obtained as a yellow solid (297 mg, quantitative) and was used to next reaction without characterization.

Step-(v) Preparation of Compound-120

Synthesis of (E)-6-(3:oxo-3-(4-phenethyl-5,6-dihydropyridin-1(2H)-yl)prop-1-en-1-yl)-3,4-dihydro-1,8-naphthyridin-2(1H)-one The process of this step was adopted from step-(ii) of compound-1. The desired compound-120 obtained as a pale yellow solid (15 mg, 6%). ¹H NMR (400 MHz, DMSO-d₆) δ 10.64 (s, 1H), 8.35 (s, 1H), 8.08 (d, J=14.6 Hz, 1H), 7.40 (d, J=15.1 Hz, 2H), 7.36-7.10 (m, 5H), 5.45 (s, 1H), 4.16 and 3.98 (rotamer and s, 2H), 3.76 and 3.64 (rotamer and s, 2H), 2.96-2.80 (m, 2H), 2.76-2.60 (m, 2H), 2.58-2.50 (m, 2H), 2.40-2.20 (m, 2H), 2.15 and 2.09 (rotamer and s, 2H); MS (ES) m/e 388.3 (M+H)⁺.

Preparation of Compound-121 Synthesis of (E)-6-(3-(3,4-dihydroisoquinolin-2(1H)-yl)-3-oxoprop-1-en-1-yl)-3,4-dihydro-1,8-naphthyridin-2(1H)-one

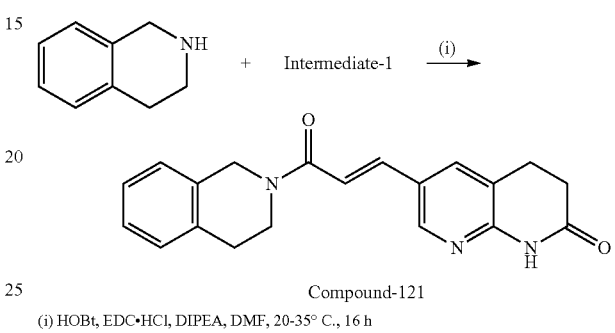

Compound-121
(i) HOBt, EDC•HCl, DIPEA, DMF, 20-35° C., 16 h

Step-(i)

The process of this step was adopted from step-(ii) of compound-1. The desired compound obtained as a white solid (50 mg, 33%).

¹H NMR (400 MHz, DMSO-d₆) δ 10.65 (s, 1H), 8.37 (s, 1H), 8.16-8.12 (m, 1H), 7.50 (d, J=15.2 Hz, 1H), 7.33 (d, J=15.1 Hz, 1H), 7.25-7.17 (m, 4H), 4.95-4.90 (m, 1H), 4.78-4.71 (m, 1H), 3.98-3.92 (m, 1H), 3.80-3.74 (m, 1H), 2.95-2.88 (m, 3H), 2.87-2.82 (m, 1H), 2.56-2.52 (m, 2H); MS (ES) m/e 334.1 (M+H)⁺.

Compounds 122-125 were prepared by the following methodologies adopted similar to described above for the Compound 121.

The compounds prepared by following the process according to compound 121 and their physicochemical characteristics are summarized herein below in the Table-VII.

TABLE-VII

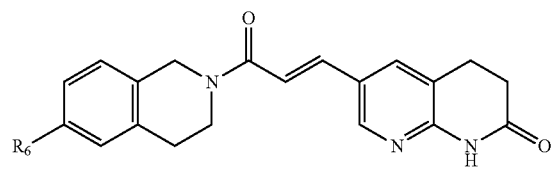

| Comp No | R₆ | ¹H NMR (400 MHz, DMSO-d₆); δ (ppm) and MS (ES) m/e |
|---|---|---|
| 122 | —Br | 10.65 (s, 1H), 8.37 (s, 1H), 8.10 (d, J = 14.7 Hz, 1H), 7.50 (d, J = 15.1 Hz, 1H), 7.43 (s, 1H), 7.38 (d, J = 8.8 Hz, 1H), 7.31 (d, J = 15.2 Hz, 1H), 7.24-7.18 (m, 1H), 4.92-4.84 (m, 1H), 4.72-4.66 (m, 1H), 3.96-3.90 (m, 1H), 3.80-3.72 (m, 1H), 2.96-2.90 (m, 3H), 2.89-2.82 (m, 1H), 2.56-2.52 (m, 2H); MS (ES) m/e 412.1 (M + H)⁺. |
| 123 | —OCH₃ | 10.64 (s, 1H), 8.36 (d, J = 1.5 Hz, 1H), 8.12-8.10 (m, 1H), 7.49 (d, J = 15.2 Hz, 1H), 7.31 (d, J = 15.2 Hz, 1H), 7.13 (d, J = 8.8 Hz, 1H), 6.77-6.71 (m, 1H), 4.84-4.80 (m, 1H), 4.76-4.72 (m, 1H), |

TABLE-VII-continued

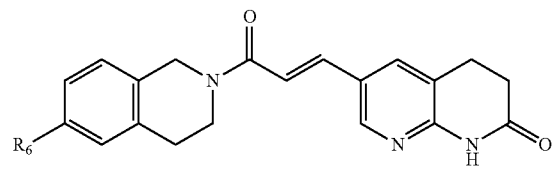

| Comp No | R_6 | $^1$H NMR (400 MHz, DMSO-$d_6$); δ (ppm) and MS (ES) m/e |
|---|---|---|
| 124 | —OH | 3.98-3.92 (m, 1H), 3.80-3.74 (m, 1H), 3.73 (s, 3H), 2.93 (t, J = 7.8 Hz, 2H), 2.91-2.87 (m, 1H), 2.87-2.79 (m, 2H), 2.56-2.52 (m, 2H); MS (ES) m/e 362.3 (M − H).<br>10.64 (s, 1H), 9.25 (s, 1H), 8.36 (d, J = 1.9 Hz, 1H), 8.10 (bs, 1H), 7.48 (d, J = 15.2 Hz, 1H), 7.29 (d, J = 15.6 Hz, 1H), 7.00 (d, J = 8.3 Hz, 1H), 6.61 (d, J = 6.4 Hz, 2H), 4.78-4.60 (m, 2H), 3.88-3.70 (m, 2H), 2.92 (t, J = 7.4 Hz, 2H), 2.2.80-2.68 (m, 2H), 2.56-2.52 (m, 2H); MS (ES) m/e 350.2 (M +H)$^+$. |
| 125 | (pyrrolidine acryloyl structure) | 10.65 (s, 1H), 8.37 (s, 1H), 8.11 (d, J = 11.8 Hz, 1H), 7.54-7.48 (m, 3H), 7.43 (d, J = 15.6 Hz, 1H), 7.33 (d, J = 15.2 Hz, 1H), 7.26 (d, J = 6.9 Hz, 1H), 6.96 (d, J = 15.6 Hz, 1H), 4.98-4.92 (m, 1H), 4.78-4.72 (m, 1H), 3.99-3.92 (m, 1H), 3.84-3.78 (m, 1H), 3.64 (t, J = 6.8 Hz, 2H), 3.39 (t, J = 6.8 Hz, 2H), 2.93 (t, J = 7.3 Hz, 2H), 2.89-2.85 (m, 2H), 2.56-2.53 (m, 2H), 1.92 (t, J = 6.8 Hz, 2H), 1.81 (t, J = 6.9 Hz, 2H); MS (ES) m/e 457.2 (M +H)$^+$. |

* Bonding position of R6.

Preparation of Compound-126

Synthesis of 6-((2-(6-bromo-3,4-dihydroisoquinolin-2(1H)-yl)-2-oxoethyl)thio)-3,4-dihydro-1,8-naphthyridin-2(1H)-one

Step-(i)

Preparation of Compound-126

The process of this step was adopted from step-(ii) of compound-1. The desired compound-126 obtained as a pale yellow sticky solid (80 mg, 44%). $^1$H NMR (400 MHz, DMSO-$d_6$) δ 10.52 (s, 1H), 8.11-8.05 (m, 1H), 7.70-7.63 (m, 1H), 7.42-7.35 (m, 2H), 7.18-7.09 (m, 1H), 4.65 and 4.54 (rotamer and s, 2H), 3.98 (d, J=10.3 Hz, 2H), 3.72-3.60 (m, 2H), 2.90-2.78 (m, 4H), 2.56-2.52 (m, 2H); MS (ES) m/e 434.0 (M+2H)$^+$.

Preparation of Compound-127

Synthesis of (E)-6-(3-(3,4-dihydroisoquinolin-2(1H)-yl)-3-oxoprop-1-en-1-yl)-3-(2-morpholinoethyl)-3,4-dihydropyrido[2,3-d]pyrimidin-2(1H)-one

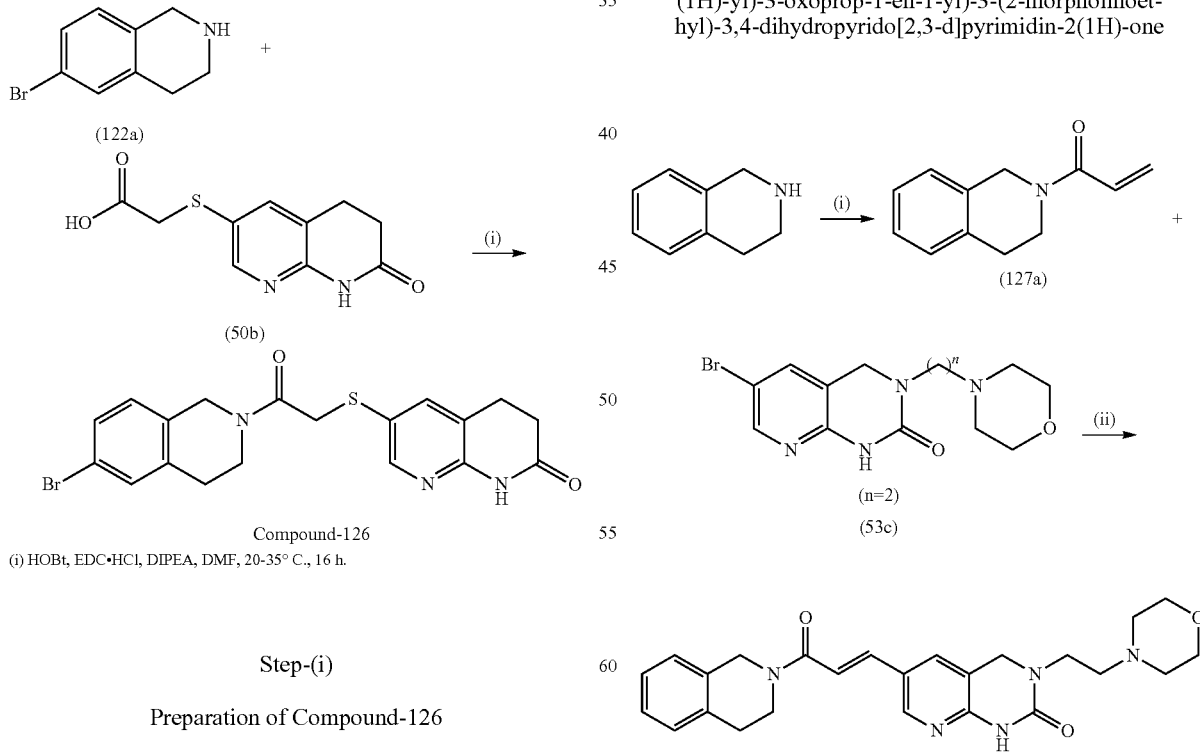

(i) HOBt, EDC•HCl, DIPEA, DMF, 20-35° C., 16 h.

(i) Acryloyl chloride, Triethylamine, CH$_2$Cl$_2$, 20-35° C., 16 h; (ii) Pd(OAc)$_2$, P(O-tolyl)$_3$, DIPEA, Propionitrile, DMF, 100° C., 16 h;

Step-(i)

Synthesis of 1-(3,4-dihydroisoquinolin-2(1H)-yl) prop-2-en-1-one (127a)

To a stirred solution of 1,2,3,4-tetrahydroisoquinoline (1 g, 7.52 mmol) in anhydrous dichloromethane (10 ml) was added triethylamine (4.17 ml, 30.00 mmol) and acryloyl chloride (0.73 ml, 9.02 mmol) at 0° C. The reaction mixture was stirred at 20-35° C. for 16 h. The progress of the reaction was monitored by TLC. After 16 h of stirring, the reaction mixture was diluted with water (50 ml) and extracted with dichloromethane (2×50 ml). The combined organic layers were washed with brine (50 ml), followed by drying over anhydrous $Na_2SO_4$ and filtering. The filtrate was rotary evaporated to get residue which was purified by column chromatography using a mixture of 40% ethyl acetate/pet ether as an eluent to get the desired compound as a pale brown liquid (800 g, 57%). $^1$H NMR (400 MHz, DMSO-$d_6$) δ 7.24-7.06 (m, 4H), 6.70-6.60 (m, 1H), 6.33 (dd, J=16.6, 1.5 Hz, 1H), 5.73 (dd, J=10.5, 1.7 Hz, 1H), 4.80 (s, 1H), 4.73 (s, 1H), 3.89 (t, J=5.8 Hz, 2H), 3.78 (t, J=5.8 Hz, 2H).

Step-(ii) Preparation of Compound-127

Synthesis of (E)-6-(3-(3,4-dihydroisoquinolin-2 (1H)-yl)-3-oxoprop-1-en-1-yl)-3-(2-morpholino ethyl)-3,4-dihydropyrido[2,3-d]pyrimidin-2(1H)-one The process of this step was adopted from step-(iv) of compound-54. The desired compound-127 obtained as an off-white solid (25 mg, 19%). $^1$H NMR (400 MHz, DMSO-$d_6$) δ 9.87 (s, 1H), 8.36 (d, J=1.5 Hz, 1H), 8.04-7.98 (m, 1H), 7.48 (d, J=15.2 Hz, 1H), 7.27 (d, J=15.6 Hz, 1H), 7.21-7.18 (m, 4H), 4.92-4.88 (m, 1H), 4.78-4.72 (m, 1H), 4.55 (s, 2H), 198-3.92 (m, 1H), 3.84-3.78 (m, 1H), 3.56 (t, J=4.4 Hz, 4H), 3.46 (t, J=6.4 Hz, 2H), 3.31-3.27 (m, 2H), 2.89-2.85 (m, 1H), 2.84-2.81 (m, 1H), 2.46-2.40 (m, 4H); MS (ES) m/e 448.2 (M+H)$^+$.

Preparation of Compound-128

Synthesis of (E)-tert-butyl 6-(3-(3,4-dihydro isoquinolin-2(1H)-yl)-3-oxoprop-1-en-1-yl)-2-oxo-2,4-dihydro-1H-spiro[[1,8]naphthyridine-3,4'-piperidine]-1'-carboxylate

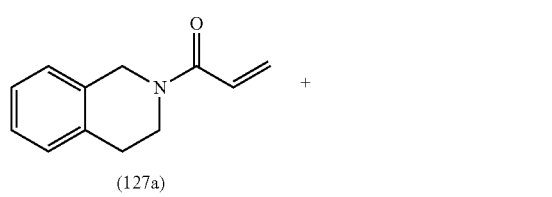

(127a)

+

(51a)

(i)

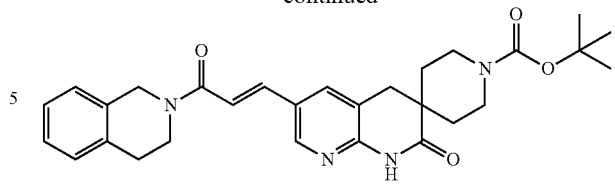

Compound-128

(i) Pd(OAc)$_2$, P(o-tolyl)$_3$, DIPEA, Propionitrile, DMF, 100° C., 16 h.

Step-(i)

The process of this step was adopted from step-(iv) of compound-54. The desired compound-128 obtained as an off-white solid (100 mg, 52%). $^1$H NMR (400 MHz, DMSO-$d_6$) δ 10.74 (s, 1H), 8.40 (s, 1H), 8.12-8.08 (m, 1H), 7.50 (d, J=15.2 Hz, 1H), 7.30 (d, J=15.6 Hz, 1H), 7.24-7.16 (m, 4H), 4.92-4.88 (m, 1H), 4.76-4.68 (m, 1H), 3.96-3.88 (m, 1H), 3.82-3.74 (m, 1H), 3.60-3.50 (m, 2H), 3.29-3.23 (m, 2H), 2.96 (s, 2H), 2.92-2.88 (m, 1H), 2.86-2.80 (m, 1H), 1.78-1.68 (m, 2H), 1.40 (s, 9H), 1.36-1.28 (m, 2H); MS (ES) m/e 503.3 (M+H)$^+$.

Preparation of Compound-129

Synthesis of (E)-6-(3-(3,4-dihydroisoquinolin-2 (1H)-yl)-3-oxoprop-1-en-1-yl)-1H-spiro[[1,8]naphthyridine-3,4'-piperidin]-2(4H)-one trifluoroacetic acid

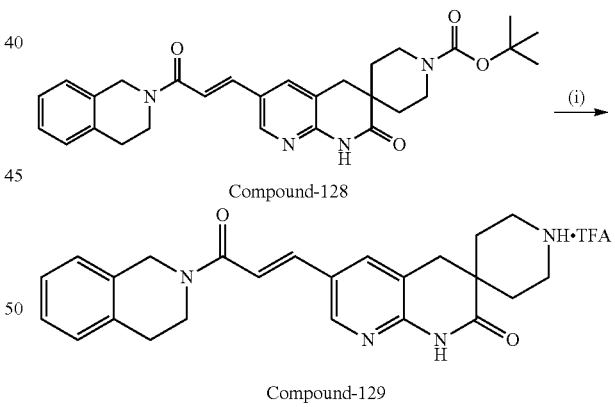

Compound-128

(i)

Compound-129

(i) TFA, CH$_2$Cl$_2$, 20-35° C., 3 h

Step-(i)

The process, of this step was adopted from step-(i) of compound-1. The desired compound-129 obtained as a pale brown solid (30 mg, 41%). $^1$H NMR (400 MHz, DMSO-$d_6$) δ 10.89 (s, 1H), 8.64-8.44 (m, 2H), 8.45 (s, 1H), 8.16-8.08 (m, 1H), 7.51 (d, J=15.2 Hz, 1H), 7.32 (d, J=15.1 Hz, 1H), 7.26-7.16 (m, 4H), 4.96-4.88 (m, 1H), 4.76-4.68 (m, 1H), 3.98-3.88 (m, 1H), 3.84-3.76 (m, 1H), 3.29-3.10 (m, 4H), 2.99 (s, 2H), 2.92-2.88 (m, 1H), 2.87-2.78 (m, 1H), 2.04-1.96 (m, 2'-1), 1.64-1.58 (m, 2H); MS (ES) m/e 403.0 (M-CF$_3$COOH)$^+$.

Preparation of Compound-130

Synthesis of (E)-7-(3-(3,4-dihydroisoquinolin-2(1H)-yl)-3-oxoprop-1-en-1-yl)-4,5-dihydro-1H-pyrido[2,3-e][1,4]diazepin-2(3H)-one

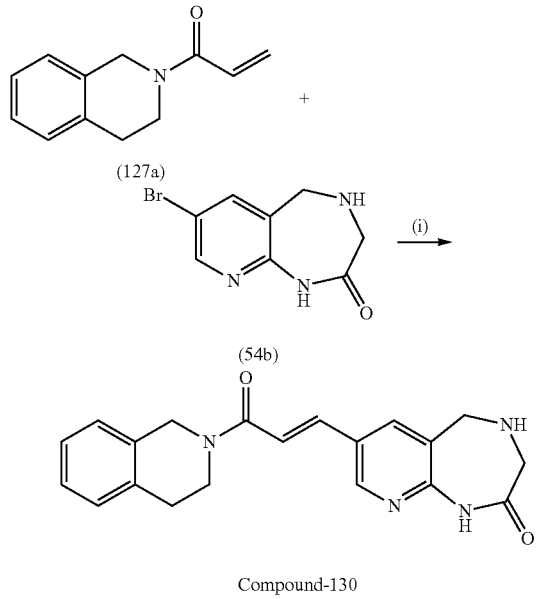

Compound-130

(i) Pd(OAc)$_2$, P(o-tolyl)$_3$, DIPEA, Propionitrile, DMF, 110° C., 16 h.

Step-(i)

The process of this step was adopted from step-(iv) of compound-54. The desired compound-130 obtained as a pale yellow solid (5 mg, 3%). $^1$H NMR (400 MHz, DMSO-d$_6$) δ 10.06 (s, 1H), 8.06 (s, 1H), 8.45 (s, 1H), 7.50 (d, J=15.1 Hz, 1H), 7.35 (d, J=15.1 Hz, 1H), 7.21-7.19 (m, 5H), 4.91-4.89 (m, 1H), 4.74-4.72 (m, 1H), 3.94-3.90 (m, 3H), 3.81-3.79 (m, 1H), 3.63 (s, 2H), 2.90-2.80 (m, 2H); MS (ES) m/e 349.1 (M+H)$^+$.

Preparation of Compound-131

Synthesis of (E)-7-(3-(3,4-dihydroisoquinolin-2(1H)-yl)-3-oxoprop-1-en-1-yl)-4-methyl-4,5-dihydro-1H-pyrido[2,3-e][1,4]diazepin-2(3H)-one

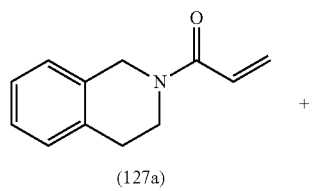

(127a)

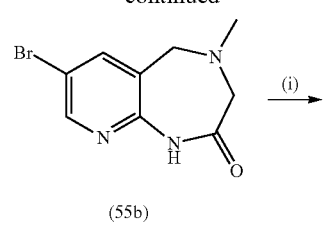

(55b)

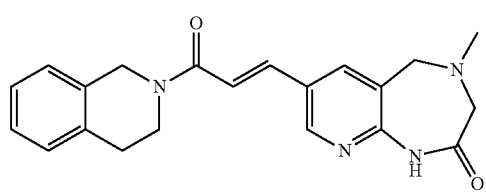

Compound-131

(i) Pd(OAc)$_2$, P(o-tolyl)$_3$, DIPEA, Propionitrile, DMF, 110° C., 16 h.

Step-(i)

The process of this step was adopted from step-(iv) of compound-54. The desired compound-131 obtained as a pale yellow solid (16 mg, 7%). $^1$H NMR (400 MHz, DMSO-d$_6$) 10:35 (s, 1H), 8.54 (d, J=1.9 Hz, 1H), 8.17 (d, J=8.8 Hz, 1H), 7.53 (d, J=15.4 Hz, 1H), 7.39 (d, J=15.4 Hz, 1H), 7.23-7.19 (m, 4H), 4.93-4.91 (m, 1H), 4.72-4.70 (m, 1H), 3.96-3.94 (m, 1H), 3.82-3.80 (m, 3H), 3.43 (s, 2H), 2.91-2.83 (m, 2H), 2.38 (s, 3H); MS (ES) m/e 363.1 (M+H)$^+$.

Preparation of Compound-132

Synthesis of (E)-7-(3-(3,4-dihydroisoquinolin-2(1H)-yl)-3-oxoprop-1-en-1-yl)-4-(2-morpholinoethyl)-4,5-dihydro-1H-pyrido[2,3-e][1,4]diazepin-2(3H)-one

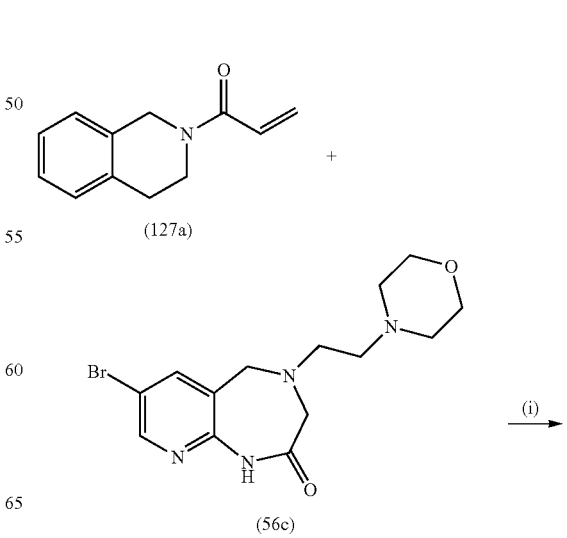

(127a)

(56c)

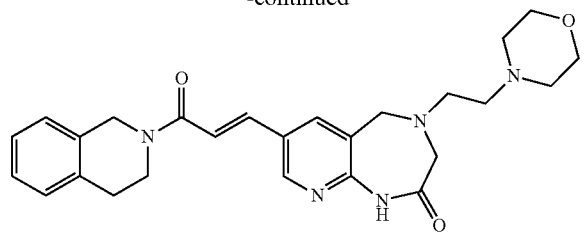

Compound-132

(i) Pd(OAc)₂, P(o-tolyl)₃, DIPEA, Propionitrile, DMF, 110° C., 16 h.

Step-(i)

The process of this step was adopted from step-(iv) of compound-54. The desired compound-132 obtained as a pale yellow solid (16 mg, 7%). $^1$H NMR (400 MHz, DMSO-d$_6$) δ 10.31 (s, 1H), 8.53 (s, 1H), 8.18 (s, 1H), 7.52 (d, J=15.1 Hz, 1H), 7.38 (d, J=15.1 Hz, 1H), 7.22-7.18 (m, 4H), 4.92-4.90 (m, 1H), 4.74-4.70 (m, 1H), 3.95-3.91 (m, 1H), 3.93 (s, 2H), 3.83-3.79 (m, 1H), 3.58 (s, 2H), 3.53 (t, J=4.1 Hz, 4H), 2.94-2.88 (m, 1H), 2.87-2.81 (m, 1H), 2.68-2.64 (m, 2H), 2.42 (t, J=6.8 Hz, 2H), 2.34-2.32 (m, 4H); MS (ES) m/e 460.3 (M–H)⁺.

Preparation of Compound-133

Synthesis of (E)-1-(5-(3-(3,4-dihydroisoquinolin-2 (1H)-yl)-3-oxoprop-1-en-1-yl)pyridin-2-yl)azetidin-2-one

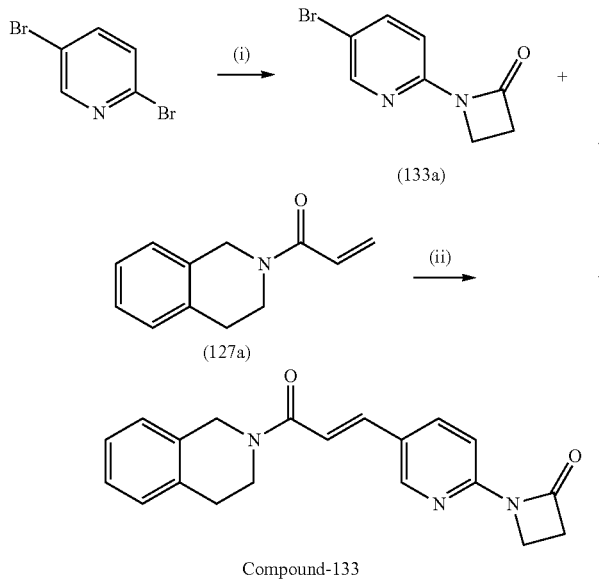

Compound-133

(i) 2-Azetidinone, Pd₂(dba)₃, Xantphos, Cs₂CO₃, Toluene, 90° C., 18 h;
(ii) Pd(OAc)₂, P(o-tolyl)₃, DIPEA, Propionitrile, DMF, 110° C., 16 h.

Step-(i)

Synthesis of 1-(5-bromopyridin-2-yl)azetidin-2-one (133a)

A solution of 2,5-dibromopyridine (500 mg, 2.10 mmol), 2-azetidinone (140 mg, 1.97 mmol) and Cs₂CO₃ (1.27 g, 3.89 mmol) in toluene (15 ml) was added Pd₂(dba)₃ (36 mg, 0.039 mmol), Xantphos (45 mg, 0.078 mmol) and the reaction mixture was purged with nitrogen for 10 minutes, then was heated at 90° C. for 18 h in seal tube. The progress of the reaction was monitored by TLC. After 18 h of stirring, the mixture was cooled to 20-35° C., filtered on celite and concentrated. The resultant residue was diluted with water (50 ml) and extracted with ethyl acetate (2×50 ml). The combined organic layers were washed with brine (50 ml), followed by drying over anhydrous Na₂SO₄ and filtering. The filtrate was rotary evaporated to get residue which was purified by column chromatography using a mixture of 50% ethyl acetate/pet ether as an eluent to get the desired compound as a creamy white solid (280 mg, 59%). $^1$H NMR (400 MHz, DMSO-d$_6$) δ 8.33 (d, J=1.9 Hz, 1H), 7.76 (dd, J=8.8, 2.5 Hz, 1H), 7.67 (d, J=8.8 Hz, 1H), 3.78 (t, J=4.9 Hz, 2H), 3.13 (t, J=4.9 Hz, 2H); MS (ES) m/e 229.0 (M+2H)⁺.

Step-(ii) Preparation of Compound-133

Synthesis of (E)-1-(5-(3-(3,4-dihydro isoquinolin-2 (1H)-yl)-3-oxoprop-1-en-1-yl)pyridin-2-yl)azetidin-2-one The process of this step was adopted from step-(iv) of compound-54. The desired compound-133 obtained as an off-white solid (40 mg, 30%). $^1$H NMR (400 MHz, DMSO-d$_6$) δ 8.61 (d, J=1.9 Hz, 1H), 8.39 (d, J=8.6 Hz, 1H), 7.61 (d, J=8.8 Hz, 1H), 7.53 (d, J=15.1 Hz, 1H), 7.37 (d, J=15.1 Hz, 1H), 7.22-7.7.17 (m, 4H), 4.92-4.88 (m, 1H), 4.72-4.70 (m, 1H), 3.94-3.88 (m, 1H), 3.82-3.76 (m, 1H), 3.73 (t, J=4.9 Hz, 2H), 3.13 (t, J=4.9 Hz, 2H), 2.94-2.88 (m, 1H), 2.86-2.82 (m, 1H); MS (ES) m/e 334.1 (M+H)⁺.

Preparation of Compound-134

Synthesis of (E)-N-(5-(3-(3,4-dihydroisoquinolin-2 (1H)-yl)-3-oxoprop-1-en-1-yl)pyridin-2-yl)-2-morpholinoacetamide

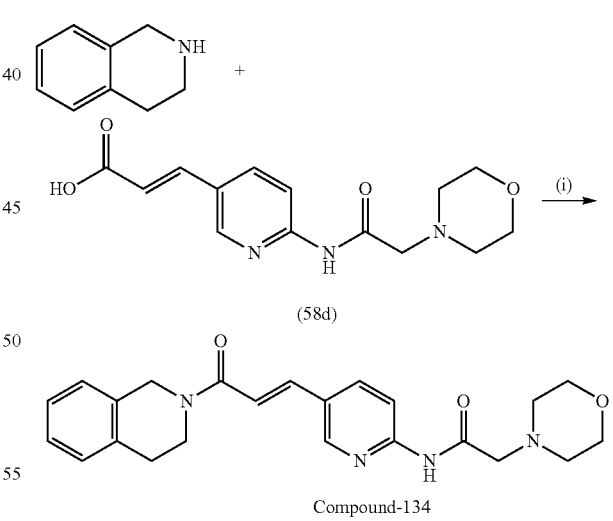

Compound-134

(i) HOBt, EDC•HCl, DIPEA, DMF, 20-35° C., 16 h

Step-(i)

The process of this step was adopted from step-(ii) of compound-1. The desired compound obtained as a white solid (50 mg, 24%).

The compound prepared by following the process according to compound 134 and their physicochemical characteristics are summarized hereinbelow in the Table-VIII.

TABLE-VIII

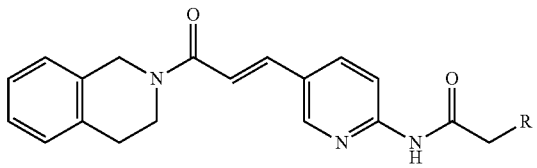

| Comp No | R | ¹HNMR (400 MHz, DMSO-D$_6$); δ (ppm) & MS (ES) m/e⁻ |
|---|---|---|
| 134 | (morpholine, *N-linked) | 10.17 (s, 1H), 8.63 (d, J = 2.7 Hz, 1H), 8.27 (d, J = 8.3 Hz, 1H), 8.12 (d, J = 8.3 Hz, 1H), 7.53 (d, J = 15.6 Hz, 1H), 7.38 (d, J = 15.6 Hz, 1H), 7.21-7.19 (m, 4H), 4.98-4.90 (m, 1H), 4.78-4.70 (m, 1H), 3.98-3.92 (m, 1H), 3.84-3.76 (m, 1H), 3.63 (t, J = 4.4 Hz, 4H), 3.22 (s, 2H), 2.98-2.88 (m, 1H), 2.88-2.80 (m, 1H), 2.55-2.52 (m, 4H); MS (ES) m/e 407.3 (M + H)⁺. |
| 135 | (imidazole, *N-linked) | 11.06 (s, 1H), 8.67 (d, J = 1.5 Hz, 1H), 8.26 (d, J = 8.4 Hz, 1H), 8.06 (d, J = 8.4 Hz, 1H), 7.63 (s, 1H), 7.52 (d, J = 15.1 Hz, 1H), 7.39 (d, J = 15.6 Hz, 1H), 7.26-7.16 (m, 5H), 6.89 (s, 1H), 4.99 (s, 2H), 4.93-4.89 (m, 1H), 4.73-4.70 (m, 1H), 3.96-3.92 (m, 1H), 3.78-3.74 (m, 1H), 2.92-2.86 (m, 1H), 2.84-2.78 (m, 1H); MS (ES) m/e 388.2 (M + H)⁺. |

Note:
* Bonding position of R.

Preparation of Compound-136

Synthesis of (E)-N-(5-(3-(3,4-dihydroisoquinolin-2(1H)-yl)-3-oxoprop-1-en-1-yl)pyridin-2-yl)-2-(1H-1,2,3-triazol-1-yl)acetamide

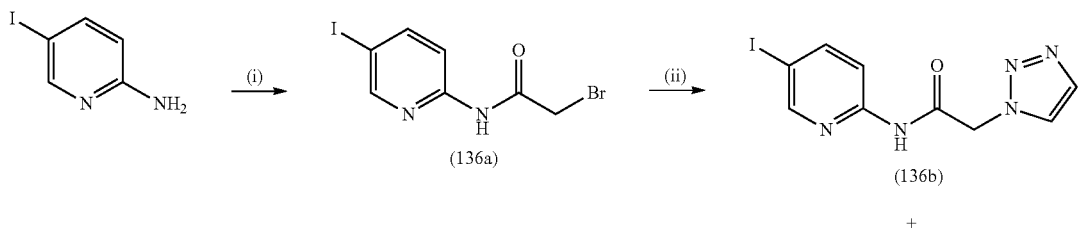

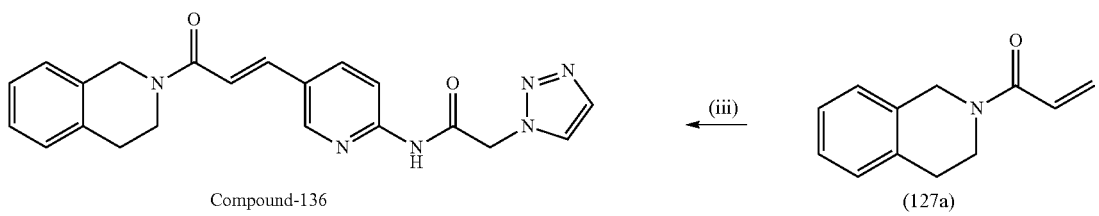

(i) Bromo acetyl bromide, DMF, 20-35° C., 16 h; (ii) 1,2,3-triazole, triethylamine, 1,4-dioxane, 90° C., 2 h; (iii) Pd(OAc)$_2$, P(o-tolyl)$_3$, DIPEA, Propionitrile, DMF, 110° C., 16 h. (Reference for Step-(i): Chemistry of Natural Compounds, 46, 1, 66-67, 2010)

Step-(ii)

Synthesis of N-(5-iodopyridin-2-yl)-2-(1H-1,2,3-triazol-1-yl)acetamide (136b)

To a stirred suspension of 136a (5.5 g, 16.17 mmol) in anhydrous 1,4-dioxane (60 ml) was added triethylamine (4.4 ml, 32.0 mmol), followed by 1,2,3-triazole (1.33 g, 19.27 mmol) and heated at 90° C. for 2 h. The progress of the reaction was monitored by TLC. After 2 h of stirring, the reaction mixture was cooled to 20-35° C., filtered and concentrated. The resultant residue was diluted with water (100 ml) and extracted with ethyl acetate (2×100 ml). The combined organic layers were washed with brine (100 ml), followed by drying over anhydrous $Na_2SO_4$ and filtering. The filtrate was rotary evaporated to get residue which was purified by column chromatography using a mixture of 40% ethyl acetate/pet ether as an eluent to get the desired compound as a white solid (1.8 g, 34%); MS (ES) m/e 203.9 (M-127)$^+$.

Step-(iii) Preparation of Compound-136

Synthesis of (E)-N-(5-(3-(3,4-dihydro isoquinolin-2 (1H)-yl)-3-oxoprop-1-en-1-yl)pyridin-2-yl)-2-(1H-1,2,3-triazol-1-yl)acetamide The process of this step was adopted from step-(iv) of compound-54. The desired compound-136 obtained as a pale yellow solid (10 mg, 6%). $^1$H NMR (400 MHz, DMSO-D6) δ 11.19 (s, 1H), 8.68 (d, J=1.9 Hz, 1H), 8.31-8.25 (m, 1H), 8.16 (s, 1H), 8.08-8.02 (m, 1H), 7.77 (s, 1H), 7.53 (d, J=15.2 Hz, 1H), 7.40 (d, J=15.6 Hz, 1H), 7.20-7.18 (m, 4H), 5.46 (s, 2H), 4.95-4.91 (m, 1H), 4.72-4.68 (m, 1H), 3.98-3.94 (m, 1H), 3.82-3.78 (m, 1H), 2.67-2.63 (m, 2H); MS (ES) m/e 389.2 (M+H)$^+$.

Preparation of Compound-137

Synthesis of (E)-tert-butyl 2-oxo-7-(3-oxo-3-(4-(thiophen-2-ylmethyl)-5,6-dihydropyridin-1(2H)-yl) prop-1-en-1-yl)-2,3-dihydro-1H-pyrido[2,3-e][1,4] diazepine-4(5H)-carboxylate

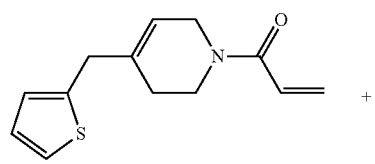

Intermediate-4

+

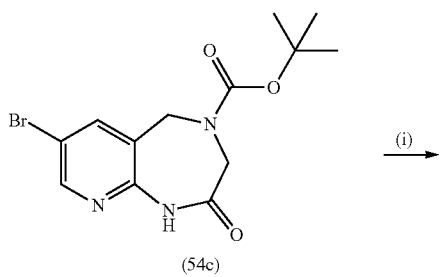

(54c)

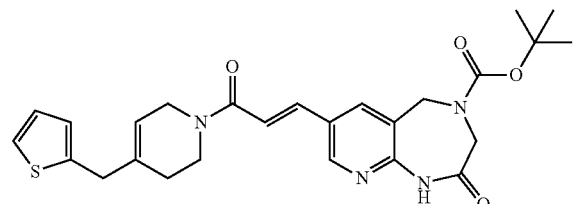

Compound-137

(i) Pd(OAc)$_2$, P(o-tolyl)$_3$, DIPEA, Propionitrile, DMF, 100° C., 16 h;

Step-(i)

The process of this step was adopted from step-(iv) of compound-54. The desired compound-137 obtained as a pale yellow solid (15 mg, 3%). $^1$H NMR (400 MHz, DMSO-D6) δ 10.37 & 10.29 (rotamer & s, 1H), 8.52-8.46 (m, 1H), 8.22-8.12 (m, 1H), 7.47 (d, J=15.6 Hz, 1H), 7.35 (d, J=4.4 Hz, 1H), 7.35-7.23 (m, 1H), 6.97-6.94 (m, 1H), 6.88 (s, 1H), 5.58 (s, 1H), 4.55 & 4.49 (rotamer & s, 2H), 4.36-4.28 (m, 2H), 4.21 & 4.04 (rotamer & s, 2H), 3.75 & 3.63 (rotamer & s, 2H), 3.55 (s, 2H), 2.10 & 2.03 (rotamer & s, 2H), 1.37 (s, 9H); MS (ES) m/e 495.3 (M+H)$^+$.

Preparation of Compound-138

Synthesis of (E)-1'-(2-hydroxyacetyl)-6-(3-oxo-3-(4-(thiophen-2-ylmethyl)-5,6-dihydropyridin-1(2H)-yl) prop-1-en-1-yl)-1H-spiroa[[1,8]naphthyridine-3,4'-piperidin]-2(4H)-one

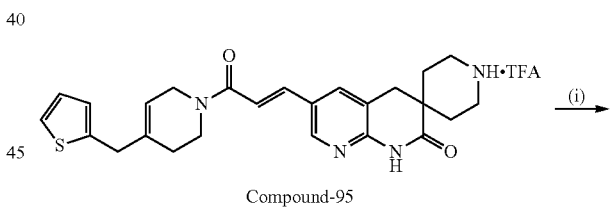

Compound-95

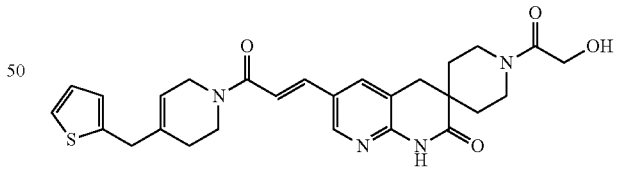

Compound-138

(i) Glycolic acid, HOBt, EDC•HCl, DIPEA, DMF, 20-35° C., 24 h

Step-(i)

The process of this step was adopted from step-(ii) of compound-1. The desired compound-138 obtained as a pale yellow solid (20 mg, 56%). $^1$H NMR (400 MHz, DMSO-d$_6$) δ 10.75 (s, 1H), 8.38 (d, J=1.5 Hz, 1H), 8.08 (s, 1H), 7.45 (d, J=15.6 Hz, 1H), 7.36-7.34 (m, 1H), 7.26-7.15 (m, 1H), 6.96 (dd, J=5.3, 3.4 Hz, 1H), 6.87 (d, J=2.4 Hz, 1H), 5.57 (s, 1H), 4.51 (t, J=5.3 Hz, 1H), 4.21-4.03 (m, 4H), 3.74-3.61 (m, 4H), 3.54 (s, 2H), 2.97 (s, 2H), 2.95-2.49 (m, 2H), 2.09-1.98 (m, 2H), 1.81-1.69 (m, 2H), 1.38-1.23 (m, 2H); MS (ES) m/e 505.3 (M−H).

Preparation of Compound-139

Synthesis of (E)-2-oxo-6-(3-oxo-3-(4-(thiophen-2-ylmethyl)-5,6-dihydropyridin-1(2H)-yl)prop-1-en-1-yl)-2,4-dihydro-1H-spiro[[1,8]naphthyridine-3,4'-piperidine]-1'-carboxamide

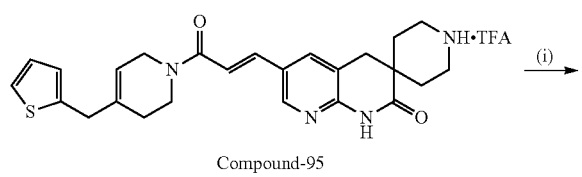

Compound-95

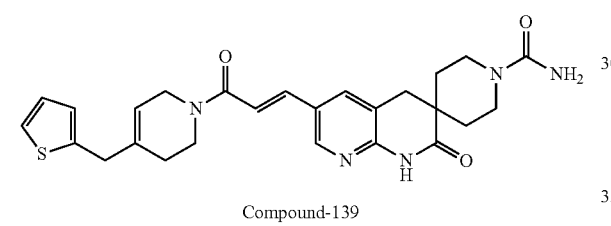

Compound-139
(i) phenyl carbamate, TEA, DMSO, 20-35° C., 48 h

Step-(i)

To a stirred solution of Compound-95 (100 mg, 0.18 mmol) in DMF (2 ml) was added triethylamine (0.07 ml, 0.54 mmol) at 0° C. and the reaction mixture was stirred at the same temperature for 15 min. After 15 min, phenyl carbamate (36 mg, 0.27 mmol) was added and the reaction mixture was stirred at 20-35° C. for 48 h. The progress of the reaction was monitored by TLC. After 48 h of stirring, the reaction mixture was diluted with water (30 ml) and extracted with dichloromethane (2×30 ml). The combined organic layers were washed with brine (30 ml), followed by drying over anhydrous $Na_2SO_4$ and filtering. The filtrate was rotary evaporated to get residue which was triturated with mixture of ethyl acetate and diethyl ether to get the desired compound as a cream solid (20 mg, 23%). $^1$H NMR (400 MHz, DMSO-$d_6$) δ 10.71 (s, 1H), 8.36 (s, 1H), 8.10 (s, 1H), 7.45 (d, J=15.1 Hz, 1H), 7.35 (d, J=4.4 Hz, 1H), 7.25-7.18 (m, 1H), 6:96 (dd, J=4.9, 3.5 Hz, 1H), 6.87 (d, J=2.9 Hz, 1H), 5.92 (s, 2H), 5.58 (s, 1H), 4.22 & 4.03 (rotamer & s, 2H), 3.74 & 3.63 (rotamer & s, 2H), 3.58-3.52 (m, 4H), 3.22-3.16 (m, 2H), 2.94 (s, 2H), 2.10 & 2.02 (rotamer & s, 2H), 1.73-1.68 (m, 2H), 1.31-1.23 (m, 2H); MS (ES) m/e 492.4 (M+H)$^+$.

Preparation of Compound-140

Synthesis of (E)-1'-(3-methylbutanoyl)-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one

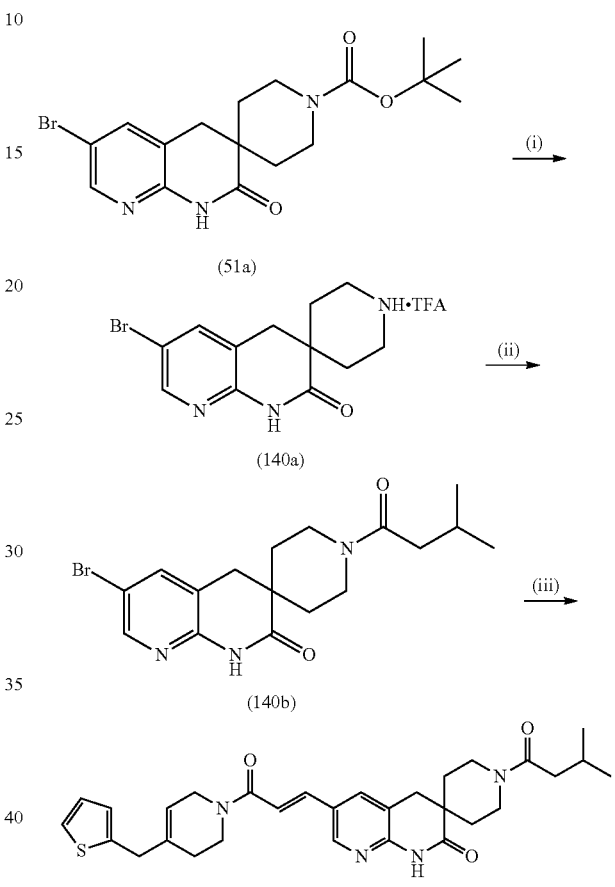

Compound-140
(i) $CF_3COOH$, $CH_2Cl_2$, 20-35° C., 2 h; (ii) 3-methylbutanoic acid, HOBt, EDC•HCl, DMF, DIPEA, 20-35° C., 16 h; (iii) Intermediate-4, Pd(OAc)$_2$, P(o-tolyl)$_3$, DIPEA, Propionitrile, DMF, 100° C., 16 h;

Step-(i)

The process of this step was adopted from step-(i) of compound-1. The desired compound (140a) obtained as an off-white solid (1.5 g, Quantitative). $^1$H NMR (400 MHz, DMSO-$d_6$) δ 10.85 (s, 1H), 8.64-8.46 (m, 2H), 8.25 (d, J=2.5 Hz, 1H), 7.88 (d, J=2.5 Hz, 1H), 3.26-3.04 (m, 4H), 2.99 (s, 2H), 2.00-1.91 (m, 2H), 1.57-1.49 (m, 2H).

Step-(ii)

The process of this step was adopted from step-(ii) of compound-1. The desired compound (140b) obtained as an off-white solid (140 mg, 76%). $^1$H NMR (400 MHz, DMSO-$d_6$) δ 10.73 (s, 1H), 8.23 (d, J=2.0 Hz, 1H), 7.86 (s, 1H), 3.80-3.72 (m, 1H), 3.70-3.62 (m, 1H), 3.48-3.36 (m, 2H), 2.98 (s, 2H), 2.17 (d, J=6.8 Hz, 2H), 2.00-1.93 (m, 1H), 1.84-1.76 (m, 1H), 1.70-1.62 (m, 1H), 1.38-1.24 (m, 2H), 0.89 (d, J=6.4 Hz, 6H).

Step-(iii) Preparation of Compound-140

Synthesis of (E)-1'-(3-methylbutanoyl)-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one The process of this step was adopted from step-(iv) of compound-54. The desired compound-140 obtained as a yellow solid (40 mg, 27%). ¹H NMR (400 MHz, DMSO-d₆) δ 10.75 (s, 1H), 8.37 (s, 1H), 8.08 (s, 1H), 7.45 (d, J=15.1 Hz, 1H), 7.35 (d, J=4.9 Hz, 1H), 7.25-7.18 (m, 1H), 6.96 (s, 1H), 6.87 (s, 1H), 5.57 (s, 1H), 4.21 & 4.03 (rota-mer & s, 2H), 3.62 & 3.54 (rotamer & s, 2H), 3.49-3.31 (m, 6H), 2.95 (s, 2H), 2.17 (d, J=6.3 Hz, 2H), 2.10-1.95 (m, 3H), 1.84-1.78 (m, 1H), 1.77-1.63 (m, 1H), 1.46-1.28 (m, 2H), 0.89 (d, J=6.3 Hz, 6H); MS (ES) m/e 533.3 (M+H)⁺.

The compounds prepared by following the process according to compound 140 and their physicochemical characteristics are summarized here in below in the table-IX.

TABLE-IX

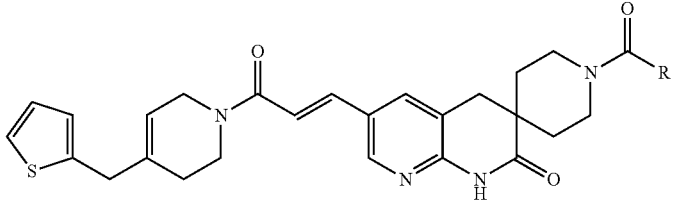

| Comp No | R | ¹H NMR (400 MHz, DMSO-d₆); δ (ppm) & MS (ES) m/e |
|---|---|---|
| 141 | 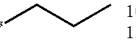 | 10.74 (s, 1H), 8.37 (d, J = 1.9 Hz, 1H), 8.08 (s, 1H), 7.45 (d, J = 15.6 Hz, 1H), 7.35 (dd, J = 5.2, 1.3 Hz, 1H), 7.26-7.20 (m, 1H), 6.96 (dd, J = 5.3, 3.5 Hz, 1H), 6.87 (d, J = 2.4 Hz, 1H), 5.57 (s, 1H), 4.21 & 4.03 (rotamer & s, 2H), 3.78-3.71 (m, 2H), 3.70-3.62 (m, 2H), 3.54 (s, 2H), 3.43-3.23 (m, 2H), 2.95 (s, 2H), 2.33-2.25 (m, 2H), 2.16-2.04 (m, 2H), 1.86-1.77 (m, 1H), 1.76-1.64 (m, 1H), 1.50 (q, J = 7.3 Hz, 2H), 1.42-1.23 (m, 2H), 0.88 (t, J = 7.4 Hz, 3H); MS (ES) m/e 517.5 (M − H). |
| 142 | 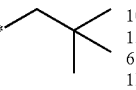 | 10.74 (s, 1H), 8.38 (d, J = 1.5 Hz, 1H), 8.08 (s, 1H), 7.45 (d, J = 15.1 Hz, 1H), 7.35 (dd, J = 4.9, 1.0 Hz, 1H), 7.26-7.20 (m, 1H), 6.96 (dd, J = 5.3, 3.4 Hz, 1H), 6.87 (d, J = 2.4 Hz, 1H), 5.57 (s, 1H), 4.21 & 4.03 (rotamer & s, 2H), 3.78-3.62 (m, 5H), 3.54 (s, 2H), 3.47-3.35 (m, 1H), 2.96 (s, 2H), 2.22 (s, 2H), 2.16-2.02 (m, 2H), 1.84-1.74 (m, 1H), 1.72-1.64 (m, 1H), 1.44-1.32 (m, 2H), 0.98 (s, 9H); MS (ES) m/e 547.5 (M + H)⁺. |

Note:
* Bonding position of R.

Preparation of Compound-143

Synthesis of (E)-8-(3-oxo-3-(4-(thiazol-2-ylmethyl)-5,6-dihydropyridin-1(2H)-yl)prop-1-en-1-yl)-2,3-dihydro-1H-pyrido[2,3-b][1,4]diazepin-4(5H)-one

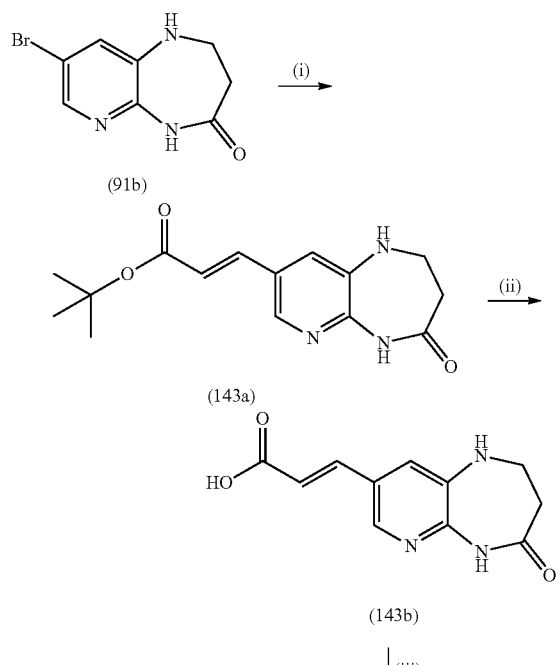

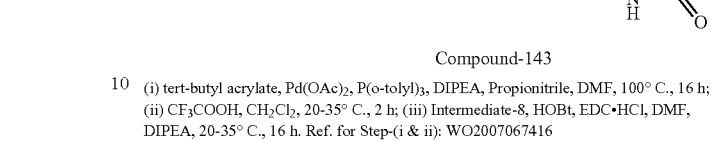

Compound-143

(i) tert-butyl acrylate, Pd(OAc)$_2$, P(o-tolyl)$_3$, DIPEA, Propionitrile, DMF, 100° C., 16 h; (ii) CF$_3$COOH, CH$_2$Cl$_2$, 20-35° C., 2 h; (iii) Intermediate-8, HOBt, EDC•HCl, DMF, DIPEA, 20-35° C., 16 h. Ref. for Step-(i & ii): WO2007067416

Step-(iii) Preparation of Compound-143

The process of this step was adopted from step-(ii) of compound-1. The desired compound-143 obtained as a pale yellow solid (30 mg, 8%).

$^1$H NMR (400 MHz, DMSO-d$_6$) δ 9.73 (s, 1H), 8.01 (s, 1H), 7.71 (d, J=3.4 Hz, 1H), 7.60 (d, J=3.4 Hz, 1H), 7.36 (t, J=7.6 Hz, 2H), 7.19-7.03 (m, 1H), 6.10-5.92 (m, 1H), 5.66 (m, 1H), 4.20 &4.04 (rotamer & s, 2H), 4.74 (s, 2H), 3.72-3.54 (m, 2H), 3.42 (t, J=5.3 Hz, 2H), 2.67-2.59 (m, 2H), 2.16-2.07 (m, 2H); MS (ES) m/e 396.0 (M+H)$^+$.

Preparation of Compound-144

Synthesis of (E)-1'-(3-hydroxypropyl)-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one

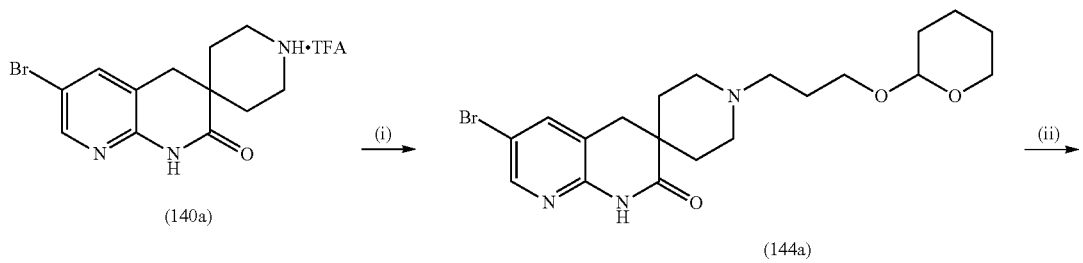

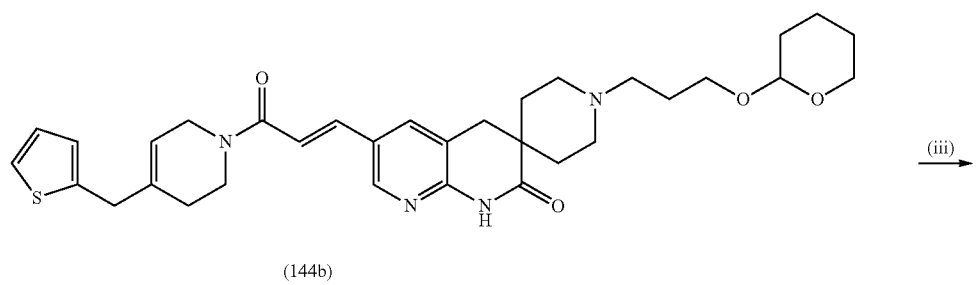

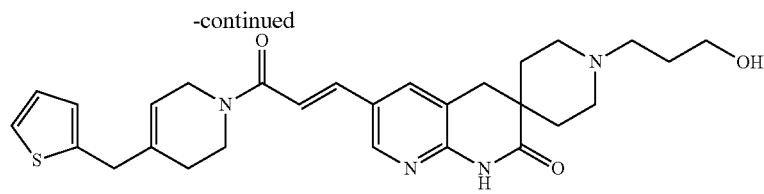

Compound-144

(i) 2-(3-bromopropoxy)tetrahydro-2H-pyran, Triethylamine, DMF, 20-35° C., 16 h; (ii) Intermediate-4, Pd(OAc)₂, P(o-tolyl)₃, DIPEA, Propionitrile, DMF, 100° C., 16 h
(iii) 2M HCl in MeOH, CH₂Cl₂, 0° C. to 20-35° C., 1 h.

Step-(i)

To a stirred solution of 140a (1.2 g, 2.93 mmol) in DMF (10 ml) were added triethylamine (1.3 ml, 8.79 mmol), 2-(3-bromopropoxy)tetrahydro-2H-pyran (0.91 g, 3.50 mmol) at 0° C. and the reaction mixture was stirred at 20-35° C. for 16 h. The progress of the reaction was monitored by TLC. After 16 h of stirring, the reaction mixture was diluted with water (50 ml) and extracted with dichloromethane (2×50 ml). The combined organic layers were washed with brine (50 ml), followed by drying over anhydrous Na₂SO₄ and filtering. The filtrate was rotary evaporated to get residue which was purified by column chromatography using a mixture of 2% methanol/dichloromethane as an eluent to get the desired compound as an off-white solid (1.05 g, 82%). ¹H NMR (400 MHz, DMSO-d₆) δ 10.63 (s, 1H), 8.21 (d, J=1.9 Hz, 1H), 7.90 (d, J=2.0 Hz, 1H), 4.53 (d, J=3.9 Hz, 1H), 3.77-3.69 (m, 1H), 3.68-3.54 (m, 2H), 3.49-3.32 (m, 3H), 2.91 (s, 2H), 2.63-2.52 (m, 2H), 2.36-2.32 (m, 2H), 2.26-2.22 (m, 2H), 1.82 (t, J=9.8 Hz, 2H), 1.77-1.57 (m, 4H), 1.52-1.40 (m, 3H), 1.38-1.26 (m, 1H).

Step-(ii)

The process of this step was adopted from step-(iv) of compound-54. The desired compound-144b obtained as a yellow solid (170 mg, 53%). ¹H NMR (400 MHz, DMSO-d₆) 10.91 (s, 1H), 8.50-8.40 (m, 1H), 8.13 (s, 1H), 7.46 (d, J=15.2 Hz, 1H), 7.35 (dd, J=4.8, 1.0 Hz, 1H), 7.26-7.10 (m, 1H), 6.96 (dd, J=4.9, 3.4 Hz, 1H), 6.87 (d, J=2.4 Hz, 1H), 5.58 (s, 1H), 4.56 (s, 1H), 4.21 & 4.04 (rotamer & s, 2H), 3.82-3.62 (m, 4H), 3.55 (s, 2H), 3.50-3.38 (m, 4H), 3.28-3.08 (m, 5H), 2.20-1.84 (m, 7H), 1.76-1.60 (m, 4H), 1.58-1.42 (m, 4H).

Step-(iii) Preparation of Compound-144

Synthesis of (E)-1'-(3-hydroxypropyl)-6-(3-oxo-3-(4-(thiophen-2-ylmethyl)-5,6-dihydropyridin-1(2H)-yl)prop-1-en-1-yl)-1H-spiro[[1,8]naph-thyridine-3,4'-piperidin]-2(4H)-one To a stirred solution of 144b (170 mg, 0.29 mmol) in DCM (3 ml) was added 2M HCl in MeOH (2 ml) at 0° C. and the reaction mixture was stirred at 20-35° C. for 1 h. The progress of the reaction was monitored by TLC. After 1 h, the reaction mixture was evaporated under vacuum, resultant residue was diluted with water (5 ml) and neutralized with NaHCO₃ solution (3 ml). The resultant precipitate was filtered, washed with water (10 ml) and dried under vacuum for 3 h to get the desired compound as an off-white solid (100 mg, 69%). ¹H NMR (400 MHz, DMSO-d₆) δ 10.65 (s, 1H), 8.33 (s, 1H), 8.13 (s, 1H), 7.44 (d, J=15.2 Hz, 1H), 7.35 (d, J=4.4 Hz, 1H), 7.26-7.16 (m, 1H), 6.96 (dd, J=4.9, 3.4 Hz, 1H), 6.88 (d, J=2.4 Hz, 1H), 5.58 (s, 1H), 4.54-4.40 (m, 1H), 4.21 & 4.04 (rotamer & s, 2H), 3.74 & 3.62 (rotamer & s, 2H), 3.54 (s, 2H), 3.42 (t, J=6.1 Hz, 2H), 2.90 (s, 2H), 2.69-2.59 (m, 2H), 2.42-2.30 (m, 2H), 2.29-2.18 (m, 2H), 2.16-2.11 (m, 1H), 2.10-2.00 (m, 1H), 1.84 (t, J=9.6 Hz, 2H), 1.56 (t, J=6.4 Hz, 2H), 1.42-1.32 (m, 2H); MS (ES) m/e 507.3 (M+H)⁺.

Preparation of Compound-146

Synthesis of (E)-1'-methyl-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one

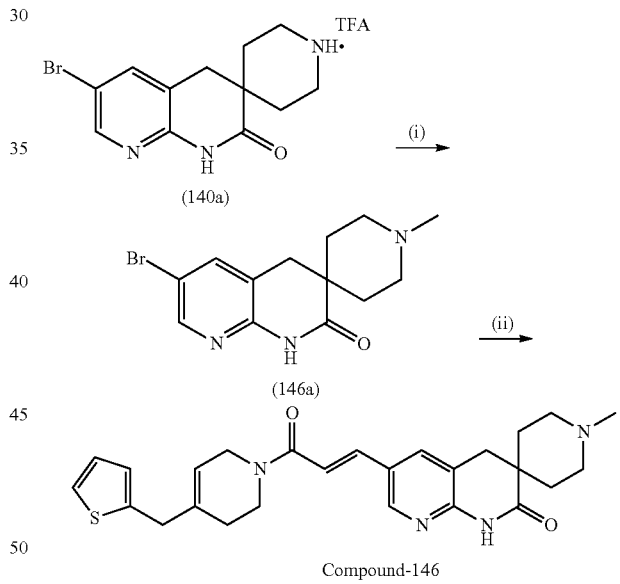

Compound-146

(i) HCHO, Triethylamine, MeOH, 20-35° C., 0.5 h, then NaBH₄, 0° C. to 20-35° C., 16 h; (ii) Intermediate-4, Pd(OAc)₂, P(o-tolyl)₃, DIPEA, Propionitrile, DMF, 100° C., 16 h;

Step-(i)

To a stirred suspension of 140a (250 mg, 0.61 mmol) in methanol (15 ml) were added triethylamine (0.25 ml, 1.83 mmol) and 37% formaldehyde solution (0.2 ml, 1.83 mmol) at 20-35° C. and the reaction mixture was stirred at 20-35° C. for 0.5 h. After 0.5 h, the reaction mixture was cooled to 0° C. and NaBH₄ (39 mg, 0.91 mmol) was added, then the reaction mixture was again stirred at 20-35° C. for 16 h. The progress of the reaction was monitored by TLC. After 16 h of stirring, the reaction mixture was diluted with water (50 ml) and extracted with ethyl acetate (2×50 ml). The combined organic layers were washed with brine (50 ml), followed by drying over anhydrous Na$_2$SO$_4$ and filtering. The filtrate was rotary evaporated to get the desired compound as a white solid (175 mg, 93%). $^1$H NMR (400 MHz, DMSO-d$_6$) δ 10.65 (s, 1H), 8.21 (d, J=2.5 Hz, 1H), 7.89 (d, J=2.0 Hz, 1H), 2.91 (s, 3H), 2.64-2.50 (m, 2H), 2.36-2.26 (m, 2H), 2.22 (s, 2H), 1.88-1.82 (m, 2H), 1.40-1.28 (m, 2H).

Step-(ii) Preparation of Compound-146

Synthesis of (E)-1'-methyl-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one The process of this step was adopted from step-(iv) of compound-54. The desired compound-146 obtained as an off-white solid (60 mg, 23%). $^1$H NMR (400 MHz, DMSO-d$_6$) δ 10.66 (s, 1H), 8.33 (s, 1H), 8.15 (s, 1H), 7.44 (d, J=15.2 Hz, 1H), 7.35 (d, J=5.4 Hz, 1H), 7.28-7.16 (m, 1H), 6.98-6.92 (m, 1H), 6.88 (s, 1H), 5.58 (s, 1H), 4.22 & 4.03 (rotamer & s, 2H), 3.75 & 3.63 (rotamer & s, 2H), 3.55 (s, 3H), 2.89 (s, 2H), 2.26-2.16 (m, 4H), 2.12-1.98 (m, 4H), 1.85 (t, J=9.8 Hz, 2H), 1.38-1.28 (m, 2H); LC-MS 463.2 (M+H)$^+$.

Preparation of Compound-147

Synthesis of (E)-3-(2-(2-oxa-7-azaspiro[3.5]nonan-7-yl)ethyl)-6-(3-oxo-3-(4-(thiophen-2-ylmethyl)-5,6-dihydropyridin-1(2H)-yl)prop-1-en-1-yl)-3,4-dihydropyrido[2,3-d]pyrimidin-2(1H)-one

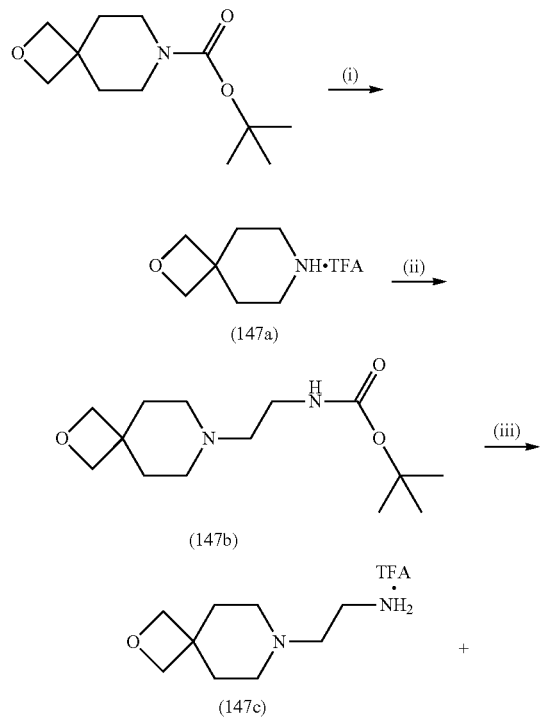

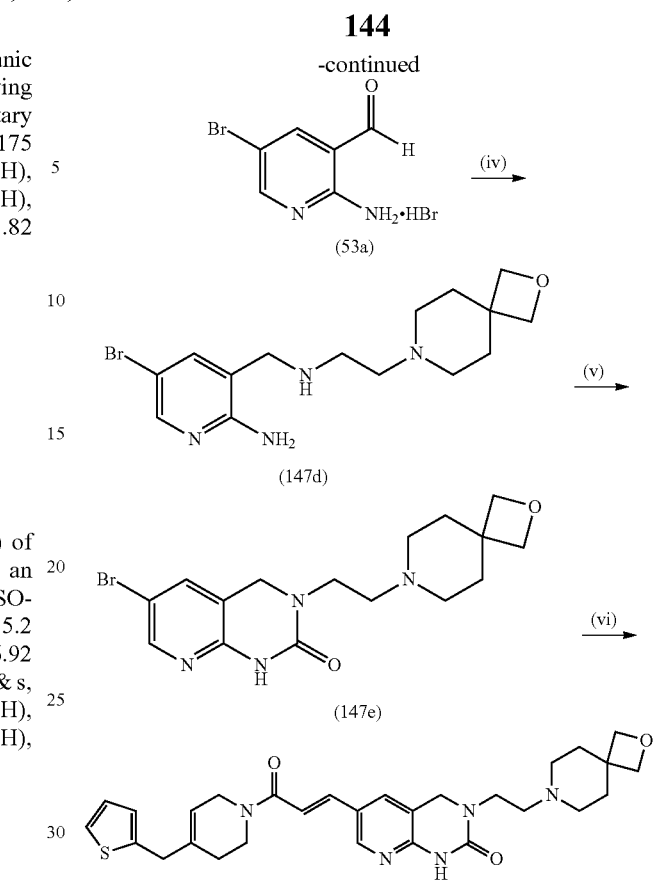

Compound-147

(i) CH$_2$Cl$_2$, TFA, 20-35° C., 4 h; (ii) tert-butyl (2-bromoethyl)carbamate, K$_2$CO$_3$, ACN, 80-90° C., 16 h; (iii) CH$_2$Cl$_2$, TFA, 20-35° C., 2 h; (iv) Triethylamine, MeOH, 20-35° C., 16 h then NaBH$_4$, 20-35° C., 4 h; (v) CDI, Dioxane, 100° C., 16 h; (vi) Intermediate-4, Pd(OAc)2, P(O-tolyl)$_3$, DIPEA, Propionitrile:DMF, 100°C., 16 h.

Step-(i)

The process of this step was adopted from step-(i) of compound-1. The desired compound (147a) obtained as a pale brown liquid (4 g, Quantitative) and was used in next reaction without characterization.

Step-(ii)

To a stirred suspension of 147a (4 g, 16.5 mmol) in acetonitrile (40 ml) was added K$_2$CO$_3$ (9.16 g, 66.3 mmol) and stirred at 20-35° C. for 10 min. After 10 min, tert-butyl (2-bromoethyl)carbamate (6.9 g, 33.2 mmol) was added and the reaction mixture was stirred 80-90° C. for 16 h. The progress of the reaction was monitored by TLC. After 16 h of stirring, the reaction mixture was diluted with water (200 ml) and extracted with ethyl acetate (2×200 ml). The combined organic layers were washed with brine (100 ml), followed by drying over anhydrous Na$_2$SO$_4$ and filtering. The filtrate was rotary evaporated to get residue which was purified by column chromatography using a mixture of 40% ethyl, acetate/pet ether as an eluentto get the desired compound as a yellow liquid (1.2 g, 27%). $^1$H NMR (400 MHz, DMSO-d$_6$) δ 6.64-6.57 (m, 1H), 4.25 (s, 4H), 2.99 (dd, J=12.8, 6.4 Hz, 2H), 2.30-2.18 (m, 6H), 1.80-1.68 (m, 4H), 1.36 (s, 9H).

Step-(iii)

The process of this step was adopted from step-(i) of compound-1. The desired compound (147c) obtained as a pale brown liquid (1.2 g, Quantitative) and was used in next reaction without characterization.

Step-(iv)

To a stirred solution of 2-(2-oxa-7-azaspiro[3.5]nonan-7-yl)ethanamine trifluoro acetic acid (147c)(1.2 g, 4.22 mmol) in MeOH (10 ml) was added triethylamine (1.7 g, 16.90 mmol) at 20-35° C. and the reaction mixture was stirred at 20-35° C. for 10 min, then 53a (1.18 g, 4.22 mmol) was added and the reaction mixture was again stirred at 20-35° C. for 16 h. After 16 h, NaBH$_4$ (0.32 g, 8.45 mmol) was added slowly portion wise at 0° C. and continued stirring at 20-35° C. for 4 h. The progress of the reaction was monitored by TLC. The excess methanol was removed under vacuum and resultant residue was diluted with ethyl acetate (100 ml). The organic layer was washed with water (50 ml), brine (50 ml), dried over anhydrous Na$_2$SO$_4$ and evaporated. The crude compound was purified by column chromatography using mixture of 3% methanol/dichloromethane as an eluent to get the desired compound as a pale yellow solid (0.4 g, 27%). LC-MS 355.1 (M+H)$^+$.

Step-(v)

To a stirred solution of 147d (0.4 g, 1.12 mmol) in 1,4 dioxane (10 ml) was added CDI (0.56 g, 3.37 mmol) at 20-35° C. and the reaction mixture was 100° C. for 16 h. The progress of the reaction was monitored by TLC. The excess 1,4-dioxane was removed under vacuum and resultant residue diluted with dichloromethane (50 ml). The organic layer was washed with water (50 ml), brine (50 ml), dried over anhydrous Na$_2$SO$_4$ and evaporated. The crude compound was purified by column chromatography using mixture of 3% methanol/dichloromethane as an eluent to get the desired compound as a pale yellow solid (0.15 g, 36%). LC-MS 381.1 (M+H)$^+$.

Step-(vi) Preparation of Compound-147

Synthesis of (E)-3-(2-(2-oxa-7-azaspiro[3.5]nonan-7-yl) ethyl)-6-(3-oxo-3-(4-(thiophen-2-ylmethyl)-5,6-dihydropyridin-1(2H)-yl)prop-1-en-1-yl)-3,4-dihydropyrido[2,3-d]pyrimidin-2(1H)-one The process of this step was adopted from step-(iv) of compound-54. The desired compound-147 obtained as a pale yellow solid (15 mg, 4%). $^1$H NMR (400 MHz, DMSO-d$_6$) δ 9.84 (s, 1H), 8.32 (s, 1H), 7.97 (s, 1H), 7.43 (d, J=15.2 Hz, 1H), 7.35 (dd, J=5.2, 1.3 Hz, 1H), 7.22-7.17 (m, 1H), 6.95 (dd, J=5.3, 3.5 Hz, 1H), 6.87 (d, J=2.5 Hz, 1H), 5.58-5.56 (m, 1H), 4.52 (s, 2H), 4.26 (s, 4H), 4.21-4.19 (m, 1H), 4.03-4.01 (m, 1H), 3.74-3.71 (m, 1H), 3.63-3.61 (m, 2H), 3.54 (s, 4H), 3.44-3.42 (m, 1H), 2.33 (t, J=1.7 Hz, 4H), 2.09-2.01 (m, 2H), 1.76-1.73 (m, 4H); MS (ES) m/e 534.2 (M+H)$^+$.

Preparation of Compound-148

Synthesis of (E)-3-(2-(6-azaspiro[2.5]octan-6-yl) ethyl)-6-(3-oxo-3-(4-(thiophen-2-ylmethyl)-5,6-dihydropyridin-1(2H)-yl)prop-1-en-1-yl)-3,4-dihydropyrido[2,3-d]pyrimidin-2(1H)-one

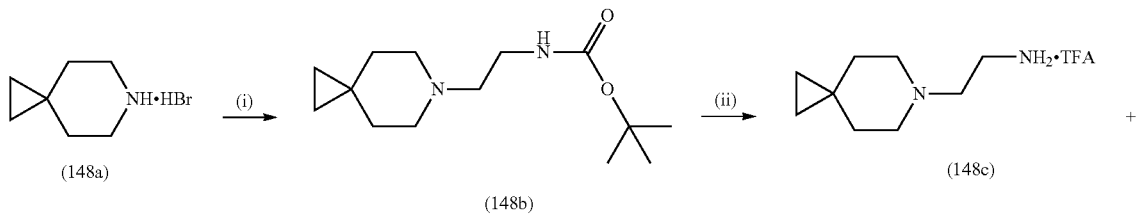

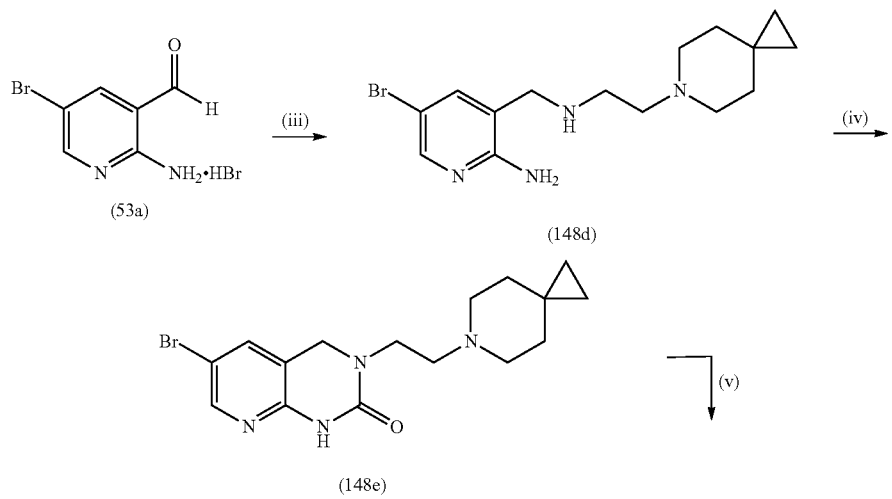

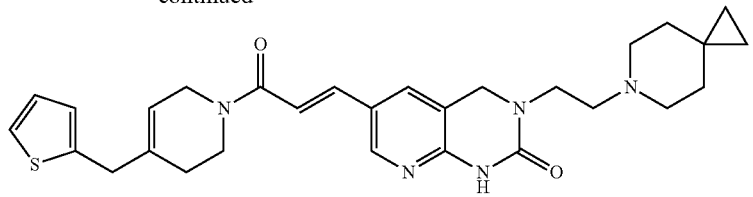

Compound-148

(i) tert-butyl (2-bromoethyl)carbamate, K₂CO₃, ACN, 80-90° C., 16 h; (ii) CH₂Cl₂, TFA, 20-35° C., 2 h; (iii) Triethylamine, MeOH, 20-35° C., 16 h then NaBH₄, 20-35° C., 4 h (iv) CDI, 1,4-dioxane, 100° C., 16 h; (v) Intermediate-4, Pd(OAc)₂, P(O-tolyl)₃, DIPEA, Propionitrile:DMF, 100° C., 16 h. (Reference for 148a: WO2011006960)

Step-(i)

The process of this step was adopted from step-(ii) of compound-147. The desired compound-148b obtained as a yellow liquid (2.1 g, 60%). LC-MS 255.2 (M+H)⁺.

Step-(ii)

The process of this step was adopted from step-(i) of compound-1. The desired compound-148c obtained as a pale brown liquid (0.6 g, Quantitative) and was used in next reaction without characterization.

Step-(iii)

The process of this step was adopted from step-(iv) of compound-147. The desired compound-148d obtained as a yellow liquid (200 mg, 32%). $^1$H NMR (400 MHz, DMSO-d$_6$) δ 7.91 (d, J=2.5 Hz, 1H), 7.51 (d, J=1.9 Hz, 1H), 6.25 (bs, 2H), 3.60 (s, 2H), 3.35-3.33 (m, 1H), 2.67-2.63 (m, 2H), 2.51-2.47 (m, 2H), 1.40-1.28 (m, 4H), 1.27-1.21 (m, 4H), 0.25 (s, 4H). MS (ES) m/e 339.1 (M+H)⁺.

Step-(iv)

The process of this step was adopted from step-(v) of compound-147. The desired compound-148e obtained as a pale yellow solid (120 mg, 56%). $^1$H NMR (400 MHz, DMSO-d$_6$) δ 9.80 (s, 1H), 8.16 (d, J=1.9 Hz, 1H), 7.76 (s, 1H), 4.51 (s, 2H), 3.41 (t, J=6.6 Hz, 2H), 3.38 (d, J=9.8 Hz, 2H), 2.49-2.43 (m, 4H), 1.42-1.30 (m, 4H), 0.23 (s, 4H); MS (ES) m/e 365.1 (M+H)⁺.

Step-(v) Preparation of Compound-148

Synthesis of (E)-3-(2-(6-azaspiro[2.5]octan-6-yl)ethyl)-6-(3-oxo-3-(4-(thiophen-2-ylmethyl)-5,6-dihydropyridin-1(2H)-yl)prop-1-en-1-yl)-3,4-dihydropyrido[2,3-d]pyrimidin-2(1H)-one The process of this step was adopted from step-(iv) of compound-54. The desired compound-148 obtained as a pale yellow solid (50 mg, 29%). $^1$H NMR (400 MHz, DMSO-d$_6$) δ 9.98 (bs, 1H), 8.35 (s, 1H), 7.97 (s, 1H), 7.44 (d, J=15.6 Hz, 1H), 7.35 (d, J=5.4 Hz, 1H), 7.30-7.16 (m, 1H), 6.96-6.94 (m, 1H), 6.87 (d, J=3.4 Hz, 1H), 5.57 (s, 1H), 4.54 (s, 2H), 4.20 & 4.03 (rotamers & s, 2H), 3.73 & 3.62 (rotamers & s, 2H), 3.60-3.54 (m, 4H), 3.39-3.23 (m, 2H), 2.44-2.32 (m, 4H), 2.09-2.02 (m, 2H), 1.23-1.19 (m, 4H), 0.36-0.26 (m, 4H); MS (ES) m/e 518.3 (M+H)⁺.

Preparation of Compound-149

Synthesis of (E)-7-(3-oxo-3-(4-(thiazol-2-ylmethyl)-5,6-dihydropyridin-1(2H)-yl)prop-1-en-1-yl)-4,5-dihydro-1H-pyrido[2,3-e][1,4]diazepin-2(3H)-one

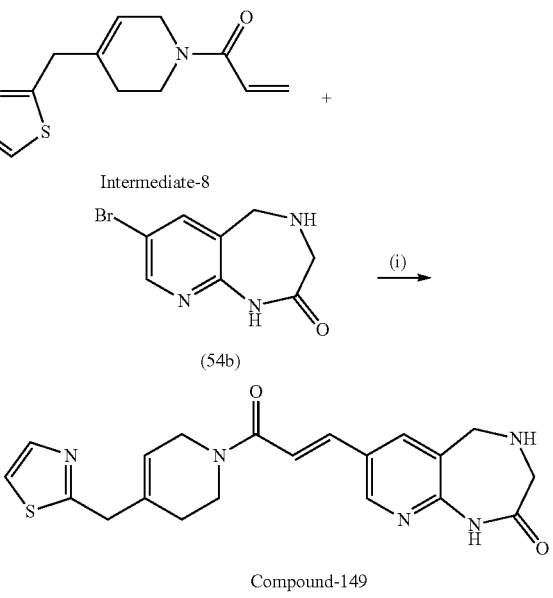

Compound-149

(i) Pd(OAc)₂, P(o-tolyl)₃, DIPEA, Propionitrile, DMF, 100° C., 16 h;

Step-(i)

The process of this step was adopted from step-(iv) of compound-54. The desired compound-149 obtained as a yellow solid (10 mg, 2%). $^1$H NMR (400 MHz, DMSO-d$_6$) 10.04 (s, 1H), 8.42 (s, 1H), 8.02-7.95 (m, 1H), 7.71 (d, J=3.4 Hz, 1H), 7.61 (d, J=3.4 Hz, 1H), 7.46 (d, J=15.2 Hz, 1H), 7.32-7.23 (m, 1H), 5.66 (s, 1H), 4.23 & 4.05 (rotamer & s, 2H), 3.90 (s, 2H), 3.75 (s, 3H), 3.62 (s, 3H), 3.14-2.96 (m, 1H), 2.23 & 2.04 (m, 2H); MS (ES) m/e 396.2 (M+H)⁺.

Preparation of Compound-150

Synthesis of (E)-tert-butyl2-(2-(2-oxo-6-(3-oxo-3-(4-(thiophen-2-ylmethyl)-5,6-dihydropyridin-1(2H)-yl)prop-1-en-1-yl)-1,2-dihydro pyrido[2,3-d]pyrimidin-3(4H)-yl)ethyl)-2,7-diazaspiro[3.5]nonane-7-carboxylate

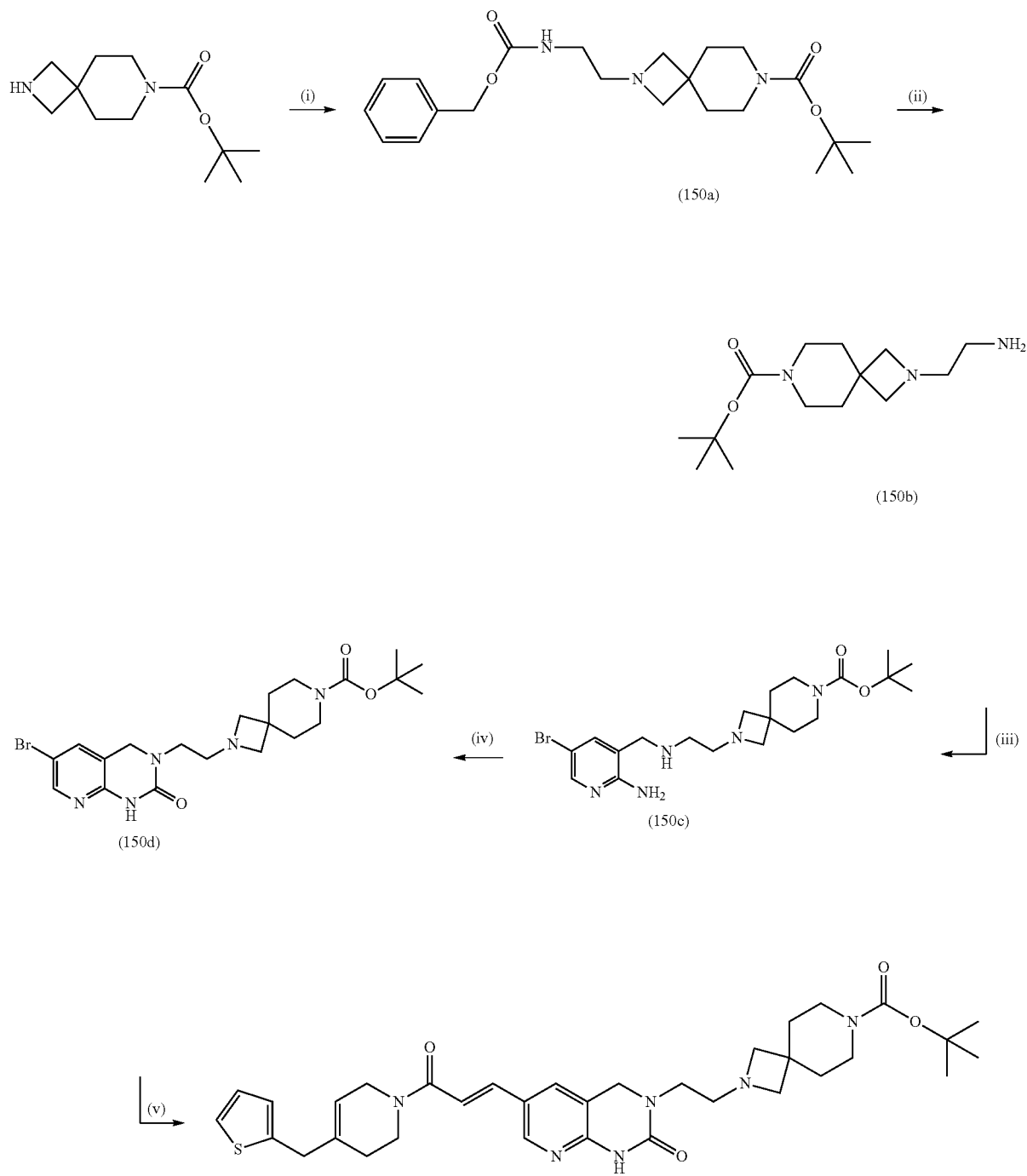

Compound-150

(i) Benzyl 2-bromoethylcarbamate, K₂CO₃, ACN, 80° C., 16 h; (ii) 10% Pd/C, MeOH, H₂ gas, 20-35° C., 16 h; (iii) 53a, Triethylamine, MeOH, 20-35° C., 16 h then NaBH₄, 0° C. to 20-35° C., 16 h; (iv) CDI, 1,4-dioxane, 80° C., 16 h; (v) Intermediate-4, Pd(OAc)₂, P(O-tolyl)₃, DIPEA, Propionitrile:DMF, 110° C., 16 h.

Step-(i)

The process of this step was adopted from step-(ii) of compound-147. The desired compound (150a) obtained as a brown liquid (1.5 g, Quantitative). $^1$H NMR (400 MHz, DMSO-$d_6$) δ 7.42-7.29 (m, 5H), 7.14-7.06 (m, 1H), 5.00 (s, 2H), 3.56-3.44 (m, 4H), 3.08 (dd, J=12.7, 6.4 Hz, 2H), 2.36-2.18 (m, 6H), 1.68-1.56 (m, 4H), 1.37 (s, 9H); LC-MS 255.2 (M+H)$^+$.

Step-(ii)

To a stirred solution of 150a (1.5 g, 3.72 mmol) in methanol (20 ml) was added 10% Pd/C (0.6 g) under nitrogen. The reaction mixture was stirred in presence of H$_2$ gas at 20-35° C. for 16 h. The progress of the reaction was monitored by TLC. After 16 h, the reaction mixture was filtered on celite and the resultant filtrate was concentrated to get the desired compound as a yellow liquid (1 g, Quantitative). LC-MS 270.3 (M+H)$^+$.

Step-(iii)

The process of this step was adopted from step-(iv) of compound-147. The desired compound (150c) obtained as a brown oily liquid (900 mg, Quantitative). LC-MS 454.2 (M+H)$^+$.

Step-(iv)

The process of this step was adopted from step-(v) of compound-147. The desired compound (150d) obtained as a brown oily liquid (700 mg, Quantitative). LC-MS 482.2 (M+2H)$^+$.

Step-(v) Preparation of Compound-150

Synthesis of (E)-tert-butyl 2-(2-(2-oxo-6-(3-oxo-3-(4-(thiophen-2-ylmethyl)-5,6-dihydropyridin-1(2H)-yl)prop-1-en-1-yl)-1,2-dihydropyrido[2,3-d]pyrimidin-3(4H)-yl)ethyl)-2,7-diazaspiro[3.5]nonane-7-carboxylate The process of this step was adopted from step-(iv) of compound-54. The desired compound-150 obtained as a pale yellow solid (60 mg, Quantitative). LC-MS 633.4 (M+H)$^+$.

Preparation of Compound-151

Synthesis of (E)-3-(2-(2,7-diazaspiro[3.5]nonan-2-yl)ethyl)-6-(3-oxo-3-(4-(thiophen-2-ylmethyl)-5,6-dihydropyridin-1(2H)-yl)prop-1-en-1-yl)-3,4-dihydropyrido[2,3-d]pyrimidin-2(1H)-one 2,2,2-trifluoroacetate

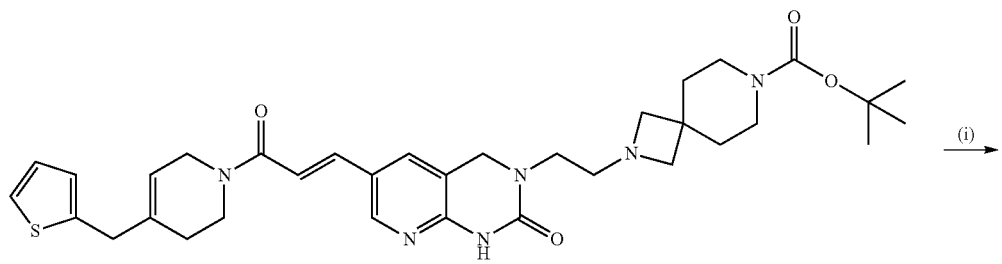

Compound-150

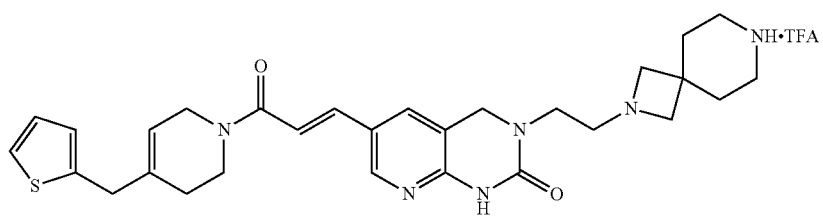

Compound-151

(i) CF$_3$COOH, CH$_2$Cl$_2$, 20-35° C., 2 h

Step-(i)

The process of this step was adopted from step-(i) of compound-1. The desired compound-151obtained as a yellow solid (40 mg, Quantitative). LC-MS 533.3 (M+H)$^+$.

Biological Screening of the Compounds of Formula (I) of the Present Invention:

The biological screening of the various substituted pyridine derivatives of formula (I) was carried out using FABI protocol designed for evaluating enzymatic assay for FABI. Following protocol was used for the evaluation purpose and the results are summarized in the table-X.

Fabiassay Protocol:

The enzymatic assay for Fab I is based on the conversion of enoyl-ACP to acyl-ACP by FabI which is accompanied by oxidation of NADH. This reaction can be monitored by measuring the decrease in absorbance at 340 nM. Total reaction volume is 100 µl which includes 10 µl compound/10% DMSO (final concentration is 1%), 25 µl enzyme (600 nM), 45 µl 100 mM sodium ADA buffer and 20 µl substrate mix. Enzyme is pre-incubated with compound/DMSO for 30 min in sodium ADA buffer at room temperature on a shaker. At the end of 30 min, 20 µl of freshly prepared substrate mix is added to the reaction. Substrate mix contains Crotonoly Co-A at a final concentration of 250 µM and 375 µM NADH. The reaction is incubated for 2 hrs at 25±5° C. on a shaker. The plate is read at 340 nm at the end of 2 hrs for NADH depletion. The NADH depletion is directly proportional to enzyme activity.

Mic by Broth Microdilution Method:

Required quantity of the test compound was weighed and dissolved in suitable solvent to yield 1 mg/ml stock solution. The stock solution was diluted in MHB/CAMHB (Mueller Hinton Broth/Cation adjusted Mueller Hinton Broth) by serial two fold dilutions of the compounds in 96 well microtitre trays. Organisms were grown in MHA over night at 35±2° C. and the inoculum was prepared by directly suspending colonies from an overnight grown culture in 0.9% saline or MHB and the optical density (OD) adjusted at 625 nm which corresponds to 0.5 Mc Farland (1–2×10$^8$ cfu/ml) and cultures were further diluted 1:1000 times. To each of the wells of the microtitre tray, 50 µL of the above diluted organism is inoculated to obtain a final in oculum density of (5±0.5)×10$^4$ cfu/well. Broth, compound and organism controls were set up. Microdilution trays were incubated at 35±2° C. for 16-20 hours in an ambient air incubator. After the incubation period, growth of organism in the wells was detected by unaided eye facilitated by a viewing device. The amount of growth in the wells containing the antibiotic is compared with the amount of growth in organism control wells (no antibiotic) to help in determining the end point. The lowest concentration of antimicrobial agent that completely inhibits growth of the organism as detected by the unaided eye was taken as MIC.

In Vivo Systemic Infection Model:

Female and male Swiss Albino mice, 4-6 weeks old, weighing 20±2 g. were used in the study. Organisms were sub-cultured on Columbia blood agar (CBA) media and incubated at 35±2° C. for 18-24 hours. Inoculum was prepared in NS and optical density (OD) adjusted at 560 nm which corresponds to 1-2×10$^8$ CFU/mL with final mucin concentration of 5% (wt/vol) and 0.5 ml of inoculum was injected intraperitoneally in to each mice. Two groups of mice left untreated, serve as control (UTC). NCEs (New chemical entities)/standard antibiotics were formulated in Tween 80+0.25% CMC or specified formulations for oral administration. NCEs/antibiotics were administered as bid. at 0 to 5 h post infection. End point was determined by survival/death in each treated and untreated groups, animals were monitored for 5 days and the ED50's were calculated by Probit analysis.

TABLE X

| Comp. No | FAB-I inhibition %@1 µM | MIC Vs MRSA (µg/ml) | | | In vivo efficacy Route and Dosing |
|---|---|---|---|---|---|
| | | MSSA | MRSA | MRSE | |
| (2) | 86 | 0.5 | 0.5 | 4 | p.o., b.i.d. × 1 day |
| (8) | 108 | 2 | 2 | 8 | — |
| (4) | 87 | 4 | 4 | 4 | — |
| (62) | 76 | 0.25 | 0.5 | 0.5 | p.o., b.i.d. × 1 day |
| (84) | 100 | 0.125 | 0.25 | 0.25 | p.o., b.i.d. × 1 day |
| (87) | 69.047619 | 0.5 | 0.5 | 0.5 | — |
| (97) | 66.8546366 | 0.5 | 0.5 | 1 | p.o., b.i.d. × 1 day |
| (65) | 90 | 0.25 | 0.25 | 0.5 | p.o., b.i.d. × 1 day |
| (70) | 63.4711779 | 1 | 1 | 2 | — |
| (66) | 84 | 0.25 | 0.25 | 0.25 | p.o., b.i.d. × 1 day |
| (107) | 95 | 4 | 4 | 4 | — |
| (67) | 63 | 2 | 1 | 2 | — |
| (113) | 36 | >128 | >128 | >128 | — |
| (108) | 99 | 8 | 8 | 8 | — |
| (109) | 74 | 1 | 1 | 2 | — |
| (100) | 77 | 128 | 128 | 128 | — |
| (88) | 87 | >128 | >128 | >128 | — |
| (93) | 93 | 0.5 | 0.5 | 1 | — |
| (90) | 89 | >128 | >128 | >128 | — |
| (91) | 93 | 0.25 | 0.5 | 0.5 | p.o., b.i.d. × 1 day |
| (94) | — | 0.5 | 0.5 | 1 | — |
| (92) | — | 0.12 | 0.25 | 0.25 | p.o., b.i.d. × 1 day |
| (96) | — | 8 | 8 | 16 | — |

The above selected compounds have protected mice from infection at ED$_{50}$ doses.

Metabolic Stability Study:

In vitro metabolic stability of the compounds was done in mouse liver microsomes prepared in house as per standard protocol. Compounds were tested at 1 µM concentration. Compounds were incubated for 15 and 60 minutes at 37° C. with 100 rpm in shaker bath. After the incubation samples were analysed by LC/MS (API-4000). Respective control (Propranalol) was included in the study.

TABLE XI

| Comp. No | Percentage of compound remained after 15 min | Percentage of compound remained after 60 min |
|---|---|---|
| (147) | 4.0% | 2.2% |
| (145) | 83.3% | 60.2% |
| (146) | 57.9% | 15.8% |
| (140) | 1.9% | 1.7% |
| (143) | 27.5% | 15.8% |
| (138) | 44.3% | 10.2% |
| (139) | 21.6% | 7.3% |
| (2) | 99.7% | 97.9% |
| (62) | 78.5% | 54.2% |
| (65) | 90.6% | 75.0% |
| (84) | 70.5 | 45.9 |
| (91) | 81.3% | 79.3% |
| (94) | 55.7% | 37.6% |
| (93) | 16.1% | 1.1% |
| (90) | 32.4% | 22.9% |
| (57) | 86.8% | 57.1% |
| (88) | 11.1% | 5.5% |

We claim:

1. A compound of formula (I):

(I)

[Chemical structure showing a pyridine ring with R₂N and R₃ substituents, connected via linker L to a C(=O) group attached to a tetrahydropyridine ring with R₄ and R₅ substituents; an O=C-R₁ group attached to N]

or a pharmaceutically acceptable salts and stereoisomer's thereof;
wherein;
$R_1$ is selected from an optionally substituted alkyl, amino, cycloalkyl, aryl, heterocyclyl, heteroaryl, heterocyclylalkyl or heteroarylalkyl;
$R_2$ is hydrogen; or
$R_1$ and $R_2$ may be taken together with the atoms to which they are attached to form an optionally substituted 4-7 membered ring containing 0-3 additional hetero atoms independently selected from N, O and S in any stable combination;
$R_3$ is selected from hydrogen, carboxy, optionally substituted alkyl or heterocyclylalkyl; or
$R_1$ and $R_3$ may be taken together with the carbon atoms to which they are attached to form an optionally substituted 6-8 membered ring containing 0-3 additional hetero atoms independently selected from N, O and S in any stable combination; wherein the optional substituent, at each occurrence, is independently selected from one or more $R_6$;
L is a linker selected from —$CH_2$—$CH_2$—, —CH=CH— or —$CH_2$—S—;
$R_4$ is selected from optionally substituted alkyl, optionally substituted alkenyl, optionally substituted alkynyl, optionally substituted alkoxy, optionally substituted amino, optionally substituted aryl, $B(OH)_2$, optionally substituted cycloalkyl, optionally substituted heterocyclyl, optionally substituted heteroaryl, optionally substituted arylalkyl, optionally substituted heteroarylalkyl, optionally substituted heterocyclylalkyl, wherein the optional substituent, in each occurrence, is independently selected from one or more $R_7$;
$R_5$ is hydrogen; or
$R_4$ and $R_5$ may be taken together with the carbon atoms to which they are attached to form an optionally substituted 5-8 membered ring optionally containing 0-4 hetero atoms independently selected from N, O and S in any stable combination; wherein the optional substituent, at each occurrence, is independently selected from alkoxy, halo, hydroxyl, an optionally substituted alkyl or an optionally substituted alkenyl;
$R_6$ is independently selected from optionally substituted alkyl, optionally substituted heterocyclylalkyl, —$COOR_8$ or two of the $R_6$ groups on the same atom combined together to form an optionally substituted spiro condensed 3-8 membered ring containing 0-3 hetero atoms independently selected from N, O and S; wherein the optional substituent is independently selected from one or more $R_8$, —$(CH_2)_{1-3}OR_8$, —$COOR_8$, —$COR_8$, —$COCH_2OR_8$, —$CONR_8R_8$, —$NR_8R_8$ or an optionally substituted heterocyclyl;
$R_7$ is independently selected from cyano, nitro, halogen, —$OR_8$, —$NR_8R_8$, —$COOR_8$, —$CONR_8R_8$, —$NR_8COR_8$, haloalkyl, haloalkoxy, —NHC(=$NR_9$)$NHR_9$, —$(CH_2)_{1-3}OR_8$, —C(=NOH)$NH_2$ or optionally substituted alkyl, optionally substituted alkoxy, optionally substituted alkenyl, optionally substituted alkynyl, optionally substituted aryloxy, cyanoalkyl, cyanoalkoxy, cycloalkyl, optionally substituted aryl, optionally substituted heterocyclyl, optionally substituted heteroaryl or optionally substituted heterocyclylalkyl;
$R_8$ at each occurrence is independently selected from hydrogen or optionally substituted alkyl, optionally substituted aryl, optionally substituted arylalkyl, cycloalkyl, heterocyclyl, heteroaryl, —$CH_2$C(=NOH)$NH_2$ or two of the $R_8$ groups on the same atom can be taken together with the atom to which they are attached to form an optionally substituted 3-8 membered ring containing 0-3 hetero atoms independently selected from N, O and S in any stable combination;
wherein the optional substituent is independently selected from —$COOC_1$-$C_4$alkyl, halogen, hydroxy, cyano, alkyl, alkoxy, nitro or haloalkoxy;
$R_9$ at each occurrence is independently selected from hydrogen or —$COOC_1$-$C_4$alkyl.

2. The compound of claim 1, wherein linker L is —CH=CH—.

3. The compound of claim 1, wherein $R_1$ is $C_1$-$C_4$alkyl or heterocyclylalkyl.

4. The compound of claim 1, wherein $R_1$ and $R_3$ can be taken together with the carbon atoms to which they are attached to form a 6-membered ring optionally substituted with one or more $R_6$.

5. The compound of claim 1, wherein $R_1$ and $R_3$ can be taken together with the carbon atoms to which they are attached to form a 7-membered ring containing one additional N atom and optionally substituted with one or more $R_6$.

6. The compound of claim 4, wherein $R_6$ is alkyl, heterocyclylalkyl or —$COOR_8$ wherein $R_8$ is $C_{1-4}$ alkyl.

7. The compound of claim 5, wherein $R_6$ is alkyl, heterocyclylalkyl or —$COOR_8$ wherein $R_8$ is $C_{1-4}$ alkyl.

8. The compound of claim 4, wherein two of the $R_6$ groups on the same atom combined together to form an optionally substituted spiro condensed 3-8 membered ring containing 0-3 hetero atoms independently selected from N, O and S; wherein the optional substituent is independently selected from alkyl, —$(CH_2)_{1-3}OR_8$, —$COOR_8$, —$COR_8$, —$COCH_2OR_8$, —$CONR_8R_8$, —$NR_8R_8$ or an optionally substituted heterocyclyl.

9. The compound of claim 5, wherein two of the $R_6$ groups on the same atom combined together to form an optionally substituted spiro condensed 3-8 membered ring containing 0-3 hetero atoms independently selected from N, O and S; wherein the optional substituent is independently selected from alkyl, —$(CH_2)_{1-3}OR_8$, —$COOR_8$, —$COR_8$, —$COCH_2OR_8$, —$CONR_8R_8$, —$NR_8R_8$ or an optionally substituted heterocyclyl.

10. The compound of claim 1, wherein $R_4$ is aryl, arylalkyl, heteroaryl, or heteroarylalkyl which may be optionally substituted with $R_7$.

11. The compound of claim 1 wherein the compound of formula (I) is a compound of Formula (IA)

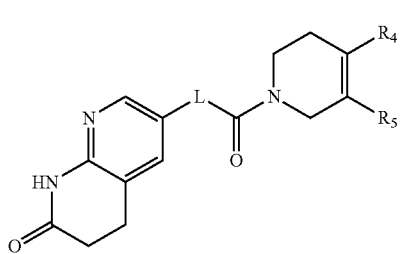

wherein L, R₄ and R₅ are as defined in claim 1; or a pharmaceutically acceptable salt thereof.

12. The compound of claim 1 wherein the compound of formula (I) is a compound of Formula (IB)

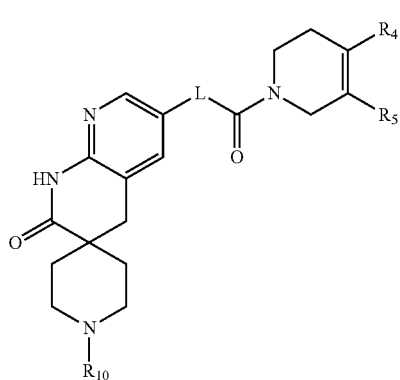

wherein $R_{10}$ is selected from optionally substituted alkyl, —(CH₂)₁₋₃OR₈, —COR₈, —COCH₂OR₈ or —CONR₈R₈; and L, R₄, R₅ and R₈ are as defined in claim 1; or a pharmaceutically acceptable salt thereof.

13. The compound of claim 1 wherein the compound of formula (I) is a compound of Formula (IC)

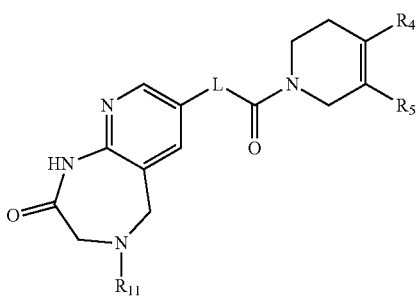

wherein $R_{11}$ is selected from hydrogen, optionally substituted alkyl, heterocyclylalkyl or —COOR₈; and L, R₄, R₅ and R₈ are as defined in claim 1;

or a pharmaceutically acceptable salt thereof.

14. The compound of claim 1 wherein the compound of formula (I) is a compound of Formula (ID)

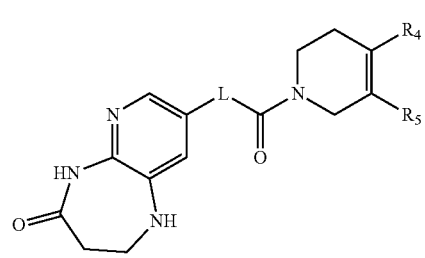

wherein L, R₄ and R₅ are as defined in claim 1; or a pharmaceutically acceptable salt thereof.

15. A compound selected from the group consisting of
(E)-(1-(3-(7-oxo-5,6,7,8-tetrahydro-1,8-naphthyridin-3-yl)acryloyl)-1,2,3,6-tetrahydropyridin-4-yl)boronic acid;
(E)-6-(3-oxo-3-(4-phenyl-5,6-dihydropyridin-1(2H)-yl)prop-1-en-1-yl)-3,4-dihydro-1,8-naphthyridin-2(1H)-one;
(E)-6-(3-(4-(3-methylbenzofuran-2-yl)-5,6-dihydropyridin-1(2H)-yl)-3-oxoprop-1-en-1-yl)-3,4-dihydro-1,8-naphthyridin-2(1H)-one;
(E)-6-(3-(5,6-dihydro-[4,4'-bipyridin]-1(2H)-yl)-3-oxoprop-1-en-1-yl)-3,4-dihydro-1,8-naphthyridin-2(1H)-one;
(E)-6-(3-(5,6'-dihydro-[3,4'-bipyridin]-1'(2'H)-yl)-3-oxoprop-1-en-1-yl)-3,4-dihydro-1,8-naphthyridin-2(1H)-one;
(E)-6-(3-oxo-3-(4-(pyrimidin-2-yl)-5,6-dihydropyridin-1(2H)-yl)prop-1-en-1-yl)-3,4-dihydro-1,8-naphthyridin-2(1H)-one;
(E)-6-(3-oxo-3-(4-(pyrimidin-5-yl)-5,6-dihydropyridin-1(2H)-yl)prop-1-en-1-yl)-3,4-dihydro-1,8-naphthyridin-2(1H)-one;
(E)-6-(3-(4-(4-fluorophenyl)-5,6-dihydropyridin-1(2H)-yl)-3-oxoprop-1-en-1-yl)-3,4-dihydro-1,8-naphthyridin-2(1H)-one;
(E)-6-(3-(4-(4-hydroxyphenyl)-5,6-dihydropyridin-1(2H)-yl)-3-oxoprop-1-en-1-yl)-3,4-dihydro-1,8-naphthyridin-2(1H)-one;
(E)-6-(3-(4-(3-hydroxyphenyl)-5,6-dihydropyridin-1(2H)-yl)-3-oxoprop-1-en-1-yl)-3,4-dihydro-1,8-naphthyridin-2(1H)-one;
(E)-6-(3-(4-(2-hydroxyphenyl)-5,6-dihydropyridin-1(2H)-yl)-3-oxoprop-1-en-1-yl)-3,4-dihydro-1,8-naphthyridin-2(1H)-one;
(E)-6-(3-(4-(4-methoxyphenyl)-5,6-dihydropyridin-1(2H)-yl)-3-oxoprop-1-en-1-yl)-3,4-dihynaphthyridin-2(1H)-one;
(E)-6-(3-(4-(3-methoxyphenyl)-5,6-dihydropyridin-1(2H)-yl)-3-oxoprop-1-en-1-yl)-3,4-dihydro-1,8-naphthyridin-2(1H)-one;
(E)-6-(3-(4-(2-methoxyphenyl)-5,6-dihydropyridin-1(2H)-yl)-3-oxoprop-1-en-1-yl)-3,4-dihydro-1,8-naphthyridin-2(1H)-one;
(E)-6-(3-oxo-3-(4-(4-(trifluoromethoxy)phenyl)-5,6-dihydropyridin-1(2H)-yl)prop-1-en-1-yl)-3,4-dihydro-1,8-naphthyridin-2(1H)-one;
(E)-6-(3-oxo-3-(4-(p-tolyl)-5,6-dihydropyridin-1(2H)-yl)prop-1-en-1-yl)-3,4-dihydro-1,8-naphthyridin-2(1H)-one;

- (E)-3-(1-(3-(7-oxo-5,6,7,8-tetrahydro-1,8-naphthyridin-3-yl)acryloyl)-1,2,3,6-tetrahydropyridin-4-yl)benzonitrile;
- (E)-4-(1-(3-(7-oxo-5,6,7,8-tetrahydro-1,8-naphthyridin-3-yl)acryloyl)-1,2,3,6-tetrahydropyridin-4-yl)benzonitrile;
- (Z)—N'-hydroxy-4-(1-((E)-3-(7-oxo-5,6,7,8-tetrahydro-1,8-naphthyridin-3-yl)acryloyl)-1,2,3,6-tetrahydropyridin-4-yl)benzimidamide;
- (E)-6-(3-(4-(4-nitrophenyl)-5,6-dihydropyridin-1(2H)-yl)-3-oxoprop-1-en-1-yl)-3,4-dihydro-1,8-naphthyridin-2(1H)-one;
- (E)-6-(3-(4-(4-aminophenyl)-5,6-dihydropyridin-1(2H)-yl)-3-oxoprop-1-en-1-yl)-3,4-dihydro-1,8-naphthyridin-2(1H)-one;
- (E)-N-(4-(1-(3-(7-oxo-5,6,7,8-tetrahydro-1,8-naphthyridin-3-yl)acryloyl)-1,2,3,6-tetrahydropyridin-4-yl)phenyl)acetamide;
- (E)-6-(3-(4-(3-nitrophenyl)-5,6-dihydropyridin-1(2H)-yl)-3-oxoprop-1-en-1-yl)-3,4-dihydro-1,8-naphthyridin-2(1H)-one;
- (E)-6-(3-(4-(3-aminophenyl)-5,6-dihydropyridin-1(2H)-yl)-3-oxoprop-1-en-1-yl)-3,4-dihydro-1,8-naphthyridin-2(1H)-one;
- (E)-N-(3-(1-(3-(7-oxo-5,6,7,8-tetrahydro-1,8-naphthyridin-3-yl)acryloyl)-1,2,3,6-tetrahydropyridin-4-yl)phenyl)acetamide;
- (E)-ethyl-4-(1-(3-(7-oxo-5,6,7,8-tetrahydro-1,8-naphthyridin-3-yl)acryloyl)-1,2,3,6-tetrahydropyridin-4-yl)benzoate;
- (E)-4-(1-(3-(7-oxo-5,6,7,8-tetrahydro-1,8-naphthyridin-3-yl)acryloyl)-1,2,3,6-tetrahydropyridin-4-yl)benzoic acid;
- (E)-4-(1-(3-(7-oxo-5,6,7,8-tetrahydro-1,8-naphthyridin-3-yl)acryloyl)-1,2,3,6-tetrahydropyridin-4-yl)benzamide;
- (E)-di-tert-butoxycarbonyl-1-(4-(1-(3-(7-oxo-5,6,7,8-tetrahydro-1,8-naphthyridin-3-yl)acryloyl)-1,2,3,6-tetrahydropyridin-4-yl)phenyl)guanidine;
- (E)-1-(4-(1-(3-(7-oxo-5,6,7,8-tetrahydro-1,8-naphthyridin-3-yl)acryloyl)-1,2,3,6-tetrahydropyridin-4-yl)phenyl)guanidine trifluoro aceticacid;
- (E)-1-(3-(1-(3-(7-oxo-5,6,7,8-tetrahydro-1,8-naphthyridin-3-yl)acryloyl)-1,2,3,6-tetrahydropyridin-4-yl)phenyl)guanidine;
- (E)-2-(4-(1-(3-(7-oxo-5,6,7,8-tetrahydro-1,8-naphthyridin-3-yl)acryloyl)-1,2,3,6-tetrahydropyridin-4-yl)phenoxy)acetonitrile;
- (Z)—N'-hydroxy-2-(4-(1-((E)-3-(7-oxo-5,6,7,8-tetrahydro-1,8-naphthyridin-3-yl)acryloyl)-1,2,3,6-tetrahydropyridin-4-yl)phenoxy)acetimidamide;
- (E)-4-((4-(1-(3-(7-oxo-5,6,7,8-tetrahydro-1,8-naphthyridin-3-yl)acryloyl)-1,2,3,6-tetrahydropyridin-4-yl)phenoxy)methyl)benzonitrile;
- (E)-4-((4-(1-(3-(7-oxo-5,6,7,8-tetrahydro-1,8-naphthyridin-3-yl)acryloyl)-1,2,3,6-tetrahydropyridin-4-yl)benzyl)oxy)benzonitrile;
- (E)-6-(3-(4-(3-(morpholinomethyl)phenyl)-5,6-dihydropyridin-1(2H)-yl)-3-oxoprop-1-en-1-yl)-3,4-dihydro-1,8-naphthyridin-2(1H)-one;
- (E)-6-(3-(4-(3,5-dihydroxyphenyl)-5,6-dihydropyridin-1(2H)-yl)-3-oxoprop-1-en-1-yl)-3,4-dihydro-1,8-naphthyridin-2(1H)-one;
- (E)-6-(3-(4-(3,4-dichlorophenyl)-5,6-dihydropyridin-1(2H)-yl)-3-oxoprop-1-en-1-yl)-3,4-dihydro-1,8-naphthyridin-2(1H)-one;
- (E)-6-(3-(4-(2-methyl-3-nitrophenyl)-5,6-dihydropyridin-1(2H)-yl)-3-oxoprop-1-en-1-yl)-3,4-dihydro-1,8-naphthyridin-2(1H)-one;
- (E)-6-(3-(4-(3-amino-2-methylphenyl)-5,6-dihydropyridin-1(2H)-yl)-3-oxoprop-1-en-1-yl)-3,4-dihydro-1,8-naphthyridin-2(1H)-one;
- (E)-N-(2-methyl-3-(1-(3-(7-oxo-5,6,7,8-tetrahydro-1,8-naphthyridin-3-yl)acryloyl)-1,2,3,6-tetrahydropyridin-4-yl)phenyl)acetamide;
- (E)-6-(3-(4-(6-methoxynaphthalen-2-yl)-5,6-dihydropyridin-1(2H)-yl)-3-oxoprop-1-en-1-yl)-3,4-dihydro-1,8-naphthyridin-2(1H)-one;
- (E)-6-(3-oxo-3-(4-(thiophen-2-yl)-5,6-dihydropyridin-1(2H)-yl)prop-1-en-1-yl)-3,4-dihydro-1,8-naphthyridin-2(1H)-one;
- (E)-6-(3-oxo-3-(4-(thiazol-2-yl)-5,6-dihydropyridin-1(2H)-yl)prop-1-en-1-yl)-3,4-dihydro-1,8-naphthyridin-2(1H)-one;
- (E)-6-(3-(4-(1-methyl-1H-imidazol-2-yl)-5,6-dihydropyridin-1(2H)-yl)-3-oxoprop-1-en-1-yl)-3,4-dihydro-1,8-naphthyridin-2(1H)-one;
- (E)-6-(3-(4-(1-methyl-1H-pyrazol-4-yl)-5,6-dihydropyridin-1(2H)-yl)-3-oxoprop-1-en-1-yl)-3,4-dihydro-1,8-naphthyridin-2(1H)-one;
- (E)-2-(4-(1-(3-(7-oxo-5,6,7,8-tetrahydro-1,8-naphthyridin-3-yl)acryloyl)-1,2,3,6-tetrahydropyridin-4-yl)benzyl)isoindoline-1,3-dione;
- (E)-2-(3-(1-(3-(7-oxo-5,6,7,8-tetrahydro-1,8-naphthyridin-3-yl)acryloyl)-1,2,3,6-tetrahydropyridin-4-yl)benzyl)isoindoline-1,3-dione;
- 6-(3-oxo-3-(4-phenyl-5,6-dihydropyridin-1(2H)-yl)propyl)-3,4-dihydro-1,8-naphthyridin-2(1H)-one;
- 6-((2-oxo-2-(4-phenyl-5,6-dihydropyridin-1(2H)-yl)ethyl)thio)-3,4-dihydro-1,8-naphthyridin-2(1H)-one;
- (E)-tert-butyl 2-oxo-6-(3-oxo-3-(4-phenyl-5,6-dihydropyridin-1(2H)-yl)prop-1-en-1-yl)-2,4-dihydro-1H-spiro[[1,8]naphthyridine-3,4'-piperidine]-1'-carboxylate;
- (E)-6-(3-oxo-3-(4-phenyl-5,6-dihydropyridin-1(2H)-yl)prop-1-en-1-yl)-1H-spiro[[1,8]naphthyridine-3,4'-piperidin]-2(4H)-one trifluoro aceticacid;
- (E)-3-(2-morpholinoethyl)-6-(3-oxo-3-(4-phenyl-5,6-dihydropyridin-1(2H)-yl)prop-1-en-1-yl)-3,4-dihydropyrido[2,3-d]pyrimidin-2(1H)-one;
- (E)-7-(3-oxo-3-(4-phenyl-5,6-dihydropyridin-1(2H)-yl)prop-1-en-1-yl)-4,5-dihydro-1H-pyrido[2,3-e][1,4]diazepin-2(3H)-one trifluoro aceticacid;
- (E)-4-methyl-7-(3-oxo-3-(4-phenyl-5,6-dihydropyridin-1(2H)-yl)prop-1-en-1-yl)-4,5-dihydro-1H-pyrido[2,3-e][1,4]diazepin-2(3H)-one;
- (E)-4-(2-morpholinoethyl)-7-(3-oxo-3-(4-phenyl-5,6-dihydropyridin-1(2H)-yl)prop-1-en-1-yl)-4,5-dihydro-1H-pyrido[2,3-e][1,4]diazepin-2(3H)-one;
- (E)-6-(3-(4-((5-methylthiazol-2-yl)methyl)-5,6-dihydropyridin-1(2H)-yl)-3-oxoprop-1-en-1-yl)-3,4-dihydro-1,8-naphthyridin-2(1H)-one;
- (E)-2-morpholino-N-(5-(3-oxo-3-(4-phenyl-5,6-dihydropyridin-1(2H)-yl)prop-1-en-1-yl)pyridin-2-yl)acetamide;
- (E)-2-(1H-imidazol-1-yl)-N-(5-(3-oxo-3-(4-phenyl-5,6-dihydropyridin-1(2H)-yl)prop-1-en-1-yl)pyridin-2-yl)acetamide;
- (E)-N-(5-(3-oxo-3-(4-phenyl-5,6-dihydropyridin-1(2H)-yl)prop-1-en-1-yl)pyridin-2-yl)-2-(1H-1,2,3-triazol-1-yl)acetamide;

(E)-N-(3-(morpholinomethyl)-5-(3-oxo-3-(4-phenyl-5,6-dihydropyridin-1(2H)-yl)prop-1-en-1-yl)pyridin-2-yl)acetamide;

(E)-6-(3-(4-benzyl-5,6-dihydropyridin-1(2H)-yl)-3-oxoprop-1-en-1-yl)-3,4-dihydro-1,8-naphthyridin-2(1H)-one;

(E)-6-(3-oxo-3-(4-(pyridin-4-ylmethyl)-5,6-dihydropyridin-1(2H)-yl)prop-1-en-1-yl)-3,4-dihydro-1,8-naphthyridin-2(1H)-one;

(E)-6-(3-(4-(4-fluorobenzyl)-5,6-dihydropyridin-1(2H)-yl)-3-oxoprop-1-en-1-yl)-3,4-dihydro-1,8-naphthyridin-2(1H)-one;

(E)-6-(3-(4-(3-fluorobenzyl)-5,6-dihydropyridin-1(2H)-yl)-3-oxoprop-1-en-1-yl)-3,4-dihydro-1,8-naphthyridin-2(1H)-one;

(E)-6-(3-(4-(2-fluorobenzyl)-5,6-dihydropyridin-1(2H)-yl)-3-oxoprop-1-en-1-yl)-3,4-dihydro-1,8-naphthyridin-2(1H)-one;

(E)-6-(3-(4-(3-chlorobenzyl)-5,6-dihydropyridin-1(2H)-yl)-3-oxoprop-1-en-1-yl)-3,4-dihydro-1,8-naphthyridin-2(1H)-one;

(E)-6-(3-(4-(4-chlorobenzyl)-5,6-dihydropyridin-1(2H)-yl)-3-oxoprop-1-en-1-yl)-3,4-dihydro-1,8-naphthyridin-2(1H)-one;

(E)-6-(3-oxo-3-(4-(4-(trifluoromethyl)benzyl)-5,6-dihydropyridin-1(2H)-yl)prop-1-en-1-yl)-3,4-dihydro-1,8-naphthyridin-2(1H)-one;

(E)-6-(3-(4-(4-methylbenzyl)-5,6-dihydropyridin-1(2H)-yl)-3-oxoprop-1-en-1-yl)-3,4-dihydro-1,8-naphthyridin-2(1H)-one;

(E)-6-(3-(4-(3-methylbenzyl)-5,6-dihydropyridin-1(2H)-yl)-3-oxoprop-1-en-1-yl)-3,4-dihydro-1,8-naphthyridin-2(1H)-one;

(E)-6-(3-(4-(2-methylbenzyl)-5,6-dihydropyridin-1(2H)-yl)-3-oxoprop-1-en-1-yl)-3,4-dihydro-1,8-naphthyridin-2(1H)-one;

(E)-4-((1-(3-(7-oxo-5,6,7,8-tetrahydro-1,8-naphthyridin-3-yl)acryloyl)-1,2,3,6-tetrahydropyridin-4-yl)methyl)benzonitrile;

(E)-3-((1-(3-(7-oxo-5,6,7,8-tetrahydro-1,8-naphthyridin-3-yl)acryloyl)-1,2,3,6-tetrahydropyridin-4-yl)methyl)benzonitrile;

(E)-2-((1-(3-(7-oxo-5,6,7,8-tetrahydro-1,8-naphthyridin-3-yl)acryloyl)-1,2,3,6-tetrahydropyridin-4-yl)methyl)benzonitrile;

(E)-6-(3-oxo-3-(4-(4-(trifluoromethoxy)benzyl)-5,6-dihydropyridin-1(2H)-yl)prop-1-en-1-yl)-3,4-dihydro-1,8-naphthyridin-2(1H)-one;

(E)-6-(3-oxo-3-(4-(3-(trifluoromethoxy)benzyl)-5,6-dihydropyridin-1(2H)-yl)prop-1-en-1-yl)-3,4-dihydro-1,8-naphthyridin-2(1H)-one;

(E)-6-(3-oxo-3-(4-(2-(trifluoromethoxy)benzyl)-5,6-dihydropyridin-1(2H)-yl)prop-1-en-1-yl)-3,4-dihydro-1,8-naphthyridin-2(1H)-one;

(E)-6-(3-(4-(2-nitrobenzyl)-5,6-dihydropyridin-1(2H)-yl)-3-oxoprop-1-en-1-yl)-3,4-dihydro-1,8-naphthyridin-2(1H)-one;

(E)-6-(3-(4-(3-nitrobenzyl)-5,6-dihydropyridin-1(2H)-yl)-3-oxoprop-1-en-1-yl)-3,4-dihydro-1,8-naphthyridin-2(1H)-one;

(E)-6-(3-(4-(3-aminobenzyl)-5,6-dihydropyridin-1(2H)-yl)-3-oxoprop-1-en-1-yl)-3,4-dihydro-1,8-naphthyridin-2(1H)-one;

(E)-6-(3-(4-(2-methoxybenzyl)-5,6-dihydropyridin-1(2H)-yl)-3-oxoprop-1-en-1-yl)-3,4-dihydro-1,8-naphthyridin-2(1H)-one;

(E)-6-(3-(4-(4-fluoro-2-methylbenzyl)-5,6-dihydropyridin-1(2H)-yl)-3-oxo prop-1-en-1-yl)-3,4-dihydro-1,8-naphthyridin-2(1H)-one;

(E)-6-(3-oxo-3-(4-(thiophen-2-ylmethyl)-5,6-dihydropyridin-1(2H)-yl)prop-1-en-1-yl)-3,4-dihydro-1,8-naphthyridin-2(1H)-one;

(E)-6-(3-(4-((5-nitrothiophen-2-yl)methyl)-5,6-dihydropyridin-1(2H)-yl)-3-oxoprop-1-en-1-yl)-3,4-dihydro-1,8-naphthyridin-2(1H)-one;

(E)-6-(3-(4-((3-methylthiophen-2-yl)methyl)-5,6-dihydropyridin-1(2H)-yl)-3-oxoprop-1-en-1-yl)-3,4-dihydro-1,8-naphthyridin-2(1H)-one;

(E)-6-(3-(4-((3-chlorothiophen-2-yl)methyl)-5,6-dihydropyridin-1(2H)-yl)-3-oxoprop-1-en-1-yl)-3,4-dihydro-1,8-naphthyridin-2(1H)-one;

(E)-N-(5-(3-oxo-3-(4-(thiophen-2-ylmethyl)-5,6-dihydropyridin-1(2H)-yl)prop-1-en-1-yl)pyridin-2-yl)acetamide;

(E)-2-morpholino-N-(5-(3-oxo-3-(4-(thiophen-2-ylmethyl)-5,6-dihydropyridin-1(2H)-yl)prop-1-en-1-yl)pyridin-2-yl)acetamide;

(E)-3-(2-morpholinoethyl)-6-(3-oxo-3-(4-(thiophen-2-ylmethyl)-5,6-dihydropyridin-1(2H)-yl)prop-1-en-1-yl)-3,4-dihydropyrido[2,3-d]pyrimidin-2(1H)-one;

(E)-8-(3-oxo-3-(4-(thiophen-2-ylmethyl)-5,6-dihydropyridin-1(2H)-yl)prop-1-en-1-yl)-2,3-dihydro-1H-pyrido[2,3-b][1,4]diazepin-4(5H)-one;

(E)-7-(3-oxo-3-(4-(thiophen-2-ylmethyl)-5,6-dihydropyridin-1(2H)-yl)prop-1-en-1-yl)-4,5-dihydro-1H-pyrido[2,3-e][1,4]diazepin-2(3H)-one trifluoro aceticacid;

(E)-4-methyl-7-(3-oxo-3-(4-(thiophen-2-ylmethyl)-5,6-dihydropyridin-1(2H)-yl)prop-1-en-1-yl)-4,5-dihydro-1H-pyrido[2,3-e][1,4]diazepin-2(3H)-one;

(E)-tert-butyl-2-oxo-6-(3-oxo-3-(4-(thiophen-2-ylmethyl)-5,6-dihydropyridin-1(2H)-yl)prop-1-en-1-yl)-2,4-dihydro-1H-spiro[[1,8]naphthyridine-3,4'-piperidine]-1'-carboxylate;

(E)-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one trifluoro aceticacid;

(E)-1'-acetyl-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one;

(E)-6-(3-oxo-3-(4-(thiazol-2-ylmethyl)-5,6-dihydropyridin-1(2H)-yl)prop-1-en-1-yl)-3,4-dihydro-1,8-naphthyridin-2(1H)-one;

(E)-6-(3-(4-((1-methyl-1H-pyrazol-4-yl)methyl)-5,6-dihydropyridin-1(2H)-yl)-3-oxoprop-1-en-1-yl)-3,4-dihydro-1,8-naphthyridin-2(1H)-one;

(E)-6-(3-(4-((1H-imidazol-1-yl)methyl)-5,6-dihydropyridin-1(2H)-yl)-3-oxo prop-1-en-1-yl)-3,4-dihydro-1,8-naphthyridin-2(1H)-one;

(E)-6-(3-(4-((1H-pyrazol-1-yl)methyl)-5,6-dihydropyridin-1(2H)-yl)-3-oxo prop-1-en-1-yl)-3,4-dihydro-1,8-naphthyridin-2(1H)-one;

(E)-6-(3-(4-((1H-1,2,3-triazol-1-yl)methyl)-5,6-dihydropyridin-1(2H)-yl)-3-oxoprop-1-en-1-yl)-3,4-dihydro-1,8-naphthyridin-2(1H)-one;

(E)-6-(3-(4-((1H-1,2,4-triazol-1-yl)methyl)-5,6-dihydropyridin-1(2H)-yl)-3-oxoprop-1-en-1-yl)-3,4-dihydro-1,8-naphthyridin-2(1H)-one;

(E)-6-(3-oxo-3-(4-(pyrrolidin-1-ylmethyl)-5,6-dihydropyridin-1(2H)-yl)prop-1-en-1-yl)-3,4-dihydro-1,8-naphthyridin-2(1H)-one;

(E)-6-(3-(4-(morpholinomethyl)-5,6-dihydropyridin-1(2H)-yl)-3-oxoprop-1-en-1-yl)-3,4-dihydro-1,8-naphthyridin-2(1H)-one;

(E)-6-(3-(4-((3-methylbenzofuran-2-yl)methyl)-5,6-dihydropyridin-1(2H)-yl)-3-oxoprop-1-en-1-yl)-3,4-dihydro-1,8-naphthyridin-2(1H)-one;

(E)-6-(3-oxo-3-(4-(phenylethynyl)-5,6-dihydropyridin-1(2H)-yl)prop-1-en-1-yl)-3,4-dihydro-1,8-naphthyridin-2(1H)-one;

(E)-6-(3-oxo-3-(4-(phenoxymethyl)-5,6-dihydropyridin-1(2H)-yl)prop-1-en-1-yl)-3,4-dihydro-1,8-naphthyridin-2(1H)-one;

(E)-6-(3-(4-((2-fluorophenoxy)methyl)-5,6-dihydropyridin-1(2H)-yl)-3-oxoprop-1-en-1-yl)-3,4-dihydro-1,8-naphthyridin-2(1H)-one;

(E)-6-(3-(4-((3-fluorophenoxy)methyl)-5,6-dihydropyridin-1(2H)-yl)-3-oxo prop-1-en-1-yl)-3,4-dihydro-1,8-naphthyridin-2(1H)-one;

(E)-6-(3-(4-((4-fluorophenoxy)methyl)-5,6-dihydropyridin-1(2H)-yl)-3-oxo prop-1-en-1-yl)-3,4-dihydro-1,8-naphthyridin-2(1H)-one;

(E)-6-(3-(4-((2-chlorophenoxy)methyl)-5,6-dihydropyridin-1(2H)-yl)-3-oxo prop-1-en-1-yl)-3,4-dihydro-1,8-naphthyridin-2(1H)-one;

(E)-6-(3-(4-((3-chlorophenoxy)methyl)-5,6-dihydropyridin-1(2H)-yl)-3-oxo prop-1-en-1-yl)-3,4-dihydro-1,8-naphthyridin-2(1H)-one;

(E)-6-(3-(4-((4-chlorophenoxy)methyl)-5,6-dihydropyridin-1(2H)-yl)-3-oxo prop-1-en-1-yl)-3,4-dihydro-1,8-naphthyridin-2(1H)-one;

(E)-6-(3-(4-((2-methoxyphenoxy)methyl)-5,6-dihydropyridin-1(2H)-yl)-3-oxoprop-1-en-1-yl)-3,4-dihydro-1,8-naphthyridin-2(1H)-one;

(E)-6-(3-(4-((4-methoxyphenoxy)methyl)-5,6-dihydropyridin-1(2H)-yl)-3-oxoprop-1-en-1-yl)-3,4-dihydro-1,8-naphthyridin-2(1H)-one;

(E)-6-(3-oxo-3-(4-((4-(trifluoromethoxy)phenoxy)methyl)-5,6-dihydropyridin-1(2H)-yl)prop-1-en-1-yl)-3,4-dihydro-1,8-naphthyridin-2(1H)-one;

(E)-6-(3-(4-((2-methoxy-4-methylphenoxy)methyl)-5,6-dihydropyridin-1(2H)-yl)-3-oxoprop-1-en-1-yl)-3,4-dihydro-1,8-naphthyridin-2(1H)-one;

(E)-6-(3-(4-((2-fluoro-4-nitrophenoxy)methyl)-5,6-dihydropyridin-1(2H)-yl)-3-oxoprop-1-en-1-yl)-3,4-dihydro-1,8-naphthyridin-2(1H)-one;

(E)-6-(3-(4-((4-ethyl-5-fluoro-2-methoxyphenoxy)methyl)-5,6-dihydropyridin-1(2H)-yl)-3-oxoprop-1-en-1-yl)-3,4-dihydro-1,8-naphthyridin-2(1H)-one;

(E)-6-(3-oxo-3-(4-phenethyl-5,6-dihydropyridin-1(2H)-yl)prop-1-en-1-yl)-3,4-dihydro-1,8-naphthyridin-2(1H)-one;

(E)-6-(3-(3,4-dihydroisoquinolin-2(1H)-yl)-3-oxoprop-1-en-1-yl)-3,4-dihydro-1,8-naphthyridin-2(1H)-one;

(E)-6-(3-(6-bromo-3,4-dihydroisoquinolin-2(1H)-yl)-3-oxoprop-1-en-1-yl)-3,4-dihydro-1,8-naphthyridin-2(1H)-one;

(E)-6-(3-(6-methoxy-3,4-dihydroisoquinolin-2(1H)-yl)-3-oxoprop-1-en-1-yl)-3,4-dihydro-1,8-naphthyridin-2(1H)-one;

(E)-6-(3-(6-hydroxy-3,4-dihydroisoquinolin-2(1H)-yl)-3-oxoprop-1-en-1-yl)-3,4-dihydro-1,8-naphthyridin-2(1H)-one;

6-((E)-3-oxo-3-(6-((E)-3-oxo-3-(pyrrolidin-1-yl)prop-1-en-1-yl)-3,4-dihydroisoquinolin-2(1H)-yl)prop-1-en-1-yl)-3,4-dihydro-1,8-naphthyridin-2(1H)-one;

6-((2-(6-bromo-3,4-dihydroisoquinolin-2(1H)-yl)-2-oxoethyl)thio)-3,4-dihydro-1,8-naphthyridin-2(1H)-one;

(E)-6-(3-(3,4-dihydroisoquinolin-2(1H)-yl)-3-oxoprop-1-en-1-yl)-3-(2-morpholinoethyl)-3,4-dihydropyrido[2,3-d]pyrimidin-2(1H)-one;

(E)-tert-butyl 6-(3-(3,4-dihydroisoquinolin-2(1H)-yl)-3-oxoprop-1-en-1-yl)-2-oxo-2,4-dihydro-1H-spiro[[1,8]naphthyridine-3,4'-piperidine]-1'-carboxylate;

(E)-6-(3-(3,4-dihydroisoquinolin-2(1H)-yl)-3-oxoprop-1-en-1-yl)-1H-spiro[[1,8]naphthyridine-3,4'-piperidin]-2(4H)-one trifluoro acetic acid;

(E)-7-(3-(3,4-dihydroisoquinolin-2(1H)-yl)-3-oxoprop-1-en-1-yl)-4,5-dihydro-1H-pyrido[2,3-e][1,4]diazepin-2(3H)-one;

(E)-7-(3-(3,4-dihydroisoquinolin-2(1H)-yl)-3-oxoprop-1-en-1-yl)-4-methyl-4,5-dihydro-1H-pyrido[2,3-e][1,4]diazepin-2(3H)-one;

(E)-7-(3-(3,4-dihydroisoquinolin-2(1H)-yl)-3-oxoprop-1-en-1-yl)-4-(2-morpholinoethyl)-4,5-dihydro-1H-pyrido[2,3-e][1,4]diazepin-2(3H)-one;

(E)-1-(5-(3-(3,4-dihydroisoquinolin-2(1H)-yl)-3-oxoprop-1-en-1-yl)pyridin-2-yl)azetidin-2-one;

(E)-N-(5-(3-(3,4-dihydroisoquinolin-2(1H)-yl)-3-oxoprop-1-en-1-yl)pyridin-2-yl)-2-morpholinoacetamide;

(E)-N-(5-(3-(3,4-dihydroisoquinolin-2(1H)-yl)-3-oxoprop-1-en-1-yl)pyridin-2-yl)-2-(1H-imidazol-1-yl)acetamide;

(E)-N-(5-(3-(3,4-dihydroisoquinolin-2(1H)-yl)-3-oxoprop-1-en-1-yl)pyridin-2-yl)-2-(1H-1,2,3-triazol-1-yl)acetamide;

(E)-tert-butyl2-oxo-7-(3-oxo-3-(4-(thiophen-2-ylmethyl)-5,6-dihydropyridin-1(2H)-yl)prop-1-en-1-yl)-2,3-dihydro-1H-pyrido[2,3-e][1,4]diazepine-4(5H)-carboxylate;

(E)-1'-(2-hydroxyacetyl)-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one;

(E)-2-oxo-6-(3-oxo-3-(4-(thiophen-2-ylmethyl)-5,6-dihydropyridin-1(2H)-yl)prop-1-en-1-yl)-2,4-dihydro-1H-spiro[[1,8]naphthyridine-3,4'-piperidine]-1'-carboxamide;

(E)-1'-(3-methylbutanoyl)-6-(3-oxo-3-(4-(thiophen-2-ylmethyl)-5,6-dihydro pyridin-1(2H)-yl)prop-1-en-1-yl)-1H-spiro[[1,8]naphthyridine-3,4'-piperidin]-2(4H)-one;

(E)-140-butyryl-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one;

(E)-1'-(3,3-dimethylbutanoyl)-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one;

(E)-8-(3-oxo-3-(4-(thiazol-2-ylmethyl)-5,6-dihydropyridin-1(2H)-yl)prop-1-en-1-yl)-2,3-dihydro-1H-pyrido[2,3-b][1,4]diazepin-4(5H)-one;

(E)-1'-(3-hydroxypropyl)-6-(3-oxo-3-(4-(thiophen-2-ylmethyl)-5,6-dihydro pyridin-1(2H)-yl)prop-1-en-1-yl)-1H-spiro[[1,8]naphthyridine-3,4'-piperidin]-2(4H)-one;

(E)-6-(3-oxo-3-(4-(thiazol-5-ylmethyl)-5,6-dihydropyridin-1(2H)-yl)prop-1-en-1-yl)-3,4-dihydro-1,8-naphthyridin-2(1H)-one;

(E)-1'-methyl-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one;

(E)-3-(2-(2-oxo-7-azaspiro[3,5]nonan-7-yl)ethyl)-6-(3-oxo-3-(4-(thiophen-2-ylmethyl)-5,6-dihydropyridin-1(2H)-yl)prop-1-en-1-yl)-3,4-dihydropyrido[2,3-d]pyrimidin-2(1H)-one;

(E)-3-(2-(6-azaspiro[2,5]octan-6-yl)ethyl)-6-(3-oxo-3-(4-(thiophen-2-ylmethyl)-5,6-dihydropyridin-1(2H)-yl)prop-1-en-1-yl)-3,4-dihydropyrido[2,3-d]pyrimidin-2(1H)-one;

(E)-7-(3-oxo-3-(4-(thiazol-2-ylmethyl)-5,6-dihydropyridin-1(2H)-yl)prop-1-en-1-yl)-4,5-dihydro-1H-pyrido[2,3-e][1,4]diazepin-2(3H)-one;

(E)-tert-butyl2-(2-(2-oxo-6-(3-oxo-3-(4-(thiophen-2-ylmethyl)-5,6-dihydropyridin-1(2H)-yl)prop-1-en-1-yl)-1,2-dihydropyrido[2,3-d]pyrimidin-3(4H)-yl)ethyl)-2,7-diazaspiro[3.5]nonane-7-carboxylate; and (E)-3-(2-(2,7-diazaspiro[3.5]nonan-2-yl)ethyl)-6-(3-oxo-3-(4-(thiophen-2-yl methyl)-5,6-dihydropyridin-1(2H)-yl)prop-1-en-1-yl)-3,4-dihydropyrido[2,3-d]pyrimidin-2(1H)-one 2,2,2-trifluoroacetate;

or a pharmaceutically acceptable salt thereof.

16. A compound selected from the group consisting of (E)-6-(3-oxo-3-(4-(thiophen-2-ylmethyl)-5,6-dihydropyridin-1(2H)-yl)prop-1-en-1-yl)-3,4-dihydro-1,8-naphthyridin-2(1H)-one;

(E)-7-(3-oxo-3-(4-(thiophen-2-ylmethyl)-5,6-dihydropyridin-1(2H)-yl)prop-1-en-1-yl)-4,5-dihydro-1H-pyrido[2,3-e][1,4]diazepin-2(3H)-one trifluoro acetic acid;

(E)-1'-acetyl-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one;

(E)-6-(3-oxo-3-(4-(thiazol-2-ylmethyl)-5,6-dihydropyridin-1(2H)-yl)prop-1-en-1-yl)-3,4-dihydro-1,8-naphthyridin-2(1H)-one;

(E)-1'-(3-methylbutanoyl)-6-(3-oxo-3-(4-(thiophen-2-ylmethyl)-5,6-dihydro pyridin-1(2H)-yl)prop-1-en-1-yl)-1H-spiro[[1,8]naphthyridine-3,4'-piperidin]-2(4H)-one;

(E)-1'-butyryl-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one;

(E)-1'-(3-hydroxypropyl)-6-(3-oxo-3-(4-(thiophen-2-ylmethyl)-5,6-dihydro pyridin-1(2H)-yl)prop-1-en-1-yl)-1H-spiro[[1,8]naphthyridine-3,4'-piperidin]-2(4H)-one;

(E)-6-(3-oxo-3-(4-(thiazol-5-ylmethyl)-5,6-dihydropyridin-1(2H)-yl)prop-1-en-1-yl)-3,4-dihydro-1,8-naphthyridin-2(1H)-one;

(E)-1'-methyl-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one; and (E)-3-(2-(2-oxo-7-azaspiro[3,5]nonan-7-yl)ethyl)-6-(3-oxo-3-(4-(thiophen-2-ylmethyl)-5,6-dihydropyridin-1(2H)-yl)prop-1-en-1-yl)-3,4-dihydropyrido[2,3-d]pyrimidin-2(1H)-one;

or a pharmaceutically acceptable salt thereof.

17. A pharmaceutical composition comprising a therapeutically effective amount of at least one compound of formula (I) according to claim 1, their pharmaceutically acceptable salts and stereoisomers thereof, with at least one pharmaceutically acceptable carrier, diluent or excipient including mixtures thereof in all ratios.

18. A method of treating a disease comprising the administration to a subject in need thereof a therapeutically effective amount of a compound according to claim 1, wherein said disease is bacterial diseases.

19. A method for inhibiting FabI comprising administering to a subject in need thereof a therapeutically effective amount of a compound according to claim 1, wherein said disease is bacterial diseases.

* * * * *

UNITED STATES PATENT AND TRADEMARK OFFICE
CERTIFICATE OF CORRECTION

PATENT NO. : 9,062,002 B2  
APPLICATION NO. : 14/361171  
DATED : June 23, 2015  
INVENTOR(S) : Mohamed Takhi et al.

It is certified that error appears in the above-identified patent and that said Letters Patent is hereby corrected as shown below:

In the specification

Column 21-22, Scheme-5, 5.1, remove the ",," after "CH$_2$".

Column 21-22, Scheme-5, 5.3, remove the "," after "CH$_2$".

Column 26, Line 48, remove the "," after "and".

Column 27, Line 55, delete "120" and insert --12-- therefor.

Column 35, Line 1, delete "E." and insert --δ-- therefor.

Column 50, Line 66, delete "their to physicochemical" and insert --their physicochemical--.

Column 65, Line 3, delete "(E)" and insert --((E)-- therefor.

Column 77, Line 41, delete "6.1-1" and insert --6.11-- therefor.

Column 106, Line 24, insert --δ-- before "11.02".

Column 125, Line 37, delete "198" and insert --3.98-- therefor.

Column 128, Line 32, insert --δ-- before "10:35".

Column 134, Line 36, delete "spiroa" and insert --spiro-- therefor.

Column 141, Line 42, insert --δ-- before "10.91".

Signed and Sealed this  
Fifteenth Day of December, 2015

Michelle K. Lee  
*Director of the United States Patent and Trademark Office*

CERTIFICATE OF CORRECTION (continued)
U.S. Pat. No. 9,062,002 B2

In the claims

Column 158, Lines 54-55, delete "dihynaphthyridin-2(1H)-one" and insert --dihydro-1,8-naphthyridin-2(1H)-one-- therefor.

Column 164, Line 44, delete "140" and insert --1'-- therefor.